United States Patent
Ogawa et al.

[11] Patent Number: 5,622,947
[45] Date of Patent: Apr. 22, 1997

[54] BENZOHETEROCYCLIC COMPOUNDS AND VASOPRESSIN ANTAGONIST AND OXYTOCIN ANTAGONIST COMPOSITIONS CONTAINING A BENZOHETEROCYCLIC COMPOUND

[75] Inventors: Hidenori Ogawa; Kazumi Kondo; Hiroshi Yamashita; Kenji Nakaya, all of Tokushima; Hajime Komatsu, Tokyo; Michinori Tanaka, Tokushima; Kazuyoshi Kitano, Tokushima; Michiaki Tominaga, Tokushima; Yoichi Yabuuchi, Tokushima, all of Japan

[73] Assignee: Otsuka Pharmaceutical Co., Ltd., Tokyo, Japan

[21] Appl. No.: 244,424

[22] PCT Filed: Oct. 15, 1993

[86] PCT No.: PCT/JP93/01483

§ 371 Date: May 25, 1994

§ 102(e) Date: May 25, 1994

[87] PCT Pub. No.: WO94/08582

PCT Pub. Date: Apr. 28, 1994

[30] Foreign Application Priority Data

Oct. 16, 1992 [JP] Japan ................... 4-277589

[51] Int. Cl.$^6$ .................. A61K 31/55; C07D 223/16
[52] U.S. Cl. .................. 514/213; 540/593; 540/594; 540/476
[58] Field of Search .................. 514/213; 540/593, 540/594, 476

[56] References Cited

U.S. PATENT DOCUMENTS 3,516,987 6/1970 Charles et al. .................. 540/593
3,542,760 11/1970 Charles et al. .................. 540/593
5,258,510 11/1993 Ogawa et al. .................. 540/476

FOREIGN PATENT DOCUMENTS

WO9408582 4/1994 WIPO .

*Primary Examiner*—Yogendra N. Gupta
*Attorney, Agent, or Firm*—Sughrue, Mion, Zinn, Macpeak & Seas

[57] ABSTRACT

An object of the present invention is to provide a vasopressin antagonist and oxytocin antagonist.

The vasopressing antagonist and oxytocin antagonist according to the present invention contain, as the active ingredient, a benzoheterocyclic compound represented by the general formula (1):

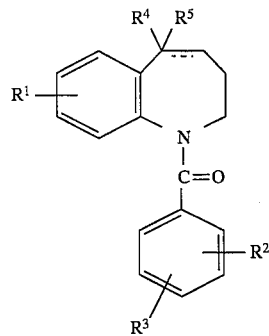

(wherein $R^1$, $R^2$, $R^3$, $R^4$, $R^5$ and the carbon-carbon bond between 4- and 5-positions in the benzoazepine skeleton are the same as defined in claims 1, 2 and 3.) or salt thereof.

28 Claims, No Drawings

BENZOHETEROCYCLIC COMPOUNDS AND VASOPRESSIN ANTAGONIST AND OXYTOCIN ANTAGONIST COMPOSITIONS CONTAINING A BENZOHETEROCYCLIC COMPOUND

TECHNICAL FIELD

The present invention relates to a vasopressin antagonist and oxytocin antagonist containing a benzoheterocyclic compound as an active ingredient.

BACKGROUND ART

Some of benzoheterocyclic compounds being used as the active ingredients in the vasopressin antagonists and oxytocin antagonists which are represented by the general formula (1) containing novel compounds.

Some benzohetrocyclic compounds having chemical structural formulae similar to those of benzoheterocyclic compounds according to the present invention are disclosed in EP-A-0382185 A2 (Publication Date: Aug. 15, 1990); WO 91/05549 (Publication Date: May 2, 1991) and EP-A-0470514A1 (Publication Date: Feb. 12, 1992). Furthermore, EP-A-0514667A1 (Publication Date: Nov. 25, 1992) discloses benzoheterocyclic compounds, and is known as the junior patent application of the present invention.

The substituents bonded at 1-position in the benzoheterocyclic compounds disclosed in these prior art references are substantially different from the substituents bonded at 1-position in the benzoheterocyclic compounds according to the present invention.

DISCLOSURE OF THE INVENTION

The benzoheterocyclic compounds or a salts thereof of the present invention are prepresented by the general formula (1) as follows:

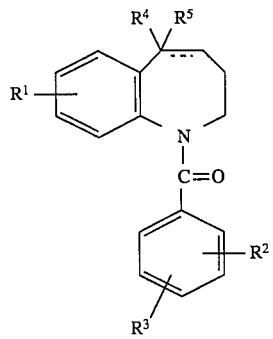

wherein, $R^1$ is a hydrogen atom, a halogen atom, a hydroxyl group, a lower alkanoyloxy group, an amino-lower alkoxy group which may have the substituents selected from the group consisting of lower alkyl group and lower alkanoyl group, a carboxy-substituted lower alkoxy group, a lower alkoxycarbonyl-substituted lower alkoxy group, or an aminocarbonyl-lower alkoxy group which may have lower alkyl groups as the substituents;

$R^4$ is a hydrogen atom, a group of the formula:

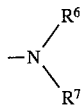

(wherein $R^6$ and $R^7$ are the same or different, and are each a hydrogen atom, a lower alkyl group, a lower alkenyl group or a benzoyl group having halogen atoms as the substituents on the phenyl ring), a lower alkenyloxy group, a hydroxyl group-substituted lower alkyl group, a group of the formula:

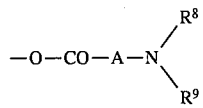

(wherein

A is a lower alkylene group;

$R^8$ and $R^9$ are the same or diffrent, and are each a hydrogen atom or a lower alkyl group; further $R^8$ and $R^9$ may form a 5- to 6-membered saturated or unsaturated heterocyclic group by combining with the adjacent nitrogen atom being bonded thereto, together with or without other nitrogen atom or oxygen atom, said heterocyclic group may be substituted with lower alkyl groups), a group of the formula $—O—R^{10}$ (wherein $R^{10}$ is an amino acid residue), a lower alkoxycarbonyl-substituted lower alkylidene group, a lower alkoxycarbonyl-substituted lower alkyl group, a carboxy-substituted lower alkyl group, a group of the formula:

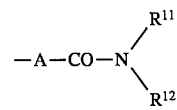

(wherein

A is the same as defined above;

$R^{11}$ and $R^{12}$ are the same or different, and are each a hydrogen atom, a lower alkyl group which may have hydroxyl groups as the substituents, a piperidinyl group which may have phenyl-lower alkyl group on the piperidine ring, a carbamoyl-substituted lower alkyl group, a pyridyl-substituted lower alkyl group, a pyridyl group, a group of the formula:

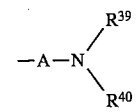

(wherein

A is a lower alkylene group;

$R^{39}$ and $R^{40}$ are the same or different, and are each a hydrogen atom or a lower alkyl group which may have hydroxyl group as the substituents;

further $R^{39}$ and $R^{40}$ may form a 5- or 6-membered saturated heterocyclic group, by combining with the adjacent nitrogen atom being bonded thereto, together with or without other nitrogen atom or oxygen atom, said heterocyclic group may have lower alkyl groups on the heterocyclic ring), a pyrazinyl-substituted lower alkyl group which may have, as the substituents, lower alkyl groups on the pyrazine ring, pyrrolyl-substituted lower alkyl group which may have, as the substituents, lower alkyl groups on the pyrrole ring, a pyrrolidinyl-substituted lower alkyl group which may have, as the substituents, lower alkyl groups on the pyrrolidine ring, or a phenyl group which may have halogen atoms on the phenyl ring;

further, $R^{11}$ and $R^{12}$ may form 5 to 7-membered saturated heterocyclic group, by combining with the adjacent nitrogen atom being bonded thereto, together with or without other nitrogen atom or oxygen atom; said heterocyclic group may be substituted with a lower alkyl group, a lower alkoxycarbonyl group, an amino group which may have the substituents selected from the group consisting of a lower alkyl group and a lower alkanoyl group, a lower alkoxycarbonyl-substituted lower alkyl group, a phenyl group which may have halogen atoms on the phenyl ring, a cyano-substituted lower alkyl group, a lower alkenyl group, an oxyranyl-substituted lower alkyl group, a carbamoyl-substituted lower alkyl group, a lower alkyl group having 1 to 2 substituents selected from the group consisting of a hydroxyl group and an amino group which may have lower alkyl group, or a pyrrolidinylcarbonyl-lower alkyl group), group of the formula:

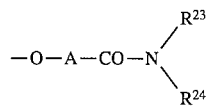

(wherein

A is the same as defined above;

$R^{23}$ and $R^{24}$ are the same or different, and are each a hydrogen atom, a lower alkyl group, a lower alkoxycarbonyl-substituted lower alkyl group, a carboxy-substituted lower alkyl group, a piperidinyl group which may have lower alkyl groups on the piperidine ring, a group of the formula:

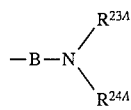

(wherein

B is an alkylene group;

$R^{23A}$ and $R^{24A}$ are the same or different, and are each a hydrogen atom or a lower alkyl group;

further $R^{23A}$ and $R^{24A}$ may form a 5- to 6-membered saturated hetero-cyclic group, by combining with the adjacnet nitrogen atom being bonded thereto, together with or without other nitrogen atom or oxygen atom), further $R^{23}$ and $R^{24}$ may form a 5- to 7-membered hetero-cyclic group group, by combining with the adjacent nitrogen atom being bonded, thereto together with or without other nitrogen atom or oxygen atom), a pyrrolidinylcarbonyl-lower alkoxy group having lower alkoxycarbonyl group on the pyrrolidine ring, a lower alkoxy-substituted lower alkanoyloxy group, a group of the formula:

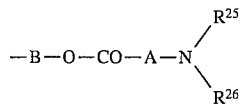

(wherein

A is the same as defined above;

B is a lower alkylene group; $R^{25}$ and $R^{26}$ are the same or different, and are each a hydrogen atom or a lower alkyl group), an amino-substituted lower alkylidene group, a group of the formula:

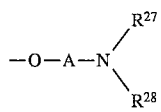

(wherein

A is the same as defined above;

$R^{27}$ and $R^{28}$ are the same or different, and are each a hydrogen atom, a lower alkyl group, a lower alkenyl group, a lower alkynyl group, a lower alkylsulfonyl group, an aminothiocarbonyl group which may have lower alkyl groups as the substituents, a group of the formula:

(wherein $R^{41}$ is a hydrogen atom or a cyano group;

$R^{42}$ is a lower alkyl group or an amino group which may have a lower alkyl groups as the substituents), a carbamoyl group, a lower alkoxycarbonyl group, a cycloalkyl group, a phenyl-lower alkyl group which may have halogen atoms as the substituents on the phenyl ring, a cyano-substituted lower alkyl group, a halogen atom-substituted lower alkylsulfonyl group, an amino-substituted lower alkyl group which may have lower alkylgroups as the substituents;

further, $R^{27}$ and $R^{28}$ may form a 5- to 10-membered single ring or binary ring saturated or unsaturated heterocyclic group, said heterocyclic group may be substituted with an oxo group, a lower alkyl group, a lower alkoxycarbonyl group, a lower alkanoyl group or a lower alkanoylamino group on the heterocyclic ring), a cyano group, a cyano-substituted lower alkyl group, a phenylsulfonyloxy group which may have lower alkyl groups as the substituents on the phenyl ring, a lower alkoxy group having hydroxy groups, a group of the formula:

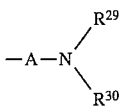

(wherein

A is the same as defined above;

$R^{29}$ is a hydrogen atom or a lower alkyl group;

$R^{30}$ is a lower alkenyl group, a cycloalkyl group or a lower alkynyl group;

further $R^{29}$ and $R^{30}$ may form a 5- to 6-memberedsaturated heterocyclic group, by combining with the adjacent nitrogen atom being bonded thereto, together with or without other nitrogen atom or oxygen atom; said heterocyclic group may be substituted with a lower alkyl group, a lower alkanoyl group, an amino group which may have the substituent selected from the group consisting of a lower alkyl group, and a lower alkanoyl group, a lower alkylsulfonyl group, a lower alkoxycarbonyl group or an aminocarbonyl group which may have lower alkyl groups as the substituents), a phenylsulfonyloxy-substituted lower alkyl group which may have lower alkyl groups as the substituents on the phenyl ring, a phthalimide-substituted lower alkyl group a cyano-substituted lower alkylidene group, a halogen atoms-substituted lower alkyl group, an imidazolyl-substituted lower alkyl group, a 1,2,4-triazolyl-substituted lower alkoxy group, a 1,2,3,4-tetrazolyl-substituted lower alkoxy group, a 1,2,3,5-tetrazolyl-substituted lower alkoxy group, a 1,2,3,4-tetrazolyl-substituted lower alkyl group, a 1,2,3,5-tetrazolyl-substituted lower alkyl group, 1,2,4-triazolyl-substituted lower alkyl group, a carboxy-substituted lower alkoxy group, a lower alkoxycarbonyl-substituted lower alkoxy group, a pyridylthio-substituted lower alkoxy group, a pyrimidinylthio-substituted lower alkoxy group which may have lower alkyl groups on the pyrimidine ring, a imidazolthio-substituted lower alkoxy group, a pyridylsulfinyl-substituted lower alkoxy group, a pyridylsulfonyl-substituted lower alkoxy group, an imidazolylsulfinyl-substituted lower alkoxy group and an imidazolylsulfonyl-substituted lower alkoxy group;

$R^5$ is a hydrogen atom or a hydroxyl group;

$R^4$ and $R^5$ may form an oxo group by combining together;

$R^2$ is a hydrogen atom, a lower alkyl group, a hydroxyl group, a halogen atom or a lower alkoxy group;

$R^3$ is a group of the formula

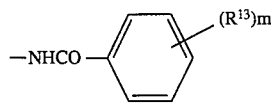

(wherein $R^{13}$ is a halogen atom, a hydrogen group, a carbamoyl group, a piperazinyl-lower alkoxy group having a lower alkanoyl group at 4-position in the piperazine ring, an imidazolyl-substituted lower alkoxy group, a piperidinyl-lower alkoxy group having lower alkanoylamino groups on the piperidine ring, a 1,2,4-triazolyl-substituted alkoxy group, an ureido-substituted lower alkoxy group which may have lower alkyl groups, or an amino-substituted lower alkoxy group which may have lower alkyl groups as the substituents;

m is 0 or an integer of 1 to 3), a phenyl-lower alkanoylamino group having 1 to 3 substituents selected from the group consisting of a halogen atom, a lower alkoxy group, a lower alkyl group and a nitro group, a group of the formula:

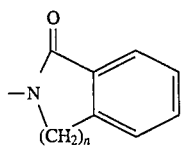

(wherein n is 1 or 2), or a group of the formula:

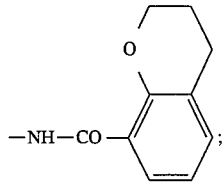

the carbon-carbon bond between 4- and 5-positions in the benzoazepin skeleton is a single bond or double bond;

provided that when $R^1$ is a hydrogen atom or a halogen atom;

$R^4$ is a hydrogen atom, a group of the formula:

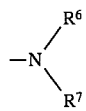

(wherein $R^6$ and $R^7$ are the same as defined above, excluding a benzoyl group having halogen atoms as the substituents on the phenyl group), a group of the formula:

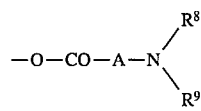

(wherein

A is the same as defined above;

$R^8$ and $R^9$ are the same or different and are each a hydrogen atom or a lower alkyl group), a hydroxy-substituted lower alkyl group, a carboxy-substituted lower alkoxy group, a lower alkoxycarbonyl-substituted lower alkoxy group, or a group of the formula:

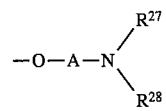

(wherein

A is the same as defined above;

$R^{27}$ and $R^{28}$ are the same or different, and are each a hydrogen atom or a lower alkyl group); and $R^5$ is a hydrogen atom or a hydroxyl group or $R^4$ and $R^5$ may form an oxo group by combinig together; further when $R^3$ is a group of the formula

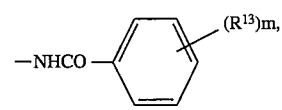

then $R^{13}$ should be of a carbamoyl group, a piperazinyl-lower alkoxy group having a lower alkanoyl group at 4-position in the piperazine ring, an imidazolyl-substituted lower alkoxy group a piperidinyl-substituted lower alkoxy group having lower alkanoylamino group on the piperidine ring, an 1,2,4-triazolyl-substituted lower alkoxy group or an ureido-substituted lower alkoxy group which may have lower alkyl groups).

According to an extensive research work made by the present inventors, there have been found the facts that each one of benzoheterocyclic compounds represented by the above-mentioned general formula (1) possess excellent vasopressin antagonistic activity and oxytocinantagonistic activity.

The vasopressin antagonists according to the present invention possess various pharmacological activities, for example, vasodilating activity, anti-hypertension, activity for inhibiting release of hepatic sugar, activity for inhibiting proliferation of mesangial cells, water diuretic activity, activity for inhibiting agglutination of platelets and anti-emetic activity, thus they are useful as vasodilators, hypotensives, water diuretics and platelets agglutination inhibitors. So that they are effective for prophilaxis and treatments of hypertension, edema, hydroperitonia, heart falilure, renal function disorder, syndrome of inappropriate secretion of vasopressin or syndrome of inappropriate secretion of antidiuretic hormone (SIADH), hepatic cirrhosis, hyponatremia, hypokalemia, diabetes mellitus, circulation insufficiency, motion sickness and the like.

The oxytocin antagonists according to the present invention possess activity for inhibiting contraction of the uterus smooth muscle, activity for inhibiting secretion of milk, activity for inhibiting synthesis and release of prostaglandins, vasodilation, thus, they are effective for prophylaxis and treatments of oxytocin related diseases, particularly early birth, prevention of birth before cesarean section, dysmenorrhea and the like.

Furthermore, the benzoheterocyclic compounds according to the present invention have the features in that they have less side-effects, while they sustain the pharmacological activities for long period of time.

More specifically, examples of the respective groups shown by general formula (1) described above include the following:

As to the lower alkoxy group, there may be exemplified straight or branched alkoxy groups having 1 to 6 carbon atoms, for example, methoxy, ethoxy, propoxy, isopropoxy, butoxy, tert-butoxy, pentyloxy and hexyloxy groups, etc.

As to the lower alkyl group, there may be exemplified straight or branched alkyl groups having 1 to 6 carbon atoms, for example, methyl, ethyl, propyl, isoporpyl, butyl, tert-butyl, pentyl and hexyl groups, etc.

Specific examples of the halogen atom are fluorine, chlorine, bromine and iodine atoms.

As to the lower alkenyl group, there may be exemplified straight or branched alkenyl groups having 2 to 6 carbon atoms, for example, vinyl, allyl, 2-butenyl, 3-butenyl, 1-methylallyl, 2-pentenyl and 2-hexenyl groups, etc.

As to the lower alkenyloxy group, there may be exemplified straight or branched alkenyloxy groups having 2 to 6 carbon atoms, for example, vinyloxy, allyloxy, 2-butenyloxy, 3-butenyloxy, 1-methylallyloxy, 2-pentenyloxy and 2-hexenyloxy groups, etc.

As to the lower alkylene group, there may be exemplified straight chain or branched chain alkylene groups having 1 to 6 carbon atoms, for example, methylene, ethylene, trimethylene, 2-methyltrimethylene, 2,2-dimethyltrimethylene, 1-methyltrimethylene, methylmethylene, ethylmethylene, tetramethylene, pentamethylene and hexamethylene groups, etc.

As to the lower alkanoyloxy group, there may be exemplified straight chain or branched chain alkanoyloxy groups having 1 to 6 carbon atoms, for example, formyloxy, acetyloxy, propionyloxy, butyryloxy, isobutyryloxy, pentanoyloxy, tert-butylcarbonyloxy and hexanoyloxy groups, etc.

As to the hydroxy-substituted lower alkyl group, there may be exemplified straight chain or branched chain alkyl groups having 1 to 6 carbon atoms which contains 1 to 3 hydroxy groups as substituent(s), for example, hydroxymethyl, 2-hydroxyethyl, 1-hydroxyethyl, 3-hydroxypropyl, 2,3-dihydroxyethyl, 4-hydroxybutyl, 3,4-dihydroxybutyl, 1,1-dimethyl-2-hydroxyethyl, 5-hydroxypentyl, 6-hydroxyhexyl, 2-methyl-3-hydroxypropyl and 2,3,4-trihydroxybutyl groups, etc.

As to the aminocarbonyl-lower alkoxy group having a lowr alkyl group as a substituent(s) means straight chain or branched chain alkoxy groups having 1 to 6 carbon atoms which contains as substituent(s) one or two straight chain or branched chain alkyl groups having 1 to 6 carbon atoms, for example, methylaminocarbonylmethoxy, 1-ethylaminocarbonylethoxy, 2-propylaminocarbonylethoxy, 3-isopropylaminocarbonylpropoxy, 4-butylaminocarbonylbutoxy, 5-pentylaminocarbonylpentyloxy, 6-hexylaminocarbonylhexyloxy, dimethylaminocarbonylmethoxy, 3-diethylaminocarbonylpropoxy, diethylaminocarbonylmethoxy, (N-ethyl-N-propylamino)carbonylmethoxy and 2-(N-methyl-N-hexylamino)carbonylethoxy groups, etc.

As to the lower alkoxycarbonyl-substituted lower alkyl group, there may be exemplified straight chain or branched chain alkoxycarbonylalkyl groups having 1 to 6 carbon atoms in which the alkoxycarbonyl moiety is a straight chain or branched chain alkoxycarbonyl group having 1 to 6 carbon atoms; specific examples are methoxycarbonylmethyl, 3-methoxycarbonylpropyl, ethoxycarbonylmethyl, 3-ethoxycarbonylpropyl, 4-ethoxycarbonylbutyl, 5-isopropoxycarbonylpentyl, 6-propoxycarbonylhexyl, 1,1-dimethyl-2-butoxycarbonylethyl, 2-methyl-3-tert-butoxycarbonylpropyl, 2-pentyloxycarbonylethyl and hexyloxycarbonylmethyl groups, etc.

As to the carboxy-substituted lower alkyl group, there may be exemplified carboxyalkyl groups in which the alkyl moiety is a straight chain or branched chain alkyl group having 1 to 6 carbon atoms; for example, carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl and 2-methyl-3-carboxypropyl groups, etc.

As to the phenyl-lower alkanoylamino group which contains as 1 to 3 substituent, on the phenyl ring, selected from the group consisting of a halogen atom, a lower alkoxy group, a lower alkyl group and nitro group, there may be exemplified phenylalkanoylamino groups which contain as 1 to 3 substituent(s), on the phenyl ring, selected from the group consisting of a straight chain or branched chain alkyl group having 1 to 6 carbon atoms, a straight chain or branched chain alkoxy group having 1 to 6 carbon atoms, a halogen atom and nitro group; for exmaple, 2-methoxyphenylacetylamino, 3-methoxyphenylacetylamino, 4-methoxyphenylacetylamino, 3-(2-ethoxyphenyl)propionylamino, 2-(3-ethoxyphenyl)propionylamino, 4-(4-ethoxyphenyl)butyrylamino, 2,2-dimethyl-3-(4-isopropoxyphenyl)propionylamino, 5-(4-pentyloxyphenyl)pentanoylamino, 2,4-dimethoxyphenylacetylamino, 4-hexyloxyphenylacetylamino, 3,4-dimethoxyphenylacetylamino, 2-(3-ethoxy-4-methoxyphenyl)propionylamino, 3-(2,3-dimethoxyphenyl)propionylamino, 4-(3,4-diethoxyphenyl)butyrylamino, 2,5-dimethoxyphenylacetylamino, 6-(2,6-dimethoxyphenyl)hexanoylamino, 3,5-dimethoxyphenylacetylamino, 3,4-dipentyloxyphenylacetylamino, 3,4,5-trimethoxyphenylacetylamino, 2-chlorophenylacetylamino, 3-chlorophenylacetylamino, 4-chlorophenylacetylamino, 2-fluorophenylacetylamino, 3-fluorophenylacetylamino, 3-(4-fluorophenyl)propionylamino, 2-(2- bromophenyl)propionylamino, 4-(3-bromophenyl)butyrylamino, 5-(4-bromophenyl)pentanoylamino, 6-(2-iodophenyl)hexanoylamino, 3-iodophenylacetylamino, 3-(4-iodophenyl)propionylamino, 4-(3,4-dichlorophenyl)-butrylamino, 3,4-dichlorophenylacetylamino, 2,6-dichlorophenylacetylamino, 2,3-dichlorophenylacetylamino, 2,4-dichlorophenylacetylamino, 3,4-difluorophenylacetylamino, 3-(3,5-dibromophenyl)propionylamino, 3,4,5-trichlorophenylacetylamino, 2-methoxy-3-chlorophenylacetylamino, 2-methylphenylacetylamino, 3-methylphenylacetylamino, 4-methylphenylacetylamino, 3-(2-ethylphenyl)propionylamino, 2-(3-ethylphenyl)propionylamino, 4-(4-ethylphenyl)butyrylamino, 5-(4-isopropylphenyl)pentanoylamino, 6-(3-butylphenyl)hexanoylamino, 3-(4-pentylphenyl)propionylamino, 4-hexylphenylacetylamino, 3,4-dimethylphenylacetylamino, 3,4-diethylphenylacetylamino, 2,4-dimethylphenylacetylamino, 2,5-dimethylphenylacetylamino, 2,6-dimethylphenylacetylamino, 3,4,5-trimethylphenylacetylamino, 3-chloro-4-methylphenylacetylamino, 3-methoxy-4-methyl-5-iodophenylacetylamino, 3,4-dimethoxy-5-bromophenylacetylamino, 3,5-diiodo-4-methoxyphenylacetylamino, 2-nitrophenylacetylamino, 3-nitrophenylacetylamino, 3,4-dinitrophenylacetylamino and 3,4,5-trinitrophenylacetylamino groups, etc.

As to the lower alkoxycarbonyl-substituted lower alkylidene group, there may be exemplified straight chain or branched chain alkylidene groups having 1 to 6 carbon atoms which are substituted with a straight chain or branched chain alkoxycarbonyl group having 1 to 6 carbon atoms; for example, ethoxycarbonylmethylidene, 2-methoxycarbonylethylidene, 3-isopropoxycarbonylpropylidene, 2-propoxycarbonylisopropylidene, 4-butoxycarbonylbutylidene, 5-pentyloxycarbonylpentylidene and 6-hexyloxycarbonylhexylidene groups, etc.

As to the 5 or 6-membered saturated or unsaturated heterocyclic group formed by combing $R^8$ and $R^9$ together with the adjacent nitrogen atom being bonded thereto, together with or without other nitrogen atom or oxygen atom, there may be exemplified pyrrolidinyl, piperidinyl, piperazinyl, morpholino, pyrrolyl, imidazolyl, 1,2,4-triazolyl, 1,2,4-triazolyl, pyrazolyl, 2-pyrrolinyl, 2-imidazolinyl, imidazolidinyl, 2-pyrazolinyl, pyazolidinyl, 1,2-dihydropyridyl and 1,2,3,4-tetrahydropyridyl groups, etc.

As to the heterocyclic groups described above which are further substituted with a lower alkyl group, there may be exemplified heterocyclic groups as described above which are substituted with 1 to 3 straight chain or branched chain alkyl groups having 1 to 6 carbon atoms; for example, 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, 2-methylimidazolyl, 3-methyl-1,2,4-triazolyl, 3-methylpyrrolyl, 3-methylpyrazolyl and 4-methyl-1,2-dihydropyridyl groups, etc.

As to the amino acid residue, there may be exemplified alanyl-, β-alanyl, arginyl, cystationyl, cystyl, glycyl, histidyl, homoseryl, isoleucyl, lanthionyl, leucyl lysyl, methionyl, norleucyl, norvalyl, ornithyl, prolyl, sarcosyl, seryl, threonyl, tyronyl, tyrosyl, valyl, α-aspartyl, β-aspartyl, aspartoyl, asparaginyl, α-glutamyl, γ-glutamyl, glutaminyl, cysteinyl, homocysteinyl, tryptophyl and dimethylglycyl groups, etc.

As to the amino-lower alkoxy group which may optionally contain as the substituents selected from the group consisting of a lower alkyl group and a lower alkanoyl group, there may be exemplified straight chain or branched chain alkoxy groups having 1 to 6 carbon atoms which may contain 1 to 2 substituents selected from the group consisting of a straight chain or branched chain alkyl group having 1 to 6 carbon atoms and a straight chain or branched chain alkanoyl group having 1 to 6 carbon atoms; there may be exemplified, aminomethoxy, 2-aminoethoxy, 1-aminoethoxy, 3-aminopropoxy, 4-amionobutoxy, 5-aminopentyloxy, 6-aminohexyloxy, 1,1-dimethyl-2-aminoethoxy, 2-methyl-3-aminopropoxy, acetylaminomethoxy, 1-acetylaminoethoxy, 2-propionylaminoethoxy, 3-isopropionylaminopropoxy, 4-butyrylaminobutoxy, 5-pentanoylaminopentyloxy, 6-hexanoylaminohexyloxy, formylaminomethoxy, methylaminomethoxy, 1-ethylaminoethoxy, 2-propylaminoethoxy, 3-isopropylaminopropoxy, 4-butylaminobutoxy, 5-pentylaminopentyloxy, 6-hexylaminohexyloxy, dimethylaminomethoxy, (N-ethyl-N-propylamino)methoxy and 2-(N-methyl-N-hexylamino)ethoxy groups, etc.

As to the lower alkoxycarbonyl-substituted lower alkoxy group, there may be exemplified straight chain or branched chain alkoxycarbonylalkoxy groups having 1 to 6 carbon atoms in which the alkoxycarbonyl moiety is a straight chain or branched chain alkoxycarbonyl group having 1 to 6 carbon atoms; for example, methoxycarbonylmethoxy, 3-methoxycarbonylpropoxy, ethoxycarbonylmethoxy, 3-ethoxycarbonylpropoxy, 4-ethoxycarbonylbutoxy, 5-isopropoxycarbonylpentyloxy, 6-propoxycarbonylhexyloxy, 1,1-dimethyl-2-butoxycarbonylethoxy, 2-methyl-3-tert-butoxycarbonylpropoxy, 2-pentyloxycarbonylethoxy and hexyloxycarbonylmethoxy groups, etc.

As the carboxy-substituted lower alkoxy group, there may be exemplified carboxyalkoxy groups in which the alkoxy moiety is a straight chain or branched chain alkoxy group having 1 to 6 carbon atoms; for exmaple, carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy and 2-methyl-3-carboxypropoxy groups, etc.

As to the piperidinyl group which may optionally contain a phenyl-lower alkyl group on the piperidine ring, there may be exemplified piperidinyl groups which may optionally contain phenylalkyl groups on the piperidine ring and in which the alkyl moiety is a straight chain or branched chain alkyl group having 1 to 6 carbon atoms; for example, piperidinyl, 1-benzyl-4-piperidinyl, 1-(2-phenylethyl)-3-piperidinyl, 1-(1-phenylethyl)-2-piperidinyl, 1-(3-phenylpropyl)-4-piperidinyl, 1-(4-phenylbutyl)-4-piperidinyl, 1-(5-phenylpentyl)-4-piperidinyl, 1-(6-phenylhexyl)-4-piperidinyl, 1-(1,1-dimethyl-2-phenylethyl)-3-piperidinyl and 1-(2-methyl-3-phenylpropyl)-2-piperidinyl groups, etc.

As to the carbamoyl-substituted lower alkyl group, there may be exemplified carbamoyl-substituted alkyl groups in which the alkyl moiety is a straight chain or branched chain alkyl group having 1 to 6 carbon atoms; for example, carbamoylmethyl, 2-carbamoylethyl, 1-carbamoylethyl, 3-carbamoylpropyl, 4-carbamoylbutyl, 5-carbamoylpentyl, 6-carbamoylhexyl, 1,1-dimethyl-2-carbamoylethyl and 2-methyl-3-carbamoylpropyl groups, etc.

As to the lower alkanoyl group, there may be exemplified straight chain or branched chain alkanoyl groups having 1 to 6 carbon atoms, for example, formyl, acetyl, propionyl, butyryl, isobutyryl, pentanoyl, tert-butylcarbonyl and hexanoyl groups, etc.

As to the amino group which may optionally contain as a substituent selected from the group consisting of a lower alkyl group and a lower alkanoyl group, there may be exemplified amino groups which may optionally contain 1 to 2 substituents selected from the group consisting of a straight chain or branched chain alkyl group having 1 to 6 carbon atoms and a straight chain or branched chain alkanoyl group having 1 to 6 carbon atoms; for exmaple, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-methyl-N-acetylamino, N-acetylamino, N-formylamino, N-propionylamino, N-butyrylamino, N-isobutyrylamino, N-pentanoylamino, N-tert-butylcarbonylamino, N-hexanoylamino and N-ethyl-N-acetylamino groups, etc.

As to the lower alkoxycarbonyl-substituted lower alkyl group, there may be exemplified straight chain or branched chain alkoxycarbonylalkyl groups having 1 to 6 carbon atoms in which the alkoxycarbonyl moiety is a straight chain or branched chain alkoxycarbonyl group having 1 to 6 carbon atoms; for exmaple, methoxycarbonylmethyl, 3-methoxycarbonylpropyl, ethoxycarbonylmethyl, 3-ethoxycarbonylpropyl, 4-ethoxycarbonylbutyl, 5-isopropxycarbonylpentyl, 6-propoxycarbonylhexyl, 1,1-dimethyl-2-butoxycarbonylethyl, 2-methyl-3-tert-butoxycarbonylpropyl, 2-pentyloxycarbonylethyl and hexyloxycarbonylmethyl groups etc.

As to the carboxy-substituted lower alkyl group, there may be exemplified carboxyalkyl groups in which the alkyl moiety is a straight chain or branched chain alkyl group having 1 to 6 carbon atoms; for exmaple, carboxymethyl, 2-carboxy-ethyl, 1-carboxyethyl, 3-carboxypropyl, 4-carboxybutyl, 5-carboxypentyl, 6-carboxyhexyl, 1,1-dimethyl-2-carboxyethyl and 2-methyl-3-carboxypropyl groups, etc.

As to the piperidinyl group which may optionally contain a lower alkyl group on the piperidine ring, there may be exemplified piperidinyl groups which may optionally contain a straight chain or branched chain alkyl group having 1 to 6 carbon atoms; for example, piperidinyl, 1-methyl-4-piperidinyl, 1-ethyl-3-piperidinyl, 1-propyl-2-piperidinyl, 1-butyl-4-piperidinyl, 1-pentyl-4-piperidinyl and 1-hexyl-4-piperidinyl groups, etc.

As to the pyrrolidinylcarbonyl-lower alkoxy group which contains a lower alkoxycarbonyl group on the pyrrolidine ring, there may be exemplified pyrrolidinylcarbonylalkoxy groups which have a straight chain or branched chain alkoxycarbonyl group of 1 to 6 carbon atoms on the pyrrolidine ring and in which the alkoxy moiety is a straight chain or branched chain alkoxy group having 1 to 6 carbon atoms; for exmaple, 2-methoxycarbonyl-1-pyrrolidinylmethoxy, 1-(2-ethoxycarbonyl-1-pyrrolidinylcarbonyl)ethoxy, 2-(3-propoxycarbonyl-1-pyrrolidinylcarbonyl)ethoxy, 3-(2-butoxycarbonyl-1-pyrrolidinylcarbonyl)propoxy, 4-(3-pentyloxycarbonyl-1-pyrrolidinylcarbonyl)butoxy, 5-(2-hexyloxycarbonyl-1-pyrrolidinylcarbonyl)pentyloxy and 6-(2-methoxycarbonyl-1-pyrrolidinylcarbonyl)hexyloxy groups, etc.

As to the lower alkoxycarbonyl group, there may be exemplified straight chain or branched chain alkoxycarbonyl groups having 1 to 6 carbon atoms, for example, methoxycarbonyl, ethoxycarbonyl, propoxycarbonyl, isopropoxycarbonyl, butoxycarbonyl, tert-butoxycarbonyl, pentyloxycarbonyl and hexyloxycarbonyl groups, etc.

As to the lower alkoxy-substituted lower alkanoyloxy group, there may be exemplified alkanoyloxy groups which are substituted with a straight chain or branched chain alkoxy group having 1 to 6 carbon atoms and in which the alkanoyloxy moiety is a straight chain or branched chain alkanoyloxy group having 2 to 6 carbon atoms; for example, methoxyacetyloxy, 3-ethoxypropionyloxy, 2-propoxypropionyloxy, 4-butoxybutyryloxy, 2,2-dimethyl-3-pentyloxypropionyloxy, 5-hexyloxypentanoyloxy and 6-methoxyhexanoyloxy groups, etc.

As to the amino group which may contain a lower alkyl group, there may be exemplified amino groups which may optionally contain 1 to 2 straight chain or branched chain alkyl groups having 1 to 6 carbon atoms as substituents; for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino and N-methyl-N-hexylamino groups, etc.

As to the amino-substituted lower alkylidene group which may optionally contain lower alkyl groups as substituents, there may be exemplified straight chain or branched chain amino-substituted alkylidene groups having 1 to 6 carbon atoms which may optionally contain 1 to 2 straight chain or branched chain alkyl groups having 1 to 6 carbon atoms as substituents; for example, aminomethylidene, 2-ethylaminoethylidene, 3-propylaminopropylidene, 2-isopropylaminopropylidene, 4-butylaminobutylidene, 5-pentylaminopentylidene, 6-hexylaminohexylidene, 3-dimethylaminopropylidene, 3-(N-methyl-N-butylamino)propylidene, 2-dipentylaminoethylidene and 4-(N-methyl-N-hexylamino)butylidene groups, etc.

As to the cyano-substituted lower alkyl group, there may be exemplified cyanoalkyl groups in which the alkyl moiety is a straight chain or branched chain alkyl group having 1 to 6 carbon atoms; for example, cyanomethyl, 2-cyanoethy, 1-cyanoethyl, 3-cyanopropyl, 4-cyanobutyl, 5-cyanopentyl, 6-cyanohexyl, 1,1-dimethyl-2-cyanoethyl and 2-methyl-3-cyanopropyl groups, etc.

As to the phthalimido-substituted lower alkyl group, there may be exemplified phthalimido-substituted alkyl groups in which the alkyl moiety is a straight chain or branched chain alkyl group having 1 to 6 carbon atoms, for example, phthalimidomethyl, 2-phthalimidoethyl, 1-phthalimidoethyl, 3-phthalimidopropyl, 4-phthalimidobutyl, 5-phthalimidopentyl, 6-phthalimidohexyl, 1,1-dimethyl-2-phthalimidoethyl and 2-methyl-3-phthalimidopropyl groups, etc.

As to the lower alkoxy group having a phenylsulfonyloxy group which may optionally contain a lower alkyl group as substituent(s) on the phenyl ring or having hydroxy group, there may be exemplified straight chain or branched chain alkoxy groups having 1 to 6 carbon atoms and having a phenylsulfonyloxy group which may optionally contain 1 to 3 straight chain or branched chain alkyl groups having 1 to 6 carbon atoms as substituent(s) on the phenyl ring or having 1 to 3 hydroxy groups; for example, (2-methylphenylsulfonyloxy)methoxy, 2-(4-methylphenylsulfonyloxy)ethoxy, 3-(phenylsulfonyloxy)propoxy, 4-(3-methylphenylsulfonyloxy)butoxy, 5-(2-ethylphenylsulfonyloxy)pentyloxy, 6-(3-propylphenylsulfonyloxy)hexyloxy, (4-butylphenylsulfonyloxy)methoxy, 2-(2-pentylphenylsulfonyloxy)ethoxy, 1-(3-hexylphenylsulfonyloxy)ethoxy, 3-(3,4-dimethylphenylsulfonyloxy)propoxy, 2-(3,4,5-trimethylphenylsulfonyloxy)ethoxy, hydroxymethoxy, 2-hydroxyethoxy, 1-hydroxyethoxy, 3-hydroxypropoxy, 2,3-dihydroxypropoxy, 4-hydroxybutoxy, 3,4-dihydroxybutoxy, 1,1-dimethyl-2-hydroxyethoxy, 5-hydroxypentyloxy, 6-hydroxyhexyloxy, 2-methyl-3-hydroxypropoxy and 2,3,4-trihydroxybutoxy groups, etc.

As to the phenylsulfonyloxy-substituted lower alkyl group which may optionally contain a lower alkyl group as substituent(s) on the phenyl ring, there may be exemplified phenylsulfonyloxy-substituted straight chain or branched chain alkyl groups having 1 to 6 carbon atoms which may optionally contain 1 to 3 straight chain or branched chain alkyl groups having 1 to 6 carbon atoms as substituent(s) on the phenyl ring; for example, (2-methylphenylsulfonyloxy)methyl, 2-(4-methylphenylsulfonyloxy)ethoxy, 3-(phenylsulfonyloxy)propyl, 4-(3-methylphenylsulfonyloxy)butyl, 5-(2-ethylphenylsulfonyloxy)pentyl, 6-(3-propylphenylsulfonyloxy)hexyl, (4-butylphenylsulfonyloxy)methyl, 2-(2-pentylphenylsulfonyloxy)ethyl, 1-(3-hexylphenylsulfonyloxy)ethyl, 3-(3,4-dimethylphenylsulfonyloxy)propyl and 2-(3,4,5-trimethylphenylsulfonyloxy)ethyl groups, etc.

As to the 5- or 6-membered saturated heterocyclic group formed by combining $R^{29}$ and $R^{30}$ or $R^{23A}$ and $R^{24A}$ together with the adjacent nitrogen atom being bonded thereto, together with or without other nitrogen atom or oxygen atom, there may be exemplified, pyrrolidinyl, piperidinyl, piperazinyl and morpholino groups, etc.

As to the heterocyclic groups described above which are substituted with a lower alkyl group, a lower alkanoyl group, an amino group which may optionally contain substituent(s) selected from the group consisting of a lower alkyl group and a lower alkanoyl group, a ower alkylsulfonyl group, a lower alkoxycarbonyl group or an aminocarbonyl group which may optionally contain a lower alkyl group as a substituent, there may be exemplified those heterocyclic groups described above which are substituted with 1 to 3 straight chain or branched chain alkyl groups having 1 to 6 carbon atoms, straight chain or branched chain alkanoyl groups having 1 to 6 carbon atoms, amino groups which may optionally contain as 1 to 2 substituents selected from the group consisting of a straight chain or branched chain alkyl group having 1 to 6 carbon atoms and a straight chain or branched chain alkanoyl group having 1 to 6 carbon atoms, a straight chain or branched chain alkylsulfonyl group having 1 to 6 carbon atoms, a straight chain or branched chain alkoxycarbonyl group having 1 to 6 carbon atoms, or an aminocarbonyl group which may optionally contain 1 to 2 straight chain or branched chain alkyl groups as substituent(s); examples of such heterocyclic groups include 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, 4-acetylpiperazinyl, 4-hexanoylpiperidinyl, 4-formylpiperidinyl, 2-propionylpyrrolidinyl, 3-butyrylmorpholino, 4-pentanoylpiperazinyl, 4-ethylaminopiperidinyl, 4-dimethylaminopiperidinyl, 3-methyl-4-acetylpiperazinyl, 3-methylaminomorpholino, 2-aminopyrrolidinyl, 3-(N-methyl-N-hexylamino)piperazinyl, 4-(N-methyl-N-butylamino)piperidinyl, 4-acetylaminopiperidinyl, 3-propionylaminopyrrolidinyl, 3-butyrylaminopiperazinyl, 3-pentanoylaminomorpholino, 4-(N-methyl-N-acetylamino)piperidinyl, 4-methylsulfonylpiperazinyl, 4-ethoxycarbonylpiperazinyl, 4-methylaminocarbonyl, piperazinyl, 4-ethylsulfonylpiperidinyl, 3-propylsulfonylmorpholino, 2-butylsulfonylpyrrodinyl, 3-methoxycarbonylmorpholino, 3-methyl-4-ethoxycarbonylpiperidinyl, 3-ethoxycarbonylpyrrolidinyl, 4-dimethylaminocarbonylpiperidinyl, 3-ethylaminocarbonylmorpholino and 2-(N-methyl-N-propylamino)carbonylpyrrolidinyl groups, etc.

As to the 5- to 7-membered saturated heterocyclic group formed by combining $R^{11}$ and $R^{12}$ together with the adjacent nitrogen atom being bonded thereto, together with or without other nitrogen atom or oxygen atom, there may be exemplified, pyrrolidinyl, piperidinyl, piperazinyl, morpholino and homopiperazinyl groups, etc.

As to the heterocyclic groups described above which are substituted with a lower alkyl group, a lower alkoxycarbonyl group, an amino group which may optionally contain as substituent(s) selected from the group consisting of a lower alkyl group and a lower alkanoyl group, a lower alkoxycarbonyl-substituted lower alkyl group, a phenyl group which may optionally contain a halogen atom on the phenyl ring, a cyano-substituted lower alkyl group, a lower alkenyl group, an oxiranyl-substituted lower alkyl group, a carbamoyl-substituted lower alkyl group, a lower alkyl group having 1 to 2 substituents selected from the group consisting of hydroxy group and an amino group which may optionally contain a lower alkyl group, or a pyrrolidinylcarbonyl lower alkyl group, there may be exemplified heterocyclic groups described above which are substituted with 1 to 3 straight chain or branched chain alkyl groups having 1 to 6 carbon atoms, straight chain or branched chain alkoxycarbonyl groups having 1 to 6 carbon atoms, an amino group which may optionally contain 1 to 2 substituent(s) selected from the group consisting of a straight or branched alkyl group having 1 to 6 carbon atoms and straight chain or branched chain alkanoyl groups having 1 to 6 carbon atoms, a straight chain or branched chain alkoxycarbonylalkyl group in which the alkoxycarbonyl moiety is a straight chain or branched chain alkoxycarbonyl group having 1 to 6 carbon atoms, a phenyl group which may optionally contain 1 to 3 halogen atoms on the phenyl ring, a cyanoalkyl group in which the alkyl moiety is a straight chain or branched chain alkyl group having 1 to 6 carbon atoms, a straight chain or branched chain alkenyl group having 2 to 6 carbon atoms, an oxiranyl substituted alkyl group in which the alkyl moiety is a straight chain or branched chain alkyl group having 1 to 6 carbon atoms, a carbamoyl-substituted alkyl group in which the alkyl moiety is a straight chain or branched chain alkyl group having 1 to 6 carbon atoms, a straight chain or branched chain alkyl group having 1 to 6 carbon atoms and having 1 to 2 substituents selected from the group consisting of hydroxy group and an amino group which may optionally contain a straight chain or branched chain alkyl group having 1 to 6 carbon atoms, or a pyrrolidinylcarbonyl alkyl group in which the alkyl moiety is a straight chain or branched chain alkyl group having 1 to 6 carbon atoms; examples of such heterocyclic groups include 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, 4-tert-butoxycarbonylpiperazinyl, 4-ethoxycarbonylpiperidinyl, 2-methoxycarbonylpyrrolidinyl, 3-pentyloxycarbonylmorpholino, 4-hexyloxycarbonylpiperazinyyl, 4-acetylaminopiperidinyl, 4-dimethylaminopiperidinyl, 3-methylaminomorpholino, 2-aminopyrrolidinyl, 3-(N-methyl-N-hexylamino)piperazinyl, 4-(N-methyl-N-acetylamino)piperidinyl, 4-methylhomopiperazinyl, 4-ethoxycarbonylhomopiperazinyl, 4-acetylaminohomopiperazinyl, 4-dimethylaminohomopiperazinyl, 4-ethoxycarbonylmethylpiperazinyl, (4-chlorophenyl)piperazinyl, 4-cyanomethylpiperazinyl, 4-allylpiperazinyl, 4-(oxiranylmethyl)piperazinyl, 4-carbamoylmethylpiperazinyl, 4-(2-hydroxyethyl)piperazinyl, 4-(2-hydroxy-3-isopropylaminopropyl)piperazinyl, 3-(3-chlorophenyl)pyrrolidinyl, 4-(2-cyanoethyl)piperidinyl, 3-(2-butenyl)morpholino, 4-(1-oxiranylethyl)homopiperazinyl, 3-(2-carbamoylethyl)piperidinyl, 2-hydroxymethylpyrrolidinyl, 2-(2-hydroxy-3-diethylaminopropyl)morpholino, 3-(2-hydroxyethyl)homopiperazinyl, 4-[(1-pyrrolidinyl)carbonylmethyl]piperazinyl, 2-[2-(1-pyrrolidinyl)carbonylethyl]pyrrolidinyl, 3-[1-(1-pyrrolidinyl)carbonylethyl]

morpholino, 4-[3-(1-pyrrolidinyl)carbonylpropyl]piperidinyl and 4-[(1-pyrrolidinyl)carbonylmethyl]homopiperazinyl groups, etc.

As to the 5- to 10-membered monocyclic or bicyclic saturated or unsaturated heterocyclic group formed by combining $R^{27}$ and $R^{28}$ together with the adjacent nitrogen atom being bonded thereto, together with or without other nitrogen atom or oxygen atom, there may be exemplified pyrrolidinyl, piperidinyl, piperazinyl, morpholino, imidazolyl, isoindolyl and 1,2,3,4,5,6,7-octahydroisoindolyl groups, etc.

As to the heterocyclic groups described above which are substituted with oxo group, a lower alkyl group, a lower alkoxycarbonyl group, a lower alkanoyl group or a lower alkanoylamino group, there may be exemplified those heterocyclic groups described above which are substituted with 1 to 3 oxo groups, straight chain or branched chain alkyl groups having 1 to 6 carbon atoms, straight chain or branched chain alkoxycarbonyl groups having 1 to 6 carbon atoms, straight chain or branched chain alkanoyl groups having 1 to 6 carbon atoms or amino groups having a straight chain or branched chain alkanoyl group of 1 to 6 carbon atoms; examples of such heterocyclic groups include 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, 2-methylmorpholino, 4-formylpiperidinyl, 4-acetylpiperazinyl, 2-propanoylmorpholino, 3-butyrylmorpholino, 3-pentanoylpyrrolidinyl, 4-hexanoylpiperidinyl, 3-methyl-4-acetylpiperazinyl, 4-methylimidazolyl, 2-acetylimidazolyl, 4-tert-butoxycarbonylpiperazinyl, 4-ethoxycarbonylpiperidinyl, 2-methoxycarbonylpyrrolidinyl, 3-pentyloxycarbonlmorpholino, 4-hexyloxycarbonylpiperazinyl, 2-tert-butoxycarbonylimidazolyl, 1,3-dioxo-1,2,3,4,5,6,7-octahydroisoindolyl, 3-pentanoylaminomorpholino, 4-acetylaminopiperidinyl, 3-propionylaminopyrrolidinyl, 3-butyrylaminopiperazinyl and 2-hexanoylaminoimidazolyl groups, etc.

As to the cyano-substituted lower alkylidene group, there may be exemplified straight chain or branched chain alkylidene groups having 1 to 6 carbon atoms, for example, cyanomethylidene, 2-cyanoethylidene, 3-cyanopropylidene, 2-cyanopropylidene, 4-cyanobutylidene, 5-cyanopentylidene and 6-cyanohexylidene groups, etc.

As to the piperazinyl-lower alkoxy group having a lower alkanoyl group at the 4-position of the piperazine ring, there may be exemplified piperazinylalkoxy groups which contains a straight or branched alkanoyl group having 1 to 6 carbon atoms on the piperazine ring at the 4-position thereof and in which the alkoxy moiety is a straight or branched alkoxy group having 1 to 6 carbon atoms; examples of such groups include 3-(4-acetyl-1-piperazinyl)propoxy, 2-(4-acetyl-1-piperazinyl)ethoxy, (4-acetyl-1-piperazinyl)-methoxy, 1-(4-propionyl-1-piperazinyl)ethoxy, 4-(4-butyryl-1-piperazinyl)butoxy, 5-(4-pentanoyl-1-piperazinyl)pentyloxy, 6-(4-hexanoyl-1-piperazinyl)hexyloxy and 3-(4-formyl-1-piperazinyl)propoxy groups, etc.

As to the lower alkyl group which may optionally contain hydroxy group, there may be exemplified straight chain or branched chain alkyl groups having 1 to 6 carbon atoms which may optionally contain 1 to 3 hydroxy groups; for examles those lower alkyl groups and hydroxy-substituted lower alkyl groups described hereinabove.

As to the pyridyl-substituted lower alkyl group, there may be exemplified pyridyl-substituted alkyl groups in which the alkyl moiety is a straight chain or branched chain alkyl group having 1 to 6 carbon atoms; for example, (2-pyridyl)methyl, (3-pyridyl)methyl, (4-pyridyl)methyl, 2-(2-pyridyl)-ethyl, 2-(3-pyridyl)ethyl, 2-(4-pyridyl)ethyl, 3-(2-pyridyl)-propyl, 3-(3-pyridyl)propyl, 3-(4-pyridyl)propyl, 4-(2-pyridyl)butyl, 4-(3-pyridyl)butyl, 4-(4-pyridyl)butyl, 5-(2-pyridyl)pentyl, 5-(3-pyridyl)pentyl, 5-(4-pyridyl)pentyl, 6-(2-pyridyl)hexyl, 6-(3-pyridyl)hexyl, 6-(4-pyridyl)-hexyl, 1,1-dimethyl-2-(2-pyridyl)ethyl, 1,1-dimethyl-2-(3-pyridyl)-ethyl, 1,1-dimethyl-(4-pyridyl)ethyl, 2-methyl-3-(2-pyridyl)propyl, 2-methyl-3-(3-pyridyl)propyl and 2-methyl-3-(4-pyridyl)propyl groups, etc.

As to the amino-substituted lower alkyl group which may optionally contain a lower alkyl group, there may be exemplified straight chain or branched chain alkyl groups having 1 to 6 carbon atoms which are substituted with an amino group that may optionally contain 1 to 2 straight chain or branched chain alkyl groups having 1 to 6 carbon atoms as the substituents; for example, aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diethylaminoethyl, 2-dimethylaminoethyl, (N-ethyl-N-propylamino)methyl and 2-(N-methyl-N-hexylamino)ethyl groups, etc.

As to the lower alkynyl group, there may be exemplified straight chain or branched chain alkynyl groups having 2 to 6 carbon atoms, for example, ethynyl, propargyl, 2-butynyl, 1-methyl-2-propargyl, 2-pentynyl and 2-hexynyl groups, etc.

As to the lower alkylsulfonyl group, there may be exemplified sulfonyl groups having a straight chain or branched chain alkyl group having 1 to 6 carbon atoms, for example, methylsulfonyl, ethylsulfonyl, propylsulfonyl, isopropylsulfonyl, butylsulfonyl, tert-butylsulfonyl, pentylsulfonyl, hexylsulfonyl, etc.

As to the lower alkanoylamino group, there may be exemplified amino groups containing a straight chain or branched chain alkanoyl group having 1 to 6 carbon atoms, for example, acetylamino, propionylamino, isopropionylamino, butyrylamino, pentanoylamino, hexanoylamino and formylamino groups, etc.

As to the cycloalkyl group, there may be exemplified cycloalkylcarbonyl groups having 3 to 8 carbon atoms, for example, cyclopropyl, cyclobutyl, cyclopentyl, cyclohexyl, cycloheptyl, cyclooctyl, etc.

As to the halogen atom-substituted lower alkyl group, there may be exemplified straight chain or branched chain alkyl groups having 1 to 6 carbon atoms which contain 1 to 3 halogen atoms as substituent(s); for example, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl and 5,6-dichlorohexyl groups, etc.

As to the imidazolyl-substituted lower alkyl group, there may be exemplified imidazolyl-substituted alkyl groups in which the alkyl moiety is a straight chain or branched chain alkyl group having 1 to 6 carbon atoms; for example, (1-imidazolyl)methyl, 2-(1-imidazolyl)ethyl, 1-(2-imidazolyl)ethyl, 3-(4-imidazolyl)propyl, 4-(5-imidazolyl)butyl, 5-(1-imidazolyl)pentyl, 6-(2-imidazolyl)hexyl, 1,1-dimethyl-2-(1-imidazolyl)ethyl and 2-methyl-3-(1-imidazlyl)-propyl groups, etc.

As to the 1,2,4-triazolyl-substituted lower alkoxy group, there may be exemplified 1,2,4-triazolyl-substituted alkoxy groups in which the alkoxy moiety is a straight chain or branched chain alkoxy group having 1 to 6 carbon atoms; for example, (1-1,2,4-triazolyl)methoxy, 2-(1-1,2,4-triazolyl)ethoxy, 1-(1-1,2,4-triazolyl)ethoxy, 3-(3-1,2,4-triazolyl)propoxy, 4-(5-1,2,4-triazolyl)butoxy, 5-(1-1,2,4-triazolyl)pentyloxy, 6-(3-1,2,4-triazolyl)hexyloxy, 1,1-dimethyl-2-(5-1,2,4-triazolyl)ethoxy and 2-methyl-3-(1-1,2,4-triazolyl)propoxy groups, etc.

As to the 1,2,3,4-tetrazolyl-substituted lower alkoxy group, there may be exemplified 1,2,3,4-tetrazolyl-substituted alkoxy groups in which the alkoxy moiety is a straight chain or branched chain alkoxy group having 1 to 6 carbon atoms; for example, (1-1,2,3,4-tetrazolyl)methoxy, 2-(1-2,3,4-tetrazolyl)ethoxy, 1-(5-1,2,3,4-tetrazolyl)ethoxy, 3-(1-1,2,3,4-tetrazolyl)propoxy, 4-(5-1,2,3,4-tetrazolyl)butoxy, 5-(1-1,2,3,4-tetrazolyl)pentyloxy, 6-(5-1,2,3,4-tetrazolyl)hexyloxy, 1,1-dimethyl-2-(1-1,2,3,4-tetrazolyl)ethoxy and 2-methyl-3-(5-1,2,3,4-tetrazolyl)propoxy groups, etc.

As to the 1,2,3,4,5-tetrazolyl-substituted lower alkoxy group, there may be exemplified 1,2,3,5-tetrazolyl-substituted alkoxy groups in which the alkoxy moiety is a straight chain or branched chain alkoxy group having 1 to 6 carbon atoms; for example, (1-1,2,3,5-tetrazolyl)methoxy, 2-(1-1,2,3,5-tetrazolyl)ethoxy, 1-(4-1,2,3,5-tetrazolyl)ethoxy, 3-(1-1,2,3,5-tetrazolyl)propoxy, 4-(4-1,2,3,5-tetrazolyl)butoxy, 5-(1-1,2,3,5-tetrazolyl)pentyloxy, 6-(4-1,2,3,5-tetrazolyl)hexyloxy, 1,1-dimethyl-2-(1-1,2,3,5-tetrazolyl)ethoxy and 2-methyl-3-(4-1,2,3,5-tetrazolyl)propoxy groups, etc.

As to the 1,2,3,4-tetrazolyl-substituted lower alkyl group, there may be exemplified 1,2,3,4-tetrazolyl-substituted alkyl groups in which the alkyl moiethy is a straight chain or branched chain alkyl group having 1 to 6 carbon atoms; for exmaple, (1-1,2,3,4-tetrazolyl)methyl, 2-(1-1,2,3,4-tetrazolyl)ethyl, 1-(5-1,2,3,4-tetrazolyl)ethyl, 3-(1-1,2,3,4-tetrazolyl)propyl, 4-(5-1,2,3,4-tetrazolyl)butyl, 5-(1-1,2,3,4-tetrazolyl)pentyl, 6-(5-1,2,3,4-tetrazolyl)hexyl, 1,1-dimethyl-2-(1-1,2,3,4-tetrazolyl)ethyl and 2-methyl-3-(5-1,2,3,4-tetrazolyl)propyl groups, etc.

As to the 1,2,3,5-tetrazolyl-substituted lower alkyl group, there may be exemplified 1,2,3,5-tetrazolyl-substituted alkyl groups in which the alkyl moiety is a straight chain or branched chain alkyl group having 1 to 6 carbon atoms; for exmaple, (1-1,2,3,5-tetrazolyl)methyl, 2-(1-1,2,3,5-tetrazolyl)ethyl, 1-(4-1,2,3,5-tetrazolyl)ethyl, 3-(1-1,2,3,5-tetrazolyl)propyl, 4-(4-1,2,3,5-tetrazolyl)butyl, 5-(1-1,2,3,5-tetrazolyl)pentyl, 6-(4-1,2,3,5-tetrazolyl)hexyl, 1,1-dimethyl-2-(1-1,2,3,5-tetrazolyl)ethyl and 2-methyl-3-(4-1,2,3,5-tetrazolyl)propyl groups, etc.

As to the 1,2,4-triazolyl-substituted lower alkyl group, there may be exemplified 1,2,4-triazolyl-substituted alkyl groups in which the alkyl moiety is a straight chain or branched chain alkyl group having 1 to 6 carbon atoms; for exmaple, (1-1,2,4-triazolyl)methyl, 2-(1-1,2,4-triazolyl)ethyl, 1-(1-1,2,4-triazolyl)ethyl, 3-(3-1,2,4-triazolyl)propyl, 4-(5-1,2,4-triazolyl)butyl, 5-(1-1,2,4-triazolyl)pentyl, 6-(3-1,2,4,-triazolyl)hexyl, 1,1-dimethyl-2-(5-1,2,4-triazolyl)ethyl and 2-methyl-3-(1-1,2,4-triazolyl)propyl groups, etc.

As to the phenyl group which may optionally contain a halogen atom on the phenyl group, there may be exemplified phenyl groups which may optionally contain 1 to 3 halogen atoms as the substituents on the phenyl ring; for exmaple, phenyl, 2-chlorophenyl, 3-chlorophenyl, 4-chlorophenyl, 2-fluorphenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl and 3,4,5-trichlorophenyl groups, etc.

As to the oxiranyl-substituted lower alkyl group, there may be exemplified oxiranyl-substituted alkyl groups in which the alkyl moiety is a straight chain or branched chain alkyl group having 1 to 6 carbon atoms; for example, oxiranylmethyl, 2-oxiranylethyl, 1-oxiranylethyl, 3-oxiranylpropyl, 4-oxiranylbutyl, 5-oxiranylpentyl, 6-oxiranylhexyl, 1,1-dimethyl-2-oxiranylethyl and 2-methyl-3-oxiranylpropyl groups, etc.

As to the lower alkyl group having 1 to 2 substituents selected from the group consisting of hydroxy group and an amino group which may optionaly contain a lower alkyl group, there may be exemplified straight chain or branched chain alkyl groups having 1 to 6 carbon atoms and having 1 to 2 substituents selected from the group consisting of hydroxy group and an amino group which may optionally contain as substituent(s) 1 to 2 straight chain or branched chain alkyl groups having 1 to 6 carbon atoms; for examples, alkyl groups include hydroxymethyl, 2-hydroxyethyl, 1-hydroxyethyl, 3-hydroxypropyl, 2,3-dihydroxyethyl, 4-hydroxybutyl, 3,4-dihydrooxybutyl, 1,1-dimethyl-2-hydroxyethyl, 5,6-dihydroxyhexyl, 5-hydroxypentyl, 6-hydroxyhexyl, 2-methyl-3-hydroxypropyl, aminomethyl, 1-aminoethyl, 2-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, ethylaminomethyl, propylaminomethyl, isopropylaminomethyl, butylaminomethyl, tert-butylaminomethyl, pentylamiinomethyl, hexylaminomethyl, dimethylaminomethyl, diethylaminomethyl, dipropylaminomethyl, dibutylaminomethyl, dipentylaminomethyl, dihexylaminomethyl, N-methyl-N-ethylaminomethyl, N-methyl-N-propylaminomethyl, N-methyl-N-butylaminomethyl, N-methyl-N-hexylaminomethyl, 1-methylaminoethyl, 2-ethylaminoethyl, 3-propylaminopropyl, 4-butylaminobutyl, 1,1-dimethyl-2-pentylaminoethyl, 5-hexylaminopentyl, 6-dimethylaminohexyl, 4-dimethylaminobutyl, 2-diethylaminoethyl, 1-(N-methyl-N-hexylamino)ethyl, 3-dihexylaminopropyl, 6-diethylaminohexyl, 4-dibutylaminobutyl, 2-(N-methyl-N-pentylamino)ethyl, 2-hydroxy-3-diethylaminopropyl, 3-hydroxy-4-methylaminobutyl, 2-hydroxy-3-isopropylaminopropyl, 5-hydroxy-6-diethylaminohexyl, 4-hydroxy-5-dimethylaminopentyl, 4-hydroxy-5-methylaminopentyl, 4-hydroxy-5-diethylaminopentyl, 5-hydroxy-6-ethylaminohexy, 5-hydroxy-6-isopropylaminohexyl and 5-hydroxy-6-aminohexyl groups, etc.

As to the imidazolyl-substituted lower alkoxy group, there may be exemplified imidazolyl-substituted alkoxy groups in which the alkoxy moiety is a straight chain or branched chain alkoxy group having 1 to 6 carbon atoms; for example, (1-imidazolyl)methoxy, 2-(1-imidazolyl)ethoxy, 1-(2-imidazolyl)ethoxy, 3-(4-imidazolyl)propoxy, 4-(5-imidazolyl)butoxy, 5-(1-imidazolyl)pentyloxy, 6-(2-imidazolyl)hexyloxy, 1,1-dimethyl-2-(1-imidazolyl)ethoxy and 2-methyl-3-(1-imidazolyl)propoxy groups, etc.

As to the piperidinyl-lower alkoxy group having a lower alkanoylamino group on the piperidine ring, there may be exemplified piperidinylalkoxy groups which contain an amino group having a straight chain or branched chain alkanoyl group of 1 to 6 carbon atoms on the piperidine ring in which the alkoxy moiety is a straight chain or branched chain alkanoyl group having 1 to 6 carbon atoms; examples include 3-(4-acetylamino-1-piperidinyl)propoxy, 2-(3-acetylamino-1-piperidinyl)ethoxy, (4-acetylamino-1-piperidinyl)methoxy, 1-(2-propionylamino-1-piperidinyl)ethoxy, 4-(4-butyrylamino-1-piperidinyl)butoxy, 5-(3- pentanoylamino-1-piperidinyl)pentyloxy, 6-(4-hexanoylamino-1-piperidinyl)hexyloxy and 3-(4-formylamino-1-piperidinyl)propoxy groups, etc.

As to the ureido-substituted lower alkoxy group which may optionally contain a lower alkyl group, there may be exemplified straight chain or branched chain alkoxy groups having 1 to 6 carbon atoms which may optionally contain as substituent(s) 1 to 2 straight chain or branched chain alkyl groups having 1 to 6 carbon atoms; for example, ureidomethoxy, 2-ureidoethoxy, 1-ureidoethoxy, 3-ureidopropoxy, 4-ureidobutoxy, 5-ureidopentyloxy, 6-ureidohexyloxy, 1,1-dimethyl-2-ureidoethoxy, 2-methyl-3-ureidopropoxy, N'-methylureidomethoxy, 1-(N'-ethylureido)ethoxy, 2-(N'-propylureido)ethoxy, 3-(N'-isopropylureido)propoxy, 4-(N'-butylureido)butoxy, 5-(N'-pentylureido)pentyloxy, 6-(N'-hexylureido)hexyloxy, N',N'-dimethylureidomethoxy, (N'-ethyl-N'-propylureido)methoxy and 2-(N'-methyl-N'-hexylureido)ethoxy groups, etc.

As to the lower alkoxycarbonyl-substituted lower alkoxy group, there may be exemplified straight chain or branched chain alkoxycarbonylalkoxy groups in which the alkoxycarbonyl moiety is a straight chain or branched chain alkoxycarbonyl group having 1 to 6 carbon atoms; for example, methoxycarbonylmethoxy, 3-methoxycarbonylpropoxy, ethoxycarbonylmethoxy, 3-ethoxycarbonylpropoxy, 4-ethoxycarbonylbutoxy, 5-isopropoxycarbonylpentyloxy, 6-propoxycarbonylhexyloxy, 1,1-dimethyl-2-butoxycarbonylethoxy, 2-methyl-3-tert-butoxycarbonylpropoxy, 2-pentyloxycarbonylethoxy and hexyloxycarbonylmethoxy groups, etc.

As to the carboxy-substituted lower alkoxy, there may be exemplified carboxyalkoxy groups in which the alkoxy moiety is a straight chain or branched chain alkoxy group having 1 to 6 carbon atoms; for example, carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy and 2-methyl-3-carboxypropoxy groups, etc.

As to the 5- to 7-membered saturated heterocyclic group formed by combining $R^{23}$ and $R^{24}$ together with the adjacent nitrogen atom being bonded thereto, together with or without other nitrogen atom or oxygen atom, there may be exemplified pyrrolidinyl, piperidinyl, piperazinyl, morpholino and homopiperazinyl groups, etc.

As to the heterocyclic groups described above which are substituted with a lower alkyl group, there may be exemplified those heterocyclic groups described above which are substituted with 1 to 3 straight chain or branched chain alkyl groups having 1 to 6 carbon atoms; examples include 4-methylpiperazinyl, 4-ethylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl and 4-methylhomopiperazinyl groups, etc.

As to the benzoyl group having halogen atom(s) on the phenyl ring as substituent(s), there may be exemplified benzoyl groups having 1 to 3 halogen atoms as substituent(s) on the phenyl ring; for example, 2-chlorobenzoyl, 3-chlorobenzoyl, 4-chlorobenzoyl, 2-fluorobenzoyl, 3-fluorobenzoyl, 4-fluorobenzoyl, 2-bromobenzoyl, 3-bromobenzoyl, 4-bromobenzoyl, 2-iodobenzoyl, 3-iodobenzoyl, 4-iodobenzoyl, 3,4-dichlorobenzoyl, 2,6-dichlorobenzoyl, 2,3-dichlorobenzoyl, 2,4-dichlorobenzoyl, 3,4-diffluorobenzoyl, 3,5-dibromobenzoyl and 3,4,5-trichlorobenzoyl groups, etc.

As to the 5- to 6-membered saturated heterocyclic group formed by combining $R^{39}$ and $R^{40}$ together with the adjacent nitrogen atom being bonded thereto, together with or without other nitrogen atom or oxygen atom, there may be exemplified pyrrolidinyl, piperidinyl, piperazinyl and morpholino groups, etc.

As to the heterocyclic groups described above which are substituted with a lower alkyl group, there may be exemplified those heterocyclic groups described above which are substituted with 1 to 3 straight chain or branched chain alkyl groups having 1 to 6 carbon atoms; examples include 4-methylpiperazinyl, 3,4-dimethylpiperazinyl, 3-ethylpyrrolidinyl, 2-propylpyrrolidinyl, 1-methylpyrrolidinyl, 3,4,5-trimethylpiperidinyl, 4-butylpiperidinyl, 3-pentylmorpholino and 4-hexylpiperazinyl groups, etc.

As to the pyrazinyl-substituted lower alkyl group which may optionally contain a lower alkyl group as substituent(s) on the pyrazine ring, there may be exemplified pyrazinylalkyl groups which may optionally contain as a substituent(s) 1 to 3 straight chain or branched chain alkyl groups having 1 to 6 carbon atoms and in which the alkyl moiety is a straight chain or branched chain alkyl group having 1 to 6 carbon atoms; for example, (2-pyrazinyl)methyl, 2-(3-pyrazinyl)ethyl, 1-(2-pyrazinyl)ethyl, 3-(2-pyrazinyl)propyl, 4-(3-pyrazinyl)butyl, 5-(2-pyrazinyl)pentyl, 6-(3-pyrazinyl)hexyl, 1,1-dimethyl-2-(2-pyrazinyl)ethyl, 2-methyl-3-(3-pyrazinyl)propyl, (5-methyl-2-pyrazinyl)methyl, 2-(2-ethyl-3-pyrazinyl)ethyl, 1-(6-propyl-2-pyrazinyl)ethyl, 3-(2-butyl-5-pyrazinyl)-propyl, 4-(3-pentyl-6-pyrazinyl)butyl, 5-(6-hexyl-3-pyrazinyl)pentyl, 6-(5-methyl-3-pyrazinyl)hexyl, 1,1-dimethyl-2-(6-methyl-2-pyrazinyl)ethyl, 2-methyl-3-(5-methyl-2-pyrazinyl)propyl, (5,6-dimethyl-2-pyrazinyl)-methyl and (3,5,6-trimethyl-2-pyrazinyl)methyl groups, etc.

As to the pyrrolyl-substituted lower alkyl group which may optionally contain a lower alkyl group as a substituent(s) on the pyrrole ring, there may be exemplified pyrrolylalkyl groups which may optionally contain as a substituent(s) 1 to 3 straight chain or branched chain alkyl groups having 1 to 6 carbon atoms and in which the alkyl moiety is a straight chain or branched chain alkyl group having 1 to 6 carbon atoms; for example, (2-pyrrolyl)methyl, 2-(2-pyrrolyl)ethyl, 1-(3-pyrrolyl)ethyl, 3-(2-pyrrolyl)propyl, 4-(3-pyrrolyl)butyl, 5-(2-pyrrolyl)pentyl, 6-(3-pyrrolyl)hexyl, 1,1-dimethyl-2-(2-pyrrolyl)ethyl, 2-methyl-3-(3-pyrrolyl)propyl, (5-ethyl-2-pyrrolyl)methyl, 2-(1-methyl-2-pyrrolyl)ethyl, 1-(3-propyl-2-pyrrolyl)ethyl, 3-(1-butyl-2-pyrrolyl)propyl, 4-(3-pentyl-5-pyrrolyl)butyl, 5-(4-hexyl-3-pyrrolyl)pentyl, 6-(2-methyl-4-pyrrolyl)hexyl, 1,1-dimethyl-2-(2-methyl-1-pyrrolyl)ethyl, 2-methyl-3-(1-methyl-3-pyrrolyl)propyl, (1,3-dimethyl-2-pyrrolyl)methyl and (1,2,3-trimethyl-4-pyrrolyl)methyl groups, etc.

As to the phenyl group having halogen atom(s) on the phenyl ring as substituent(s), there may be exemplified phenyl groups having 1 to 3 halogen atoms as substituent(s) on the phenyl ring; for example, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-idophenyl, 3-iodophenyl, 4-iodophenyl, 3,4-dichlorophenyl, 2,6-dichlorophenyl, 2,3-dichlorophenyl, 2,4-dichlorophenyl, 3,4-difluorophenyl, 3,5-dibromophenyl and 3,4,5-trichlorophenyl groups, etc.

As to the pyrrolidinylcarbonyl-lower alkyl group, there may be exemplified pyrrolidinylcarbonylalkyl groups in which the alkyl moiety is a straight chain or branched chain alkyl group having 1 to 6 carbon atoms; for example (1-pyrrolidinyl)carbonylmethyl, 2-(1-pyrrolidinyl)carbonylethyl, 1-(1-pyrrolidinyl)carbonylethyl, 3-(2-pyrrolidinyl)-carbonylpropyl, 4-(3-pyrrolidinyl)carbonylbutyl, 5-(1-pyrrolidinyl)carbonylpentyl, 6-(1-pyrrolidinyl)carbonylhexyl, 1,1-dimethyl-2-(2-pyrrolidinyl)carbonylethyl and 2-methyl-3-(3-pyrrolidinyl)carbonylpropyl groups, etc.

As to the aminothiocarbonyl group which may optionally contain a lower alkyl group as substituent(s), there may be exemplified aminothiocarbonyl groups which may optionally contain as substituent(s) 1 to 2 straight chain or branched chain alkyl groups having 1 to 6 carbon atoms; for example, aminothiocarbonyl, methylaminothiocarbonyl, ethylaminothiocarbonyl, propylaminothiocarbonyl, isopropylaminothiocarbonyl, butylaminothiocarbonyl, tert-butylaminothiocarbonyl, pentylaminothiocarbonyl, hexylaminothiocarbonyl, dimethylaminothiocarbonyl, diethylaminothiocarbonyl, dipropylaminothiocarbonyl, dibutylaminothiocarbonyl, dipentylaminothiocarbonyl, dihexylaminothiocarbonyl, N-methyl-N-ethylaminothiocarbonyl, N-ethyl-N-propylaminothiocarbonyl, N-methyl-N-butylaminothiocarbonyl and N-methyl-N-hexylaminothiocarbonyl groups, etc.

As to the phenyl-lower alkyl group which may optionally contain a halogen atom as substituent(s) on the phenyl ring, there may be exemplified phenylalkyl groups in which the alkyl moiety is a straight chain or branched chain alkyl group having 1 to 6 carbon atoms and which may optionally contain 1 to 3 halogen atoms on the phenyl ring; for example, benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-chlorobenzyl, 2-(3-chlorophenyl)ethyl, 2-fluorobenzyl, 1-(4-chlorophenyl)ethyl, 3-(2-fluorophenyl)propyl, 4-(3-fluorophenyl)butyl, 5-(4-fluorophenyl)pentyl, 1,1-dimethyl-2-(2-bromophenyl)ethyl, 6-(3-bromophenyl)hexyl, 4-bromobenzyl, 2-(2-iodophenyl)ethyl, 1-(3-iodophenyl)ethyl, 3-(4-iodophenyl)propyl, 3,4-dichlorobenzyl, 3,5-dichlorobenzyl, 2,6-dichlorobenzyl, 2,3-dichlorobenzyl, 2,4-dichlorobenzyl, 3,4-difluorobenzyl, 3,5-dibromobenzyl, 3,4,5-trichlorobenzyl, 3,5-dichloro-4-hydroxybenzyl, 3,5-dimethyl-4-hydroxybenzyl and 2-methoxy-3-chlorobenzyl groups, etc.

As to the halogen-substituted lower alkylsulfonyl group, there may be exemplified straight chain or branched chain alkyl groups having 1 to 6 carbon atoms which contains as substituent(s) 1 to 3 halogen atoms; for example, trifluoromethylsufonyl, trichloromethylsulfonyl, trichloromethylsufonyl, chloromethylsulfonyl, bromomethylsulfonyl, fluoromethylsulfonyl, iodomethylsulfonyl, difluoromethylsulfonyl, dibromomethylsulfonyl, 2-chloroethylsulfonyl, 2,2,2-trifluoroethylsulfonyl, 2,2,2-trichloroethylsulfonyl, 3-chloropropylsulfonyl, 2,3-dichloropropylsulfonyl, 4,4,4-trichlorobutylsulfonyl, 4-fluorobutylsulfonyl, 5-chloropentylsulfonyl, 3-chloro-2-methylpropylsulfonyl, 5-bromohexylsulfonyl and 5,6-dichlorohexylsulfonyl groups, etc.

As to the aminocarbonyl group which may optionally contain as substituent(s) lower alkyl groups, there may be exemplified aminocarbonyl groups which may optionally contain as a substituent(s) one or two straight chain or branched chain alkyl groups having 1 to 6 carbon atoms; for example, aminocarbonyl, methylaminocarbonyl, ethylaminocarbonyl, propylaminocarbonyl, isopropylaminocarbonyl, butylaminocarbonyl, tert-butylaminocarbonyl, pentylaminocarbonyl, hexylaminocarbonyl, dimethylaminocarbonyl, diethylaminocarbonyl, dipropylaminocarbonyl, dibutylaminocarbonyl, dipentylaminocarbonyl, dihexylaminocarbonyl, N-methyl-N-ethylaminocarbonyl, N-ethyl-N-propylaminocarbonyl, N-methyl-N-butylaminocarbonyl and N-methyl-N-hexylaminocarbonyl groups, etc.

As to the pyridylthio-substituted lower alkoxy group, there may be exemplified pyridylthio-substituted alkoxy groups in which the alkoxy moety is a straight chain or branched chain alkoxy group having 1 to 6 carbon atoms; for example, (2-pyridyl)thiomethoxy, (3-pyridyl)thiomethoxy, (4-pyridyl)thiomethoxy, 2-(2-pyridyl)thioethoxy, 2-(3-pyridyl)thioethoxy, 2-(4-pyridyl)thioethoxy, 3-(2-pyridyl)thiopropoxy, 3-(3-pyridyl)thiopropoxy, 3-(4-pyridyl)thiopropoxy, 4-(2-pyridyl)thiobutoxy, 4-(3-pyridyl)thiobutoxy, 4-(4-pyridyl)thiobutoxy, 5-(2-pyridyl)thiopentyloxy, 5-(3-pyridyl)thiopentyloxy, 5-(4-pyridyl)thiopentyloxy, 6-(2-pyridyl)thiohexyloxy, 6-(3-pyridyl)thiohexyloxy, 6-(4-pyridyl)thiohexyloxy, 1,1-dimethyl-2-(2-pyridyl)thioethoxy, 1,1-dimethyl-2-(3-pyridyl)thioethoxy, 1,1-dimethyl-(4-pyridyl)thioethoxy, 2-methyl-3-(2-pyridyl)thiopropoxy, 2-methyl-3-(3-pyridyl)thiopropoxy and 2-methyl-3-(4-pyridyl)thiopropoxy groups, etc.

As to the pyridylsulfinyl-substituted lower alkoxy group, there may be exemplified pyridylsulfinyl-substituted alkoxy groups in which the alkoxy moiety is a straight chain or branched chain alkoxy group having 1 to 6 carbon atoms; for example, (2-pyridyl)sulfinylmethoxy, (3-pyridyl)sulfinylmethoxy, (4-pyridyl)sulfinylmethoxy, 2-(2-pyridyl)sulfinylethoxy, 2-(3-pyridyl)sulfinylethoxy, 2-(4-pyridyl)sulfinylethoxy, 3-(2-pyridyl)sulfinylpropoxy, 3-(3-pyridyl)sulfinylpropoxy, 3-(4-pyridyl)sulfinylpropoxy, 4-(2-pyridyl)sulfinylbutoxy, 4-(3-pyridyl)sulfinylbutoxy, 4-(4-pyridyl)sulfinylbutoxy, 5-(2-pyridyl)sulfinylpentyloxy, 5-(3-pyridyl)sulfinylpentyloxy, 5-(4-pyridyl)sulfinylpentyloxy, 6-(2-pyridyl)sulfinylhexyloxy, 6-(3-pyridyl)sulfinylhexyloxy, 6-(4-pyridyl)sulfinylhexyloxy, 1,1-dimethyl-2-(2-pyridyl)sulfinylethoxy, 1,1-dimethyl-2-(3-pyridyl)sulfinylethoxy, 1,1-dimethyl-(4-pyridyl)sulfinylethoxy, 2-methyl-3-(2-pyridyl)sulfinylpropoxy, 2-methyl-3-(3-pyridyl)sulfinylpropoxy and 2-methyl-3-(4-pyridyl)sulfinylpropoxy groups, etc.

As to the pyridylsulfonyl-substituted lower alkoxy group, there may be exemplified pyridylsulfonyl-substituted alkoxy groups in which the alkoxy moiety is a straight chain or branched chain alkoxy group having 1 to 6 carbon atoms; for example, (2-pyridyl)sulfonylmethoxy, (3-pyridyl)sulfonylmethoxy, (4-pyridyl)sulfonylmethoxy, 2-(2-pyridyl)sulfonylethoxy, 2-(3-pyridyl)sulfonylethoxy, 2-(4-pyridyl)sulfonylethoxy, 3-(2-pyridyl)sulfonylpropoxy, 3-(3-pyrfidyl)sulfonylpropoxy, 3-(4-pyridyl)sulfonylpropoxy, 4-(2-pyridyl)sulfonylbutoxy, 4-(3-pyridyl)sulfonylbutoxy, 4-(4-pyridyl)sulfonylbutoxy, 5-(2-pyridyl)sulfonylpentyloxy, 5-(3-pyridyl)sulfonylpentyloxy, 5-(4-pyridyl)sulfonylpentyloxy, 6-(2-pyridyl)sulfonylhexyloxy, 6-(3-pyridyl)sulfonylhexyloxy, 6-(4-pyridyl)sulfonylhexyloxy, 1,1-dimethyl-2-(2-pyridyl)sulfonylethoxy, 1,1-dimethyl-2-(3-pyridyl)sulfonylethoxy, 1,1-dimethyl-(4-pyridyl)sulfonylethoxy, 2-methyl-3-(2-pyridyl)sulfonylpropoxy, 2-methyl-3-(3-pyridyl)sulfonylpropoxy and 2-methyl-3-(4-pyridyl)sulfonylpropoxy groups, etc.

As to the imidazolylthio-substituted lower alkoxy group, there may be exemplified imidazolylthio-substituted alkoxy groups in which the alkoxy moiety is a straight chain or branched chain alkoxy group having 1 to 6 carbon atoms; for exmaple, (2-imidazolyl)thiomethoxy, 2-(2-imidazolyl)thioethoxy, 1-(2-imidazolyl)thioethoxy, 3-(4-imidazolyl)thiopropoxy, 4-(5-imidazolyl)thiobutoxy, 5-(4-imidazolyl)thiopentyloxy, 6-(2-imidazolyl)thiohexyloxy, 1,1-dimethyl-2-(2-imidazolyl)thioethoxy and 2-methyl-3-(5-imidazolyl)thiopropoxy groups, etc.

As to the imidazolylsulfinyl-substituted lower alkoxy group, there may be exemplified imidazlylsulfonyl-substituted alkoxy groups in which the alkoxy moiety is a straight chain or branched chain alkoxy group having 1 to 6 carbon atoms; for example, (2-imidazolyl)sulfinylmethoxy, 2-(2-imidazolyl)sulfinylethoxy, 1-(2-imidazolyl)sulfinylethoxy, 3-(4-imidazolyl)sulfinylpropoxy, 4-(5-imidazolyl)sulfinylbutoxy, 5-(4-imidazolyl)sulfinylpentyloxy, 6-(2-imidazolyl)-sulfinylhexyloxy, 1,1-dimethyl-2-(2-imidazolyl)sulfinylethoxy and 2-methyl-3-(5-imidazolyl)sulfinylpropoxy groups, etc.

As to the imidazolylsulfonyl-substituted lower alkoxy group, there may be exemplified imidazolylsulfonyl-substituted alkoxy groups in which the alkoxy moiety is a straight chain or branched chain alkoxy group having 1 to 6 carbon atoms; for example, (2-imidazolyl)sulfonylmethoxy, 2-(2-imidazolyl)sulfonylethoxy, 1-(2-imidazolyl)sulfonylethoxy, 3-(4-imidazolyl)sulfonylpropoxy, 4-(5-imidazolyl)sulfonylbutoxy, 5-(4-imidazolyl)sulfonylpentyloxy, 6-(2-imidazolyl)sulfonylhexyloxy, 1,1-dimethyl-2-(2-imidazolyl)sulfonylethoxy and 2-methyl-3-(5-imidazolyl)sulfonylpropoxy groups, etc.

As to the pyrimidinylthio-substituted lower alkoxy group which may optionally contain a lower alkyl group on the pyrimidine ring, there may be exemplified pyrimidinylthioalkoxy groups which may optionally contain 1 to 3 straight chain or branched chain alkyl groups having 1 to 6 carbon atoms on the pyrimidine ring and in which the alkoxy moiety is a straight chain or branched chain alkoxy group having 1 to 6 carbon atoms; for exmaple, (2-pyrimidinyl)thiomethoxy, 2-(2-pyrimidinyl)thioethoxy, 1-(4-pyrimidinyl)thioethoxy, 3-(5-pyrimidinyl)thiopropoxy, 4-(6-pyrimidinyl)thiobutoxy, 5-(2-pyrimidinyl)thiopentyloxy, 6-(4-pyrimidinyl)thiohexyloxy, 1,1-dimethyl-2-(2-pyrimidinyl)thioethoxy, 2-methyl-3-(4-pyrimidinyl)thiopropoxy, 2-(6-methyl-2-pyrimidinyl)thioethoxy, (4-ethyl-2-pyrimidinyl)thiomethoxy, 1-(5-propyl-4-pyrimidinyl)thioethoxy, 3-(2-butyl-5-pyrimidinyl)thiopropoxy, 4-(6-pentyl-2-pyrimidinyl)thiobutoxy, 5-(5-hexyl-2-pyrimidinyl)thiopentyloxy, 6-(6-methyl-2-pyrimidinyl)thiohexyloxy, 2-(4,6-dimethyl-2-pyrimidinyl)thioethoxy and (4,5,6-trimethyl-2-pyrimidinyl)thiomethoxy groups, etc.

As to the amino-substituted lower alkoxy group which may optionally contain as a substituent a lower alkyl group, there may be exemplified straight chain or branched chain alkoxy groups having 1 to 6 carbon atoms which may optionally contain as substituent(s) 1 to 2 straight chain or branched chain alkyl groups having 1 to 6 carbon atoms; for example, aminomethoxy, 2-aminoethoxy, 1-aminoethoxy, 3-aminopropoxy, 4-aminobutoxy, 5-aminopentyloxy, 6-aminohexyloxy, 6-aminohexyloxy, 1,1-dimethyl-2-aminoethoxy, 2-methyl-3-aminopropoxy, melthylaminomethoxy, 1-ethylaminoethoxy, 2-propylaminoethoxy, 3-isopropylaminopropoxy, 4-isopropylaminobutoxy, 4-butylaminobutoxy, 4-tert-butylaminobutoxy, 5-pentylaminopentyloxy, 6-hexylaminohexyloxy, dimethylaminomethoxy, 2-diethylaminoethoxy, 2-dimethylaminoethoxy, (N-ethyl-N-propylamino)melthoxy and 2-(N-methyl-N-hexylamino)ethoxy groups, etc.

As to the pyrrolidinyl-substituted lower alkyl group, there may be exemplified pyrrolidinylalkyl groups which may optionally contain as substituent(s) 1 to 3 straight chain or branched chain alkyl groups and in which the alkyl moiety is a straight chain or branched chain alkyl group having 1 to 6 carbon atoms; for example, (2-pyrrolidinyl)methyl, 2-(2-pyrrolidinyl)ethyl, 1-(3-pyrrolidinyl)ethyl, 3-(2-pyrrolidinyl)propyl, 4-(3-pyrrolidinyl)butyl, 5-(2-pyrrolidinyl)pentyl, 6-(3-pyrrolidinyl)hexyl, 1,1-dimethyl-2-(2-pyrrolidinyl)ethyl, 2-methyl-3-(3-pyrrolidinyl)propyl, (5-ethyl-2-pyrrolidinyl)methyl, 2-(1-methyl-2-pyrrolidinyl)-ethyl, 1-(3-propyl-2-pyrrolidinyl)ethyl, 3-(1-butyl-2-pyrrolidinyl)propyl, 4-(3-pentyl-5-pyrrolidinyl)butyl, 5-(4-hexyl-3-pyrrolidinyl)pentyl, 6-(2-methyl-4-pyrrolidinyl)hexyl, 1,1-dimethyl-2-(4-methyl-3-pyrrolidinyl)ethyl, 2-methyl-3-(1-methyl-3-pyrrolidinyl)propyl, (1,3-dimethyl-2-pyrrolidinyl)methyl and (1,2,3-trimethyl-4-pyrrolidinyl)methyl groups, etc.

The compounds of the present invention can be produced by various processes.

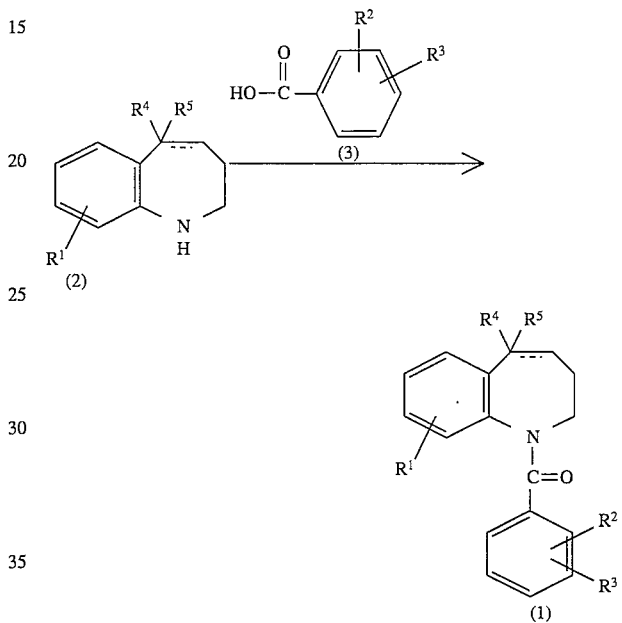

In the above, $R^1$, $R^2$, $R^3$, $R^4$, $R^5$ and the bond between the 4- and 5-position carbons of the benzoazepine skeleton are the same as defined above.

The process shown by the reaction formula 1 is a process in which a benzoheterocyclic compound of the general formula (2) is reacted with a carboxylic acid of the general formula (3) according to an ordinary amide-bond-formation reaction. In the amide-bond-formation reaction, the known conditions for amide-bond-formation reaction can be applied easily. The process includes, for example, (a) a mixed acid anhydride process which comprises reacting a carboxylic acid (3) with an alkylhalocarboxylic acid to form a mixed acid anhydride and reacting the anhydride with an amine (2); (b) an active ester process which comprises converting a carboxylic acid (3) into an active ester such as p-nitro-phenyl ester, N-hydroxysuccinimide ester, 1-hydroxybenzo-triazole ester or the like and reacting the active ester with an amine (2); a carbodiimide process which comprises subjecting a carboxylic acid (3) and an amine (2) to a condensation reaction in the presence of an activating agent such as dicyclohexylcarbodiimide, carbonyldiimidazole or the like; and other processes. The other processes include, for example, a process which comprises converting a carboxylic acid (3) into a carboxylic acid anhydride using a dehydrating agent such as acetic anhydride or the like and reacting the carboxylic acid anhydride with an amine (2); a process which comprises reacting an ester of a carboxylic acid (3) and a lower alcohol with an amine (2) at a high pressure at a high temperature; and a process which comprises reacting an acid halide of a carboxylic acid (3), i.e. a carboxylic acid halide with an amine (2).

The mixed acid anhydride used in the mixed acid anhydride process (a) can be obtained by a general Schotten-Baumann reaction. The anhydride is reacted with an amine (2) generally without being isolated, whereby the compound of the general formula (1) according to the present invention can be produced. The Schotten-Baumann reaction is conducted in the presence of a basic compound. The basic compound is a compound conventionally used in the Schotten-Baumann reaction and includes, for example, organic bases such as triethylamine, trimethylamine, pyridine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and the like, and inorganic bases such as potassium carbonate, sodium carbonate, potassium hydrogencarbonate, sodium hydrogencarbonate and the like. The reaction is conducted generally at about −20° C. to 100° C., preferably at about 0°–50° C., and the reaction time is about 5 minutes to 10 hours, preferably about 5 minutes to 2 hours. The reaction of the resulting mixed acid anhydride with an amine (2) is conducted generally at about −20° C. to 150° C., preferably at about 10°–50° C., and the reaction time is about 5 minutes to 10 hours, preferably about 5 minutes to 5 hours. The mixed acid anhydride process (a) is conducted generally in a solvent. The solvent may be any solvent conventionally used in the mixed acid anhydride process, and can be exemplified by halogenated hydrocarbons such as chloroform, dichloro-methane, dichloroethane and the like; aromatic hydrocarbons such as benzene, toluene, xylene and the like; ethers such as diethylether, diisopropyl ether, tetrahydrofuran, dimethoxyethane and the like; esters such as methyl acetate, ethyl acetate and the like; aprotic polar solvents such as N,N-dimethylformamide, dimethyl sulfoxide, acetonitrile, hexamethylphosphoric triamide and the like; and mixtures thereof. The alkylhalocarboxylic acid used in the mixed acid anhydride process (a) includes, for example, methyl chloroformate, methyl bromoformate, ethyl chloroformate, ethyl bromoformate and isobutyl chloroformate. The proportions of the carboxylic acid (3), the alkylhalocarboxylic acid and the amine (2) used in the process are generally equal moles. However, the carboxylic acid (3) and the alkylhalocarboxylic acid may be used each in an amount of about 1–1.5 moles per mole of the amine (2).

The process which comprises reacting a carboxylic acid halide with an amine (2) [this is a process included in the other processes (d)], can be conducted in the presence of a basic compound in an appropriate solvent. The basic compound can be selected from various known basic compounds and can be exemplified by not only the basic compounds usable in the above Schotten-Baumann reaction but also sodium hydroxide, potassium hydroxide, sodium hydride and potassium hydride. The solvent can be exemplified by not only the solvents usable in the mixed acid anhydride process (a) but also alcohols (e.g. methanol, ethanol, propanol, butanol, 3-methoxy-1-butanol, ethyl cellosolve and methyl cellosolve), pyridine, acetone and water. The proportions of the amine (2) and the carboxylic acid halide used are not particularly restricted and can be appropriately selected from a wide range, but the carboxylic acid halide is used in an amount of generally at least about 1 mole, preferably about 1–5 moles per mole of the amine (2). The reaction is conducted generally at about −20° C. to 180° C., preferably at about 0°–150° C. and is complete generally in about 5 minutes to 30 hours.

The amide-bond-formation reaction shown by the reaction formula 1 can also be carried by a process which comprises reacting a carboxylic acid (3) with an amine (2) in the presence of a phosphorus compound as condensating agent. The phosphorus compound includes triphenylphosphine, diphenylphosphinyl chloride, phenyl N-phenylphosphoramide chloridate, diethyl chlorophosphate, diethyl cyanophosphate, diphenyl phosphoric azide, bis(2-oxo-3-oxazolidinyl)phosphinic chloride, etc.

The reaction is conducted in the presence of the same solvent and basic compound as used in the above-mentioned process which comprises reacting a carboxylic acid halide with an amine (2), generally at about −20° C. to 150° C., preferably at about 0°–100° C., and is complete generally in about 5 minutes to 30 hours. The amounts of the condensating agent and the carboxylic acid (3) used are each at least about 1 mole, preferably about 1–2 moles per mole of the amine (2).

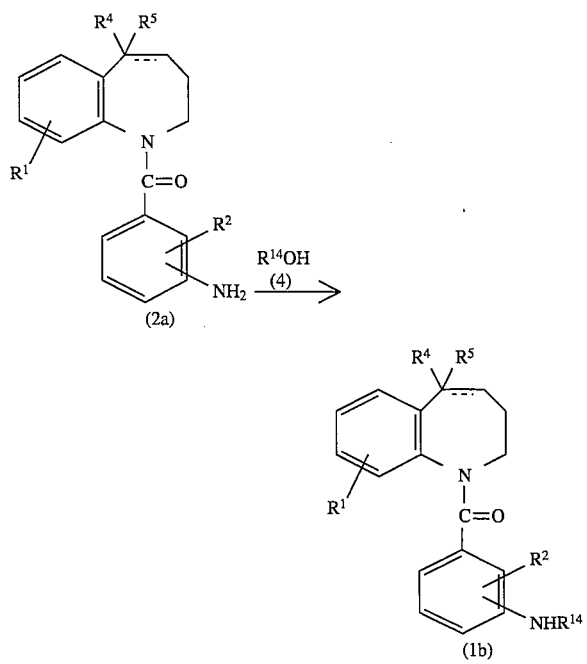

In the above, $R^1$, $R^2$, $R^4$, $R^5$ and the bond between the 4- and 5-position carbons of the benzoazepine skeleton are the same as defined above. $R^{14}$ is a group represented by the following formula

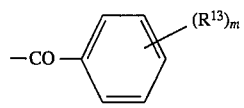

($R^{13}$ and m are the same as defined above), a phenyl-lower alkanoyl group having, on the phenyl ring, 1–3 substituents selected from the group consisting of halogen atoms, lower alkoxy groups, lower alkyl groups and a nitro group, or a group represented by the following formula.

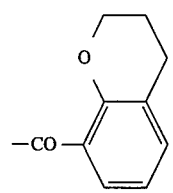

The reaction of the compound (2a) with the compound (4) can be conducted under the same conditions as in the reaction of the reaction formula 1 between the compound (2) and the compound (3).

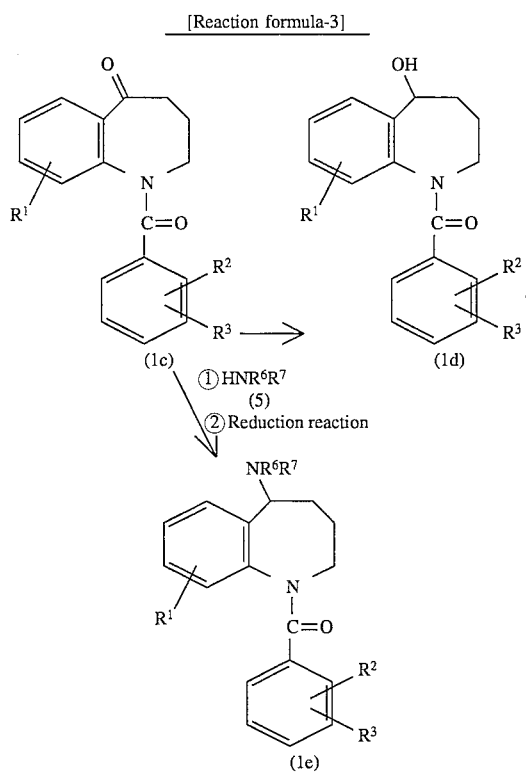

In the above, $R^1$, $R^2$, $R^3$, $R^6$ and $R^7$ are the same as defined above.

The reaction for converting a compound (1c) into a compound (1d) can be conducted by a reduction reaction.

to 100° C. for about 10 minutes to 15 hours. When lithium aluminum hydride or diborane is used as the reducing agent, it is preferable to use an anhydrous solvent such as tetrahydrofuran, diethyl ether, diisopropyl ether or diglyme.

The reduction for converting a compound (1c) into a compound (1e) is conducted in the absence of any solvent or in the presence of an appropriate solvent, in the presence or absence of a dehydrating agent. The solvent includes, for example, alcohols such as methanol, ethanol, isopropanol and the like; aromatic hydrocarbons such as benzene, toluene, xylene and the like; halogenated hydrocarbons such as dichloromethane, dichloroethane, chloroform, carbon tetrachloride and the like; aprotic polar solvents such as dimethylformamide, dimethylacetamide, N-methylpyrrolidone and the like; and mixtures thereof. The dehydrating agent includes, for example, desiccants generally used for solvent dehydration, such as molecular sieve and the like; mineral acids such as hydrochloric acid, sulfuric acid, boron trifluoride and the like; and organic acids such as p-toluenesulfonic acid and the like. The reaction is conducted generally at room temperature to 250° C., preferably at about 50°–200° C. and is complete generally in about 1–48 hours. The amount of the compound (5) used is not particularly restricted but is generally at least equimolar, preferably equimolar to a large excess to the compound (1c). The amount of the dehydrating agent used is generally a large excess when a desiccant is used, and is a catalytic amount when an acid is used.

In the subsequent reduction reaction, various methods can be used. It can be conducted by catalytic hydrogenation in the presence of a catalyst in an appropriate solvent. The solvent includes, for example, water; alcohols such as methanol, ethanol, isopropanol and the like; hydrocarbons such as hexane, cyclohexane and the like; ethers such as diethylene glycol dimethyl ether, dioxane, tetrahydrofuran, diethyl ether and the like; esters such as ethyl acetate, methyl acetate and the like; aprotic polar solvents such as dimethylformamide and the like; and mixtures thereof.

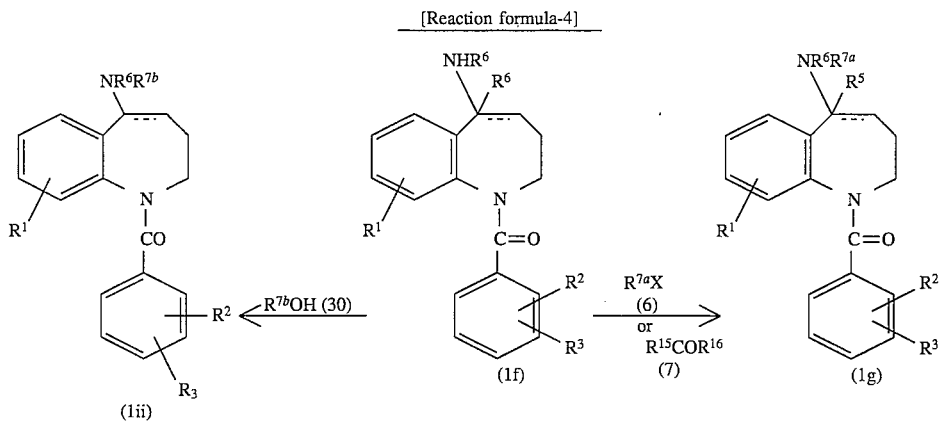

In the reduction reaction, the reduction can be preferably conducted using a hydride as a reducing agent. The hydride as reducing agent includes, for example, lithium aluminum hydride, lithium boron hydride, sodium boron hydride and diborane. The amount of the hydride used is at least 1 mole, preferably 1–15 moles per mole of the raw material. This reduction reaction is conducted generally using an appropriate solvent such as water, lower alcohol (e.g. methanol, ethanol or isopropanol), ether (e.g. tetrahydrofuran, diethyl ether, diisopropyl ether or diglyme) or mixture thereof, generally at about –60° C. to 150° C., preferably at –30° C.

In the above, $R^1$, $R^2$, $R^3$, $R^5$ $R^6$ and the bond between the 4- and 5-position carbons of the benzoazepine skeleton are the same as defined above. $R^{7a}$ is a lower alkyl group or a lower alkenyl group. $R^{15}$ and $R^{16}$ are each a hydrogen atom or a lower alkyl group. X is a halogen atom. $R^{7b}$ is a benzoyl group having halogen substituent(s) on the phenyl ring.

The reaction of the compound (1f) with the compound (6) is conducted generally in an appropriate inactive solvent in the presence or absence of a basic compound.

The inactive solvent includes, for example, aromatic hydrocarbons such as benzene, toluene, xylene and the like;

ethers such as tetrahydrofuran, dioxane, diethylene glycol dimethyl ether and the like; halogenated hydrocarbons such as dichloromethane, chloroform, carbon tetrachloride and the like; lower alcohols such as methanol, ethanol, isopropanol, butanol, tert-butanol and the like; acetic acid; ethyl acetate; acetone; acetonitrile; pyridine; dimethyl sulfoxide; dimethylformamide; hexamethylphosphoric triamide; and mixtures thereof. The basic compound includes, for example, carbonates such as sodium carbonate, potassium carbonate, sodium hydrogencarbonate, potassium hydrogencarbonate and the like; metal hydroxides such as sodium hydroxide, potassium hydroxide and the like; sodium hydride; potassium; sodium; sodium amide; metal alcoholates such as sodium methylate, sodium ethylate and the like; and organic bases such as pyridine, N-ethyldiisopropylamine, dimethylaminopyridine, triethylamine, 1,5-diazabicyclo-[4.3.0]nonene-5 (DBN), 1,8-diazabicyclo[5.4.0]undecene-7 (DBU), 1,4-diazabicyclo[2.2.2]octane (DABCO) and the like. The proportions of the compound (1f) and the compound (6) are not particularly restricted and can be appropriately selected from a wide range, but the compound (6) is used in an amount of preferably at least about 1 mole, more preferably about 1–10 moles per mole of the compound (1f). The reaction is conducted generally at about 0°–200° C., preferably at about 0°–170° C. and is complete generally in about 30 minutes to 75 hours. In the reaction system may be used an alkali metal halide (e.g. sodium iodide or potassium iodide), etc.

The reaction of the compound (1f) with the compound (7) is conducted in the absence of any solvent or in the presence of an appropriate solvent in the presence of a reducing agent. The solvent can be exemplified by water; alcohols such as methanol, ethanol, isopropanol and the like; acetonitrile; formic acid; acetic acid; ethers such as dioxane, diethyl ether, diglyme, tetrahydrofuran and the like; aromatic hydrocarbons such as benzene, toluene, xylene and the like; and mixtures thereof. The reducing agent can be exemplified by formic acid; alkali metal salts of fatty acids, such as sodium formate and the like; hydride reducing agents such as sodium borohydride, sodium cyanoborohydride, lithium aluminum hydride and the like; and catalytic reducing agents such as palladium black, palladium-carbon, platinum oxide, platinum black, Raney nickel and the like.

When formic acid is used as the reducing agent, the appropriate reaction temperature is generally about room temperature to 200° C., preferably about 50°–150° C., and the reaction is complete in about 1–10 hours. The amount of formic acid used is preferably a large excess to the compound (1f).

When a hydride reducing agent is used, the appropriate reaction temperature is generally about −30° C. to 100°, preferably about 0°–70° C., and the reaction is complete in about 30 minutes to 12 hours.

The appropriate amount of the reducing agent used is generally about 1–20 moles, preferably about 1–6 moles per mole of the compound (1f). When lithium aluminum hydride is used as the reducing agent, it is preferable to use, as the solvent, an ether (e.g. diethyl ether, dioxane, tetrahydrofuran or diglyme) or an aromatic hydrocarbon (e.g. benzene, toluene or xylene).

When a catalytic reducing agent is used, the reaction is conducted in a hydrogen atmosphere of generally about normal pressure to 20 atm., preferably about normal pressure to 10 atm. in the presence of a hydrogen donor (e.g. formic acid, ammonium formate, cyclohexene or hydrazine hydrate) generally at about −30° C. to 100° C., preferably at about 0°–60° C., and is complete generally in about 1–12 hours. The amount of the catalytic reducing agent used is generally about 0.1–40% by weight, preferably about 1–20% by weight based on the compound (1f).

The reaction of the compound (1f) with the compound (30) can be conducted under the same conditions as in the reaction of the compound (2) with the compound (3) in the reaction formula-1.

The appropriate amount of the compound (7) used is generally at least equimolar, preferably equimolar to a large excess to the compound (1f).

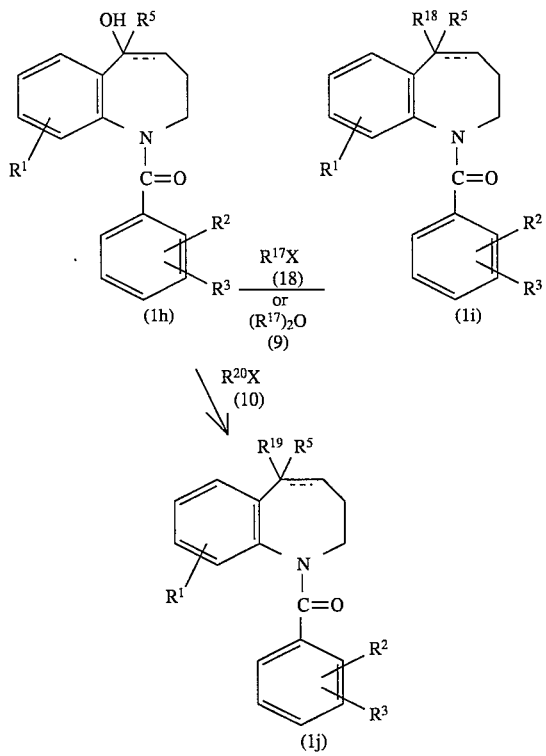

[Reaction formula-5]

In the above, $R^1$, $R^2$, $R^3$, X, $R^5$ and the bond between the 4- and 5-position carbons of the benzoazepine skeleton are the same as defined above. $R^{18}$ is a lower alkanoyloxy group having halogen substituent(s), or a lower alkoxy-substituted lower alkanoyloxy group. $R^{19}$ is a lower alkenyloxy group, a group —O—CO—A—NR$^8$R$^9$ (A, $R^8$ and $R^9$ are the same as defined above), a group —OACONR$^{23}$R$^{24}$ (A, $R^{23}$ and $R^{24}$ are the same as defined above), a pyrrolidinylcarbonyl-lower alkoxy group having lower alkoxycarbonyl group(s) on the pyrrolidine ring, a group —OANR$^{27}$R$^{28}$ (A, $R^{27}$ and $R^{28}$ are the same as defined above), a phenylsulfonyloxy group having lower alkyl substituent(s) on the phenyl ring, a hydroxyl group-containing lower alkoxy group, a 1,2,4-triazolyl-substituted lower alkoxy group, a 1,2,3,4-tetrazolyl-substituted lower alkoxy group, a 1,2,3,5-tetrazolyl-substituted lower alkoxy group, a pyridylthio-substituted lower alkoxy group, a pyrimidinylthio-substituted lower alkoxy group which may have lower alkyl group(s) on the pyrimidine ring, an imidazolylthio-substituted lower alkoxy group, a pyridylsulfinyl-substituted lower alkoxy group, a pyridylsulfonyl-substituted lower alkoxy group, an imidazolylsulfinyl-substituted lower alkoxy group or an imidazolylsulfonyl-substituted lower alkoxy group. $R^{20}$ is a lower alkenyl group, a group —CO—A—NR$^8$R$^9$ (A, $R^8$ and $R^9$ are the same as defined above), a group —ACONR$^{23}$R$^{24}$ (A, $R^{23}$ and $R^{24}$ are the same as defined above), a pyrrolidinylcarbonyl-lower alkyl group having lower alkoxycarbonyl group(s) on the pyrrolidine ring, a group —ANR$^{27}$R$^{28}$ (A, R$^{27}$ and R$^{28}$ are the same as defined above), a phenylsulfonyloxy group having lower alkyl substituent(s) on the phenyl ring, a hydroxyl group-containing lower alkyl group, a 1,2,4-triazolyl-substituted lower alkyl group, a 1,2,3,4-tetrazolyl-substituted lower alkyl group, a 1,2,3,5-tetrazolyl-substituted lower alkyl group, a pyridylthio-substituted lower alkyl group, a pyrimidinylthio-substituted lower alkyl group which may have lower alkyl group(s) on the pyrimidine ring, an imidazolylthio-substituted lower alkyl group, a pyridylsulfinyl-substituted lower alkyl group, a pyridylsulfonyl-substituted lower alkyl group, an imidazolylsulfinyl-substituted lower alkyl group or an imidazolylsulfonyl-substituted lower alkyl group. R$^{17}$ is a lower alkanoyl group having halogen substituent(s) or a lower alkoxy-substituted lower alkanoyl group.

The reaction of the compound (1h) with the compound (8) or (9) can be conducted under the same conditions as in the reaction of the compound (1f) with the compound (6) in the reaction formula-4.

The reaction of the compound (1h) with the compound (10) can be conducted under the same conditions as in the reaction of the compound (1f) with the compound (6) in the reaction formula 4.

When the R$^{18}$ of the compound (1i) is a lower alkanoyl group having halogen substituent(s), the compound (1i) can be reacted with a compound HNR$^8$R$^9$ (11) (R$^8$ and R$^9$ are the same as defined above) under the same conditions as in the reaction of the compound (1f) with the compound (6) in the reaction formula 4, to obtain a compound (1j) wherein the R$^{19}$ is a group —O—CO—A—NR$^8$R$^9$ (A, R$^8$ and R$^9$ are the same as defined above).

[Reaction formula-6]

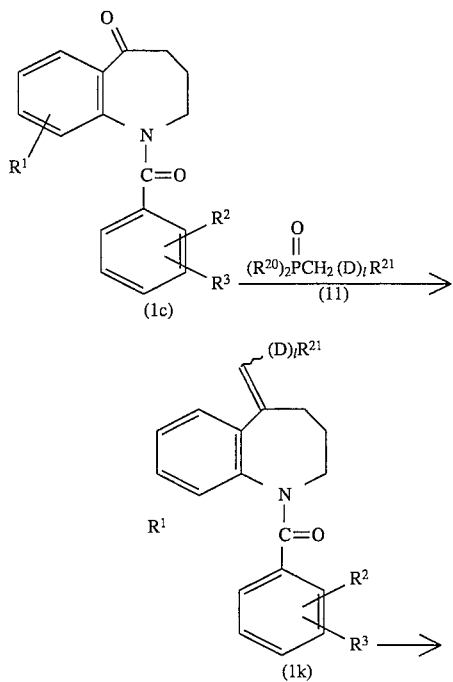

[Reaction formula-6]

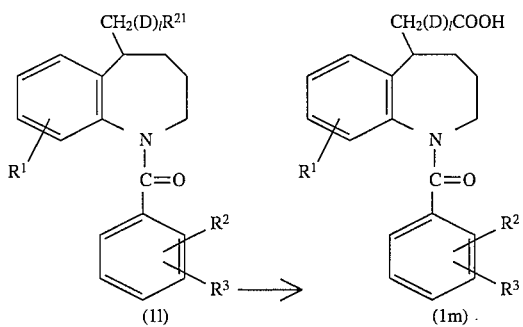

In the above, R$^1$, R$^2$ and R$^3$ are the same as defined above. R$^{20}$ is a lower alkoxy group. R$^{21}$ is a lower alkoxycarbonyl group, a cyano group or an amino group which may have lower alkyl substituent(s). D is a lower alkylene group. l is 0 or 1.

The reaction of the compound (1c) with the compound (11) is conducted in the presence of a basic compound in an appropriate solvent. The basic compound can be exemplified by inorganic bases such as metallic sodium, metallic potassium, sodium hydride, sodium amide, sodium hydroxide, potassium hydroxide, sodium carbonate, potassium carbonate, sodium hydrogencarbonate and the like; metal alcoholates such as sodium methylate, sodium ethylate, potassium tert-butoxide and the like; alkyl- or aryllithiums or lithium amides such as methyllithium, n-butyllithium, phenyllithium, lithium diisopropylamide and the like; and organic bases such as pyridine, piperidine, quinoline, triethylamine, N,N-dimethylaniline and the like. The solvent can be any solvent as long as it gives no adverse effect on the reaction. The solvent includes, for example, ethers such as diethyl ether, dioxane, tetrahydrofuran, monoglyme, diglyme and the like; aromatic hydrocarbons such as benzene, toluene, xylene and the like; aliphatic hydrocarbons such as n-hexane, heptane, cyclohexane and the like; amines such as pyridine, N,N-dimethylaniline and the like; aprotic polar solvents such as N,N-dimethylformamide, dimethyl sulfoxide, hexamethylphosphoric triamide and the like; and alcohols such as methanol, ethanol, isopropanol and the like. The appropriate reaction temperature is generally about –80° C. to 150° C., preferably about –80° C. to 120° C. The reaction is complete generally in about 0.5–15 hours.

The reaction for converting the compound (1k) into a compound (1l) is conducted under the same conditions as in the reduction reaction in the reaction formula 3 for converting the compound (1c) into a compound (1e). When hydrogen is used as a reducing agent in the reduction reaction, the addition of a metal halide (e.g. nickel chloride) allows the reaction to proceed favorably.

When the compound (1l) is a compound (1l) wherein the R$^{21}$ is a lower alkoxycarbonyl group, the reaction for converting the compound (1l) into a compound (1m) can be carried out in an appropriate solvent or in the absence of any solvent in the presence of an acid or a basic compound. The solvent includes, for example, water; lower alcohols such as methanol, ethanol, isopropanol and the like; ketones such as acetone, methyl ethyl ketone and the like; ethers such as dioxane, tetrahydrofuran, ethylene glycol dimethyl ether and the like; fatty acids such as acetic acid, formic acid and the like; and mixtures thereof. The acid includes, for example, mineral acids such as hydrochloric acid, sulfuric acid, hydrobromic acid and the like; and organic acids such as formic acid, acetic acid, aromatic sulfonic acids and the like.

The basic compound includes, for example, metal carbonates such as sodium carbonate, potassium carbonate and the like; and metal hydroxides such as sodium hydroxide, potassium hydroxide, calcium hydroxide and the like. The reaction favorably proceeds generally at about room temperature to 200° C., preferably at about room temperature to 150° C., and is complete generally in about 10 minutes to 25 hours.

[Reaction formula-7]

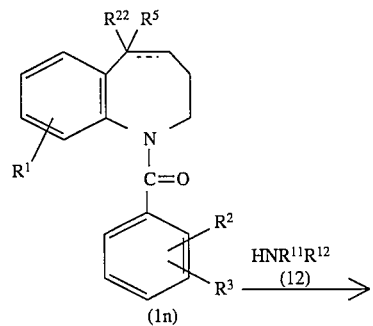

In the above, $R^1$, $R^2$, $R^3$, $R^5$, $R^{11}$, $R^{12}$, A and the bond between the 4- and 5-position carbons of the benzoazepine skeleton are the same as defined above. $R^{22}$ is a carboxy-substituted lower alkyl group.

The reaction of the compound (1n) with the compound (12) can be conducted under the same conditions as in the reaction of the compound (2) with the compound (3) in the reaction formula 1.

[Reaction formula-8]

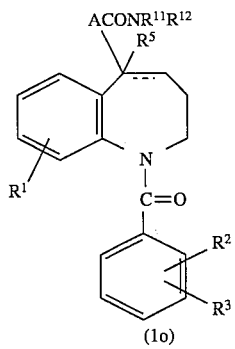

In the above, $R^1$, $R^2$, $R^3$, $R^5$, $R^{10}$ and the bond between the 4- and 5-position carbons of the benzoazepine skeleton are the same as defined above.

The reaction of the compound (1p) with the compound (13) is conducted in an appropriate solvent in the presence of a basic compound. In the system of the reaction, it is advisable to use a condensing agent such as dicyclohexylcarbodiimide, carbonyldiimidazole, 1-ethyl-3-(3'-dimethylaminopropyl)carbodiimide or the like. The basic compound and solvent can be any basic compound and solvent used in the reaction of the compound (1f) with the compound (6) in the reaction formula 4. The appropriate amount of the compound (13) used is at least 1 mole, preferably about 1–2 moles per mole of the compound (1p). The reaction is conducted at 0°–100° C., preferably at about 0°–70° C. and is complete in about 1–15 hours.

When the compound (13) is used in the reaction, it is possible to protect the amino group moiety of the amino acid residue of the $R^{10}$, with an ordinary amino acid-protecting group such as phenyl-lower alkoxycarbonyl group (e.g. benzyloxycarbonyl group), lower alkoxycarbonyl group (e.g. tert-butoxycarbonyl group) or the like, react the resulting product with a compound (1p) and deprotecting said protecting group by an ordinary deprotection reaction such as catalytic reduction, hydrolysis or the like to obtain a compound (1q).

The compound (2a) as starting material can be produced, for example, by the following reaction formula.

[Reaction formul-9]

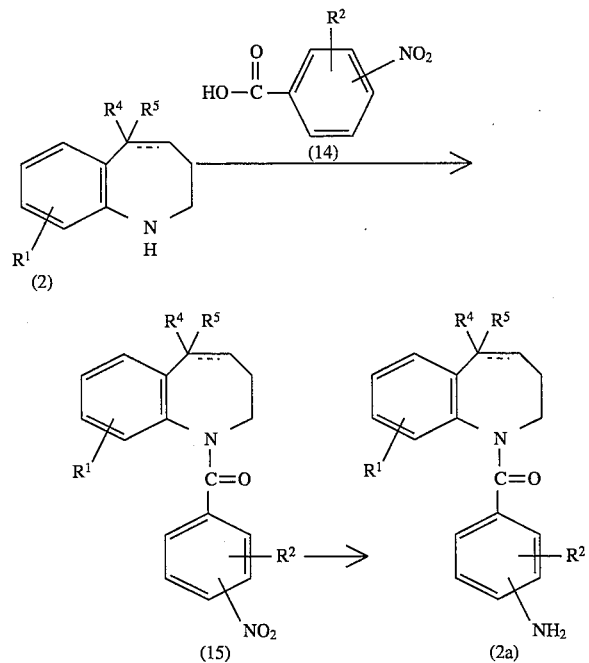

In the above, $R^1$, $R^2$, $R^4$, $R^5$ and the bond between the 4- and 5-position carbons of the benzoazepine skeleton are the same as defined above.

The reaction of the compound (2) with the compound (14) can be conducted under the same conditions as in the reaction of the compound (2) with the compound (3) in the reaction formula-3.

The reaction for converting the compound (15) into a compound (2a) is conducted, for example, by (1) reducing the compound (15) with a catalytic reduction catalyst in an appropriate solvent or (2) reducing the compound (15) in an appropriate inactive solvent using, as a reducing agent, a mixture between a metal or a metal salt and an acid or a mixture between a metal or a metal salt and an alkali metal hydroxide, a sulfide or an ammonium salt.

In the case (1) using a catalytic reduction catalyst, the solvent includes, for example, water; alcohols such as methanol, ethanol, isopropanol and the like; hydrocarbons such as hexane, cyclohexane and the like; ethers such as dioxane, tetrahydrofuran, diethyl ether, diethylene glycol dimethyl ether and the like; esters such as ethyl acetate, methyl acetate and the like; aprotic polar solvents such as N,N-dimethylformamide and the like; and mixtures thereof. The catalytic reduction catalyst includes, for example, palladium, palladium black, palladium-carbon, platinum, platinum oxide, copper chromite and Raney nickel. The appropriate amount of the catalyst used is generally about 0.02–1 time the amount of the starting material. The appropriate reaction temperature is generally about −20° C. to 150° C., preferably about 0°–100° C., the appropriate hydrogen pressure used is generally 1–10 atm. The reaction is complete generally in about 0.5–10 hours. An acid such as hydrochloric acid or the like may be used in the reaction.

In the case (2) using a mixture as a reducing agent, there is used, as the reducing agent, a mixture between iron, zinc, tin or stannous chloride and a mineral acid (e.g. hydrochloric acid or sulfuric acid), or a mixture between iron, ferrous sulfate, zinc or tin and an alkali metal hydroxide (e.g. sodium hydroxide), a sulfide (e.g. ammonium sulfide), ammonia water or an ammonium salt (ammonium chloride). The inert solvent can be exemplified by water, acetic acid, methanol, ethanol and dioxane. The conditions for the reduction reaction can be appropriately selected depending upon the reducing agent used. For example, when stannous chloride and hydrochloric acid are used as a reducing agent, the reaction is preferably conducted at about 0°–80° C. for about 0.5–10 hours. The reducing agent is used in an amount of at least 1 mole, generally 1–5 moles per mole of the raw material compound.

A compound (1) wherein the $R^1$ is a hydroxyl group, can also be obtained by dealkylating a compound (1) wherein the $R^1$ is a lower alkoxy group. The dealkylation reaction can be conducted by heat-treating said compound in a mixture between an acid (e.g. hydrobromic acid or hydrochloric acid) and a solvent (e.g. water, methanol, ethanol or isopropyl alcohol) at 30°–150° C., preferably 50°–120° C., or by hydrolyzing said compound. The hydrolysis is conducted in an appropriate solvent the presence of an acid. The solvent includes, for example, water; lower alcohols such as methanol, ethanol, isopropyl alcohol and the like; ethers such as dioxane, tetrahydrofuran and the like; halogenated hydrocarbons such as dichloromethane, chloroform, carbon tetrachloride and the like; polar solvents such as acetonitrile and the like; and mixtures thereof. The acid includes, for example, mineral acids such as hydrochloric acid, hydrobromic acid and the like; Lewis acids such as boron trifluoride, aluminum chloride, boron tribromide and the like; iodides such as sodium iodide, potassium iodide and the like; and mixtures of said Lewis acid and said iodide. The reaction proceeds favorably generally at room temperature to 150° C., preferably at room temperature to 100° C., and is complete generally in about 0.5–15 hours.

[Reaction formula-10]

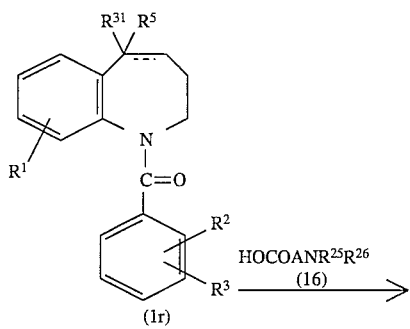

[Reaction formula-10]
-continued

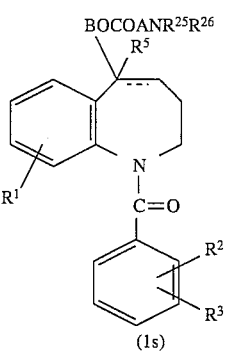

In the above, $R^1$, $R^2$, $R^3$, $R^5$ $R^{25}$, $R^{26}$, A, B and the bond between the 4- and 5-position carbons of the benzoazepine skeleton are the same as defined above. $R^{31}$ is a hydroxyl group-substituted lower alkyl group.

The reaction of the compound (1r) with the compound (16) is conducted under the same conditions as in the reaction of the compound (1p) with the compound (13) in the reaction formula 8.

[Reaction formula-11]

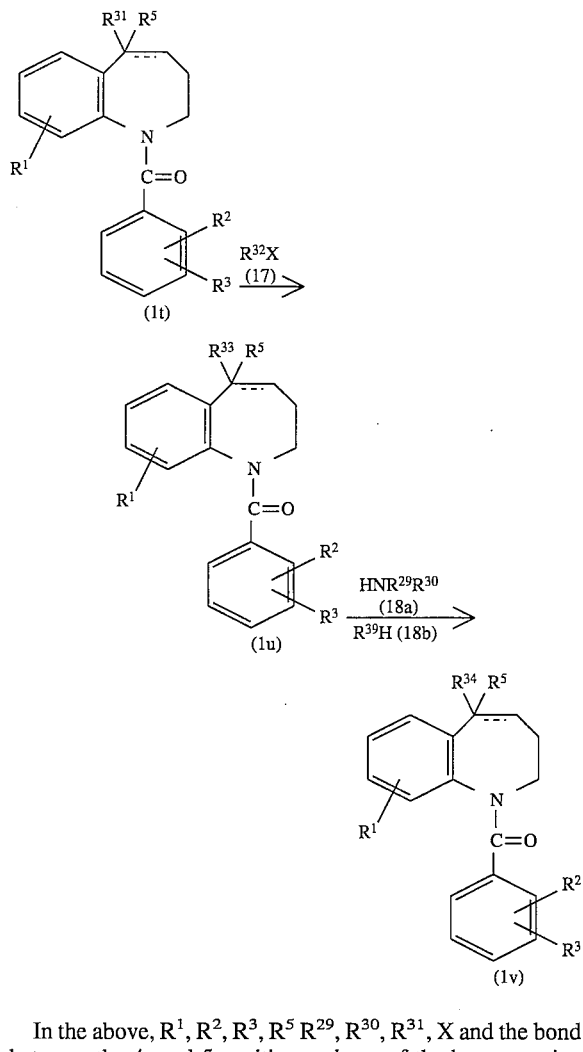

In the above, $R^1$, $R^2$, $R^3$, $R^5$ $R^{29}$, $R^{30}$, $R^{31}$, X and the bond between the 4- and 5-position carbons of the benzoazepine skeleton are the same as defined above. $R^{32}$ is a phenylsulfonyl group which may have lower alkyl substituent(s) on the phenyl ring. $R^{33}$ is a phenylsulfonyloxy-substituted lower alkyl group which may have lower alkyl substituent(s) on the phenyl ring. $R^{34}$ is a group —$ANR^{29}R^{30}$ (A, $R^{29}$ and $R^{30}$ are the same as defined above). $R^{39}$ is an imidazolyl group, a 1,2,4-triazolyl group, a 1,2,3,4-tetrazolyl group or a 1,2,3,5-tetrazolyl group.

The reaction of the compound (1t) with the compound (17) is conducted under the same conditions as in the reaction of the compound (1f) with the compound (6) in the reaction formula-4. The reaction of the compound (1u) with the compound (18a) or compound (18b) is conducted also under the same conditions as in the reaction of the compound (1f) with the compound (6) in the reaction formula-4.

[Reaction formula-12]

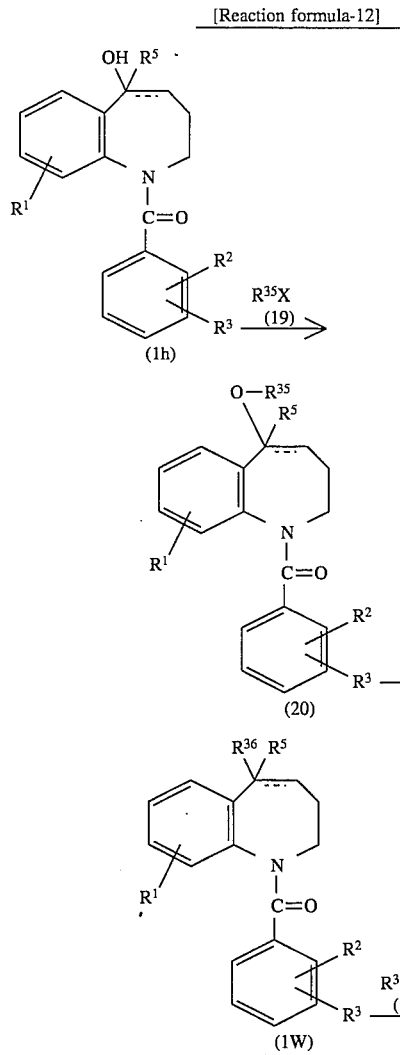

[Reaction formula-12]
—continued

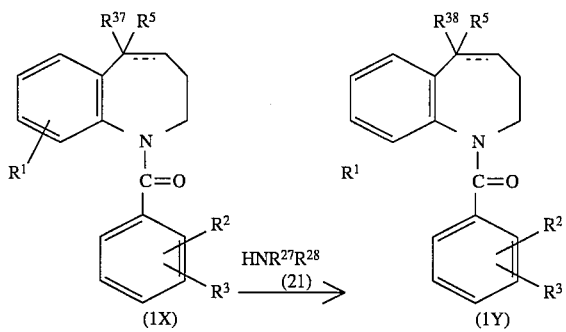

In the above, $R^1, R^2, R^3, R^5 R^{27}, R^{28}$, X, $R^{32}$ and the bond between the 4- and 5-position carbons of the benzoazepine skeleton are the same as defined above. $R^{35}$ is a lower alkoxycarbonyl-substituted lower alkyl group or a lower alkoxycarbonyl group. $R^{36}$ is a hydroxyl group-containing lower alkoxy group. $R^{37}$ is a lower alkoxy group having a phenylsulfonyloxy group which may have lower alkyl substituent(s) on the phenyl ring. $R^{38}$ is a group —$OANR^{27}R^{28}$ (A, $R^{27}$ and $R^{28}$ are the same as defined above).

The reaction of the compound (1h) with the compound (19) is conducted under the same conditions as in the reaction of the compound (1f) with the compound (6) in the reaction formula 4. The reaction for converting the compound (20) into a compound (1w) is conducted under the same conditions as in the reaction for converting the compound (1c) into a compound (1d) in the reaction formula 3. The reaction of the compound (1w) with the compound (17) is conducted under the same conditions as in the reaction of the compound (1f) with the compound (6) in the reaction formula 4. The reaction of the compound (1x) with the compound (21) is conducted also under the same conditions as in the reaction of the compound (1f) with the compound (6) in the reaction formula-4.

[Reaction formula-13]

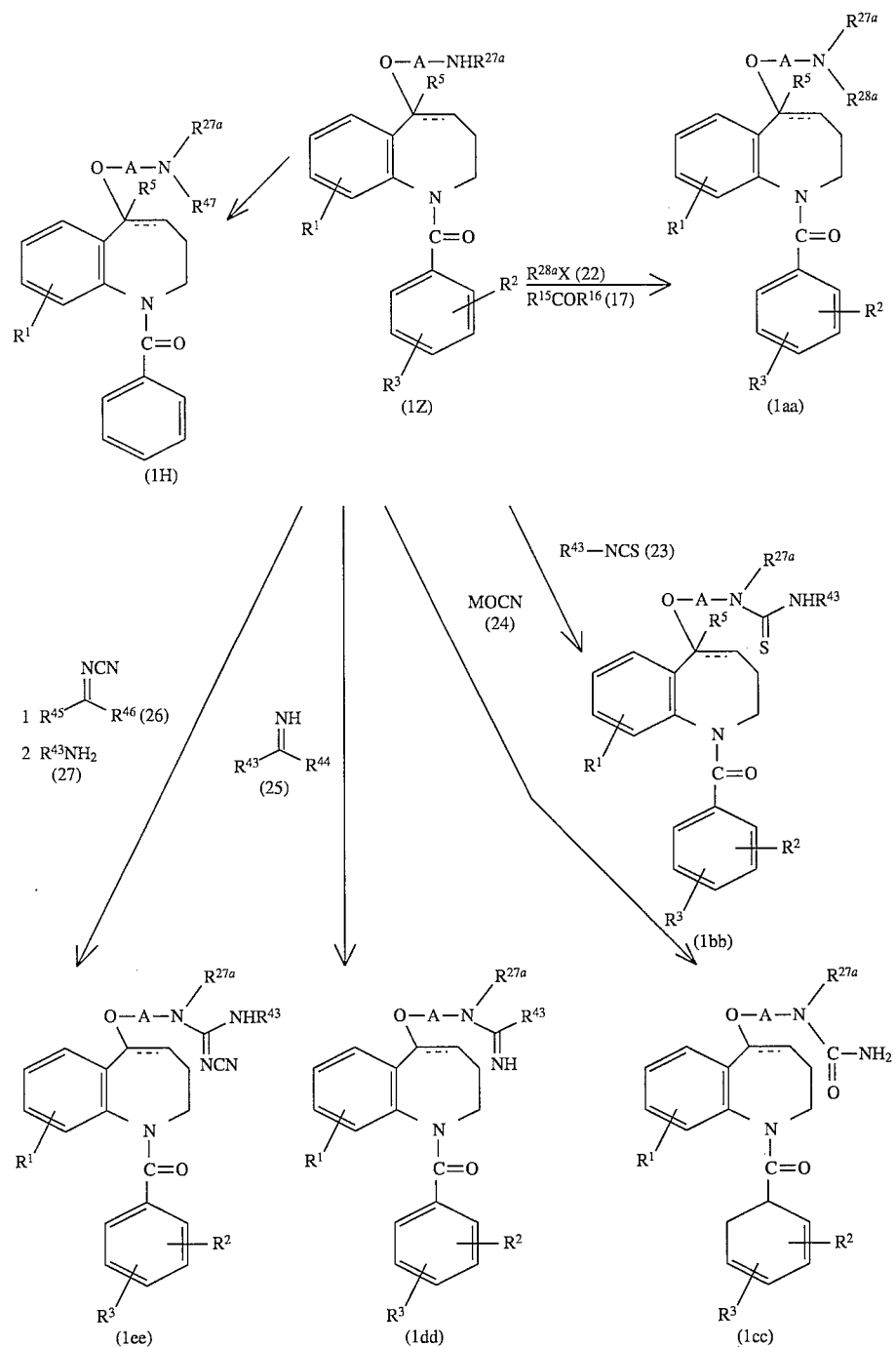

In the above, $R^1$, $R^2$, $R^3$, $R^5$, X and the bond between the 4- and 5-position carbons of the benzoazepine skeleton are the same as defined above. $R^{27a}$ is a hydrogen atom, a lower alkyl group, a lower alkenyl group, a lower alkinyl group, a lower alkylsulfonyl group, an aminothiocarbonyl group which may have lower alkyl substituent(s), a group $$\begin{array}{c} N-R^{41} \\ \| \\ -C-R^{42} \end{array}$$

[$R^{41}$ is a hydrogen atom or a cyano group. $R^{42}$ is a lower alkyl group or an amino group which may have lower alkyl substituent(s).], a carbamoyl group, a lower alkoxycarbonyl group, a cycloalkyl group, a phenyl-lower alkyl group which may have halogen substituent(s) on the phenyl ring, a cyano-substituted lower alkyl group, a halogen-substituted lower alkylsulfonyl group or a lower alkyl group having an amino substituent which may have lower alkyl group(s). $R^{28a}$ is a lower alkyl group, a lower alkenyl group, a lower alkinyl group, a lower alkylsulfonyl group, a lower alkoxycarbonyl group, a cycloalkyl group, a phenyl-lower alkyl group which may have halogen substituent(s) on the phenyl ring, a cyano-substituted lower alkyl group, a halogen-substituted lower alkylsulfonyl group or a lower alkyl group having an amino substituent which may have lower alkyl group(s). $R^{43}$ is a lower alkyl group. M is an alkali metal such as sodium, potassium or the like. $R^{44}$ is a lower alkoxy group. $R^{45}$ and $R^{46}$ are each a lower alkylthio group. $R^{47}$ is a lower alkylsulfonyl group or a halogen-substituted lower alkylsulfonyl group.

The reaction of the compound (1z) with the compound (22) or the compound (7) can be conducted under the same conditions as in the reaction of the compound (1f) with the compound (6) or the compound (7) in the reaction formula-4. The reaction of the compound (1z) with the compound (23) is conducted in the presence or absence of a basic compound, preferably in the absence of any basic compound, in an appropriate solvent or in the absence of any solvent. The solvent and basic compound can be any solvent and basic compound used in the reaction of the carboxylic acid halide with the amine (2) in the reaction formula-1.

The appropriate amount of the compound (23) used is generally about 1–5 moles, preferably about 1–3 moles per mole of the compound (1z). The reaction is conducted generally at about 0°–200° C., preferably at room temperature to 150° C. generally in about 5 minutes to 30 hours. In the reaction, a boron compound such as boron trifluoride ethyl etherate or the like may be used.

The reaction of the compound (1z) with the compound (24) can be conducted in the presence of an acid in an appropriate solvent. The acid includes, for example, organic acids such as acetic acid, trifluoroacetic acid and the like and mineral acids such as hydrochloric acid, sulfuric acid and the like. The solvent can be any solvent used in the reaction of the carboxylic acid halide with the amine (2) in the reaction formula-1.

The reaction of the compound (1z) with the compound (25) can be conducted under the same conditions as in the above reaction of the compound (1z) with the compound (23).

The reaction of the compound (1z) with the compound (26) can be conducted under the same conditions as in the above reaction of the compound (1z) with the compound (23). The product obtained thereby is reacted with a compound (27) without being isolated, whereby a compound (1ee) can be obtained. The reaction with the compound (27) can be conducted in the same solvent as used in the reaction of the compound (1z) with the compound (26), generally at 0°–150° C., preferably at about 0°–100° C. generally in about 1–10 hours. The appropriate amount of the compound (27) used is at least 1 mole, generally 1–25 moles per mole of the compound (1z).

The reaction of the compound (1z) with the compound (28) can be conducted under the same conditions as in the reaction of the carboxylic acid halide with the amine (2) in the reaction formula-1.

[Reaction formula-14]

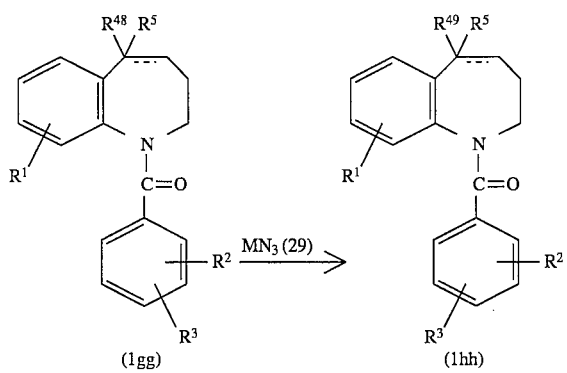

In the above, $R^1$, $R^2$, $R^3$, $R^5$, M and the bond between the 4- and 5-position carbons of the benzoazepine skeleton are the same as defined above. $R^{48}$ is a cyano-substituted lower alkyl group. $R^{49}$ is a 1,2,3,4-tetrazolyl-substituted lower alkyl group.

The reaction of the compound (1gg) with the compound (29) can be conducted in an appropriate solvent in the presence of an ammonium halide such as ammonium chloride or the like.

The appropriate amount of the compound (29) used is at least 1 mole, preferably 1–2 moles per mole of the compound (1gg). The reaction is conducted generally at room temperature to 200° C., preferably at room temperature to 150° C. and is complete in about 1–10 hours.

When the compound of the general formula (1) is a compound of the general formula (1) wherein the $R^4$ is an imidazolylthio-substituted lower alkoxy group or a pyridylthio-substituted lower alkoxy group, the compound can be converted by oxidation into a compound of the general formula (1) wherein the $R^4$ is an imidazolylsulfinyl-substituted lower alkoxy group or an imidazolylsulfonyl-substituted lower alkoxy group, or a pyridylsulfinyl-substituted lower alkoxy group or a pyridylsulfonyl-substituted lower alkoxy group.

The oxidation reaction for converting the imidazolylthio-substituted lower alkoxy group into an imidazolylsulfinyl-substituted lower alkoxy group, the oxidation reaction for converting the imidazolylsulfinyl-substituted lower alkoxy group into an imidazolylsulfonyl-substituted lower alkoxy group, the oxidation reaction for converting the pyridylthio-substituted lower alkoxy group into a pyridylsulfinyl-substituted lower alkoxy group, and the oxidation reaction for converting the pyridylsulfinyl-substituted lower alkoxy group into a pyridylsulfonyl-substituted lower alkoxy group are conducted in an appropriate solvent in the presence of an oxidizing agent. The solvent can be exemplified by water; organic acids such as formic acid, acetic acid, trifluoroacetic acid and the like; alcohols such as methanol, ethanol and the like; halogenated hydrocarbons such as chloroform, dichloromethane and the like; and mixtures thereof. The oxidizing agent includes, for example, peracids such as performic acid, peracetic acid, trifluoroperacetic acid, perbenzoic acid, m-chloroperbenzoic acid, o-carboxyperbenzoic acid and the like; hydrogen peroxide; sodium metaperiodate; bichromic acid; bichromates such as sodium bichromate, potassium bichromate and the like; permanganic acid; permanganates such as potassium permanganate, sodium permanganate and the like; and lead salts such as lead tetraacetate and the like. The appropriate amount of the oxidizing agent used is at least 1 mole, preferably 1–2.5 moles per mole of the starting material. In the cases of the oxidation reaction for converting the imidazolylthio-substituted lower alkoxy group into an imidazolylsulfonyl-substituted lower alkoxy group and the oxidation reaction for converting the pyridylthio-substituted lower alkoxy group into a pyridylsulfonyl-substituted lower alkoxy group, the appropriate amount of the oxidizing agent used is at least 2 moles, preferably 2–4 moles per mole of the oxidizing agent. The reaction is conducted generally at 0°–150° C., preferably at about 0°–100° C. and is complete in about 10 minutes to 15 hours.

When the compound of the general formula (1) is a compound of the general formula (1) wherein the $R^2$ is a lower alkoxy group, can be converted by dealkylation into a compound of the general formula (1) wherein the $R^2$ is a hydroxyl group.

The dealkylation can be conducted by heating said compound at 30°–150° C. preferably at 50°–120° C. in a mixture of an acid (e.g. hydrobromic acid or hydrochloric acid) and a solvent(e.g. water, methanol, ethanol, isopropyl alcohol or acetic acid). Alternatively, the dealkylation can be conducted by hydrolysis. The hydrolysis is conducted in an appropriate solvent in the presence of an acid. The solvent includes, for example, water; lower alcohols such as methanol, ethanol, isopropanol and the like; ethers such as dioxane, tetrahydrofuran and the like; halogenated hydrocarbons such as dichloromethane, chloroform, carbon tetrachloride and the like; polar solvents such as acetonitrile and the like; and mixtures thereof. The acid includes, for example, mineral acids such as hydrochloric acid, sulfuric acid, hydrobromic acid and the like; Lewis acids such as boron trifluoride, aluminum chloride, boron tribromide and the like; iodides such as sodium iodide, potassium iodide and the like; and mixtures of said Lewis acid and said iodide. The reaction proceeds favorably generally at room temperature to 150° C., preferably at room temperature to 100° C., and is complete generally in about 0.5–15 hours.

Of the compounds (1) used as an active ingredient in the present invention, those having an acidic group can each form a salt with a pharmacologically acceptable basic compound. The basic compound can be exemplified by metal hydroxides such as sodium hydroxide, potassium hydroxide, lithium hydroxide, calcium hydroxide and the like; alkali metal carbonates or bicarbonates such as sodium carbonate, sodium hydrogencarbonate and the like; and alkali metal alcoholates such as sodium methylate, potassium ethylate and the like. Of the compounds (1) used as an active ingredient in the present invention, those having basicity can easily form a salt with an ordinary phamacologically acceptable acid. The acid can be exemplified by inorganic acids such as sulfuric acid, nitric acid, hydrochloric acid, hydrobromic acid and the like; and organic acids such as acetic acid, p-toluenesulfonic acid, ethanesulfonic acid, oxalic acid, maleic acid, fumaric acid, citric acid, succinnic acid, benzoic acid and the like. These salts can also be used as an active ingredient in the present invention, similarly to the compounds (1) of free form. Incidentally, the compounds (1) include stereoisomers and optical isomers and these isomers can also be used as an active ingredient in the present invention.

Each of the intended compounds (1) obtained by the above reaction formulas can be separated from the reaction system by an ordinary means and can further be purified. There can be used, as the separation and purification means, various methods such as distillation, recrystallization, column chromatography, ion-exchange chromatography, gel chromatography, affinity chromatography, preparative thin-layer chromatography, solvent extraction and the like.

Each of the thus obtained active ingredient compounds is effective as a vasopressin antagonist and is used in the form of ordinary pharmaceutical preparation. The pharmaceutical preparation is prepared by using diluents or excipients ordinarily used, such as filler, bulking agent, binder, humectant, disintegrator, surfactant, lubricant and the like. The pharmaceutical preparation can be used in various forms depending upon the purpose of remedy, and the typical forms include tables, pills, a powder, a solution, a suspension, an emulsion, granules, suppositories, an injection (e.g. solution or suspension), etc. In preparing tablets, various carriers conventionally known in the art can be used. The carriers can be exemplified by excipients such as lactose, white sugar, sodium chloride, glucose, urea, starch, calcium carbonate, kaolin, crystalline cellulose, silicic acid and the like; binders such as water, ethanol, propanol, simple syrup, glucose solution, starch solution, gelatin solution, carboxymethyl cellulose, shellac, methyl cellulose, potassium phosphate, polyvinylpyrrolidone and the like; disintegrators such as dry starch, sodium alginate, powdered agar, powdered laminarin, sodium hydrogencarbonate, calcium carbonate, polyoxyethylene sorbitan-fatty acid esters, sodium lauryl sulfate, stearic acid monoglyceride, starch, lactose and the like; disintegration inhibitors such as white sugar, stearin, cacao butter, hydrogenated oil and the like; absorption promoters such as quaternary ammonium salts, sodium lauryl sulfate and the like; humectants such as glycerine, starch and the like; adsorbents such as starch, lactose, kaolin, bentonite, colloidal silicic acid and the like; and lubricants such as refined talc, stearic acid salts, boric acid powder, polyethylene glycol and the like. The tablets can be prepared, as necessary, in the form of ordinary coated tablets, such as sugar-coated tablets, gelatin-coated tablets, enteric-coated tablets or film-coated tablets, or in the form of double-layered tablets or multi-layered tablets. In preparing pills, various carriers conventionally known in the art can be used. The carriers can be exemplified by excipients such as glucose, lactose, starch, cacao butter, hardened vegetable oils, kaolin, talc and the like; binders such as powdered acacia, powdered tragacanth, gelatin, ethanol and the like; and disintegrators such as laminarin, agar and the like. In preparing suppositories, various carriers conventionally known in the art can be used. The carriers can be exemplified by a polyethylene glycol, cacao butter, a higher alcohol, a higher alcohol ester, gelatin and a semi-synthetic glyceride. Capsules can be prepared generally by mixing the active ingredient compound with various carriers shown above and filling the mixture into a hard gelatin capsule or a soft capsule by an ordinary method. In preparing an injection (solution, emulsion or suspension), it is sterilized and is preferably made isotonic to the blood. In preparing the solution, emulsion or suspension, there can be used all of the diluents conventionally used in the art, such as water, ethyl alcohol, polyethylene glycol, propylene glycol, ethoxylated isostearyl alcohol, polyoxy-isostearyl alcohol and polyoxyethylene sorbitan-fatty acid ester. In this case, the injection may contain sodium chloride, glucose or glycerine in an amount sufficient to make the injection isotonic, and may further contain a solubilizing agent, a buffer solution, a soothing agent, etc. all ordinarily used. The pharmaceutical preparation may furthermore contain, as necessary, a coloring agent, a preservative, a perfume, a flavoring agent, a sweetening agent and other drugs.

The amount of the active ingredient compound to be contained in the vasopressin antagonist of the present invention is not particularly restricted and can be appropriately selected from a wide range, but the appropriate amount is generally about 1–70% by weight, preferably 5–50% by weight in the pharmaceutical preparation.

The method for administering the vasopressin antagonist of the present invention is not particularly restricted. The vasopressin antagonist can be administered in various methods depending upon the form of preparation, the age, sex and other conditions of patient, the disease condition of patient, etc. For example, tablets, pills, a solution, a suspension, an emulsion, granules or capsules are administered orally. An injection is intravenously administered singly or in admixture with an ordianry auxiliary solution of glucose, amino acids or the like, or, as necessary, is singly administered intramuscularly, intradermally, subcutaneously or intraperitoneally. Suppositories are administered intrarectally.

The dose of the vasopressin antagonist of the present invention is appropriately selected depending upon the administration method, the age, sex and other conditions of patient, the disease condition of patient, etc., but the appropriate dose is generally about 0.6–50 mg per kg of body weight per day in terms of the amount of the active ingredient, i,e, the present compound of the general formula (1). The pharmaceutical prepartion contains about 10–1,000 mg of the active ingredient compound in each unit of administration form.

EXAMPLES

The present invention is described in more detail below by showing Preparation Examples for preparing some of the vasopressin antagonists of the present invention, Reference Examples for producing some of the raw materials used for production of the active ingredient compounds to be contained in the vasopressin antagonists of the present invention, Examples for producing said active ingredient compounds, and Test Examples for examining the efficacies of said active ingredient compounds.

| Preparation Example 1 | |
|---|---|
| 7-Hydroxy-5-methylamino-1-[4-(2-chlorobenzoylamino)-benzoyl]-2,3,4,5-tetrahydro-1H-benzoazepine | 150 g |
| Avicel (trade mark for microcrystalline cellulose, manufactured by Asahi Chemical Industry Co., Ltd.) | 40 g |
| Corn starch | 30 g |
| Magnesium stearate | 2 g |
| Hydroxypropyl methyl cellulose | 10 g |
| Polyethylene glycol 6,000 | 3 g |
| Castor oil | 40 g |
| Ethanol | 40 g |

The active ingredient compound of the present invention, Avicel, corn starch and magnesium stearate are mixed and ground. Then, the mixture is made into tablets using a tablet machine of R 10 mm (sugar coating). The tablets are each covered with a coating film consisting of hydroxypropyl methyl cellulose, polyethylene glycol 6,000, castor oil and ethanol, to prepare film-coated tablets.

| Preparation Example 2 | |
|---|---|
| 5-Dimethylamino-1-[4-(4-carbamoylbenzoyl-amino)benzoyl]-2,3,4,5-tetrahydro-1H-benzoazepine | 150 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinylpyrrolidone | 15.0 g |
| Polyethylene glycol (Carbowax 1,500) | 4.5 g |
| Polyethylene glycol (Carbowax 6,000) | 45.0 g |
| Corn starch | 30.0 g |

| -continued | |
|---|---|
| Preparation Example 2 | |
| Dry sodium stearate | 3.0 g |
| Dry magnesium stearate | 3.0 g |
| Ethanol | Appropriate amount |

The active ingredient compound of the present invention, citric acid, lactose, dicalcium phosphate, Pluronic F-68 and sodium lauryl sulfate are mixed.

The mixture is sifted using a No. 60 screen and then wet-pelletized using an alcoholic solution containing polyvinylpyrrolidone, Carbowax 1,500 and Carbowax 6,000. As necesary, the mixture is made into a paste by adding ethanol. Corn starch is added, after which mixing is conducted until uniform particles are formed. The resulting mixture is sifted using a No. 10 screen and placed in a tray. The mixture in the tray is dried in an oven of 100° C. for 12–14 hours. The dried particles are sifted using a No. 16 screen, then mixed with dry sodium lauryl sulfate and dry magnesium stearate, and compressed into desired forms using a tablet-making machine.

The core portion of each of the tablets obtained is treated with a varnish and then covered with talc for prevention of moisture absorption. An undercoating layer is formed on the surface of the core portion. Varnish coating is conducted a plurality of times for internal use. Further, an undercoating layer and smooth coating are applied in order to make completely round and smooth tablets. Color coating is conducted until a desired color is obtained. Then, drying and grinding are conducted in this order to obtain tablets of uniform lustre.

| Preparation Example 3 | |
|---|---|
| 5-Dimethylamino-1-{4-[2-(3-methylphenyl)acetylamino]-benzoyl}-2,3,4,5-tetrahydro-1H-benzoazepine | 5 g |
| Polyethylene glycol (molecular weight = 4,000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 10.0 ml |

The two parabens, sodium metabisulfite and sodium chloride are dissolved in distilled water for injection, of about half of the above amount at 80° C. with stirring. The resulting solution is cooled to 40° C. Therein are dissolved the active ingredient compound of the present invention, polyethylene glycol and polyoxyethylene sorbitan monooleate in this order. To the resulting solution is added the remaining amount of distilled water for injection. The solution is filtered for sterilization using an appropriate filter paper to prepare an injection.

Reference Example 1

38.8 g of potassium carbonate was added to a solution of 50 g of 5-dimethylamino-2,3,4,5-tetrahydro-1H-benzoazepine dissolved in 400 ml of acetone and 200 ml of water. To the solution was added 40 g of p-nitrobenzoyl chloride with ice-cooling and stirring. The resulting mixture was stirred overnight at room temperature. The reaction mixture was mixed with an appropriate amount of water. The resulting crystals were collected by filtration and dried to obtain 71 g of 5-dimethylamino-1-(4-nitro-benzoyl)-2,3,4,5-tetrahydro-1H-benzoazepine.

A light yellow powder
Melting point: 139°–142° C.

Reference Example 2

5 g of 10% palladium-carbon was dispersed in 500 ml of ethanol. Thereto was added 64.1 g of 5-dimethylamino-1-(4-nitrobenzoyl)-2,3,4,5-tetrahydro-1H-benzoazepine. The mixture was subjected to catalytic reduction at normal temperature at normal pressure. After the reduction, 10% palladium-carbon was removed by filtration. The filtrate was concentrated under reduced pressure to obtain 56.1 g of 5-dimethylamino-1-(4-aminobenzoyl)-2,3,4,5-tetrahydro-1H-benzoazepine.

A white powder
Melting point: 120°–122° C.

Reference Example 3

In 15 ml of chloroform were dissolved 0.7 g of 5-hydroxy-7-chloro-1-[2-methoxy-4-(2methylbenzoylamino)benzoyl]-2,3,4,5-tetrahydro-1H-benzoazepine, 0.83 g of dimethylaminopyridine and 0.72 g of dimethylaminopyridine hydrochloride. Thereto was added 0.56 g of N-tert-butoxy-carbonyl-L-methionine and 0.93 g of dicyclohexylcarbodi-imide. The mixture was stirred at room temperature for 3 hours. 3 ml of methanol and 0.7 ml of acetic acid were added, and the mixture was stirred at room temperature for 30 minutes. The resulting insolubles were removed by filtration. The filtrate was mixed with a 5% aqueous sodium hydrogensulfate solution, followed by extraction with dichloromethane. The dichloromethane layer was washed with a saturated aqueous sodium hydrogencarbonate solution and a saturated aqueous sodium chloride solution in this order and dried over magnesium sulfate. The resulting dichloromethane solution was concentrated for solvent removal. The residue was purified by silica gel column chromatography [elutant: dichloromethane/methanol=150/1] to obtain 1.27 g of 5-(N-tert-butoxycarbonyl-L-methionyloxy)-7-chloro-1-[2-methoxy-4-(2-methylbenzoylamino)benzoyl]-2,3,4,5-tetrahydro-1H-benzo-azepine.

$^1$H-NMR (CDCl$_3$) δ: 1.29–2.92, 3.35–5.40, 6.09–6.35 (total 30H, m, 1.45(s), 1.47(s)), 6.61–8.00 (12H, m)

The following compounds were obtained in the same manner as in Reference Example 3, using respective starting materials.

5-(N-tert-butoxycarbonyl-L-alanyloxy)-1-[2-chloro-4-(2-methylbenzoylamino)benzoyl]-2,3,4,5-tetrahydro-1H-benzoazepine $^1$H-NMR (CDCl$_3$) δ: 0.95–3.05, 3.29–5.22, 5.95–6.27 (total 23H, m), 6.86–8.17 (13H, m)

5-(N-tert-butoxycarbonyl-glycyloxy)-1-[2-chloro-4-(2-methyl-benzoylamino)benzoyl]-2,3,4,5-tetrahydro-1H-benzoazepine $^1$H-NMR (CDCl$_3$) δ: 1.30–3.09, 3.69–5.29, 5.91–6.35 (total 21H, m), 6.77–8.48 (13H, m)

5-(N-tert-butoxycarbonyl-L-methionyloxy-1-[2-chloro-4-(2-methylbenzoylamino)benzoyl]-2,3,4,5-tetrahydro-1H-benzo-azepine $^1$H-NMR (CDCl$_3$) δ: 1.05–3.06, 3.25–3.63, 4.01–5.37 (total 26H, m), 5.97–6.28 (1H, m), 6.72–8.72 (13H, m)

Reference Example 4

The following compounds were obtained in the same manner as in Reference Example 1, using respective starting materials.

5-(3-Hydroxypropoxy)-7-chloro-1-(2-methoxy-4-nitrobenzoyl)-2,3,4,5-tetrahydro-1H-benzoazepine Light yellow and amorphous $^1$H-NMR (CDCl$_3$) δ: 1.4–2.6 (7H, m), 2.7–3.0 (1H, m), 3.0–4.1 (7H, m), 4.3–5.1 (2H, m), 6.6–7.0 (2H, m), 7.1–8.0 (4H, m)

5-[3-(p-Toluenesulfonyloxy)propoxy]-7-chloro-1-(2-methoxy-4-nitrobenzoyl)-2,3,4,5-tetrahydro-1H-benzoazepine Light yellow and amorphous $^1$H-NMR (CDCl$_3$) δ:

$^1$H-NMR (CDCl$_3$) δ: 1.35–2.65 (9H, m), 2.65–3.0 (1H, m), 3.05–3.95 (5H, m), 3.95–4.45 (2H, m), 4.5–5.05 (2H, m), 6.6–7.05 (2H, m), 7.1–8.05 (8H, m)

5-(2-Hydroxyethoxy)-7-chloro-1-(2-methoxy-4-nitrobenzoyl)-2,3,4,5-tetrahydro-1H-benzoazepine Light yellow and amorphous $^1$H-NMR (CDCl$_3$) δ: 1.35–2.6 (4H, m), 2.7–3.0 (1H, m), 3.0–4.1 (7H, m), 4.35–5.0 (2H, m), 6.6–7.0 (2H, m), 7.1–8.05 (5H, m)

5-[2-(p-Toluenesulfonyloxy)ethoxy]-7-chloro-1-(2-methoxy-4-nitrobenzoyl)-2,3,4,5-tetrahydro-1H-benzoazepine Colorless and amorphous $^1$H-NMR (CDCl$_3$) δ: 1.35–2.6 (7H, m), 2.65–2.95 (1H, m), 3.0–3.95 (5H, m), 4.1–5.05 (4H, m), 6.55–7.05 (2H, m), 7.05–7.6 (4H, m), 7.65–8.0 (4H, m)

5-Methoxycarbonylmethyl-7-chloro-1-(2-methoxy-4-nitrobenzoyl)-2,3,4,5-tetrahydro-1H-benzoazepine Light yellow and amorphous $^1$H-NMR (CDCl$_3$) δ: 1.2–1.5 (1H, m), 1.5–2.3 (3H, m), 2.6–2.95 (2H, m), 2.95–3.25 (1H, m), 3.3–4.2 (7H, m), 4.45–5.15 (1H, m), 6.65–6.85 (1H, m), 6.85–7.0 (1H, m), 7.02 (1H, d, J=1.8 Hz), 7.1–8.05 (3H, m)

5-Methoxycarbonylmethyl-7-chloro-1-(4-nitrobenzoyl)-2,3,4,5-tetrahydro-1H-benzoazepine A light yellow prism $^1$H-NMR (CDCl$_3$) δ: 1.2–1.75 (2H, m), 1.75–2.3 (2H, m), 2.6–3.15 (2H, m), 3.15–3.4 (1H, m), 3.76 (3H, s), 4.05–5.2 (2H, m), 6.54 (1H, d, J=8.3 Hz), 6.92 (1H, dd, J=8.3 Hz, 2.2 Hz), 7.1–7.25 (1H, m), 7.52 (2H, d, J=8.8 Hz), 8.06 (2H, dd, J=8.8 Hz, 2 Hz)

5-[2-(p-Toluenesulfonyloxy)ethyl]-7-chloro-1-(2-methoxy-4-nitrobenzoyl)-2,3,4,5-tetrahydro-1H-benzoazepine Light yellow and amorphous $^1$H-NMR (CDCl$_3$) δ: 1.0–1.4 (1H, m), 1.4–2.15 (4H, m), 2.15–2.4 (1H, m), 2.4–2.55 (3H, m), 2.9–3.3 (2H, m), 3.35–4.5 (6H, m), 6.6–8.0 (10H, m)

5-Cyanomethyl-7-chloro-1-(3-methoxy-4-nitrobenzoyl)-2,3,4,5-tetrahydro-1H-benzoazepine A white powder $^1$H-NMR (CDCl$_3$) δ: 1.38–2.37, 2.66–4.22, 4.41–4.68, 5.03–5.24 [total 12H, m, (3.79(s))], 6.55–8.00 [6H, m, (6.76 (dd, J=1.6 Hz, 8.3 Hz)), [6.92 (d, J=1.4 Hz)], [7.23 (d, J=2.0 Hz))]

5-Ethoxycarbonylmethyl-7-chloro-1-(3-methoxy-4-nitrobenzoyl)-2,3,4,5-tetrahydro-1H-benzoazepine A white powder $^1$H-NMR (CDCl$_3$) δ: 1.25–2.26, 2.61–4.66, 5.01–5.25 [total 17H, m, (1.28 (3H, t, J=7.1 Hz)) (3.83 (3H, s))], 6.57 (1H, d, J=9.5 Hz), 6.85–7.31 (4H, m), 7.63 (1H, d, J=8.3 Hz)

Methyl N-{[7-fluoro-1-(2-chloro-4-nitrobenzoyl)-2,3,4,5-tetrahydro-1H-benzoazepin-5-yl]oxymethylcarbonyl}-L-alanate A yellow oil ¹H-NMR (CDCl₃) δ: 1.37–1.53 (3H, m), 1.54–4.25 (8H, m), 4.40–5.05 (3H, m), 6.65–8.35 (7H, m)

Methyl N-{[7-fluoro-1-(2-chloro-4-nitrobenzoyl)-2,3,4,5-tetrahydro-1H-benzoazepin-5-yl]oxymethylcarbonyl}-L-prolinate A yellow oil ¹H-NMR (CDCl₃) δ; 1.37–4.19 (16H, m), 4.23–5.07 (3H, m), 6.56–8.43 (6H, m)

5-Methoxycarbonylmethyl-7-chloro-1-(2-methyl-4-nitrobenzoyl)-2,3,4,5-tetrahydro-1H-benzoazepine A yellow powder ¹H-NMR (CDCl₃) δ: 1.50–2.31 (4H, m), 2.45–5.20 (5H, m), 2.57, 2.61 (3H, s), 3.75 (3H, s), 6.55 (1H, d, J=8.4 Hz), 6.89 (1H, dd, J=2.3 Hz, 8.4 Hz), 7.09 (1H, d, J=2.3 Hz), 7.16 (1H, d, J=8.4 Hz), 7.78 (1H, dd, J=2.2 Hz, 8.4 Hz), 8.00 (1H, d, J=2.2 Hz)

5-Methoxycarbonylmethyl-7-chloro-1-(2-chloro-4-nitrobenzoyl)-2,3,4,5-tetrahydro-1H-benzoazepine A yellow powder Melting point: 133°–134° C.

¹H-NMR (CDCl₃) δ: 1.05–2.28 (4H, m), 2.57–3.05 (2H, m), 3.06–3.32 (1H, m), 3.33–3.85 (1H, m), 3.74 (3H, s), 4.39–4.67 (1H, m), 6.78–7.19 (3H, m), 7.38 (1H, d, J=8.2 Hz), 7.93 (1H, dd, J=8.2 Hz, 2.1 Hz), 8.17 (1H, d, J=2.1 Hz)

5-Methoxycarbonylmethyl-7-chloro-1-(3-methoxy-4-nitrobenzoyl)-2,3,4,5-tetrahydro-1H-benzoazepine A slightly yellow powder Melting point: 139.5°–141° C.

¹H-NMR (CDCl₃) δ: 1.16–2.31 (4H, m), 2.61–3.09 (2H, m), 3.12–3.40 (1H, m), 3.41–5.23 (2H, m), 3.72 (3H, s), 3.83 (3H, s), 6.58 (1H, d, J=8.3 Hz), 6.85–7.24 (4H, m), 7.63 (1H, d, J=8.3 Hz)

5-[2-(p-Toluenesulfonyloxy)ethoxy]-7-chloro-1-(2-methyl-4-nitrobenzoyl)-2,3,4,5-tetrahydro-1H-benzoazepine Yellow and amorphous ¹H-NMR (CDCl₃) δ: 1.12–5.14 (17H, m), 6.50 (1H, dd, J=16 Hz, 8.4 Hz), 6.91 (1H, d, J=8.4 Hz), 7.10–8.45 (8H, m)

5-[3-(p-Toluenesulfonyloxy)propoxy]-7-chloro-1-(2-methyl-4-nitrobenzoyl)-2,3,4,5-tetrahydro-1H-benzoazepine Slightly yellow and amorphous ¹H-NMR (CDCl;₃) δ: 1.09–3.08 (13H, m), 3.09–5.18 (6H, m), 6.50 (1H, dd, J=17.8 Hz, 8.4 Hz), 6.84–8.42 (9H, m)

5-(2-Methoxyacetyloxy)-7-chloro-1-(4-nitrobenzoyl)-2,3,4,5-tetrahydro-1H-benzoazepine Yellow and amorphous ¹H-NMR (CDCl₃) δ: 1.7–3.2 (5H, m), 3.36, 3.46 (total 3H, s), 4.10, 4.29 (total 2H, s), 4.7–5.2 (1H, m), 6.1–6.2 (1H, m), 6.57 (1H, d, J=8.3 Hz), 6.9–7.1 (1H, m), 7.2–7.5 (1H, m), 7.5–7.6 (2H, m), 8.0–8.2 (2H, m)

5-Methoxycarbonylmethyl-7-fluoro-1-(4-nitrobenzoyl)-2,3,4,5-tetrahydro-1H-benzoazepine A light yellow oil ¹H-NMR (CDCl₃) δ: 1.22–1.70 (2H, m), 1.77–2.23 (2H, m), 2.65–3.04 (2H, m), 3.12–3.30 81H, m), 3.75 (3H, s), 4.07–4.35 (1H, m), 4.40–5.18 (1H, m), 6.44–6.70 (2H, m), 6.80–7.05 (1H, m), 7.40–7.60 (2H, m), 7.95–8.10 (2H, m), 8.15–8.28 (1H, m)

5-Hydroxy-7-fluoro-1-(2-methoxy-4-nitrobenzoyl)-2,3,4,5-tetrahydro-1H-benzoazepine Light yellow and amorphous ¹H-NMR (CDCl₃) δ: 1.52–2.36 (4H, m), 2.68–2.95 (1H, m), 3.12 (3H, brs), 3.44–4.03 (3H, m), 4.65–5.17 (2H, m), 6.50–6.76 (2H, m), 6.80–8.03 (4H, m)

5-(3-Morpholinopropoxy)-7-fluoro-1-(2-methyl-4-nitrobenzoyl)-2,3,4,5-tetrahydro-1H-benzoazepine Light yellow and amorphous ¹H-NMR (CDCl₃) δ: 1.43–2.62 (11H, m), 2.53, 2.59 (3H, s), 2.72–3.03 (1H, m), 3.10–3.83 (7H, m), 4.36–5.07 (2H, m), 6.46–6.71 (2H, m), 6.86–8.20 (4H, m)

5-[3-(1-Imidazolyl)propoxy]-7-fluoro-1-(2-methyl-4-nitro-benzoyl)-2,3,4,5-tetrahydro-1H-benzoazepine A light yellow oil ¹H-NMR (CDCl₃) δ: 1.37–2.63 (6H, m), 2.52, 2.59, 2.60 (total 3H, s), 2.73–3.05 (1H, m), 3.10–3.80 (2H, m), 3.96–5.07 (4H, m), 6.46–6.72 (2H, m), 6.85–7.20 (4H, m), 7.26–8.23 (3H, m)

5-Methoxycarbonylmethyl-7-fluoro-1-(2-methoxy-4-nitrobenzoyl)-2,3,4,5-tetrahydro-1H-benzoazepine Light yellow and amorphous ¹H-NMR (CDCl₃) δ: 1.19–2.26 (4H, m), 2.57–2.90 (2H, m), 2.95–3.20 (1H, m), 3.35–4.27 (4H, m), 3.75 (3H, s), 4.48–5.12 (1H, m), 6.52–6.67 (1H, m), 6.71–8.02 (5H, m)

5-[2-(p-Toluenesulfonyloxy)ethoxy]-7-fuoro-1-(2-methoxy-4-nitrobenzoyl)-2,3,4,5-1H-benzoazepine A lighty yellow oil H-NMR (CDCl₃) δ: 1.34–1.88 (2H, m), 1.95–2.38 (2H, m), 2.40, 2.43, 2.45 (total 3H, s), 2.70–2.91 (1H, m), 3.43–4.00 (5H, m), 4.13–4.47 (2H, m), 4.56–5.03 (2H, m), 6.54–7.96 (10H, m)

5-(3-Hydroxypropoxy)-7-fluoro-1-(2-methyl-4-nitrobenzoyl)-2,3,4,5-tetrahydro-1H-benzoazepine Light yellow and amorphous ¹H-NMR (CDCl₃) δ: 1.38–2.67 (8H, m), 2.53, 2.59 (total 3H, s), 2.72–3.08 (1H, m), 3.14–3.93 (5H, m), 4.25–5.11 (2H, m), 6.47–6.73 (2H, m), 6.86–8.18 (4H, m)

5-[3-(p-Toluenesulfonyloxy)propoxy]-7-fluoro-1-(2-methyl-4-nitrobenzoyl)-2,3,4,5-tetrahydro-1H-benzoazepine Light yellow and amorphous ¹H-NMR (CDCl₃) 1.38–2.63 (6H, m), 2.42, 2.44 (total 3H, s), 2.52, 2.57, 2.58 (total 3H, s), 2.73–3.03 (1H, m), 3.10–3.83 (2H, m), 4.05–5.03 (4H, m), 6.45–6.70 (2H, m), 6.86–8.19 (8H, m)

5-[3-(1-Pyrrolidinyl)propoxy]-7-fluoro-1-(2-methyl-4-nitro-benzoyl)-2,3,4,5-tetrahydro-1H-benzoazepine hydroiodide Light yellow and amorphous ¹H-NMR (CDCl₃) δ: 1.40–1.90 (2H, m), 1.95–2.63 (7H, m), 2.53, 2.58, 2.59 (total 3H, s), 2.75–3.90 (10H, m), 4.42–4.98 (2H, m), 5.22 (1H, brs), 6.47–6.68 (2H, m), 6.92–7.38 (2H, m), 7.56–8.32 (2H, m)

5-(2-Hydroxyethoxy)-7-fluoro-1-(2-ethyl-4-nitrobenzoyl)-2,3,4,5-tetrahydro-1H-benzoazepine A light yellow oil ¹H-NMR (CDCl₃) δ: 1.38–2.63 (5H, m), 2.53, 2.58, 2.59 (total 3H, s), 2.76–3.93 (4H, m), 4.40–5.00 (2H, m), 6.49–8.18 (6H, m)

5-Hydroxy-7-fluoro-1-(2-methyl-4-nitrobenzoyl)-2,3,4,5-tetrahydro-1H-benzoazepine A light yellow powder ¹H-NMR (DMSO-d₆) δ: 1.40–2.31 (4H, m), 2.49, 2.54, 2.55 (total 3H, s), 2.62–3.43 (1H, m), 4.55–5.06 (2H, m), 5.77 (1H, brs), 6.66–6.98 (2H, m), 7.10–7.50 (2H, m), 7.60–8.36 (2H, m)

7-Hydroxymethyl-7-fluoro-1-(2-methoxy-4-nitrobenzoyl)-2,3,4,5,-tetrahydro-1H-benzoazepine Light yellow and amorphous $^1$H-NMR (CDCl$_3$) δ: 1.13–1.40 (1H, m), 1.46–2.31 (3H, m), 2.40–3.50 (2H, m), 2.66 (1H, brs), 3.55–4.13 (5H, m), 4.53–5.03 (1H, m), 6.57 (1H, dt, J=8.5 Hz, 2.8 Hz), 6.67–7.18 (2H, m), 7.28–8.03 (3H, m)

5-(2-Hydroxyethyl)-7-chloro-1-(2-methyl-4-nitrobenzoyl)-2,3,4,5-tetrahydro-1H-benzoazepine White and amorphous $^1$H-NMR (CDCl$_3$) δ: 1.38–2.35 (7H, m), 2.36–4.00 (7H, m), 4.30–4.53 (1H, m), 6.57 (1H, d, J=8.3 Hz), 6.89 (1H, dd, J=2.2 Hz, 8.3 Hz), 7.03 (1H, d, J=8.3 Hz), 7.13 (1H, d, J=2.2 Hz), 7.67–7.82 (1H, m), 7.91–8.08 (1H, m)

5-[2-(p-Toluenesulfonyloxy)ethyl]-7-chloro-1-(2-methyl-4-nitrobenzoyl)-2,3,4,5-tetrahydro-1H-benzoazepine A white powder $^1$H-NMR (CDCl$_3$) δ: 1.07–2.78 [13H,m (2.46, s)], 2.79–3.38 (2H, m), 3.97–4.48 (2H, m), 6.56 (1H, d, J=8.2 Hz), 6.90 (1H, dd, J=2.2 Hz, 8.2 Hz), 7.02 (1H, d, J=2.2 Hz), 6.93 (1H, d, J=8.4 Hz), 7.20–7.64 (2H, m), 7.72–7.91 (3H, m), 7.98 (1H, d, J=2.1 Hz)

Reference Example 5

The following compounds were obtained in the same manner as in Reference Example 2, using respective starting materials.

5-[3-(p-Toluenesulfonyloxy)propoxy]-7-chloro-1-(2-methoxy-4-aminobenzoyl)-2,3,4,5-tetrahydro-1H-benzoazepine Pink and amorphous $^1$H-NMR (CDCl$_3$) δ: 1.3–2.35 (6H, m), 2.44 (3H, s), 2.55–4.0 (8H, m), 4.25 (2H, t, J=6 Hz), 4.5–5.15 (2H, m), 5.93 (1H, s), 6.1–6.45 (1H, m), 6.66 (1H, d, J=8.4 Hz), 6.88 (1H, dd, J=8.4 Hz, 2.4 Hz), 6.99 (1H, d, J=8 Hz), 7.29 (1H, s), 7.35 (2H, d, J=8.2 Hz), 7.81 (2H, d, J=8.3 Hz)

5-[2-(p-Toluenesulfonyloxy)ethoxy]-7-chloro-1-(2-methoxy-4-aminobenzoyl)-2,3,4,5-tetrahydro-1H-benzoazepine Light yellow and amorphous $^1$H-NMR (CDCl$_3$) δ: 1.3–2.35 (4H, m), 2.45 (3H, s), 2.65–2.95 (1H, m), 3.05–4.0 (7H, m), 4.0–5.1 (4H, m), 5.90 (1H, brs), 6.05–6.4 (1H, m), 6.64 (1H, d, J=8.3 Hz), 6.75–7.15 (2H, m), 7.15–7.55 (3H, m), 7.83 (2H, d, J=8.2 Hz)

5-Methoxycarbonylmethyl-7-chloro-1-(2-methoxy-4-amino-benzoyl)- 2,3,4,5-tetrahydro-1H-benzoazepine Light yellow and amorphous $^1$H-NMR (CDCl$_3$) δ: 1.15–2.3 (4H, m), 2.55–3.25 (3H, m), 3.3–4.05 (9H, m), 4.1–4.7 (1H, m), 5.85–6.45 (2H, m), 6.65–6.8 (1H, m), 6.8–7.4 (3H, m)

5-Methoxycarbonylmethyl-7-chloro-1-(4-aminobenzoyl)-2,3,4,5-tetrahydro-1H-benzoazepine A colorless prism (recrystallized from ethanol)

$^1$H-NMR (CDCl$_3$) δ: 1.15–2.3 (4H, m), 2.5–3.05 (2H, m), 3.05–3.3 (1H, m), 3.3–4.3 (6H, m), 4.35–5.3 (1H, m), 6.43 (2H, d, J=8.5 Hz), 6.61 (1H, d, J=8.4 Hz), 6.85–7.0 (1H, m), 7.0–7.4 (3H, m)

5-[2-(p-Toluenesulfonyloxy)ethyl]-7-chloro-1-(2-methoxy-4-aminobenzoyl)-2,3,4,5-tetrahydro-1H-benzoazepine Light yellow and amorphous $^1$H-NMR (CDCl$_3$) δ: 1.0–2.4 (6H, m), 2.46 (3H, s), 2.5–4.4 (10H, m), 5.85–7.25 (6H, m), 7.3–7.5 (2H, m), 7.65–7.9 (2H, m)

5-Cyanomethyl-7-chloro-1-(3-methoxy-4-aminobenzoyl)-2,3,4,5-tetrahydro-1H-benzoazepine A white powder $^1$H-NMR (CDCl$_3$) δ: 1.21–2.33, 2.40–4.70, 5.05–5.39 (total 14H, m), 6.38–7.42 (4H, m), 6.43 (1H, d, J=8.1H), 7.04 (1H, dd, J=2.3 Hz, 8.4 Hz)

5-Ethoxycarbonylmethyl-7-chloro-1-(3-methoxy-4-amino-benzoyl)-2,3,4,5-tetrahydro-1H-benzoazepine Colorless and amorphous $^1$H-NMR (CDCl$_3$) δ: 1.11–2.28 [7H, m, (1.27 (t, J=7.1 Hz))], 2.49–4.61, 5.01–5.35 (total 12H, 3.68(s)), 6.40 (1H, d, J=8.0 Hz), 6.49–7.44 (4H, m), 6.95 (1H, dd, J=2.3 Hz, 8.3 Hz)

5-Methoxycarbonylmethyl-7-chloro-1-(2-methyl-4-aminobenzoyl)-2,3,4,5-tetrahydro-1H-benzoazepine White and amorphous $^1$H-NMR (CDCl$_3$) δ: 0.83–2.47 (4H, m), 2.37 (3H, s), 2.48–5.25 (7H, m), 3.72 (3H, s), 6.16 (1H, d, J=8.3 Hz), 6.41 (1H, s), 6.54 (1H, d, J=8.3 Hz), 6.64 (1H, d, J=8.2 Hz), 6.90 (1H, d, J=8.2 Hz), 7.00–7.42 (1H, m)

Methyl N-{[7-fluoro-1-(2-chloro-4-aminobenzoyl)-2,3,4,5-tetrahydro-1H-benzoazepin-5-yl]oxymethylcarbonyl}-L-alanate Slightly yellow and amorphous $^1$H-NMR (CDCl$_3$) δ: 1.35–1.51 (3H, m), 1.51–5.14 (15H, m), 6.10–7.42 (7H, m)

Methyl N-{[7-fluoro-1-(2-chloro-4-aminobenzoyl)-2,3,4,5-tetrahydro-1H-benzoazepin-5-yl]oxymethylcarbonyl}-L-prolinate Slightyly yellow and amorphous $^1$H-NMR (CDCl$_3$) δ: 1.33–2,64 (8H, m), 2.64–3.00 (1H, m), 3.01–4.44 (9H, m), 4.45–5.13 (3H, m), 6.12–7.46 (6H, m)

5-Methoxycarbonylmethyl-7-chloro-1-(2-chloro-4-aminobenzoyl)-2,3,4,5-tetrahydro-1H-benzoazepine Yellow and amorphous $^1$H-NMR (CDCl$_3$) δ: 1.09–2.36 (4H, m), 2.45–5.19 (7H, M), 3.71 (3H, s), 6.12–7.50 (2H, m), 6.27 (1H, dd. J=2.1 Hz. 8.3 Hz), 6.54 (1H, d, J=2.1 Hz), 6.92 (1H, d, J=2.1 Hz), 7.05 (1H, dd, J=2.1 Hz, 6.1 Hz)

5-Methoxycarobnylmethyl-7-chloro-1-(3-methoxy-4-aminobenzoyl)-2,3,4,5-tetrahydro-1H-benzoazepine Slightly yellow and amorphous $^1$-NMR (CDCl$_3$) δ: 1.01–2.29 (4H, m), 2.44–3.31 (3H, m), 3.32–5.29 (4H, m), 3.68 (3H, s), 3.71 (3H, s), 6.41 (1H, d, J=8.0 Hz), 6.50–6.78 (2H, m), 6.79–6.91 (1H, m), 6.95 (1H, d, J=8.4 Hz), 7.04–7.24 (1H, m)

5-[2-(p-Toluenesulfonyloxy)ethoxy]-7-chloro-1-(2-methyl-4-aminobenzoyl)-2,3,4,5-tetrahydro-1H-benzoazepine Yellow and amorphous $^1$H-NMR (CDCl$_3$) δ: 1.01–2.52 (4H, m), 2.32 (3H, s), 2.43 (3H, s), 2.53–4.78 (9H, m), 5.86–8.03 (10H, m)

5-[3-(p-Toluenesulfonyloxy)propoxy]-7-chloro-1-(2-methyl-4-aminobenzoyl)-2,3,4,5-tetrahydro-1H-benzoazepine Slightly yellow and amorphous $^1$H-NMR (CDCl$_3$) δ: 1.13–3.03 (7H, m), 2.33, 2.43 (6H, each s), 3.04–5.18 (8H, m), 5.98–8.07 (10H, m)

5-(2-Methoxyacetyloxy)-7-chloro-1-(4-aminobenzoyl)-2,3,4,5-tetrahydro-1H-benzoazepine A white powder Melting point: 166°–169° C. (recrystallized from dichloromethane-diethyl ether)

5-Methoxycarbonylmethyl-7-fluoro-1-(4-aminobenzoyl)-2,3,4,5-tetrahydro-1H-benzoazepine A light yellow oil $^1$H-NMR (CDCl$_3$) δ: 1.06–2.20 (4H, m), 2.40–3.22 (3H, m), 3.26–4.28 (3H, m), 3.71 (3H, s), 4.35–5.30 (1H, m), 6.23–6.45 (2H, m), 6.53–6.72 (2H, m), 6.75–7.20 (3H, m)

5-(3-Morpholinopropoxy)-7-fluoro-1-(2-methyl-4-aminobenzoyl)-2,3,4,5-tetrahydro-1H-benzoazepine Light yellow and amorphous $^1$H-NMR (CDCl$_3$) δ; 1.41–2.63 (10H, m), 2.33 (3H, s), 2.75–3.00 (1H, m), 3.32–3.92 (8H, m), 4.27–5.16 (2H, m), 5.98–6.75 (4H, m), 6.80–7.38 (2H, m)

5-[2-(p-Toluenesulfonyloxy)ethoxy]-7-fluoro-1-(2-methoxy-4-aminobenzoyl)-2,3,4,5-tetrahydro-1H-benzoazepine A light yellow oil $^1$H-NMR (CDCl$_3$) δ: 1.29–2.30 (4H, m), 2.45 (3H, s), 2.62–2.88 (1H, m), 2.96–3.97 (4H, m), 3.46 (3H, s), 4.08–4.43 (2H, m), 4.52–5.07 (2H, m), 5.86–6.00 (1H, m), 6.06–6.38 (1H, m), 6.47–6.75 (2H, m), 6.90–7.40 (2H, m), 7.36 (2H, d, J=8.2 Hz), 7.82 (2H, d, J=8.2 Hz)

5-[3-(1-Pyrrolidinyl)propoxy]-7-fluoro-1-(2-methyl-4-amino-benzoyl)-2,3,4,5-tetrahydro-1H-benzoazepine Light yellow and amorphous $^1$H-NMR (CDCl$_3$) δ: 1.40–2.70 (16H, m), 2.33 (3H, s), 2.73–2.96 (1H, m), 3.30–3.86 (4H, m), 4.28–5.14 (2H, m), 6.00–6.25 (1H, m), 6.30–6.72 (4H, m), 6.75–7.35 (1H, m)

5-[2-(1,3-Dioxo-1,2,3,4,5,6,7-octahydroisoindol-2-yl)ethoxy]-7-fluoro-1-(2-methyl-4-aminobenzoyl)-2,3,4,5-tetrahydro-1H-benzoazepine A colorless oil $^1$H-NMR (CDCl$_3$) δ: 1.30–2.47 (13H, m), 2.33 (3H, s), 2.66–4.01 (8H, m), 4.32–5.13 (2H, m), 6.04–6.26 (4H, m), 6.80–7.36 (2H, m)

5-Methoxycarbonylmethyl-7-fluoro-1-(2-methoxy-4-aminobenzoyl)-2,3,4,5-tetrahydro-1H-benzoazepine Light yellow and amorphous $^1$H-NMR (CDCl$_3$) δ: 1.41–2.15 (4H, m), 2.57–3.14 (3H, m), 3.35–4.31 (3H, m), 3.59 (3H, s), 3.74 (3H, s), 4.45–5.15 (1H, m), 5.88–6.17 (2H, m), 6.51–7.07 (4H, m)

5-[2-(p-Toluenesulfonyloxy)ethyl]-7-chloro-1-(2-methyl-4-aminobenzoyl)-2,3,4,5-tetrahydro-1H-benzoazepine Yellow and amorphous $^1$H-NMR (CDCl$_3$) δ: 1.10–2.53 [13H, m (2.31, 2.45, each 3H, each s)], 2.54–4.46 (6H, m), 5.95–6.70 (3H, m), 6.71–7.56 [5H, m (7.36, 2H, d, J=8.1 Hz)], 7.80 (2H, d, J=8.1 Hz]

Reference Example 6

The following compound was obtained in the same manner as in Reference Example 1, using appropriate starting materials.

5-Ethoxycarbonylmethoxy-7-chloro-1-(2-methoxy-4-nitrobenzoyl)-2,3,4,5-tetrahydro-1H-benzoazepine A light yellow powder Melting point: 123°–124° C.

Reference Example 7

The following compounds were obtained in the same manner as in Reference Example 2, using respective starting materials.

5-(2-Chloroanilino)carbonylmethyl-7-chloro-1-(2-methoxy-4-aminobenzoyl)-2,3,4,5-tetrahydro-1H-benzoazepine Colorless and amorphous $^1$H-NMR (CDCl$_3$) δppm: 1.09–2.31 (5H, m), 2.32–5.74 (6H, m), 3.84 (3H, s), 5.80–8.82 (11H, m)

5-Methoxycarbonylmethoxy-7-chloro-1-(2-methoxy-4-aminobenzoyl)-2,3,4,5-tetrahydro-1H-benzoazepine Colorless and amorphous $^1$H-NMR (CDCl$_3$) δppm: 1.17–2.59 (4H, m), 2.60–5.19 (13H, m), 5.83–7.55 (6H, m)

5-Carboxymethyl-7-chloro1-1-(2-methoxy-4-aminobenzoyl)-2,3,4,5-tetrahydro-1H-benzoazepine Colorless and amorphous $^1$H-NMR (CDCl$_3$) δppm: 1.08–2.24 (5H, m), 2.42–4.67 (6H, m), 3.52 (3H, s), 5.78–7.46 (7H, m)

5-(2-Chlorobenzoyl)amino-7-chloro-1-[2-methoxy-4-aminobenzoyl)-2,3,4,5-tetrahydro-1H-benzoazepine A brown powder Melting point: 205°–206° C. (recrystallized from acetone-n-hexane)

Example 1

38.8 g of potassium carbonate was added to a solution of 50 g of 5-dimethylamino-2,3,4,5-tetrahydro-1H-benzoazepine dissolved in 400 ml of acetone and 200 ml of water. To the mixture was added 66.5 g of 4-[2-(2-chlorophenyl)acetylamino]benzoyl chloride with ice-cooling and stirring. The mixture was stirred overnight at room temperature. The reaction mixture was mixed with water, followed by extraction with dichloromethane. The dichloromethane layer was dried over magnesium sulfate and then subjected to vacuum distillation to remove the solvent. The residue was purified by silica gel column chromatography and then recrystallized from methanol to obtain 99.3 g of 5-dimethylamino-1-{4-[2-(2-chlorophenyl)acetylamino]benzoyl}-2,3,4,5-tetrahydro-1H-benzoazepine.

A white powder

Melting point: 187°–189° C.

Example 2

15 ml of thionyl chloride was added to 0.44 g of 2-chlorophenylacetic acid. The mixture was stirred at room temperature for 2 hours. The reaction mixture was subjected to distillation to remove the remaining thionyl chloride and then to azeotropy with toluene twice to completely remove the thionyl chloride. The residue was dissolved in 10 ml of dichloromethane. 0.36 ml of triethylamine was added, with ice-cooling, to a dichloromethane solution containing 0.40 g of 5-dimethylamino-1-(4-aminobenzoyl)-2,3,4,5-tetrahydro-1H-benzoazepine. Thereto was dropwise added the above obtained 2-(2-chlorophenyl)acetyl chloride solution. The resulting mixture was stirred at room temperature for 1 hour. The reaction mixture was water-washed twice, then dried over magnesium sulfate and concentrated. The residue was purified by silica gel column chromatography (elutant: chloroform/methanol=200/1) and then recrystallized from methanol-diethyl ether to obtain 0.29 g of 5-dimethylamino-1-{4-[2-(2-chlorophenyl)acetylamino]benzoyl}-2,3,4,5-tetrahydro-1H-benzoazepine.

A white powder

Melting point: 187°–189° C.

Tables 1 to 42 (Examples 3 to 85) and their NMR data appear here.

The following compounds were obtained in the same manner as in Examples 1 and 2, using respective raw materials.

TABLE 1

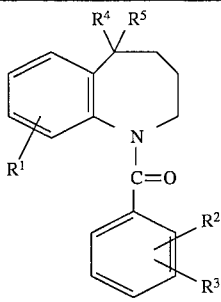

Example 3
Structure:

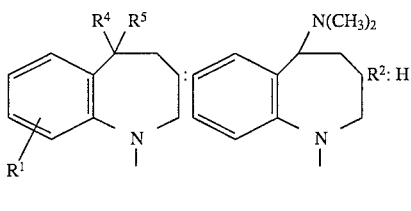

$R^3$: 4-NHCCH$_2$— (with CH$_3$ on ring, C=O)

Crystal form: white powder
Recrystallization solvent: methanol-diethyl ether
Melting point: 153–154.5° C.
Form: free

TABLE 2

Example 4
Structure:

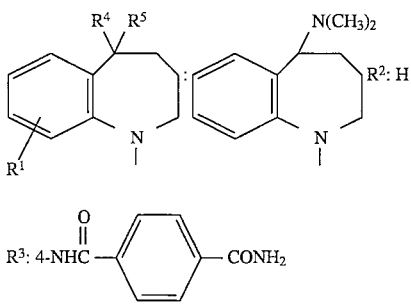

$R^3$: 4-NHC(=O)—C$_6$H$_4$—CONH$_2$

Crystal form: white powder
Recrystallization solvent: diethyl ether
Melting point: 226–231° C.
Form: free TABLE 2-continued Example 5
Structure:

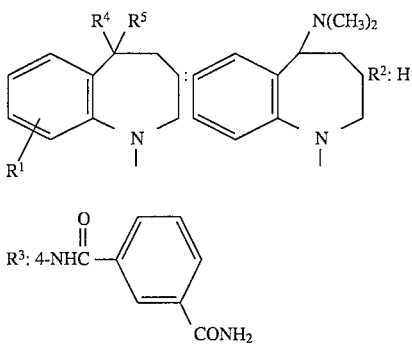

$R^3$: 4-NHC(=O)—C$_6$H$_4$—CONH$_2$

Crystal form: white powder
Recrystallization solvent: ethanol-n-hexane
Melting point: 224–229° C.
Form: free

TABLE 3

Example 6
Structure:

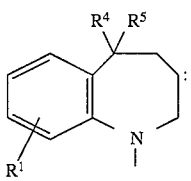

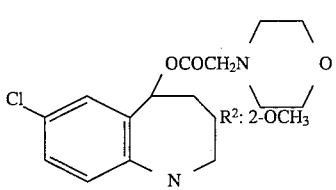

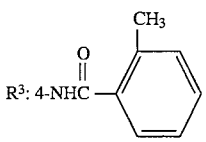

$R^3$: 4-NHC(=O)—C$_6$H$_4$—CH$_3$

Crystal form: white powder
Recrystallization solvent: ethanol-diethyl ether
Melting point: 179–181° C.
Form: hydrochloride Example 7
Structure:

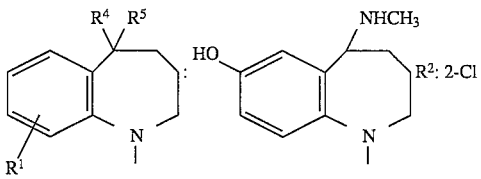

TABLE 3-continued

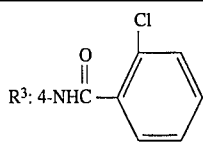

Crystal form: colorless and amorphous
Form: free
NMR: 1)

TABLE 4

Example 8
Structure:

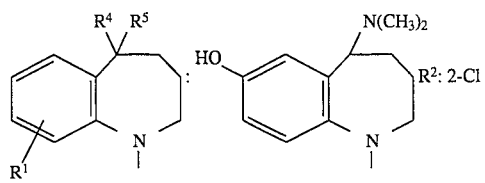

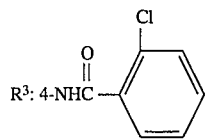

Crystal form: colorless and amorphous
Form: free
NMR: 2)

Example 9
Structure:

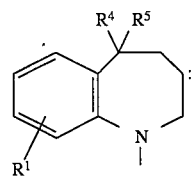

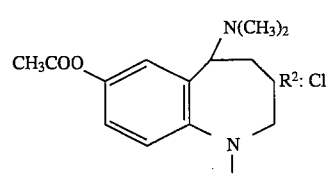

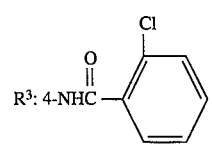

Crystal form: colorless and amorphous
Form: free
NMR: 3)

TABLE 5

Example 10
Structure:

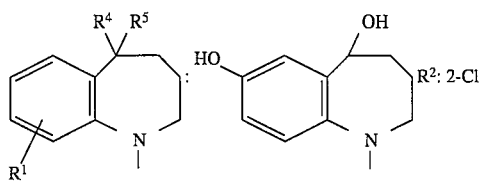

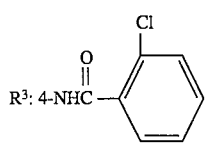

Crystal form: colorless and amorphous
Form: free
NMR: 4)

Example 11
Structure:

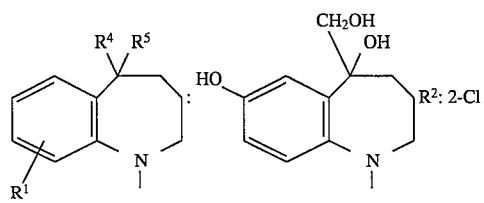

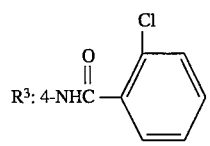

Crystal form: colorless and amorphous
Form: free
NMR: 5)

TABLE 6

Example 12
Structure:

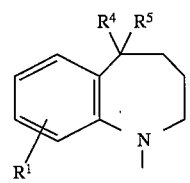

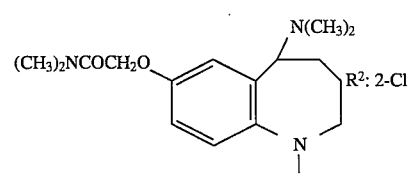

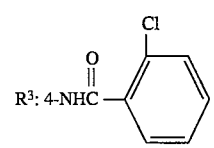

TABLE 6-continued

Crystal form: colorless and amorphous
Form: free
NMR: 6)

Example 13
Structure:

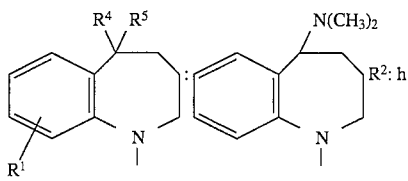
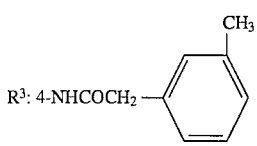

R³: 4-NHCOCH₂—⟨phenyl with CH₃⟩

Crystal form: colorless and amorphous
Form: free
NMR: 7)

TABLE 7

Example 14
Structure:

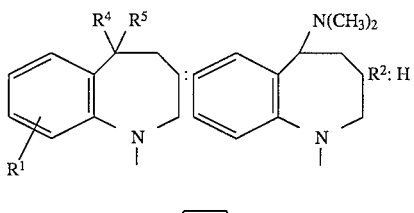

R³: 4-NHCOCH₂—⟨phenyl⟩—CH₃

Crystal form: colorless and amorphous
Form: free
NMR: 8)

Example 15
Structure:

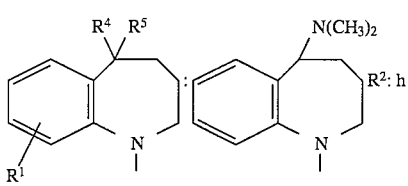
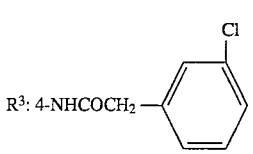

R³: 4-NHCOCH₂—⟨phenyl with Cl⟩

Crystal form: colorless and amorphous
Form: free
NMR: 9)

TABLE 8

Example 16
Structure:

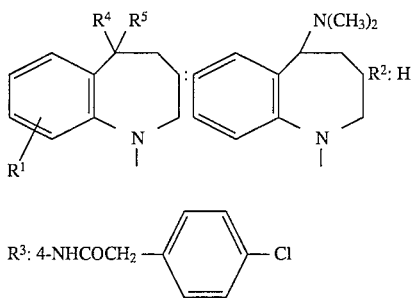

R³: 4-NHCOCH₂—⟨phenyl⟩—Cl

Crystal form: colorless and amorphous
Form: free
NMR: 10)

Example 17
Structure:

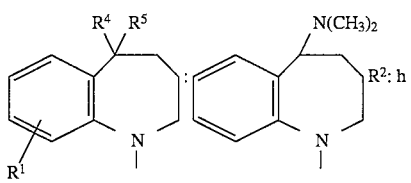

R³: 4-NHCOCH₂—⟨phenyl with OCH₃⟩

Crystal form: colorless and amorphous
Form: free
NMR: 11)

TABLE 9

Example 18
Structure:

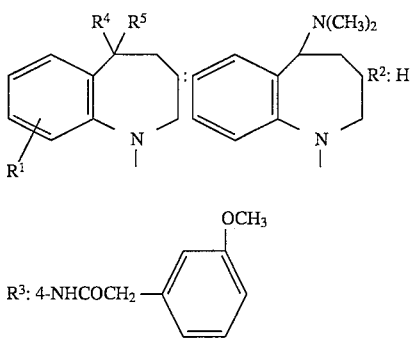

R³: 4-NHCOCH₂—⟨phenyl with OCH₃⟩

Crystal form: colorless and amorphous
Form: free
NMR: 12)

TABLE 9-continued

Example 19
Structure:

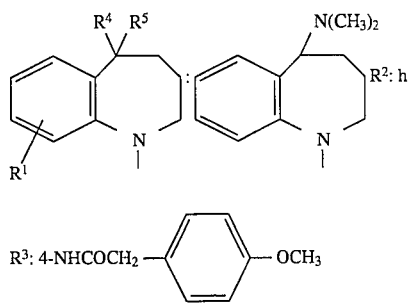

R³: 4-NHCOCH₂—⟨phenyl⟩—OCH₃

Crystal form: colorless and amorphous
Form: free
NMR: 13)

TABLE 10

Example 20
Structure:

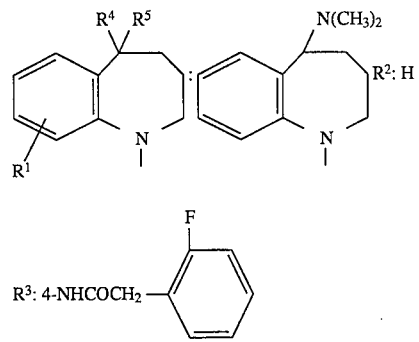

R³: 4-NHCOCH₂—⟨phenyl-F⟩

Crystal form: white powder
Recrystallization solvent: methanol-diethyl ether
Melting point: 189.5–191° C.
Form: free Example 21
Structure:

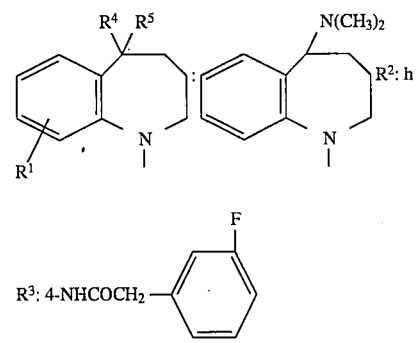

R³: 4-NHCOCH₂—⟨phenyl-F⟩

Crystal form: colorless and amorphous
Form: free
NMR: 14)

TABLE 11

Example 22
Structure:

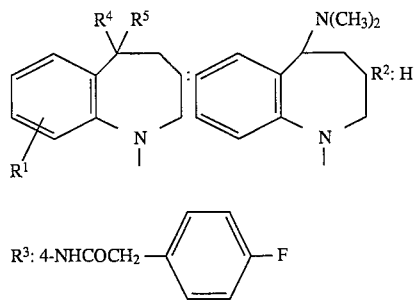

R³: 4-NHCOCH₂—⟨phenyl⟩—F

Crystal form: colorless and amorphous
Form: free
NMR: 15)

Example 23
Structure:

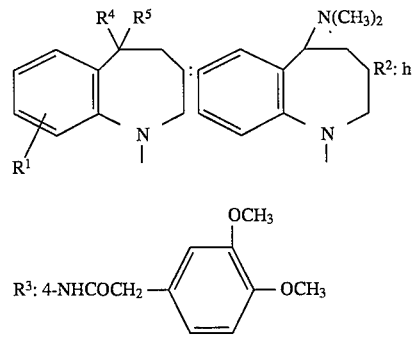

R³: 4-NHCOCH₂—⟨phenyl(OCH₃)⟩—OCH₃

Crystal form: colorless and amorphous
Form: free
NMR: 16)

TABLE 12

Example 24
Structure:

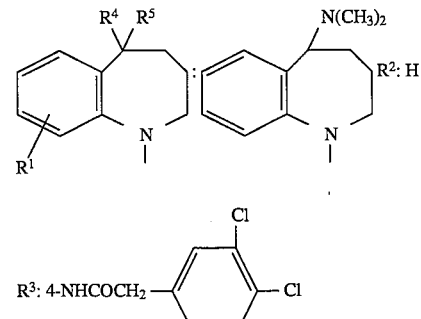

R³: 4-NHCOCH₂—⟨phenyl(Cl)⟩—Cl

Crystal form: colorless and amorphous
Form: free
NMR: 17)

TABLE 12-continued

Example 25
Structure:

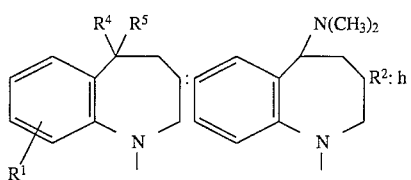

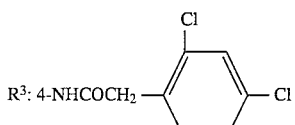
R³: 4-NHCOCH₂—

Crystal form: colorless and amorphous
Form: free
NMR: 18)

TABLE 13

Example 26
Structure:

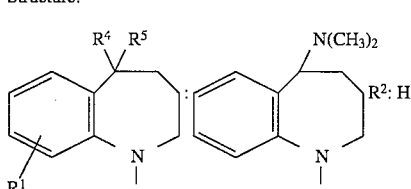

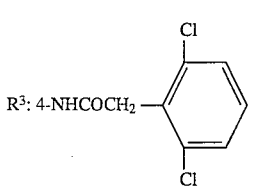
R³: 4-NHCOCH₂—

Crystal form: colorless and amorphous
Form: free
NMR: 19)

Example 27
Structure:

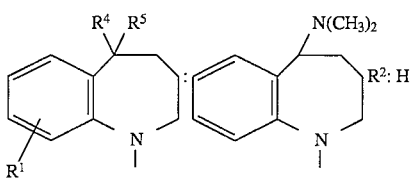

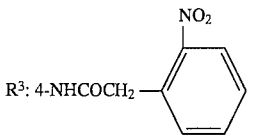
R³: 4-NHCOCH₂—

Crystal form: colorless and amorphous
Form: free
NMR: 20)

TABLE 14

Example 28
Structure:

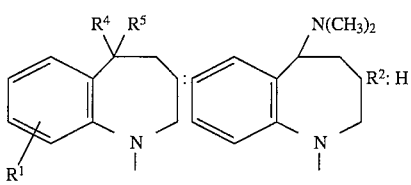

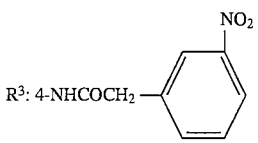
R³: 4-NHCOCH₂—

Crystal form: colorless and amorphous
Form: free
NMR: 21)

Example 29
Structure:

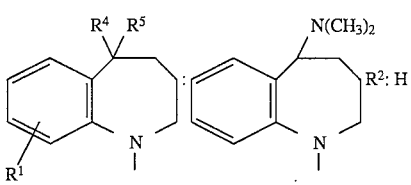

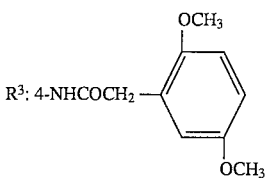
R³: 4-NHCOCH₂—

Crystal form: colorless and amorphous
Form: free
NMR: 22)

TABLE 15

Example 30
Structure:

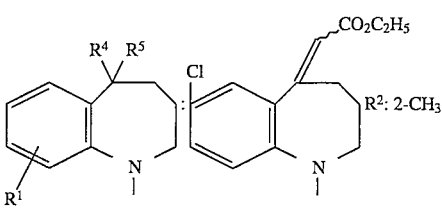

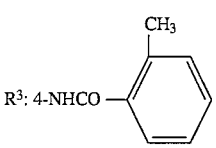
R³: 4-NHCO—

Crystal form: colorless and amorphous
Form: free
NMR: 23)

TABLE 15-continued

Example 31
Structure:

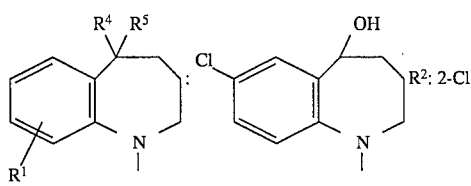

R³: 4-NHCOCH₂—⟨CH₃ phenyl⟩

Crystal form: white powder
Recrystallization solvent: methanol-diethyl ether
Melting point: 192.5–194.5° C.
Form: free

TABLE 16

Example 32
Structure:

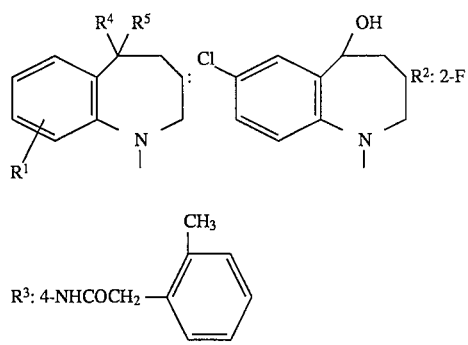

R³: 4-NHCOCH₂—⟨CH₃ phenyl⟩

Crystal form: white powder
Recrystallization solvent: methanol-diethyl ether
Melting point: 210–21° C.
Form: free Example 33
Structure:

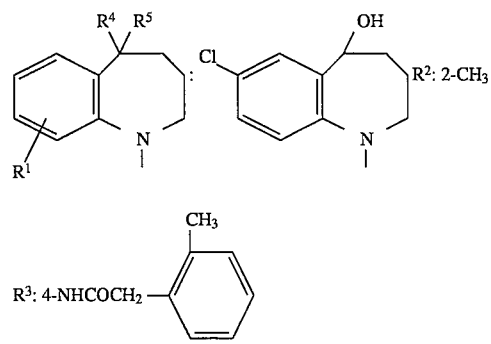

R³: 4-NHCOCH₂—⟨CH₃ phenyl⟩

Crystal form: white powder
Recrystallization solvent: methanol-diethyl ether
Melting point: 221–222° C.
Form: free

TABLE 17

Example 34
Structure:

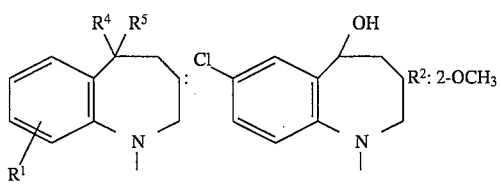

R³: 4-NHCOCH₂—⟨CH₃ phenyl⟩

Crystal form: colorless and amorphous
Form: free
NMR: 24)

Example 35
Structure:

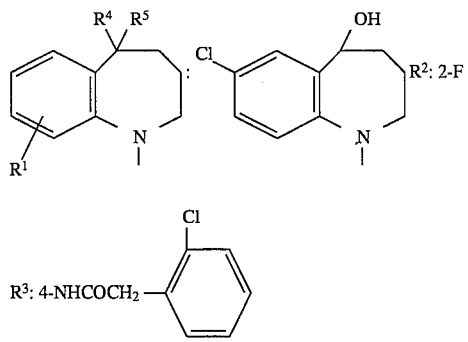

R³: 4-NHCOCH₂—⟨Cl phenyl⟩

Crystal form: white powder
Recrystallization solvent: methanol-diethyl ether
Melting point: 175–176° C.
Form: free

TABLE 18

Example 36
Structure:

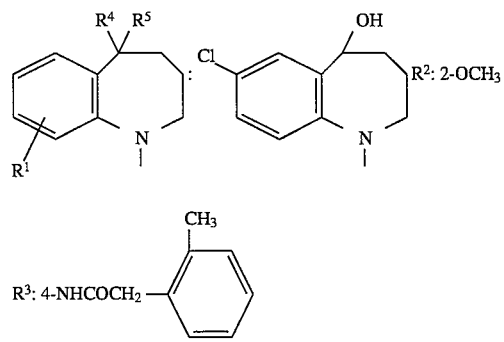

R³: 4-NHCOCH₂—⟨CH₃ phenyl⟩

Crystal form: white powder
Recrystallization solvent: methanol-solvent ether
Melting point: 212–215° C.
Form: free

TABLE 18-continued

Example 37
Structure:

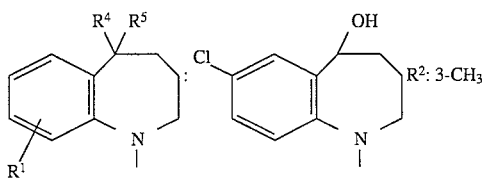

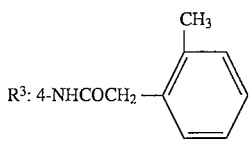

R³: 4-NHCOCH₂—

Crystal form: white powder
Recrystallization solvent: methanol-diethyl ether
Melting point: 210–211° C.
Form: free

TABLE 19

Example 38
Structure:

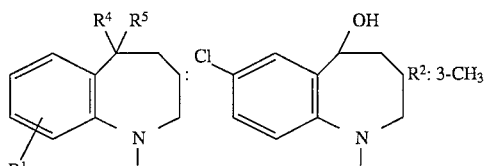

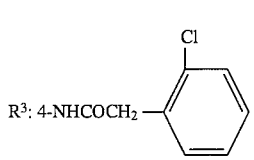

R³: 4-NHCOCH₂—

Crystal form: white powder
Recrystallization solvent: methanol
Melting point: 217–218° C.
Form: free Example 39
Structure:

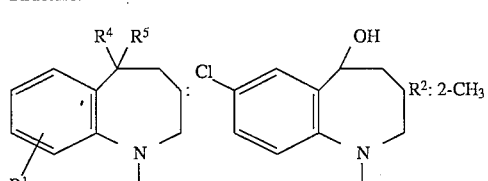

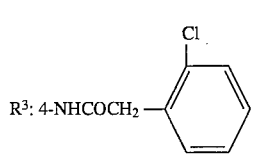

R³: 4-NHCOCH₂—

Crystal form: white powder
Recrystallization solvent: methanol
Melting point: 245–247° C.
Form: free

TABLE 20

Example 40
Structure:

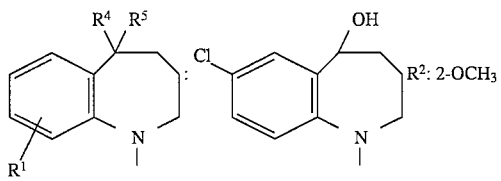

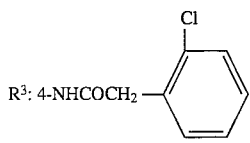

R³: 4-NHCOCH₂—

Crystal form: colorless and amorphous
Form: free
NMR: 25)

Example 41
Structure:

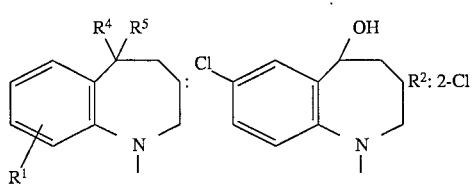

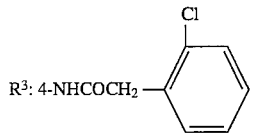

R³: 4-NHCOCH₂—

Crystal form: white powder
Recrystallization solvent: methanol-diethyl ether
Melting point: 214–216° C.
Form: free

TABLE 21

Example 42
Structure:

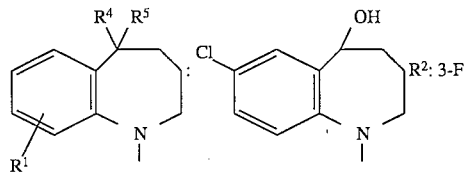

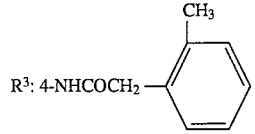

R³: 4-NHCOCH₂—

Crystal form: colorless and amorphous
Recrystallization solvent: methanol
Melting point: 208.5–209° C.
Form: free TABLE 21-continued Example 43
Structure:

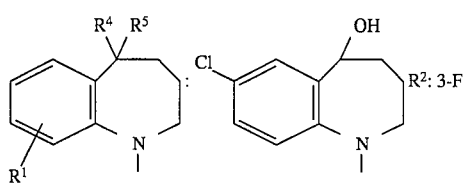

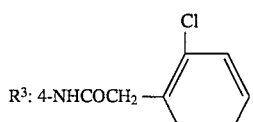

Crystal form: white powder
Recrystallization solvent: methanol
Melting point: 184–186° C.
Form: free

TABLE 22

Example 44
Structure:

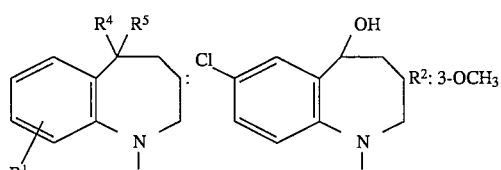

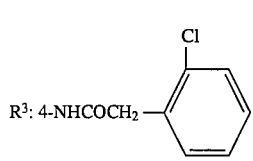

Crystal form: white powder
Recrystallization solvent: methanol-diethyl ether
Melting point: 195–196° C.
Form: free Example 45
Structure:

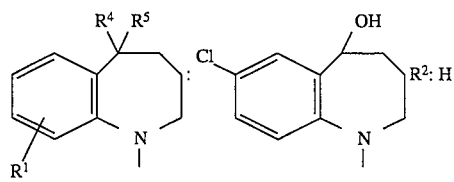

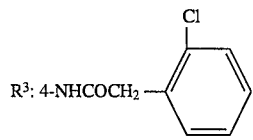

Crystal form: white powder
Recrystallization solvent: methanol-diethyl ether
Melting point: 214–215° C.
Form: free

TABLE 23

Example 46
Structure:

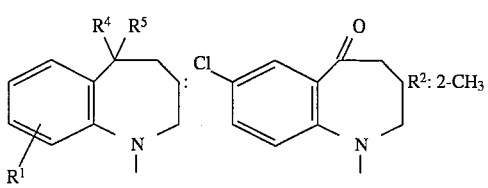

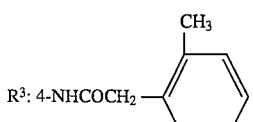

Crystal form: white powder
Recrystallization solvent: methanol-diethyl ether
Melting point: 145–146.5° C.
Form: free Example 47
Structure:

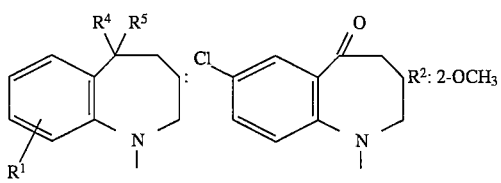

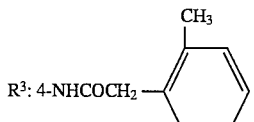

Crystal form: white powder
Recrystallization solvent: methanol-diethyl ether
Melting point: 241–241.5° C.
Form: free

TABLE 24

Example 48
Structure:

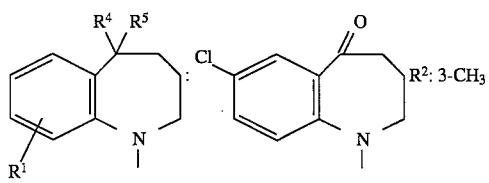

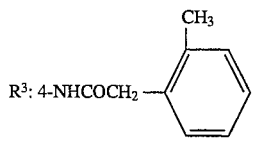

Crystal form: white powder
Recrystallization solvent: methanol-diethyl ether
Melting point: 119–120° C.
Form: free TABLE 24-continued Example 49
Structure:

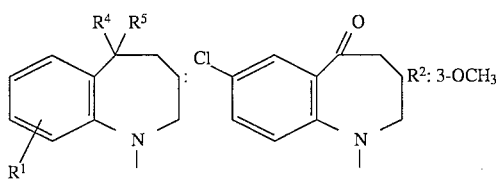

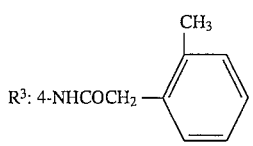

Crystal form: white powder
Recrystallization solvent: methanol-diethyl ether
Melting point: 142.5–146.5° C.
Form: free

TABLE 25

Example 50:
Structure:

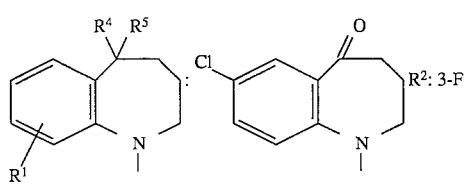

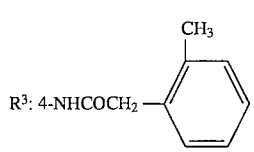

Crystal form: white powder
Recrystallization solvent: methanol-diethyl ether
Melting point: 145–146° C.
Form: free Example 51
Structure:

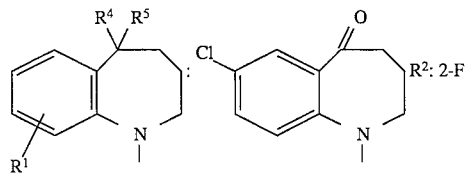

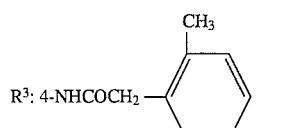

Crystal form: colorless and amorphous
Form: free
NMR: 26)

TABLE 26

Example 52
Structure:

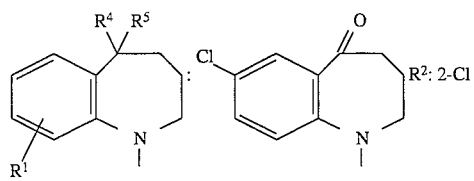

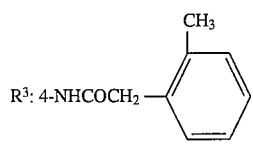

Crystal form: colorless and amorphous
Form: free
NMR: 27)

Example 53
Structure:

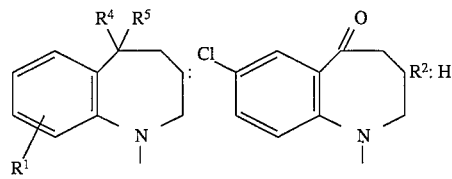

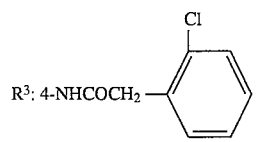

Crystal form: white powder
Recrystallization solvent: methanol-diethyl ether
Melting point: 199–202° C.
Form: free

TABLE 27

Example 54
Structure:

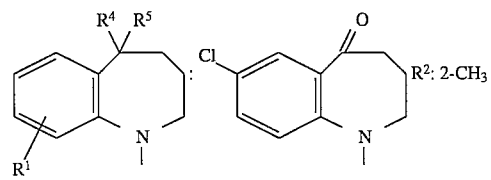

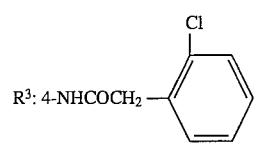

Crystal form: white powder
Recrystallization solvent: methanol-diethyl ether
Melting point: 171–172° C.
Form: free

TABLE 27-continued

Example 55
Structure:

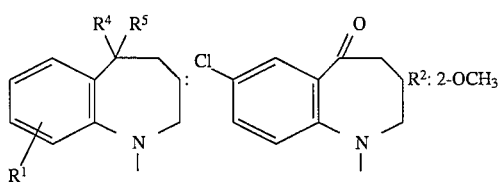

R³: 4-NHCOCH₂—

Crystal form: white powder
Recrystallization solvent: methanol-diethyl ether
Melting point: 243.5–245° C.
Form: free

TABLE 28

Example 56
Structure:

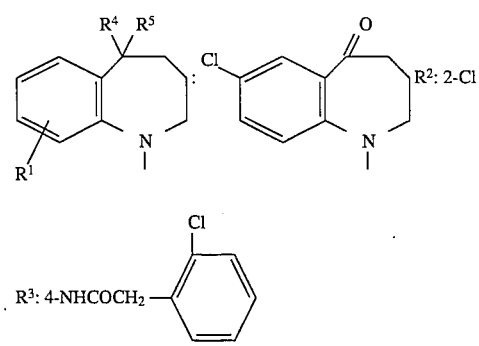

R³: 4-NHCOCH₂—

Crystal form: white powder
Recrystallization solvent: methanol-diethyl ether
Melting point: 239–240° C.
Form: free Example 57
Structure:

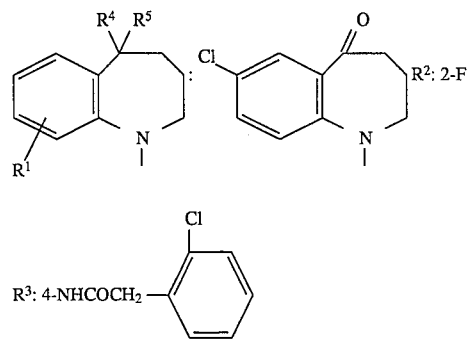

R³: 4-NHCOCH₂—

Crystal form: white powder
Recrystallization solvent: methanol-diethyl ether
Melting point: 162–163° C.
Form: free

TABLE 29

Example 58
Structure:

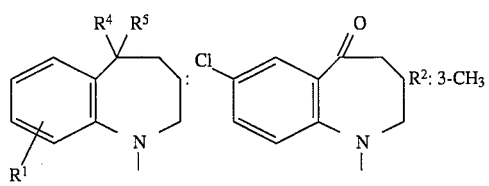

R³: 4-NHCOCH₂—

Crystal form: white powder
Recrystallization solvent: methanol-diethyl ether
Melting point: 134–135° C.
Form: free Example 59
Structure:

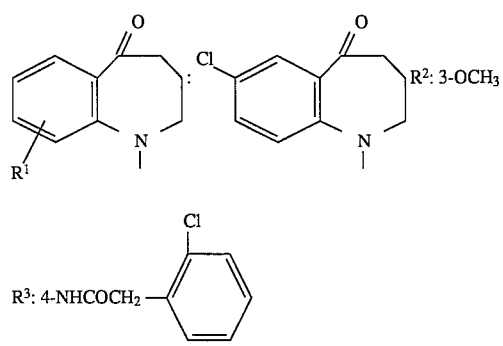

R³: 4-NHCOCH₂—

Crystal form: white powder
Recrystallization solvent: methanol-diethyl ether
Melting point: 177–178° C.
Form: free

TABLE 30

Example 60
Structure:

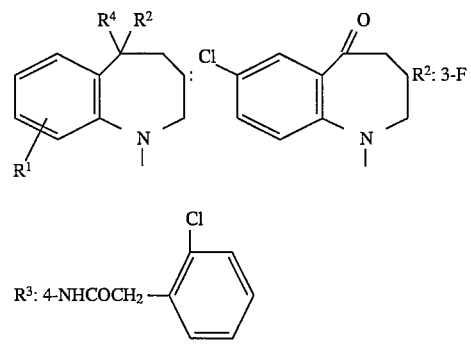

R³: 4-NHCOCH₂—

Crystal form: white powder
Recrystallization solvent: methanol-diethyl ether
Melting point: 168–169° C.Form: free

TABLE 30-continued

Example 61
Structure:

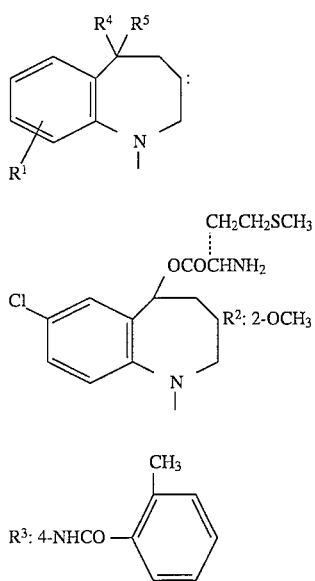

Crystal form: colorless and amorphous
Form: free
NMR: 28)

TABLE 31

Example 62
Structure:

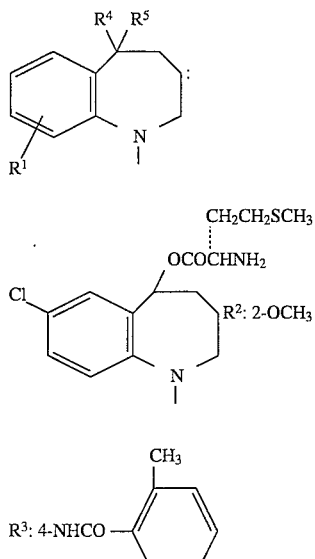

Crystal form: colorless and amorphous
Form: free
NMR: 29)

TABLE 31-continued

Example 63
Structure:

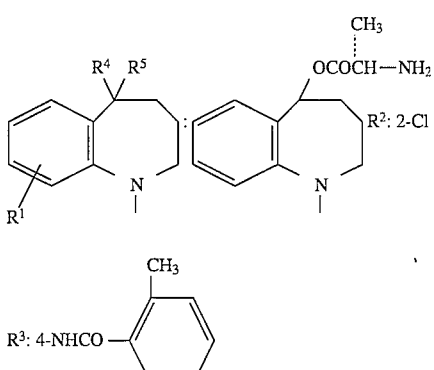

Crystal form: colorless and amorphous
Form: free
NMR: 30)

TABLE 32

Example 64
Structure:

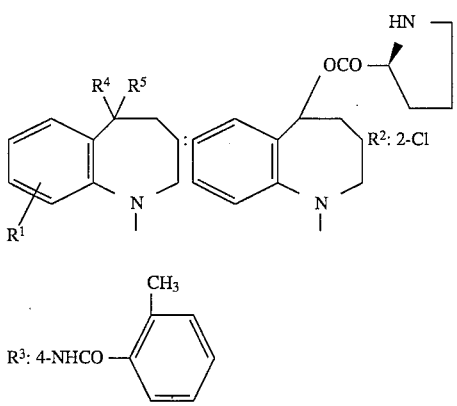

Crystal form: colorless and amorphous
Form: free
NMR: 31)

Example 65
Structure:

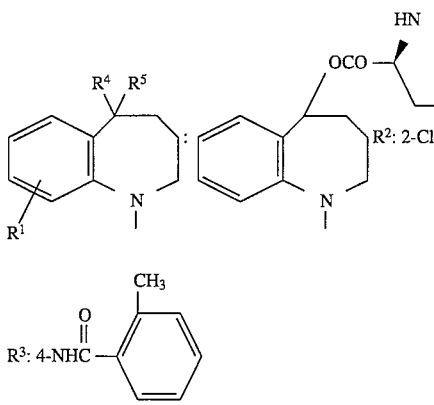

Crystal form: colorless and amorphous

TABLE 32-continued

Form: free
NMR: 32)

TABLE 33

Example 66
Structure:

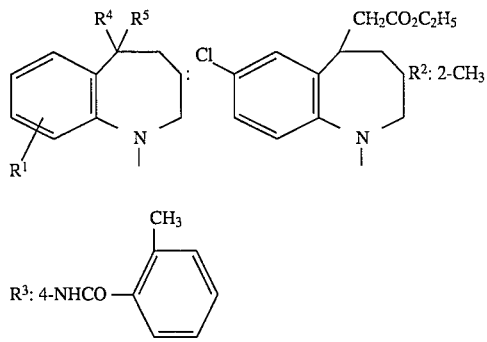

R³: 4-NHCO—⟨o-CH₃-phenyl⟩

Crystal form: colorless and amorphous
Form: free
NMR: 33)

Example 67
Structure:

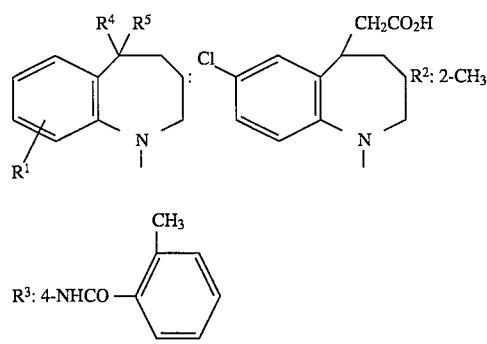

R³: 4-NHCO—⟨o-CH₃-phenyl⟩

Crystal form: colorless and amorphous
Form: free
NMR: 34)

TABLE 34

Example 68
Structure:

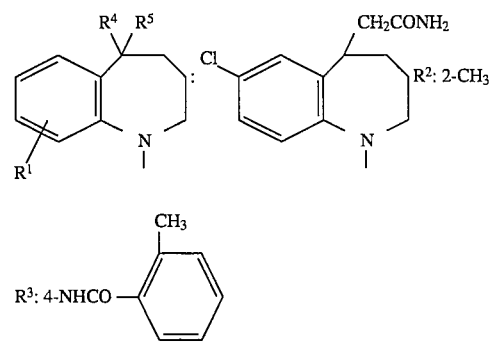

R³: 4-NHCO—⟨o-CH₃-phenyl⟩

Crystal form: colorless and amorphous
Form: free

TABLE 34-continued

NMR: 35)

Example 69
Structure:

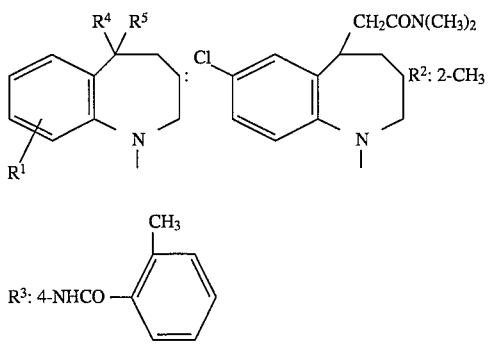

R³: 4-NHCO—⟨o-CH₃-phenyl⟩

Crystal form: colorless and amorphous
Form: free
NMR: 36)

TABLE 35

Example 70
Structure:

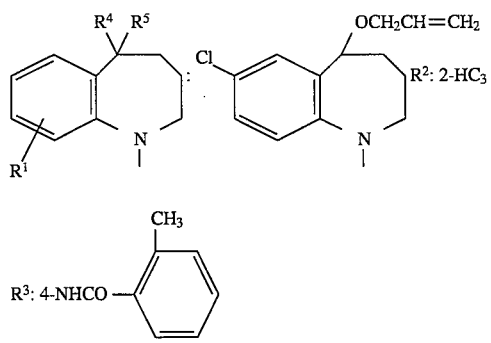

R³: 4-NHCO—⟨o-CH₃-phenyl⟩

Crystal form: colorless and amorphous
Form: free
NMR: 37)

Example 71
Structure:

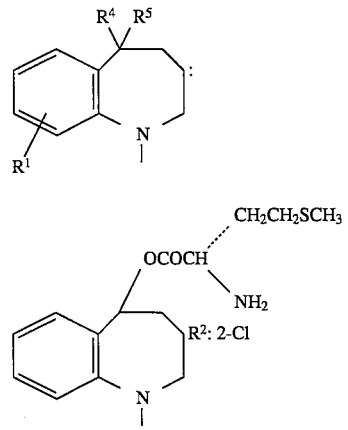

TABLE 35-continued
R³: 4-NHCO— 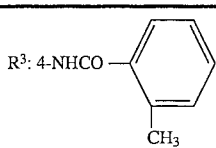
Crystal form: colorless and amorphous
Form: free
NMR: 38)
TABLE 36
Example 72
Structure:
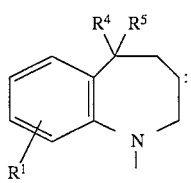
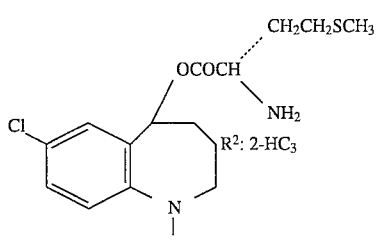
R³: 4-NHCO— 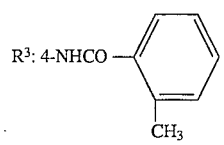
Crystal form: colorless and amorphous
Form: free
NMR: 39)
Example 73
Structure:
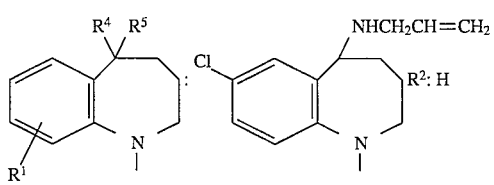
R³: 4-NHCOCH₂— 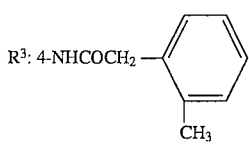
Crystal form: white powder
Recrystallization solvent: methanol-diethyl ether
TABLE 36-continued
Melting point: 128–130° C.
Form: free

TABLE 37

Example 74
Structure:

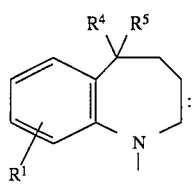

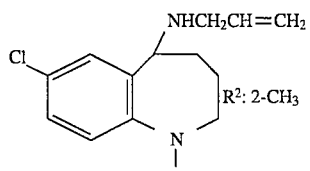

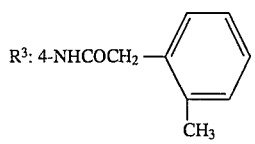

Crystal form: white powder
Recrystallization solvent: methanol-diethyl ether
Melting point: 139–140° C.
Form: free Example 75
Structure:

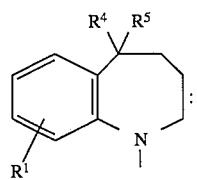

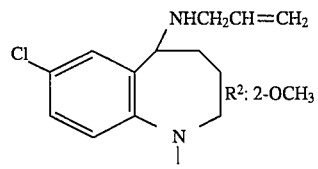

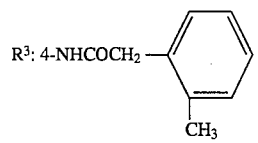

Crystal form: colorless and amorphous
Form: free
NMR: 40)

TABLE 38

Example 76
Structure:

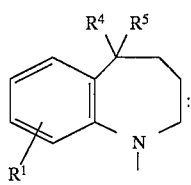

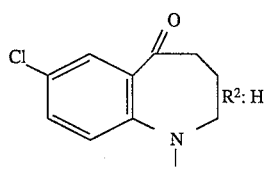

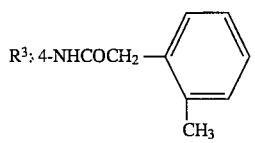

Crystal form: white powder
Recrystallization solvent: methanol-diethyl ether
Melting point: 194–196° C.
Form: free Example 77
Structure:

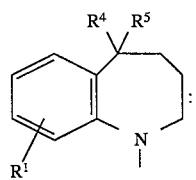

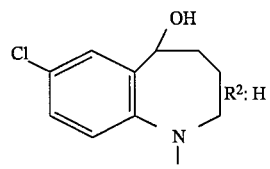

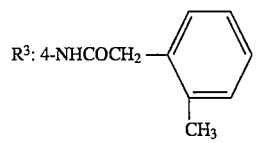

Crystal form: white powder
Recrystallization solvent: methanol-diethyl ether
Melting point: 241–243° C.
Form: free

TABLE 39

Example 78
Structure:

TABLE 39-continued

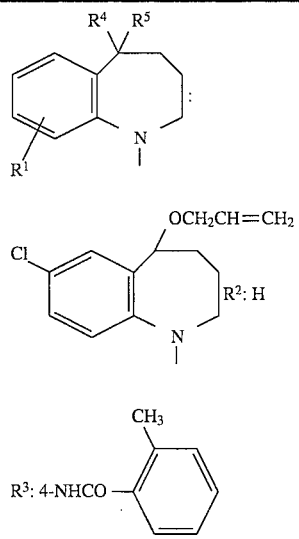

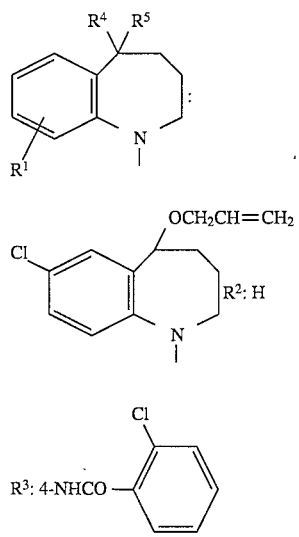

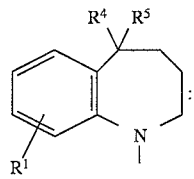

Crystal form: white powder
Recrystallization solvent: dichloromethane-diethyl ether
Melting point 136–138° C.
Form: free

TABLE 40

Example 80
Structure:

TABLE 40-continued

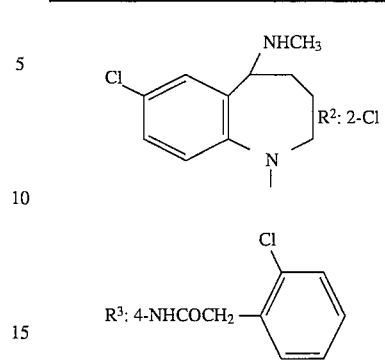

Crystal form: white powder
Recrystallization solvent: methanol-diethyl ether
Melting point: 178–179° C.
Form: free Example 81
Structure:

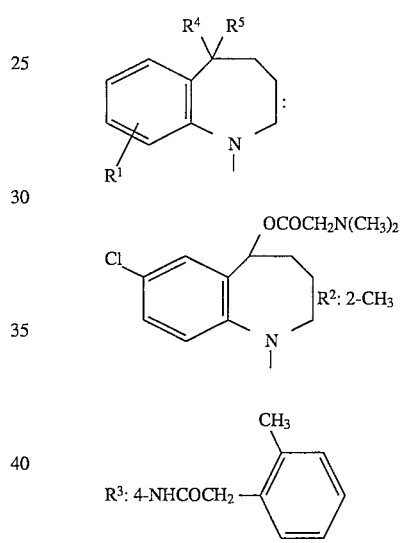

Crystal form: colorless and amorphous
Form: free
NMR: 41)

TABLE 41

Example 82
Structure:

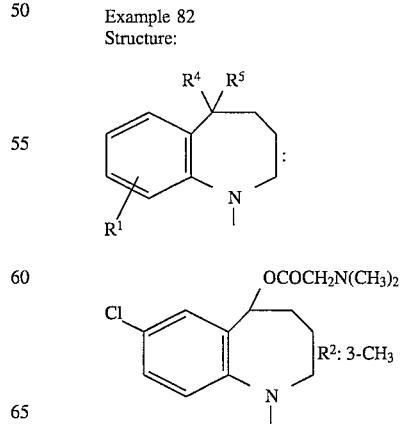

TABLE 41-continued

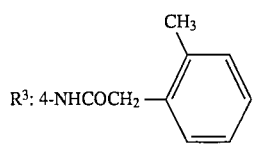

Crystal form: colorless and amorphous
Form: free
NMR: 42)

Example 83
Structure:

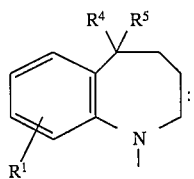

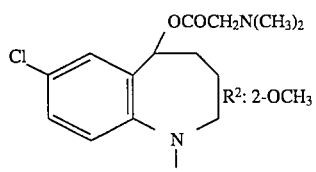

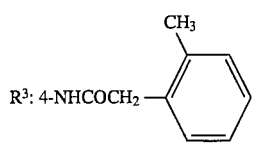

Crystal form: colorless and amorphous
Form: free
NMR: 43)

TABLE 42

Example 84
Structure:

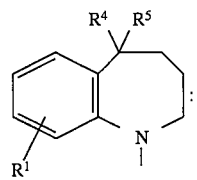

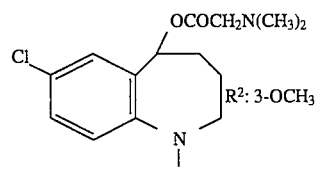

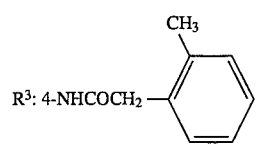

Crystal form: colorless and amorphous
Form: free

TABLE 42-continued

NMR: 44)

Example 85
Structure:

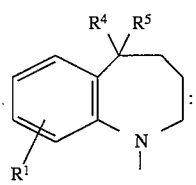

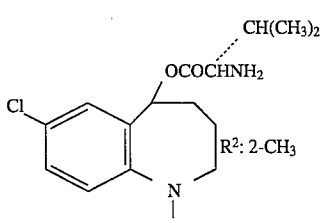

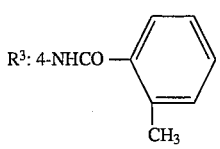

Crystal form: colorless and amorphous
Form: free
NMR: 45)

1) $^1$H-NMR (CDCl$_3$) δ: 1.41–1.72 (2H, m), 1.86–2.13 (1H, m), 2.19–2.48 (1H, m), 2.64–3.18 (4H, m), 4.20–4.83 (2H, m), 6.44–7.10 (3H, m), 7.17–8.15 (7H, 9.32 (1H, brs), 9.91 (1H, s), 10.72 (1H, s)

2) $^1$H-NMR (CDCl$_3$) δ: 1.40–3.20 (11H, m), 3.27–5.05 (2H, m), 6.38–8.37 (11H, m)

3) $^1$H-NMR (CDCl$_3$) δ: 1.40–3.30 (14H, m), 3.30–5.20 (2H, m), 6.70–8.60 (11H, m)

4) $^1$H-NMR (CDCl$_3$) δ: 1.47–5.16 (7H, m), 6.30–8.23 (11H, m) 8.90–9.10 (1H, m), 10.10–10.55 (1H, m)

5) $^1$H-NMR (DMSO-d$_6$) δ: 1.30–5.28 (9H, m), 6.19–8.13 (11H, m), 9.44–9.60 (1H, m), 10.56–10.94 (1H, m)

6) $^1$H-NMR (CDCl$_3$) δ: 1.46–5.10 (21H, m), 6.43–8.44 (11H, m)

7) $^1$H-NMR (CDCl$_3$) δ: 1.00–2.55 (10H, m), 2.33 (3H, s), 2.57–3.14 (1H, m), 3.39–3.78 (1H, m), 3.61 (2H, s), 3.84–5.20 (1H, m), 6.40–7.71 (12H, m)

8) $^1$H-NMR (CDCl$_3$) δ: 1.05–2.57 (10H, m), 2.35 (3H, s), 2.57–3.15 (1H, m), 3.30–3.82 (1H, m), 3.63 (2H, s), 3.89–5.19 (1H, m), 6.42–7.70 (12H, m)

9) $^1$H-NMR (CDCl$_3$) δ: 1.10–3.18 (11H, m), 3.32–3.80 (1H, m), 3.57 (2H, s), 3.95–5.20 (1H, m), 6.43–7.68 (12H, m), 8.13–8.44 (1H, m)

10) $^1$H-NMR (CDCl$_3$) δ: 1.06–3.21 (11H, m), 3.313.90 (1H, m), 3.54 (2H, s), 3.90–5.18 (1H, m), 6.38–7.65 (12H, m), 8.26–8.62 (1H, m)

11) $^1$H-NMR (CDCl$_3$) δ: 1.10–3.14 (11H, m), 3.34–3.75 (1H, m), 3.65 (2H, s), 3.89 (3H, s), 3.95–5.20 (1H, 6.45–7.70 (12H, m), 7.72–8.05 (1H, m)

12) $^1$H-NMR (CDCl$_3$) δ: 1.09–3.16 (11H, m), 3.35–5.20 (2H, m), 3.61 (2H, s), 3.78 (3H, s), 6.38–7.64 (12H, m), 7.70 (1H, s)

13) ¹H-NMR (CDCl₃) δ: 1.10–3.25 (11H, m), 3.36–3.71 (3H, m), 3.75–3.90 (3H, m), 3.95–5.20 (1H, m), 6.42–7.68 (12H, m)

14) ¹H-NMR (CDCl₃) δ: 1.08–3.21 (11H, m), 3.36–3.79 (1H, m), 3.59 (2H, s), 3.91–5.19 (1H, m), 6.45–7.65 (12H, m), 8.04–8.35 (1H, m)

15) ¹H-NMR (CDCl₃) δ: 1.08–3.20 (11H, m), 3.34–3.79 (1H, m), 3.58 (2H, s), 3.90–5.19 (1H, m), 6.43–7.65 (12H, m), 7.91–8.20 (1H, m)

16) ¹H-NMR (CDCl₃) δ: 1.11–3.13 (11H, m), 3.35–3.72 (1H, m), 3.61 (2H, s), 3.86 (3H, s), 3.88 (3H, s), 3.94–5.20 (1H, m), 6.45–7.69 (11H, m)

17) ¹H-NMR (CDCl₃) δ: 1.10–3.27 (11H, m), 3.36–3.75 (1H, m), 3.49 (2H, s), 3.90–5.20 (1H, m), 6.41–7.84 (11H, m), 8.81–9.59 (1H, m)

18) ¹H-NMR (CDCl₃) δ: 1.10–3.20 (11H, m), 3.35–3.66 (1H, m), 3.73 (2H, s), 3.91–5.20 (1H, m), 6.48–7.65 (11H, m), 7.68–7.94 (1H, m)

19) ¹H-NMR (CDCl₃) δ: 1.08–3.21 (11H, m), 3.38–3.68 (1H, m), 4.00 (2H, s), 3.95–5.20 (1H, m), 6.45–7.70 (11H, m), 8.15 (1H, s)

20) ¹H-NMR (CDCl₃) δ: 1.08–3.25 (11H, m), 3.36–3.69 (1H, m), 3.91 (2H, s), 3.88–5.20 (1H, m), 6.45–7.72 (11H, m), 7.85–8.13 (1H, m), 8.85 (1H, s)

21) ¹H-NMR (CDCl₃) δ: 1.10–3.30 (11H, m), 3.39–3.95 (3H, m), 3.95–5.20 (1H, m), 6.45–7.82 (10H, m), 7.94–8.36 (2H, m), 8.82–9.17 (1H, m)

22) ¹H-NMR (CDCl₃) δ: 1.06–3.11 (11H, m) 3.35–3.70 (1H, m), 3.62 (2H, s), 3.74 (3H, s), 3.86 (3H, s), 3.92–5.20 (1H, m), 6.45–7.67 (11H, m), 7.81–8.16 (1H, m)

23) ¹H-NMR (CDCl₃) δ: 1.04–5.10 (17H, m), 5.96–6.17 (1H, m), 6.52–7.86 (11H, m)

24) ¹H-NMR (CDCl₃) δ: 1.41–1.89 (2H, m), 1.90–2.24 (2H, m), 2.31 (3H, s), 2.47–2.89 (2H, m), 3.45 (3H, s), 3.69 (2H, s), 4.57–5.13 (2H, m), 6.39–6.76 (2H, m), 6.78–6.95 (1H, m), 6.95–7.41 (7H, m), 7.41–7.65 (1H, m)

25) ¹H-NMR (CDCl₃) δ: 1.45–1.92 (2H, m), 1.92–2.28 (2H, m), 2.50–2.96 (2H, m), 3.45 (3H, s), 3.81 (2H, s), 4.64–5.20 (2H, m), 6.28–7.12 (3H, m), 7.13–7.50 (5H, m), 7.50–7.64 (1H, m), 7.65–7.99 (1H, m)

26) ¹H-NMR (CDCl₃) δ: 1.52–2.54 (2H, m), 2.27 (3H, s), 2.70–2.98 (2H, m), 2.98–5.52 (2H, m), 3.65 (2H, s), 6.56–6.87 (1H, m), 6.97–7.43 (8H, m), 7.78 (1H, d, J=2.4 Hz), 7.91–8.15 (1H, m)

27) ¹H-NMR (CDCl₃) δ: 1.76–2.40 (2H, m), 2.29 (3H, s), 2.86 (2H, t, J=6.0 Hz), 3.00–5.32 (2H, m), 3.69 (2H, s), 6.46–8.05 (10H, m)

28) ¹H-NMR (CDCl₃) δ: 1.47–2.92, 3.44–4.11 (total 21H, m), 4.66–5.12 (1H, m), 5.85–6.30 (1H, m), 6.61–8.10 (11H, m) [α]_D²⁴=+90° (methanol, c=0.2) (measured for hydrochloride)

29) ¹H-NMR (CDCl₃) δ: 1.48–2.88, 3.45–4.09 (total 21H, m), 4.60–5.05 (1H, m), 5.85–6.31 (1H, m), 6.62–7.78 (10H, m), 7.92–8.41 (1H, m) [α]_D²⁴=−107° (methanol, c=0.2) (measured for hydrochloride)

30) ¹H-NMR (CDCl₃) δ: 1.21–3.06, 3.40–3.87 (total 14H, m), 4.54–5.05 (1H, m), 5.88–6.22 (1H, m), 6.83–8.09, 8.33–8.59, 8.82–9.03 (total 12H, m) [α]_D²⁴=+90° (methanol, c=0.2) (measured for hydrochloride)

31) ¹H-NMR (CDCl₃) δ: 1.50–3.22, 3.54–3.99 (total 16H, m), 4.41–4.90 (1H, m), 5.88–6.22 (1H, m), 6.79–8.04 (11H, m), 9.05–9.63 (1H, m) [α]_D²⁴=+54° (methanol, c=0.2) (measured for hydrochloride)

32) ¹H-NMR (CDCl₃) δ: 1.51–4.12 (16H, m), 4.60–5.17 (1H, m), 5.89–5.29 (1H, m), 6.71–8.50, 9.85–10.36 (total 12H, m) [α]_D²⁴=−68° (methanol, c=0.2) (measured for hydrochloride)

33) ¹H-NMR (CDCl₃) δ: 1.04–4.63 (20H, m), 6.42–7.74 (11H, m)

34) ¹H-NMR (CDCl₃) δ: 1.08–2.23 (4H, m), 2.23–2.55 (6H, m), 2.55–3.00 (2H, m), 3.00–5.10 (3H, m), 6.68–7.90 (10H, m), 10.13–10.50 (1H, m)

35) ¹H-NMR (CDCl₃) δ: 1.49–2.43 (3H, m), 2.43–2.61 (6H, m), 2.61–2.92 (2H, m), 2.92–3.99 (3H, m), 4.48–4.97 (1H, m), 5.80 (1H, brs), 6.44 (1H, brs), 6.53–7.83 (11H, m)

36) ¹H-NMR (CDCl₃) δ: 1.43–2.38 (3H, m), 2.38–2.77 (8H, m), 2.77–3.33 (8H, m), 3.33–5.10 (2H, m), 6.36–8.04 (11H, m)

37) ¹H-NMR (CDCl₃) δ: 1.43–2.13 (2H, m), 3.13–2.63 (7H, m), 2.63–3.75 (2H, m), 3.75–4.82 (4H, m), 4.97–5.50 (2H, m), 5.83–6.15 (1H, m), 6.51–7.73 (11H, m)

38) Isomer A; colorless and amorphous ¹H-NMR (CDCl₃) δ: 0.95–4.18, 4.61–5.18 (total 19H, m), 5.85–6.29 (1H, m); 6.90–8.35 (12H, m)

Isomer B; colorless and amorphous ¹H-NMR (CDCl₃) δ: 0.94–4.33, 4.61–5.23 (total 19H, m), 5.84–6.28 (1H, m), 6.76–7.91 (11H, m), 9.25–9.76 (1H, m)

39) Isomer A; colorless and amorphous ¹H-NMR (CDCl₃) δ: 1.46–2.98, 3.22–4.05 (total 21H, m), 4.67–5.19 (1H, m), 5.79–6.22 (1H, m), 6.50–7.81 (11H, m)

[α]_D²⁴=+112° (methanol, C=0.2) (measured for hydrochloride)

Isomer B; colorless and amorphous ¹H-NMR (CDCl₃) 1.42–2.98, 3.30–4.01 (total 21H, m), 4.58–5.20 (1H, m), 5.85–6.21 (1H, m), 6.43–8.14 (11H, m)

[α]_D²⁴—143° (methanol, C=0.2) (measured for hydrochloride)

40) ¹H-NMR (CDCl₃) δ: 1.30–2.30 (4H, m), 2.31 (3H, s), 2.95–3.54 (3H, m), 2.71 (2H, s), 2.80–4.60 (2H, m), 5.01–5.39 (2H, m), 5.70–6.05 (1H, m), 6.41–6.63 (1H, m), 6.80–7.43 (9H, m), 7.50–7.67 (1H, m)

41) ¹H-NMR (CDCl₃) δ: 1.49–1.97 (2H, m), 2.02–2.30 (2H, m), 2.30–2.61 (12H, m), 2.68–2.95 (1H, m), 3.11–3.49 (2H, m), 3.62–3.86 (2H, m), 4.68–5.15 (1H, m), 5.90–6.19 (1H, m), 6.41–6.60 (1H, m), 6.60–7.02 (3H, m), 7.05–7.40 (6H, m), 7.40–7.52 (1H, m)

42) ¹H-NMR (CDCl₃) δ: 1.55–1.94 (2H, m), 1.95–2.59 (14H, m), 2.60–2.91 (1H, m), 2.91–3.47 (2H, m), 3.75 (2H, s), 4.60–5.20 (1H, m), 5.90–6.22 (1H, m), 6.40–6.66 (1H, m), 6.72–7.41 (9H, m), 7.77–8.04 (1H, m)

43) ¹H-NMR (CDCl₃) δ: 1.53–1.94 (2H, m), 2.0–2.25 (2H, m), 2.25–2.52 (9H, m), 2.58–2.92 (1H, m), 3.07–3.41 (2H, m), 3.53 (3H, s), 3.60–3.91 (2H, m), 4.66–5.13 (1H, m), 6.39–7.55 (10H, m), 7.60–7.80 (1H, m)

44) ¹H-NMR (CDCl₃) δ: 1.62–1.98 (2H, m), 1.98–2.58 (11H, m), 2.64–2.98 (1H, m), 2.99–3.44 (2H, m), 3.44–3.60 (3H, m), 3.72 (2H, s), 4.60–5.21 (1H, m), 5.91–6.28 (1H, m), 6.44–7.120 (4H, m), 7.10–7.49 (5H, m), 7.72 (1H, s), 8.00–8.36 (1H, m)

45) Isomer A; Colorless and amorphous ¹H-NMR (CDCl₃) δ: 0.67–3.62, 4.67–5.20 (total 22H, m), 5.87–6.31 (1H, m), 6.49–7.85 (11H, m)

[α]_D²⁴ =−133° (methanol, C=0.2) (measured for hydrochloride)

Isomer B; Colorless and amorphous ¹H-NMR (CDCl₃) δ: 0.81–3.65, 4.65–5.18 (total 22H, m), 5.86–6.28 (1H, m), 6.44–8.03 (11H, m)

$[\alpha]_D^{24}$=+126° (methanol, C=0.2) (measured for hydrochloride)

Example 86

0.85 g of 60% sodium hydride was added to 200 ml of tetrahydrofuran. Thereto was dropwise added 4.68 ml of ethyl diethylphosphonoacetate with ice-cooling and stirring. The mixture was stirred for 10 minutes with ice-cooling. To the reaction mixture was added 2.10 g of 5-oxo-7-chloro-1-[2-methyl-4-(2-methylbenzoylamino)benzoyl]-2,3,4,5-tetra-hydro-1H-benzoazepine. The mixture was stirred at room temperature for 6 hours. The reaction mixture was poured into 200 ml of ice water. The resulting mixture was subjected to extraction with 300 ml of ethyl acetate. The extract was washed with 300 ml of an aqueous sodium chloride solution, then dried over magnesium sulfate, and subjected to distillation to remove the solvent. The residue was purified by silica gel column chromatography (elutant: ethyl acetate/n-hexane=1/2) to obtain 2.22 g of 5-ethoxycarbonylmethylidene-7-chloro-1-[2-methyl-4-(2-methylbenzoyl-amino)benzoyl]-2,3,4,5-tetrahydro-1H-benzoazepine as a mixture of the E form and the Z form.

Colorless and amorphous $^1$H-NMR (CDCl$_3$) δ: 1.04–5.10 (17H, m), 5.96–6.17 (1H, m), 6.52–7.86 (11H, m)

Example 87

In 30 ml of a 1:1 mixture of tetrahydrofuran and methanol were dissolved 0.30 g of 5-ethoxycarbonylmethylidene-7-chloro-1-[2-methyl-4-(2-methylbenzoylamino)-benzoyl]-2,3,4,5-tetrahydro-1H-benzoazepine and 0.55 g of nickel chloride hexahydrate. Thereto was slowly added 0.26 g of sodium borohydride with ice-cooling and stirring. The mixture was stirred for 10 minutes with ice-cooling. The resulting insolubles were removed by filtration with Celite. The filtrate was concentrated. The residue was purified by silica gel column chromatography (elutant: ethyl acetate/n-hexane=1/1) to obtain 0.13 g of 5-ethoxycarbonylmethyl-7-chloro-1-[2-methyl-4-(2-methylbenzoylamino)benzoyl]-2,3,4,5-tetrahydro-1H-benzoazepine.

Colorless and amorphous $^1$H-NMR (CDCl$_3$) δ: 1.04–4.63 (20H, m), 6.42–7.74 (11H, m)

Example 88

672 mg of N-benzyloxycarbonyl-L-valine and 1.42 g of dicyclohexylcarbodiimide were added to a solution of 1.0 g of 5-hydroxy-7-chloro-1-[2-methyl-4-(2-methylbenzoylamino)benzoyl]-2,3,4,5-tetrahydro-1H-benzoazepine, 1.26 g of dimethylaminopyridine and 1.10 g of dimethylaminopyridine hydrochloride dissolved in 20 ml of chloroform. The mixture was stirred at room temperature for 7 hours. Thereto were added 3 ml of methanol and 0.7 ml of acetic acid, and the mixture was stirred at room temperature for 30 minutes. The resulting insolubles were removed by filtration. To the filtrate was added a 5% aqueous sodium hydrogensulfate solution. The mixture was subjected to extraction with dichloromethane. The extract was washed with a saturated aqueous sodium hydrogencarbonate solution and a saturated aqueous sodium chloride solution in this order, then dried over magnesium sulfate, and subjected to vacuum distillation to remove the solvent to obtain 2.0 g of crude 5-N-benzyl-oxycarbonyl-L-valyloxy-7-chloro-1-[2-methyl-4-(2-methyl-benzoylamino)benzoyl]-2,3,4,5-tetrahydro-1H-benzoazepine. This crude product was dissolved in a mixed solvent consisting of 15 ml of acetic acid and 15 ml of ethyl acetate. To the solution was added 0.3 g of 5% Pd-C. The mixture was subjected to hydrogenolysis at normal temperature at normal pressure. Then, the catalyst was removed by filtration. The filtrate was concentrated. The residue was purified by silica gel column chromatography (elutant: ethyl acetate) to obtain 0.48 g of an isomer A and 0.47 g of an isomer B both of 5-L-valyloxy-7-chloro-1-[2-methyl-4-(2-methylbenzoylamino)benzoyl]-2,3,4,5-tetrahydro-1H-benzoazepine.

Isomer A

Rf value: 0.3 (developer: ethyl acetate/methanol=10/1)

$^1$H-NMR (CDCl$_3$) δ: 0.67–3.62, 4.67–5.20 (total 22H, m), 5.87–6.31 (1H, m), 6.49–7.85 (11H, m)

$[\alpha]_D^{24}$=−133° (methanol, c=0.2) (measured for hydrochloride)

Isomer B

Rf value: 0.4 (developer: ethyl acetate/methanol=10/1)

$^1$H-NMR (CDCl$_3$) δ: 0.81–3.65, 4.65–5.18 (total 22H,m), 5.86–6.28 (1H, m), 6.44–8.03 (11H, m)

$[\alpha]_D^{24}$=+126° (methanol, c=0.2) (measured for hydrochloride)

Example 89

A uniform solution of 1.27 g of 5-(N-tert-butoxycarbonyl-L-methionyloxy)-7-chloro-1-[2-methoxy-4-(2-methylbenzoylamino)benzoyl]-2,3,4,5-tetrahydro-1H-benzo-azepine, 2.5 ml of trifluoroacetic acid and 0.6 ml of anisole was stirred at room temperature for 2 hours. The most part of trifluoroacetic acid was removed by distillation under reduced pressure. To the residue was added a 0.2N aqueous sodium hydroxide solution to make the residue alkaline. The mixture was subjected to extraction with dichloromethane. The dichloromethane layer was water-washed, then dried over magnesium sulfate and concentrated. The residue was purified by silica gel column chromatography (elutant: ethyl acetate) to obtain 0.34 g of an isomer A and 0.35 g of an isomer B both of 5-(L-methionyloxy)-7-chloro-1-[2-methoxy-4-(2-methylbenzoylamino)benzoyl]-2,3,4,5-tetrahydro-1H-benzoazepine.

Isomer A

Colorless and amorphous

Rf value: 0.5 (developer: ethyl acetate/methanol=10/1)

$^1$H-NMR (CDCl$_3$) δ: 1.47–2.92, 3.44–4.11 (total 21H, m), 4.66–5.12 (1H, m), 5.85–6.30 (1H, m), 6.61–8.10 (11H, m)

$[\alpha]_D^{24}$=+96° (methanol, c=0.2) (measured for hydrochloride)

Isomer B

Colorless and amorphous

Rf value: 0.4 (developer: ethyl acetate/methanol=10/1)

$^1$H-NMR (CDCl$_3$) δ: 1.48–2.88, 3.45–4.09 (total 21H, m), 4.60–5.05 (1H, m), 5.85–6.31 (1H, m), 6.62–7.78 (10H, m), 7.92–8.41 (1H, m)

$[\alpha]_D^{24}$=−107° (methanol, c=0.2) (measured for hydrochloride)

Tables 43 to 109 (Examples 90 to 221) and their NMR data appear here.

The following compounds were obtained in the same manner as in Examples 1 and 2, using respective raw materials.

TABLE 43
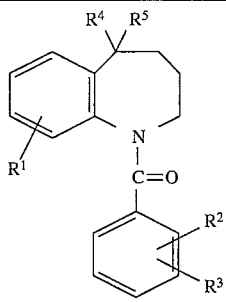
Example 90
Structure:
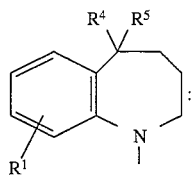
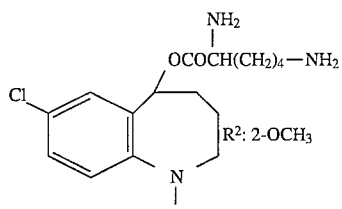
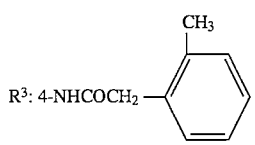
R³: 4-NHCOCH₂—
Crystal form: colorless and amorphous
Form: dihydrochloride
NMR: 46)
TABLE 44
Example 91
Structure:
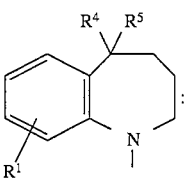
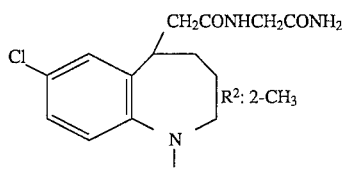
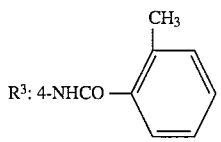
R³: 4-NHCO—
Crystal form: colorless and amorphous
Form: free
NMR: 47)
Example 92
Structure:
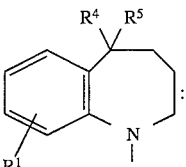
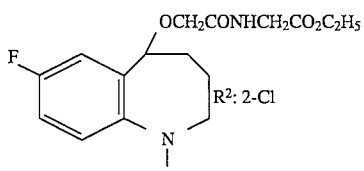
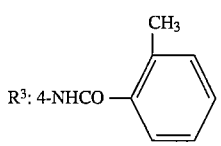
R³: 4-NHCO—
Crystal form: colorless and amorphous
Form: free
NMR: 48)

TABLE 45

Example 93
Structure:

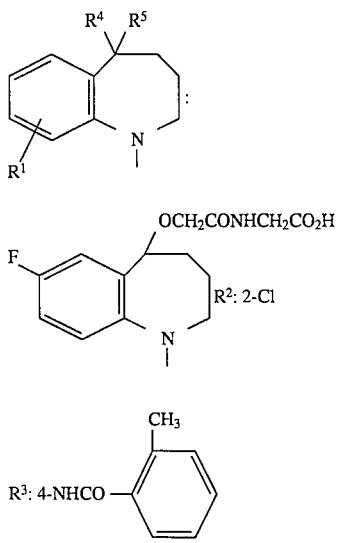

R²: 2-Cl

R³: 4-NHCO—[o-tolyl with CH₃]

Crystal form: colorless and amorphous
Form: free
NMR: 49)

Example 94
Structure:

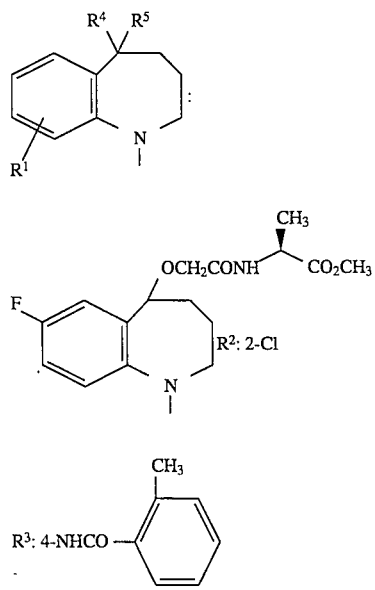

R²: 2-Cl

R³: 4-NHCO—[o-tolyl with CH₃]

Crystal form: colorless and amorphous
Form: free
NMR: 50)

TABLE 46

Example 95
Structure:

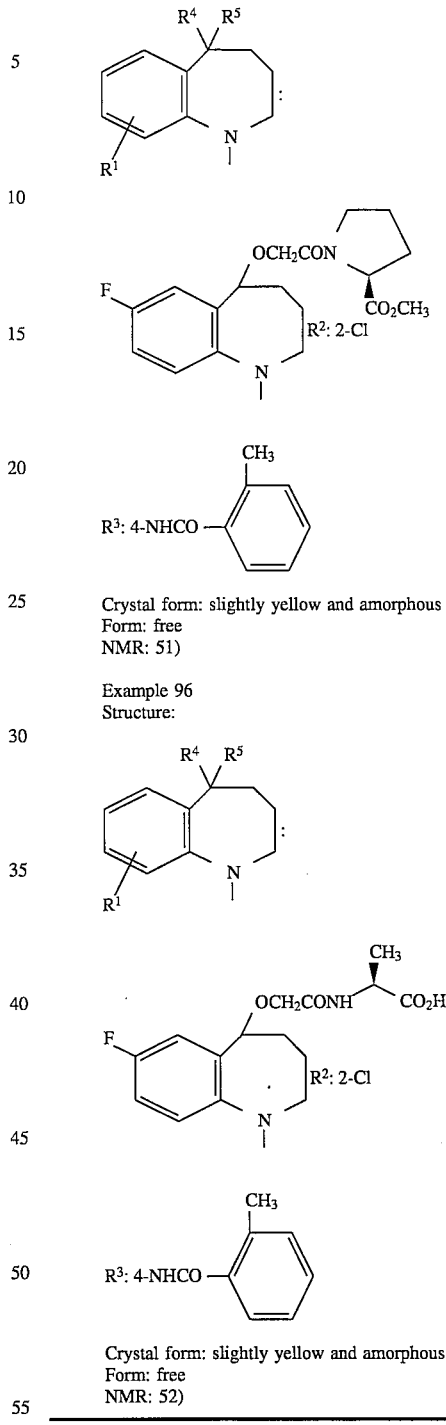

R²: 2-Cl

R³: 4-NHCO—[o-tolyl with CH₃]

Crystal form: slightly yellow and amorphous
Form: free
NMR: 51)

Example 96
Structure:

R²: 2-Cl

R³: 4-NHCO—[o-tolyl with CH₃]

Crystal form: slightly yellow and amorphous
Form: free
NMR: 52)

TABLE 47

Example 97
Structure:

TABLE 47-continued

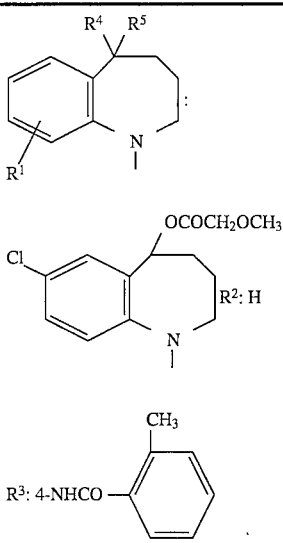

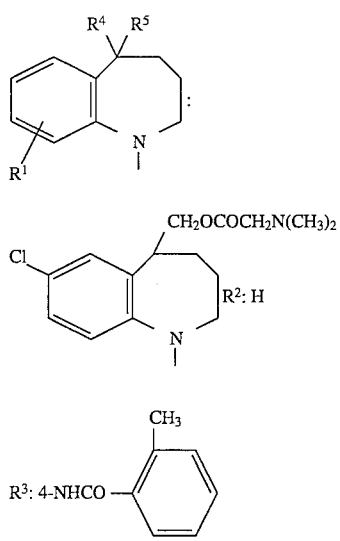

Crystal form: white powder
Recrystallization solvent: dichloromethane-diethyl ether
Melting point: 149–152° C.
Form: free Example 98
Structure:

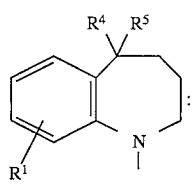

Crystal form: colorless and amorphous
Form: hydrochloride
NMR: 53)

TABLE 48

Example 99
Structure:

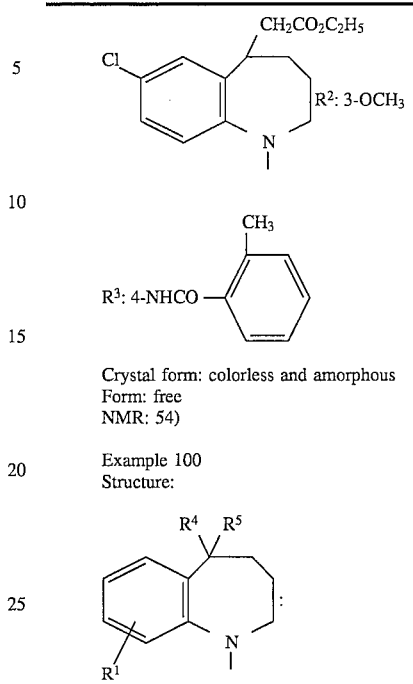

Crystal form: colorless and amorphous
Form: free
NMR: 54)

Example 100
Structure:

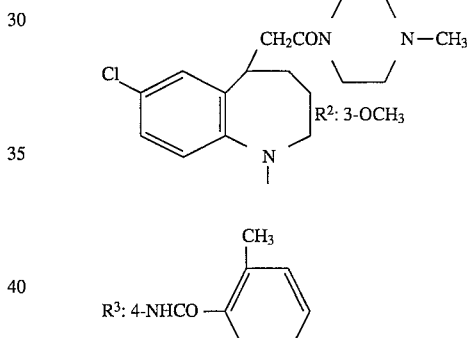

Crystal form: colorless and amorphous
Recrystallization solvent: ethanol-diethyl ether-n-hexane
Melting point: 182–184° C.
Form: free

TABLE 49

Example 101
Structure:

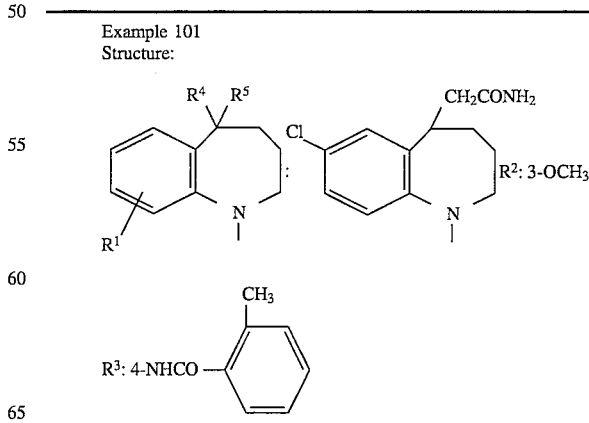

TABLE 49-continued

Crystal form: colorless and amorphous
Form: free
NMR: 55)

Example 102
Structure:

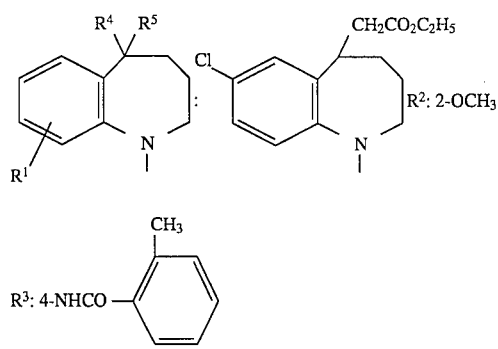

R³: 4-NHCO— (with CH₃ on phenyl ring)

Crystal form: colorless prism
Recrystallization solvent: ethanol
Melting point: 191–193° C.
Form: free

TABLE 50

Example 103
Structure:

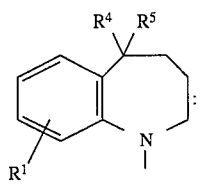

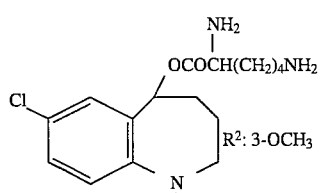

R³: 4-NHCO— 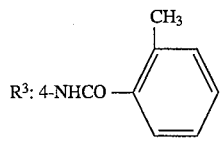

Crystal form: colorless and amorphous
Form: dihydrochloride
NMR: 56)

Example 104
Structure:

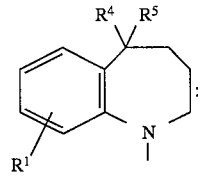

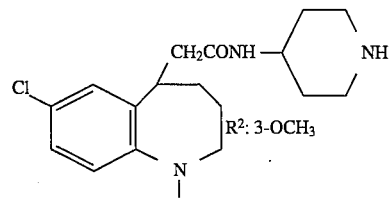

R³: 4-NHCO— 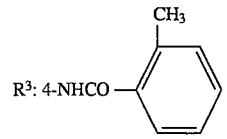

Crystal form: colorless and amorphous
Form: hydrochloride
NMR: 57)

TABLE 51

Example 105
Structure:

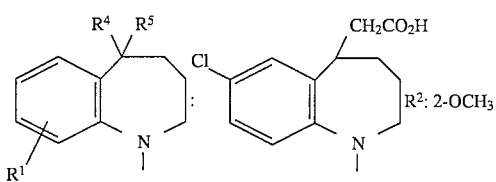

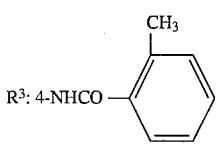

R³: 4-NHCO—

Crystal form: white powder
Recrystallization solvent: ethyl acetate
Melting point: 243.5–244.5° C.
Form: free Example 106
Structure:

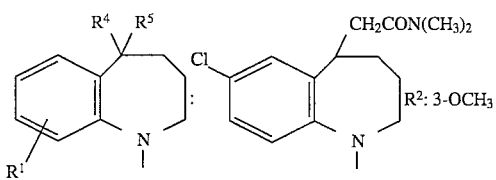

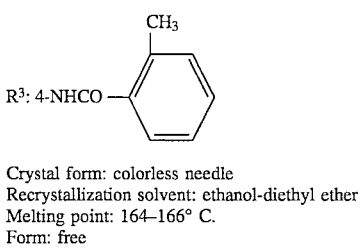

Crystal form: colorless needle
Recrystallization solvent: ethanol-diethyl ether
Melting point: 164–166° C.
Form: free

TABLE 52

Example 107
Structure:

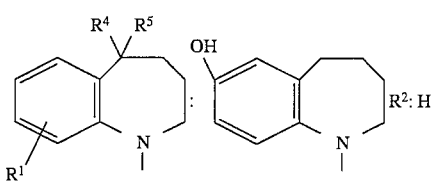

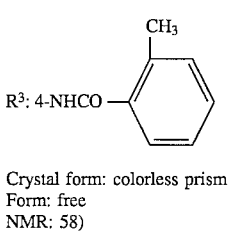

Crystal form: colorless prism
Form: free
NMR: 58)

TABLE 52-continued

Example 108
Structure:

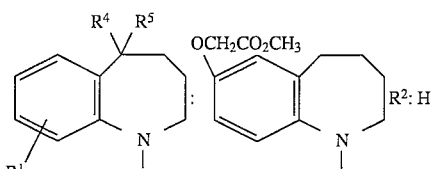

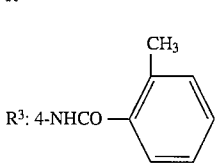

R³: 4-NHCO—

Crystal form: colorless needle
Recrystallization solvent: methanol-diethyl ether
Melting point: 141–144° C.
Form: free

TABLE 53

Example 109
Structure:

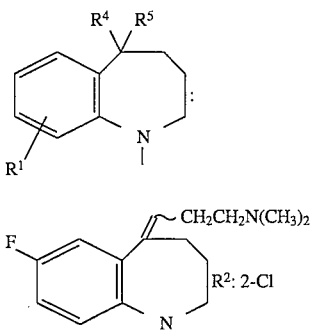

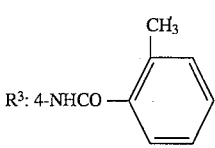

R³: 4-NHCO—

Crystal form: yellow and amorphous
Form: hydrochloride
NMR: 59)

Example 110
Structure:

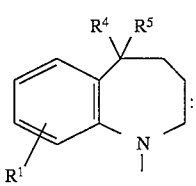

TABLE 53-continued

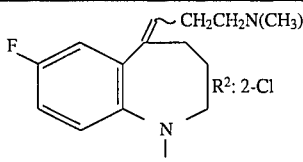

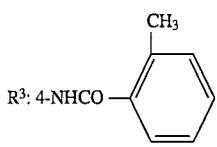

Crystal form: yellow and amorphous
Form: hydrochloride
NMR: 60)

TABLE 54

Example 111
Structure:

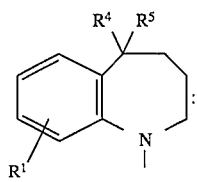

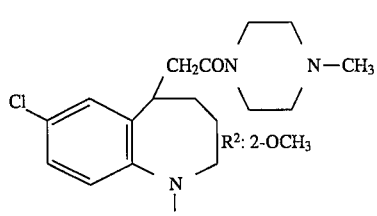

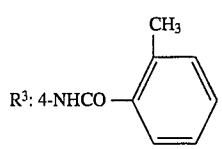

Crystal form: colorless and amorphous
Form: hydrochloride
NMR: 61)

Example 112
Structure:

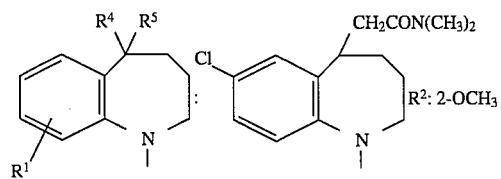

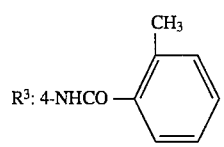

Crystal form: colorless and amorphous
Form: free

TABLE 54-continued

NMR: 62)

TABLE 55

Example 113
Structure:

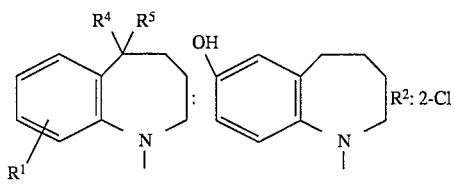

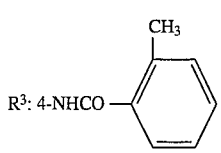

Crystal form: white powder
Recrystallization solvent: ethanol-chloroform
Melting point: 254–258° C.
Form: free Example 114
Structure:

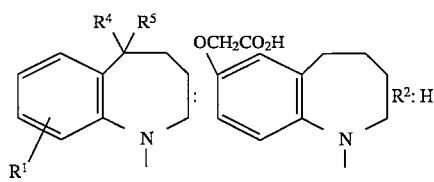

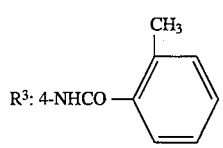

Crystal form: white powder
Recrystallization solvent: ethanol
Melting point: 258–261° C.
Form: free

TABLE 56

Example 115
Structure:

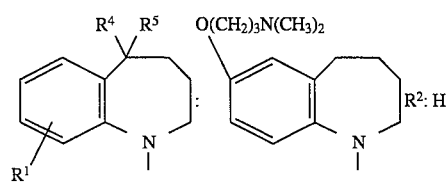

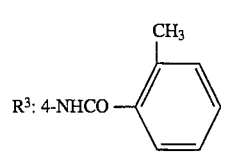

Crystal form: colorless and amorphous

TABLE 56-continued

Form: free
NMR: 63)

Example 116
Structure:

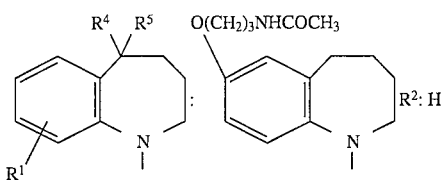

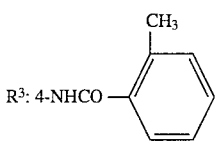

Crystal form: colorless and amorphous
Form: free
NMR: 64)

TABLE 57

Example 117
Structure:

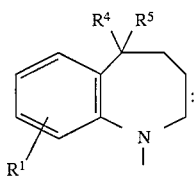

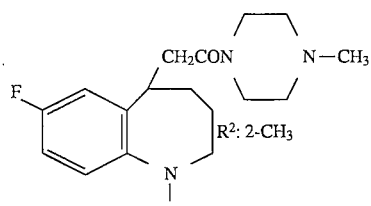

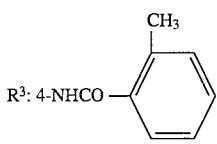

Crystal form: colorless and amorphous
Form: free
NMR: 65)

Example 118
Structure:

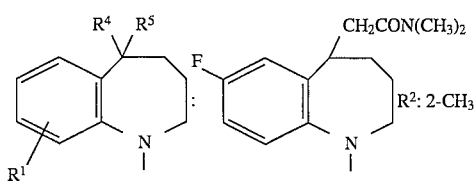

TABLE 57-continued

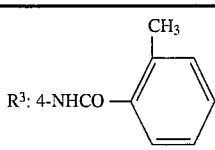

Crystal form: colorless and amorphous
Form: free
NMR: 66)

TABLE 58

Example 119
Structure:

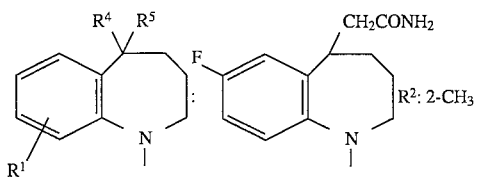

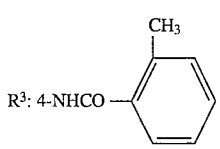

Crystal form: white powder
Recrystallization solvent: ethanol-water
Melting point: 260–263° C. (decomposed)
Form: free Example 120
Structure:

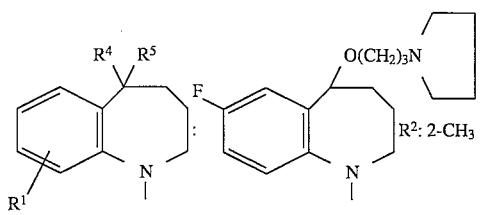

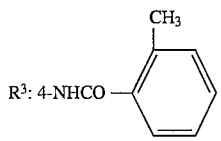

Crystal form: colorless and amorphous
Form: free
NMR: 67)

TABLE 59

Example 121
Structure:

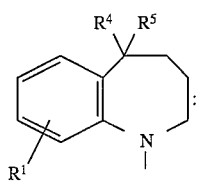

TABLE 59-continued

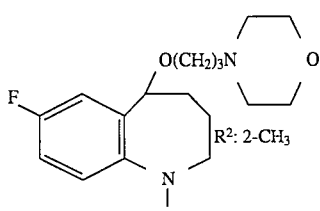

R²: 2-CH₃

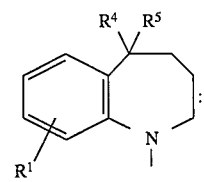

R³: 4-NHCO—

Crystal form: colorless and amorphous
Form: free
NMR: 68)

Example 122
Structure:

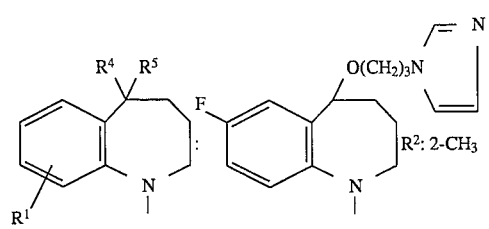

R²: 2-CH₃

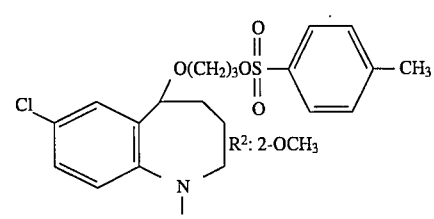

R³: 4-NHCO—

Crystal form: colorless and amorphous
Form: free
NMR: 69)

TABLE 60

Example 123
Structure:

TABLE 60-continued

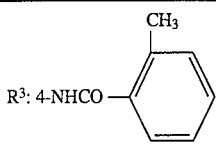

R³: 4-NHCO—

Crystal form: colorless and amorphous
Form: free
NMR: 70)

Example 124
Structure:

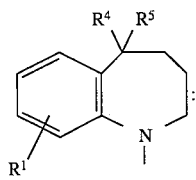

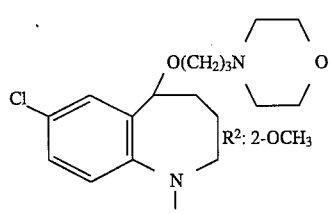

R²: 2-OCH₃

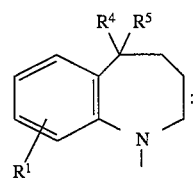

R³: 4-NHCO—

Crystal form: light yellow and amorphous
Form: hydrochloride
NMR: 71)

TABLE 61

Example 125
Structure:

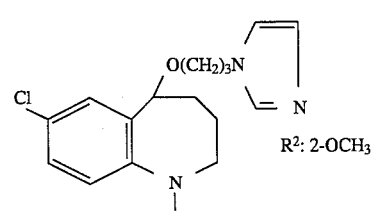

R²: 2-OCH₃

R³: 4-NHCO—

TABLE 61-continued

Crystal form: colorless and amorphous
Form: hydrochloride
NMR: 72)

Example 126
Structure:

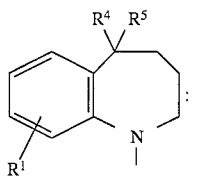

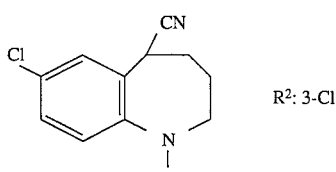 R²: 3-Cl

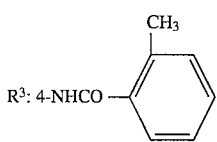 R³: 4-NHCO—

Crystal form: colorless prism
Recrystallization solvent: ethanol-dichloromethane
Melting point: 213–215.5° C.
Form: free

TABLE 62

Example 127
Structure:

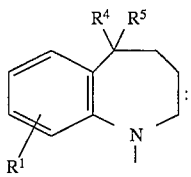

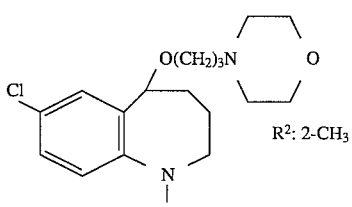 R²: 2-CH₃

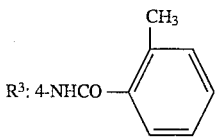 R³: 4-NHCO—

Crystal form: colorless and amorphous
Form: hydrochloride
NMR: 73)

TABLE 62-continued

Example 128
Structure:

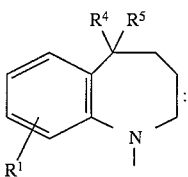

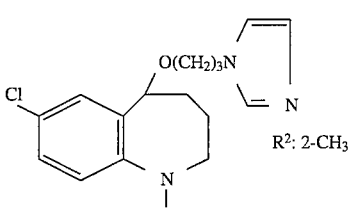 R²: 2-CH₃

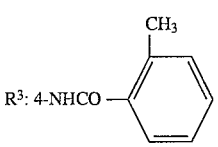 R³: 4-NHCO—

Crystal form: colorless and amorphous
Form: dihydrochloride
NMR: 74)

TABLE 63

Example 129
Structure:

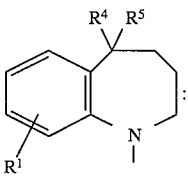

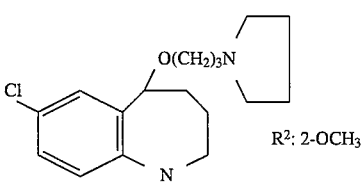 R²: 2-OCH₃

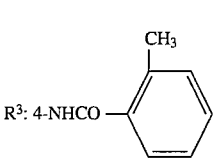 R³: 4-NHCO—

Crystal form: slightly yellow and amorphous
Form: hydrochloride
NMR: 75)

TABLE 63-continued

Example 130
Structure:

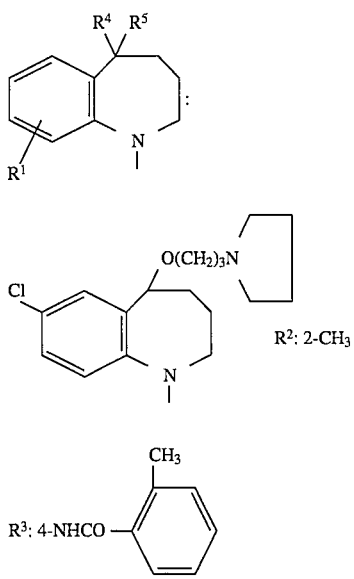

$R^2$: 2-CH$_3$ $R^3$: 4-NHCO-

Crystal form: slightly yellow and amorphous
Form: hydrochloride
NMR: 76)

TABLE 64

Example 131
Structure:

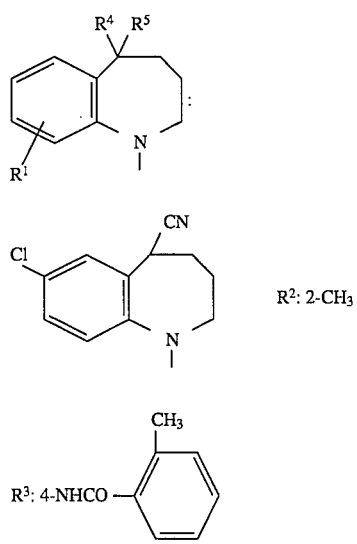

$R^2$: 2-CH$_3$ $R^3$: 4-NHCO-

Crystal form: colorless and amorphous
Form: free
NMR: 77)

Example 132
Structure:

TABLE 64-continued

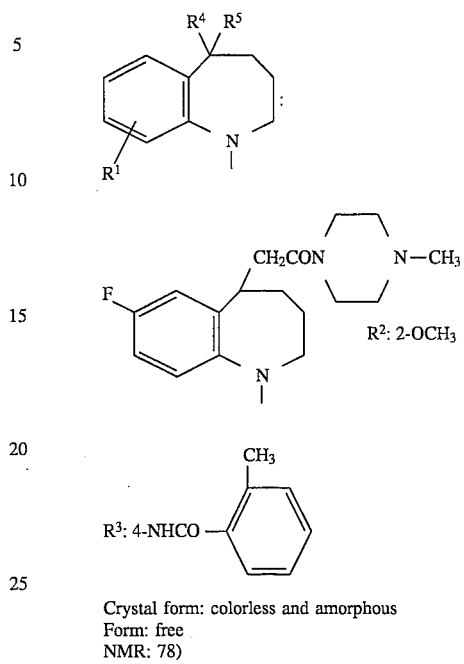

$R^2$: 2-OCH$_3$ $R^3$: 4-NHCO-

Crystal form: colorless and amorphous
Form: free
NMR: 78)

TABLE 65

Example 133
Structure:

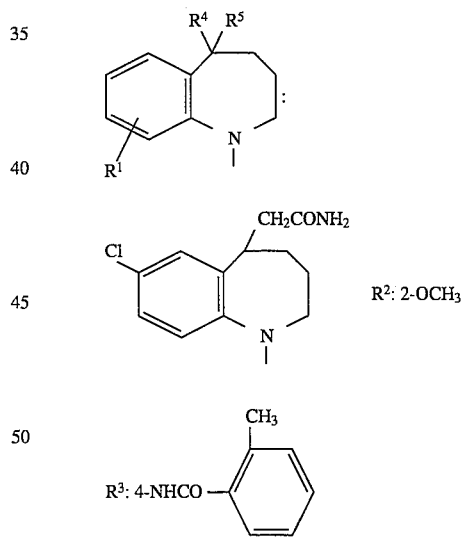

$R^2$: 2-OCH$_3$ $R^3$: 4-NHCO-

Crystal form: colorless needle
Recrystallization solvent: dichloromethane-methanol
Form: free
Melting point: 202.5–203.5° C.

TABLE 65-continued

Example 134
Structure:

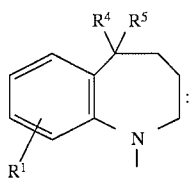

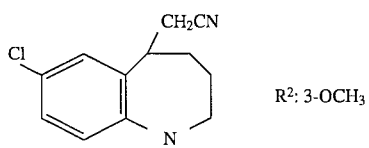   R²: 3-OCH₃

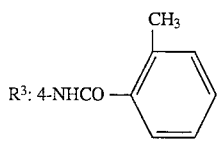   R³: 4-NHCO—

Crystal form: colorless needle
Recrystallization solvent: ethyl acetate-diethyl ether
Form: free
Melting point: 164–167° C.

TABLE 66

Example 135
Structure:

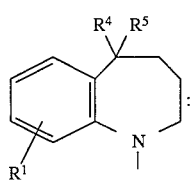

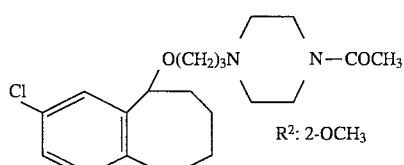   R²: 2-OCH₃

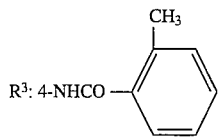   R³: 4-NHCO—

Crystal form: light yellow and amorphous
Form: hydrochloride
NMR: 79)

TABLE 66-continued

Example 136
Structure:

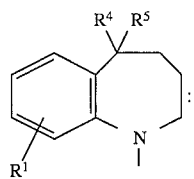

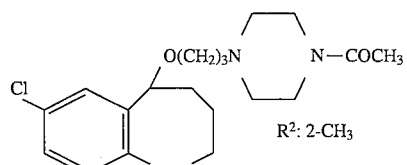   R²: 2-CH₃

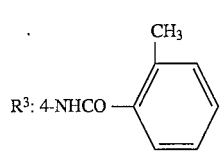   R³: 4-NHCO—

Crystal form: colorless and amorphous
Form: hydrochloride
NMR: 80)

TABLE 67

Example 137
Structure:

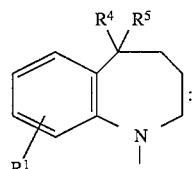

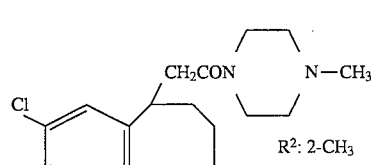   R²: 2-CH₃

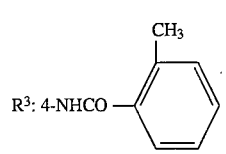   R³: 4-NHCO—

Crystal form: colorless and amorphous
Form: hydrochloride
NMR: 81)

TABLE 67-continued

Example 138
Structure:

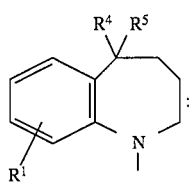

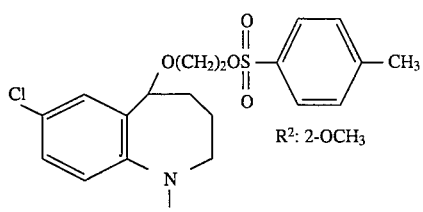

R²: 2-OCH₃

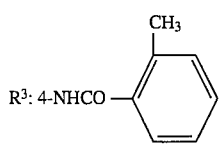

R³: 4-NHCO

Crystal form: colorless and amorphous
Form: free
NMR: 82)

TABLE 68

Example 139
Structure:

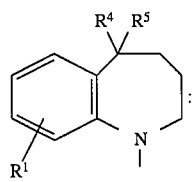

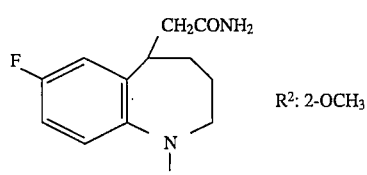

R²: 2-OCH₃

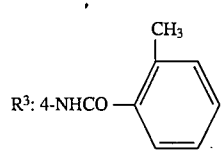

R³: 4-NHCO

Crystal form: white powder
Recrystallization solvent: ethanol-water
Melting point: 260–261° C.
Form: free

TABLE 68-continued

Example 140
Structure:

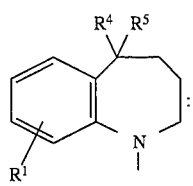

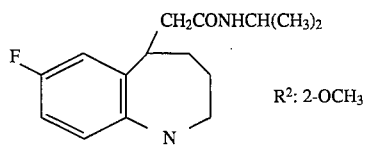

R²: 2-OCH₃

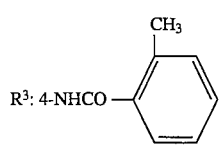

R³: 4-NHCO

Crystal form: colorless and amorphous
Form: free
NMR: 83)

TABLE 69

Example 141
Structure:

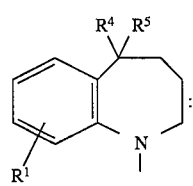

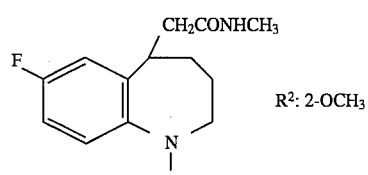

R²: 2-OCH₃

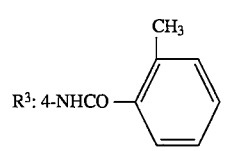

R³: 4-NHCO

Crystal form: colorless and amorphous
Form: free
NMR: 84)

Example 142
Structure:

TABLE 69-continued

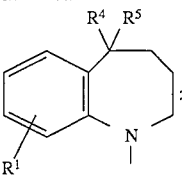

Crystal form: colorless and amorphous
Form: free
NMR: 85)

TABLE 70

Example 143
Structure:

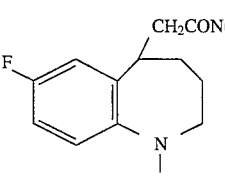

Crystal form: colorless and amorphous
Form: dihydrochloride
NMR: 86)

Example 144
Structure:

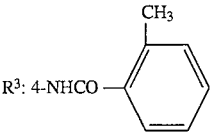

TABLE 70-continued

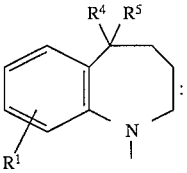

Crystal form: colorless and amorphous
Form: hydrochloride
NMR: 87)

TABLE 71

Example 145
Structure:

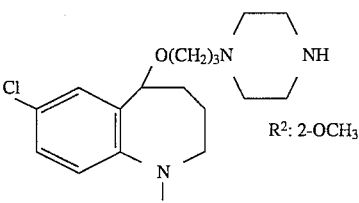

Crystal form: colorless and amorphous
Form: hydrochloride
NMR: 88)

Example 146
Structure:

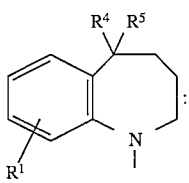

TABLE 71-continued
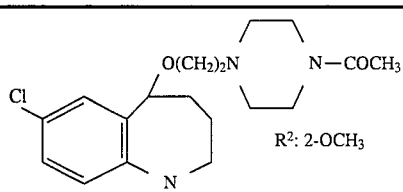
R²: 2-OCH₃
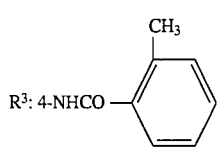
R³: 4-NHCO—
Crystal form: light yellow and amorphous
Form: hydrochloride
NMR: 89)
TABLE 72
Example 147
Structure:
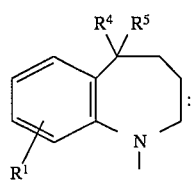
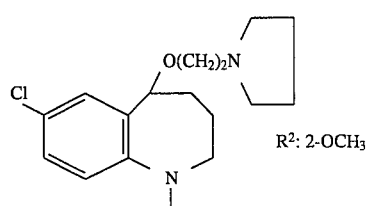
R²: 2-OCH₃
TABLE 72-continued
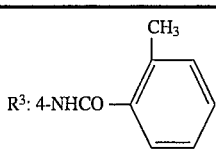
R³: 4-NHCO—
Crystal form: light yellow and amorphous
Form: hydrochloride
NMR: 90)
Example 148
Structure:
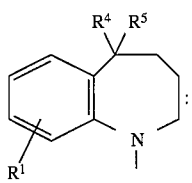
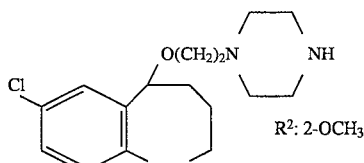
R²: 2-OCH₃
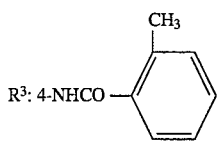
R³: 4-NHCO—
Crystal form: colorless and amorphous
Form: dihydrochloride
NMR: 91)

TABLE 73

Example 149
Structure:

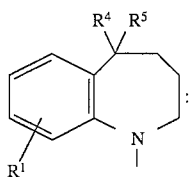

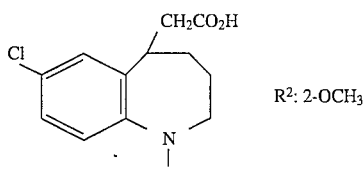 R²: 2-OCH₃

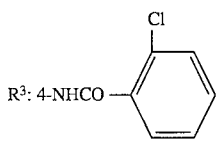

R³: 4-NHCO—

Crystal form: white powder
Recrystallization solvent: dichloromethane-diethyl ether
Melting Point: 190–193° C.
Form: free Example 150
Structure:

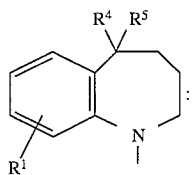

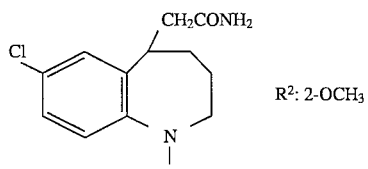 R²: 2-OCH₃

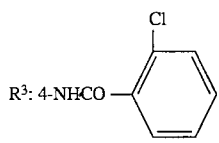

R³: 4-NHCO—

Crystal form: colorless prism
Recrystallization solvent: ethanol-hexane
Melting Point: 168–175° C.
Form: free
NMR: 92)

TABLE 74

Example 151
Structure:

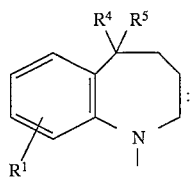

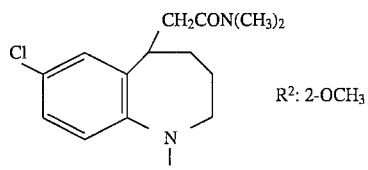 R²: 2-OCH₃

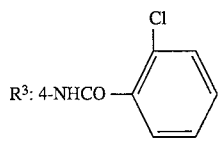

R³: 4-NHCO—

Crystal form: colorless prism
Recrystallization solvent: ethyl acetate-diethyl ether
Melting Point: 153–155° C.
Form: free Example 152
Structure:

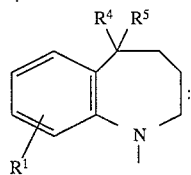

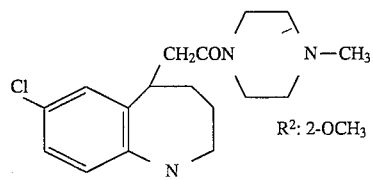 R²: 2-OCH₃

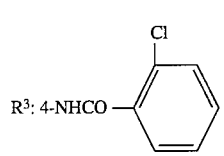

R³: 4-NHCO—

Crystal form: colorless and amorphous
Form: hydrochloride
NMR: 93)

TABLE 75
Example 153
Structure:
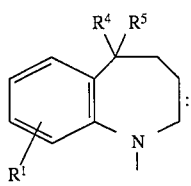
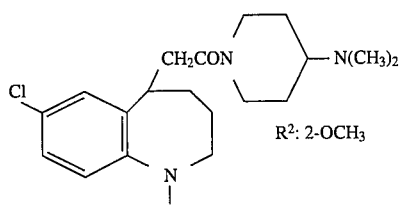
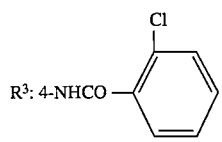
Crystal form: colorless and amorphous
Form: hydrochloride
NMR: 94)
Example 154
Structure:
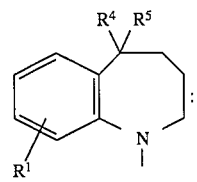
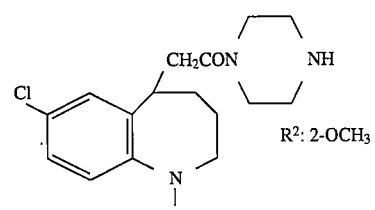
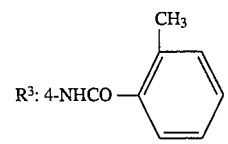
Crystal form: colorless and amorphous
Form: hydrochloride
NMR: 95)
TABLE 76
Example 155
Structure:
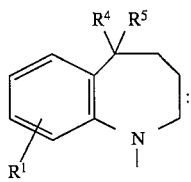
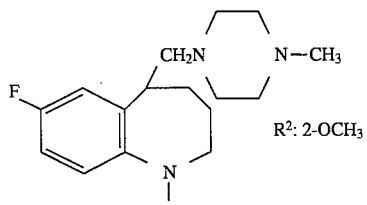
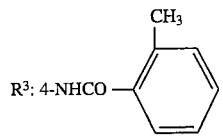
Crystal form: colorless and amorphous
Form: free
NMR: 96)
Example 156
Structure:
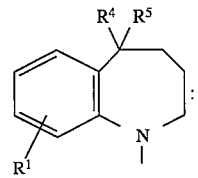
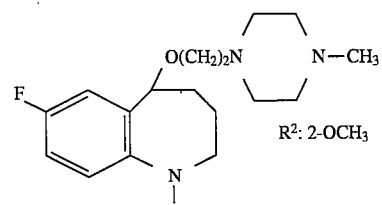
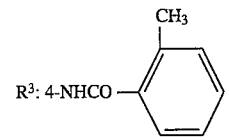
Crystal form: colorless and amorphous
Form: free
NMR: 97)

TABLE 77

Example 157
Structure:

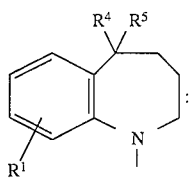

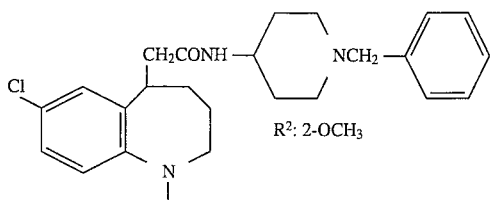

R²: 2-OCH₃

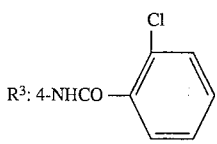

R³: 4-NHCO—

Crystal form: colorless and amorphous
Form: hydrochloride
NMR: 98)

Example 158
Structure:

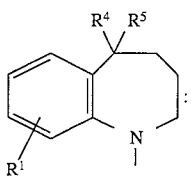

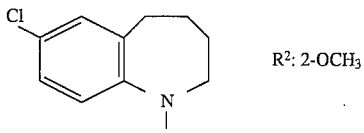

R²: 2-OCH₃

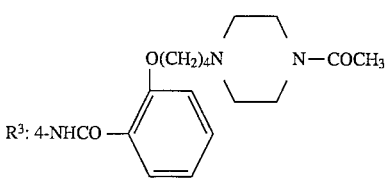

R³: 4-NHCO—

Crystal form: colorless needle
Recrystallization solvent: ethanol-diethyl ether
Melting point: 99–102° C.
Form: free

TABLE 78

Example 159
Structure:

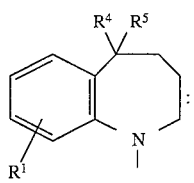

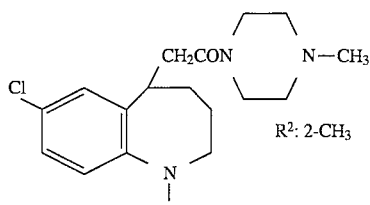

R²: 2-CH₃

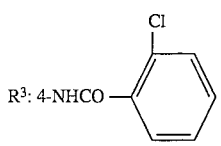

R³: 4-NHCO—

Crystal form: colorless and amorphous
Form: hydrochloride
NMR: 99)

Example 160
Structure:

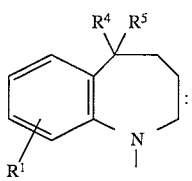

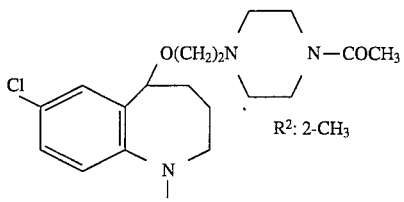

R²: 2-CH₃

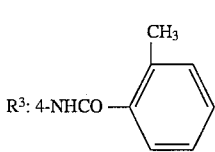

R³: 4-NHCO—

Crystal form: slightly yellow and amorphous
Form: hydrochloride
NMR: 100)

TABLE 79

Example 161
Structure:

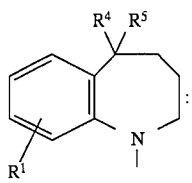

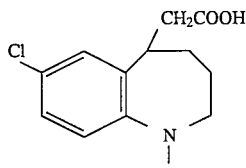  R²: 2-Cl

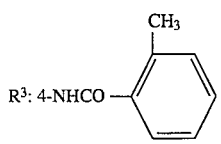

Crystal form: white powder
Recrystallization solvent: ethyl acetate-diethyl ether
Melting point: 227° C.
Form: free
NMR: 101)

Example 162
Structure:

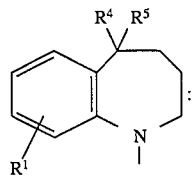

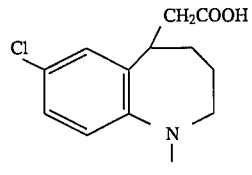  R²: 2-CH₃

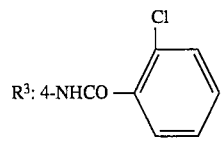

Crystal form: white powder
Recrystallization solvent: ethyl acetate-n-hexane
Melting point: 231–232° C.
Form: free
NMR: 102)

TABLE 80

Example 163
Structure:

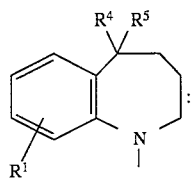

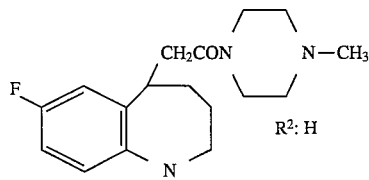  R²: H

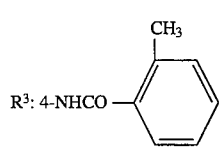

Crystal form: colorless and amorphous
Form: free
NMR: 103)

Example 164
Structure:

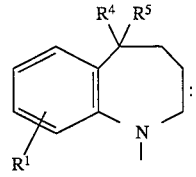

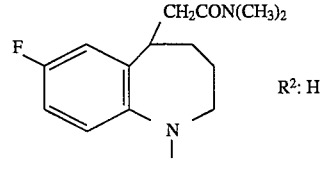  R²: H

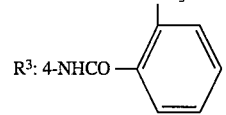

Crystal form: colorless and amorphous
Form: free
NMR: 104)

TABLE 81
Example 165
Structure:
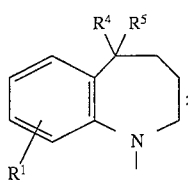
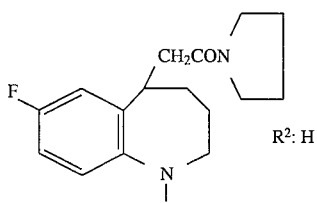   R²: H
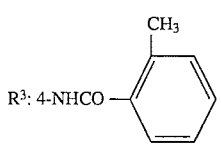   R³: 4-NHCO—
Crystal form: colorless and amorphous
Form: free
NMR: 105)
Example 166
Structure:
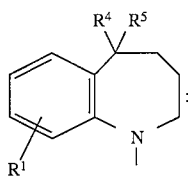
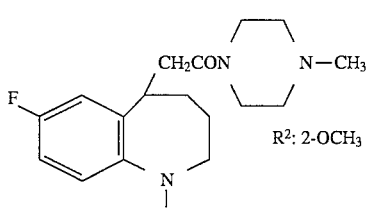   R²: 2-OCH₃
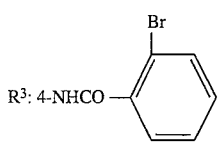   R³: 4-NHCO—
Crystal form: colorless and amorphous
Form: free
NMR: 106)
TABLE 82
Example 167
Structure:
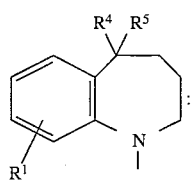
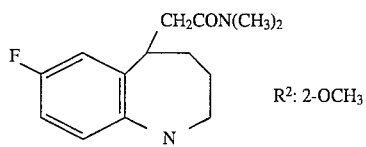   R²: 2-OCH₃
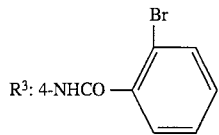   R³: 4-NHCO—
Crystal form: colorless and amorphous
Form: free
NMR: 107)
Example 168
Structure:
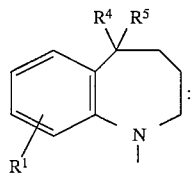
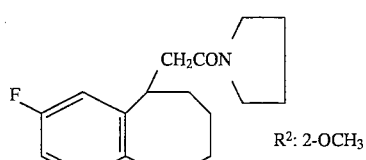   R²: 2-OCH₃
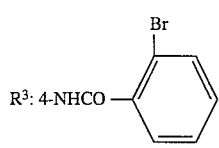   R³: 4-NHCO—
Crystal form: colorless and amorphous
Form: free
NMR: 108)

TABLE 83

Example 169
Structure:

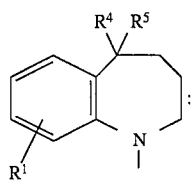

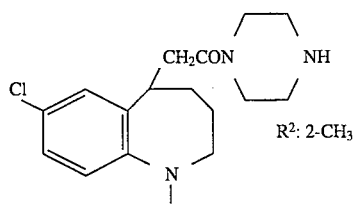

R²: 2-CH₃

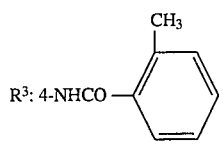

R³: 4-NHCO—

Crystal form: white powder
Recrystallization solvent: ethanol-diethyl ether
Melting point: 196° C.
Form: hydrochloride Example 170
Structure:

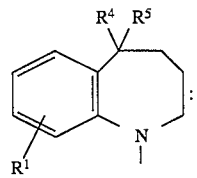

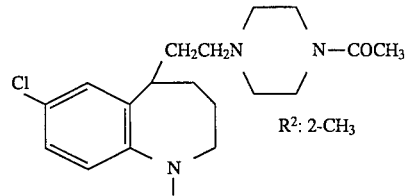

R²: 2-CH₃

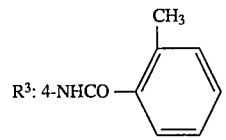

R³: 4-NHCO—

Crystal form: colorless and amorphous
Form: free
NMR: 109)

TABLE 84

Example 171
Structure:

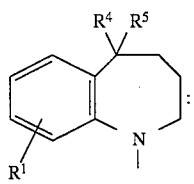

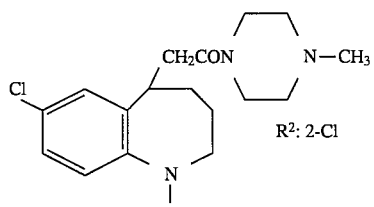

R²: 2-Cl

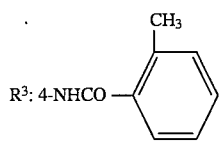

R³: 4-NHCO—

Crystal form: white powder
Recrystallization solvent: ethanol-diethyl ether
Melting point: 182–183° C.
Form: hydrochloride Example 172
Structure:

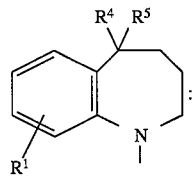

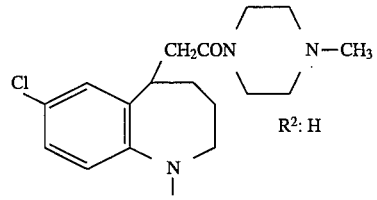

R²: H

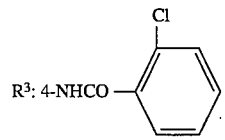

R³: 4-NHCO—

Crystal form: colorless prism
Recrystallization solvent: ethanol-diethyl ether
Melting point: 193–195° C. (decomposed)
Form: hydrochloride

TABLE 85

Example 173
Structure:

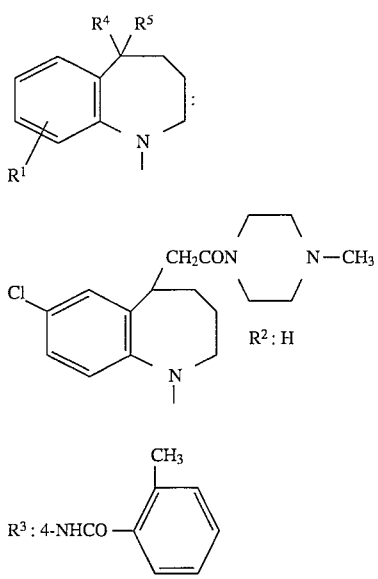

R²: H

R³: 4-NHCO—⟨CH₃ phenyl⟩

Crystal form: colorless prism
Recrystallization solvent: ethanol-diethyl ether
Melting point: 190–193°C. (decomposed)
Form: hydrocholoride Example 174
Structure:

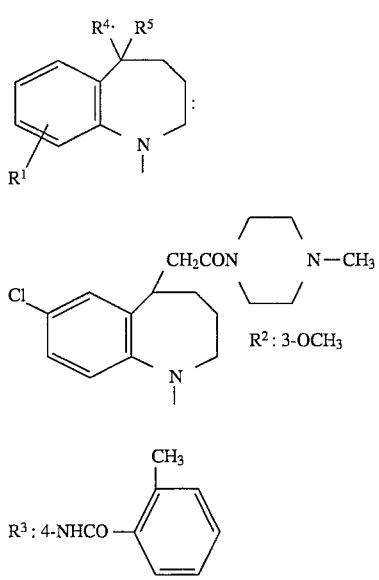

R²: 3-OCH₃

R³: 4-NHCO—⟨CH₃ phenyl⟩

Crystal form: white powder
Recrystallization solvent: ethanol-diethyl ether
Melting point: 208–209°C.
Form: hydrochloride

TABLE 86

Example 175
Structure:

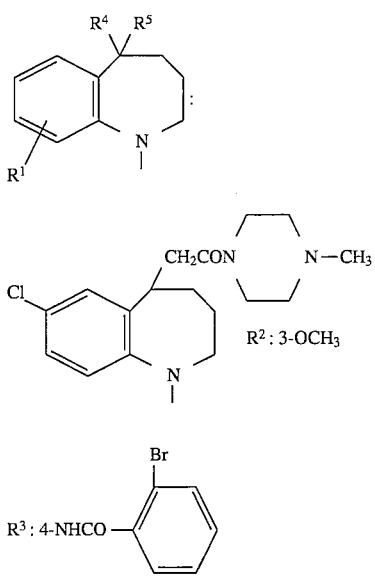

R²: 3-OCH₃

R³: 4-NHCO—⟨Br phenyl⟩

Crystal form: white powder
Recrystallization solvent: ethanol-acetone-
    diethyl ether
Melting point: 215–217°C.
Form: hydrochloride Example 176
Structure:

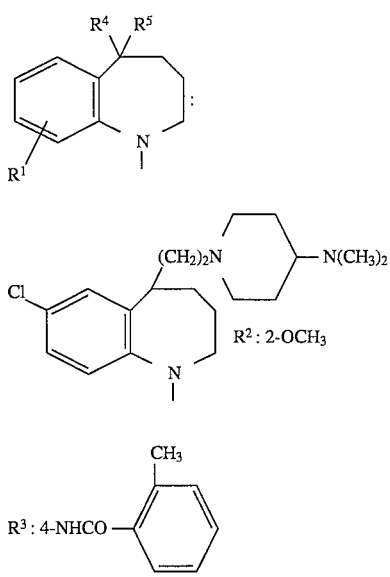

R²: 2-OCH₃

R³: 4-NHCO—⟨CH₃ phenyl⟩

Crystal form: colorless needle
Recrystallization solvent: ethanol-diethyl ether
Melting point: 222–224°C.
Form: dihydrochloride

TABLE 87

Example 177
Structure:

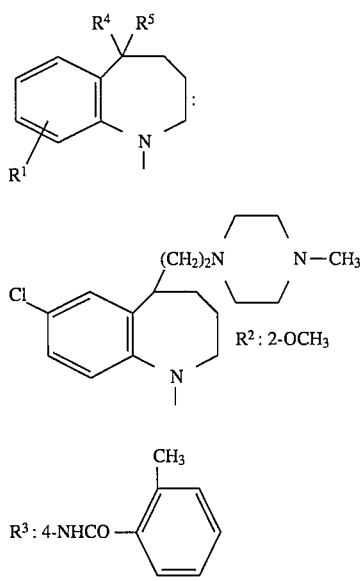

R²: 2-OCH₃

R³: 4-NHCO-(2-CH₃-phenyl)

Crystal form: colorless needle
Recrystallization solvent: ethanol-diethyl ether
Melting point: 214–216°C.
Form: dihydrochloride Example 178
Structure:

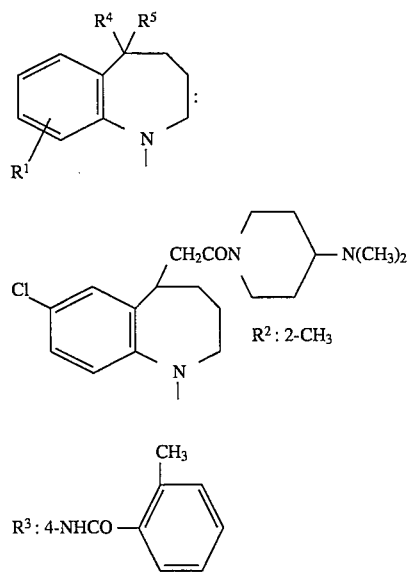

R²: 2-CH₃

R³: 4-NHCO-(2-CH₃-phenyl)

Crystal form: white powder
Recrystallization solvent: ethanol-diethyl ether
Melting point: 254–256°C.
Form: hydrochloride

TABLE 88

Example 179
Structure:

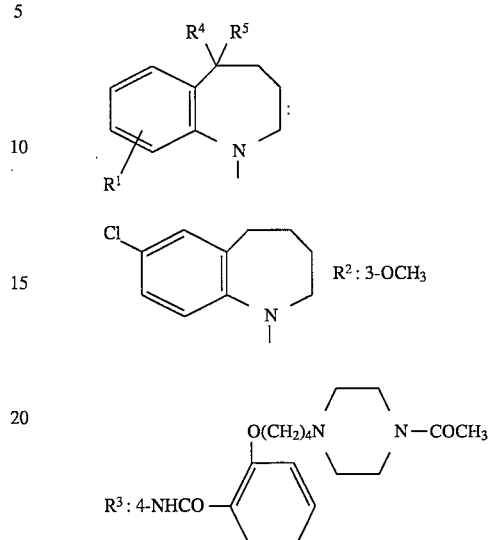

R²: 3-OCH₃

R³: 4-NHCO-(2-O(CH₂)₄N-piperazine-N-COCH₃-phenyl)

Crystal form: colorless needle
Recrystallization solvent: ethanol-diethyl ether
Melting point: 148–150°C.
Form: free Example 180
Structure:

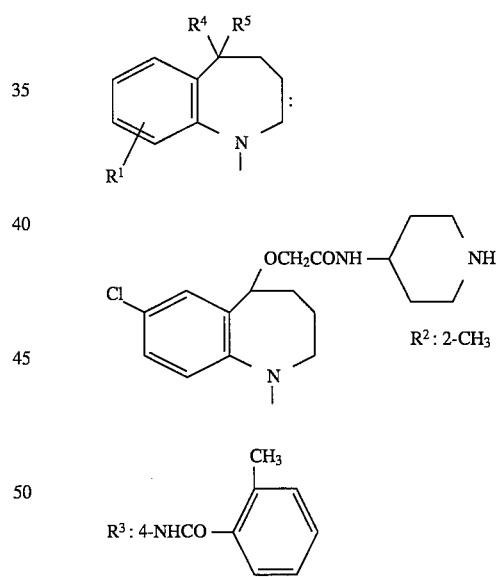

R²: 2-CH₃

R³: 4-NHCO-(2-CH₃-phenyl)

Crystal form: colorless and amorphous
Form: hydrochloride
NMR: 110)

TABLE 89

Example 181
Structure:

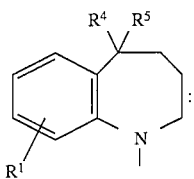

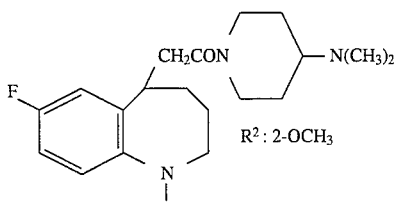

R²: 2-OCH₃

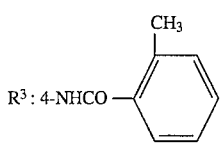

R³: 4-NHCO

Crystal form: colorless and amorphous
Form: free
NMR: 111)

Example 182
Structure:

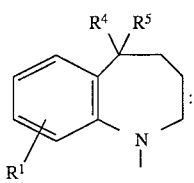

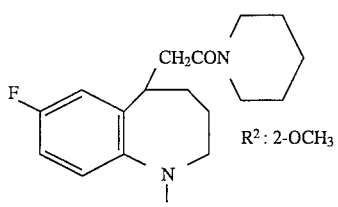

R²: 2-OCH₃

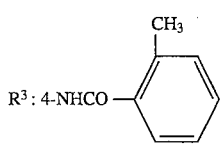

R³: 4-NHCO

Crystal form: colorless and amorphous
Form: free
NMR: 112)

TABLE 90

Example 183
Structure:

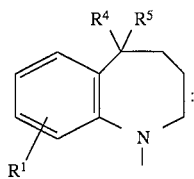

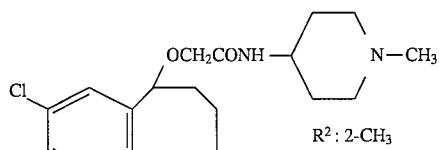

R²: 2-CH₃

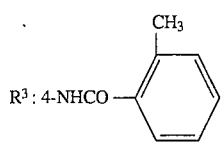

R³: 4-NHCO

Crystal form: white powder
Recrystallization solvent: ethanol-diethyl ether
Melting point: 186–188°C.
Form: hydrochloride Example 184
Structure:

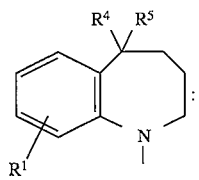

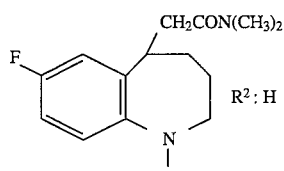

R²: H

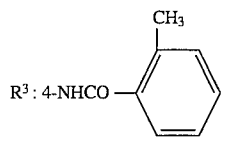

R³: 4-NHCO

Crystal form: white powder
Recrystallization solvent: dichloromethane-diethyl ether
Melting point: 239.5–240.5°C.
Form: free

TABLE 91

Example 185
Structure:

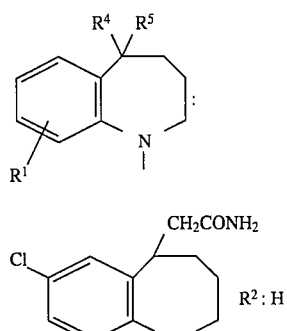

R²: H

R³: 4-NHCO—[2-CH₃-phenyl]

Crystal form: white powder
Recrystallization solvent: dichloromethane-
       diethyl ether
Melting point: 253–255°C.
Form: free Example 186
Structure:

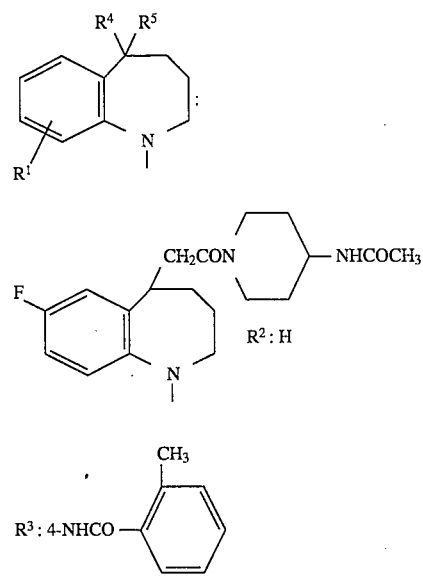

R²: H

R³: 4-NHCO—[2-CH₃-phenyl]

Crystal form: colorless and amorphous
Form: free
NMR: 113)

TABLE 92

Example 187
Structure:

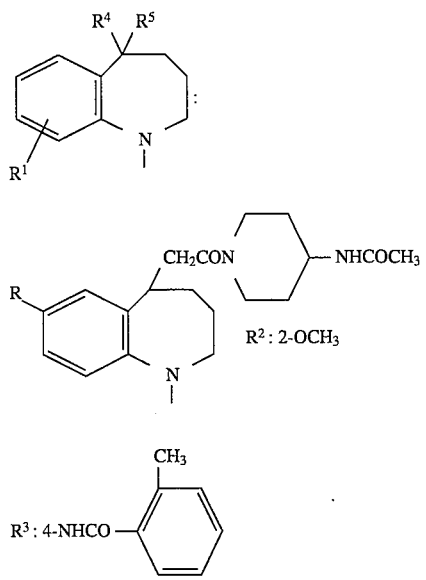

R²: 2-OCH₃

R³: 4-NHCO—[2-CH₃-phenyl]

Crystal form: colorless and amorphous
Form: free
NMR: 114)

Example 188
Structure:

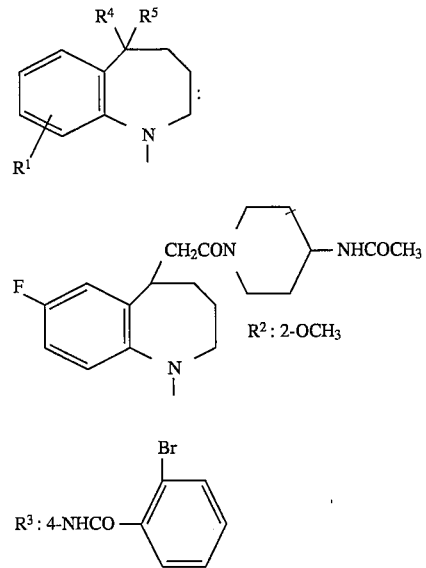

R²: 2-OCH₃

R³: 4-NHCO—[2-Br-phenyl]

Crystal form: colorless and amorphous
Form: free
NMR: 115)

TABLE 93

Example 189
Structure:

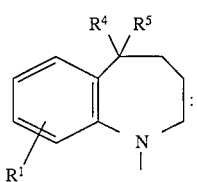

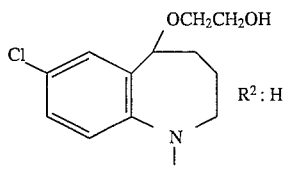

R²: H

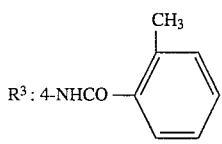

R³: 4-NHCO—

Crystal form: white powder
Recrystallization solvent: dichloromethane-
                          diethyl ether
Melting point: 185–187.5°C.
Form: free Example 190
Structure:

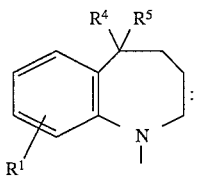

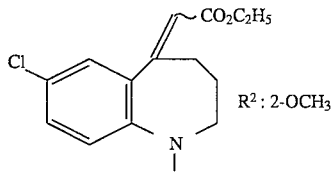

R²: 2-OCH₃

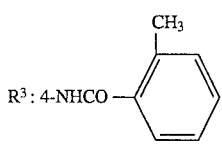

R³: 4-NHCO—

Crystal form: light yellow oil
Form: free
NMR: 116)

TABLE 94

Example 191
Structure:

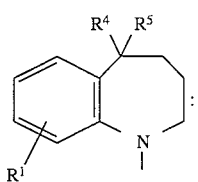

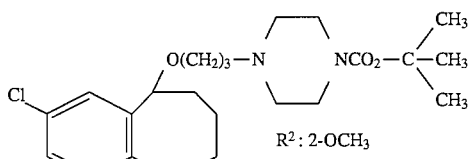

R²: 2-OCH₃

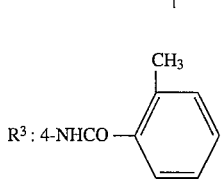

R³: 4-NHCO—

Crystal form: light yellow and amorphous
Form: free
NMR: 117)

Example 192
Structure:

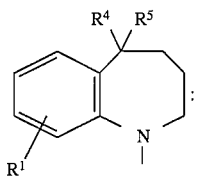

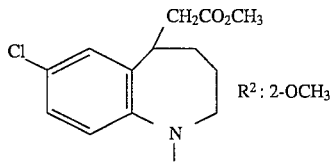

R²: 2-OCH₃

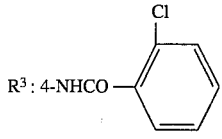

R³: 4-NHCO—

Crystal form: light yellow and amorphous
Form: free
NMR: 118)

TABLE 95
Example 193
Structure:
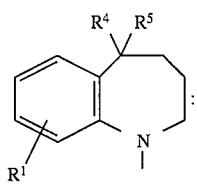
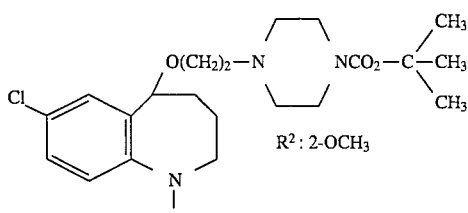
R²: 2-OCH₃
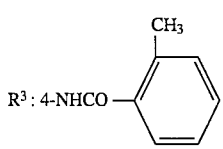
R³: 4-NHCO
Crystal form: colorless and amorphous
Form: free
NMR: 119)
Example 194
Structure:
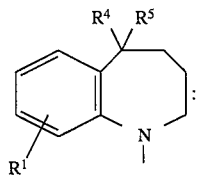
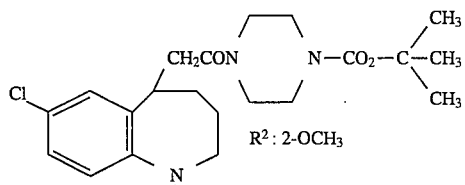
R²: 2-OCH₃
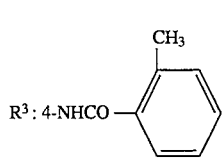
R³: 4-NHCO
Crystal form: white powder
Melting point: 145–147°C.
Form: free
TABLE 96
Example 195
Structure:
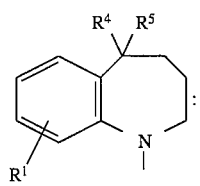
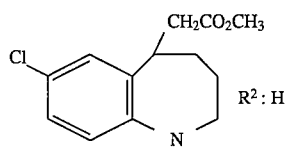
R²: H
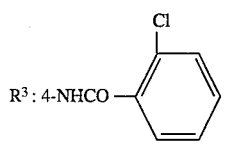
R³: 4-NHCO
Crystal form: colorless and amorphous
Form: free
NMR: 120)
Example 196
Structure:
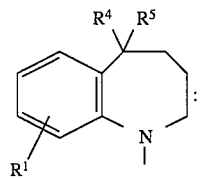
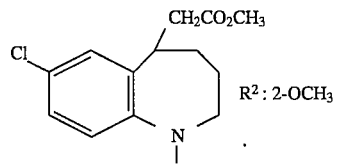
R²: 2-OCH₃
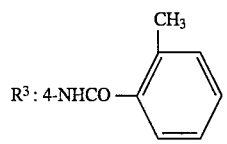
R³: 4-NHCO
Crystal form: colorless and amorphous
Form: free
NMR: 121)

TABLE 97

Example 197
Structure:

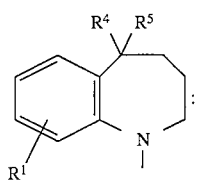

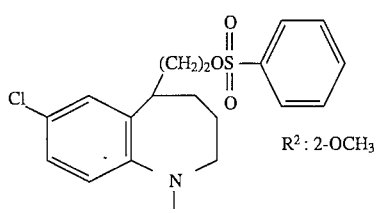

R²: 2-OCH₃

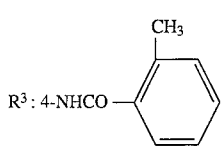

R³: 4-NHCO—

Crystal form: light yellow and amorphous
Form: free
NMR 122)

Example 198
Structure:

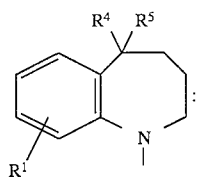

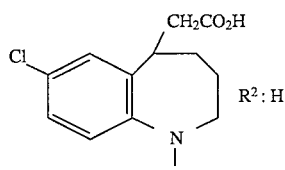

R²: H

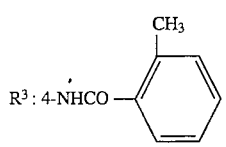

R³: 4-NHCO—

Crystal form: colorless and amorphous
Form: free
NMR: 123)

TABLE 98

Example 199
Structure:

TABLE 98-continued

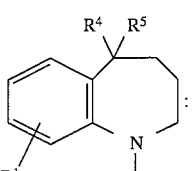

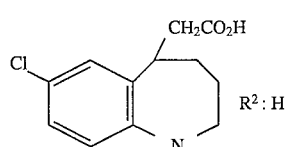

R²: H

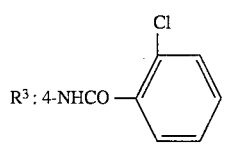

R³: 4-NHCO—

Crystal form: colorless and amorphous
Form: free
NMR: 124)

Example 200
Structure:

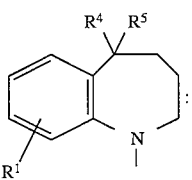

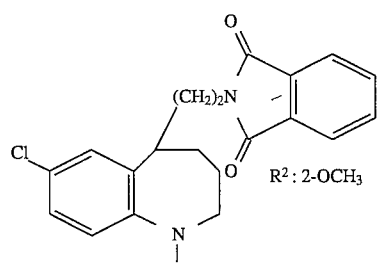

R²: 2-OCH₃

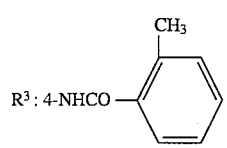

R³: 4-NHCO—

Crystal form: white powder
Form: free
NMR: 125)

TABLE 99

Example 201

TABLE 99-continued

Structure:

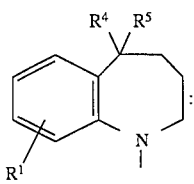

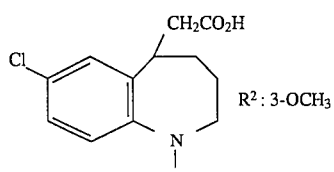 R²: 3-OCH₃

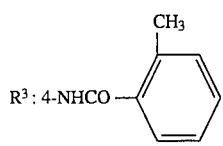 R³: 4-NHCO

Crystal form: colorless and amorphous
Form: free
NMR: 126)

Example 202
Structure:

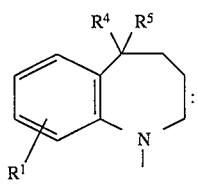

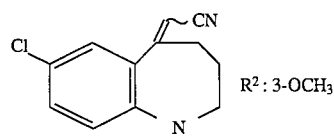 R²: 3-OCH₃

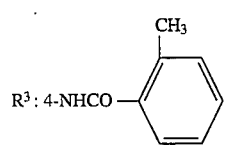 R³: 4-NHCO

Crystal form: colorless and amorphous
Form: free
NMR: 127)

TABLE 100

Example 203
Structure:

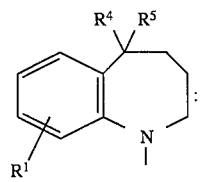

TABLE 100-continued

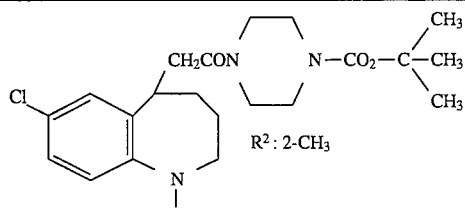 R²: 2-CH₃

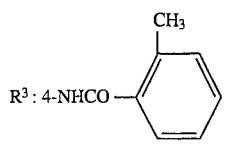 R³: 4-NHCO

Crystal form: colorless and amorphous
Form: free
NMR: 128)

Example 204
Structure:

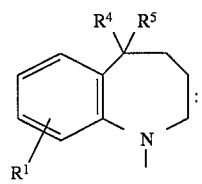

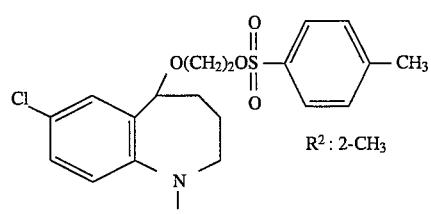 R²: 2-CH₃

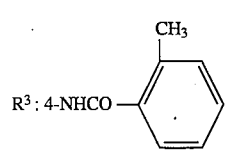 R³: 4-NHCO

Crystal form: colorless and amorphous
Form: free
NMR: 129)

TABLE 101

Example 205:
Structure:

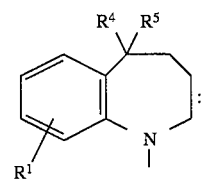

TABLE 101-continued

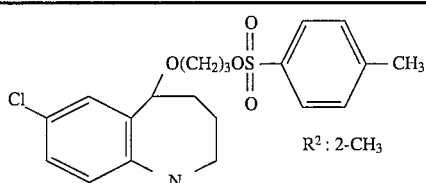

R²: 2-CH₃

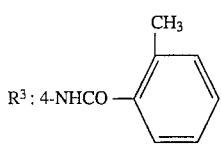

R³: 4-NHCO-

Crystal form: colorless and amorphous
form: free
NMR: 130)

Example 206
Structure:

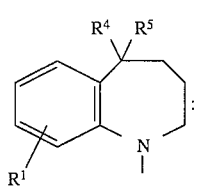

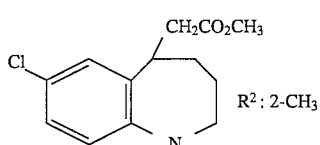

R²: 2-CH₃

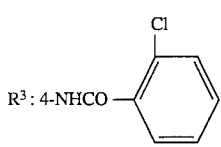

R³: 4-NHCO-

Crystal form: colorless and amorphous
Form: free
NMR: 131)

TABLE 102

Example 207
Structure:

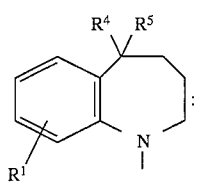

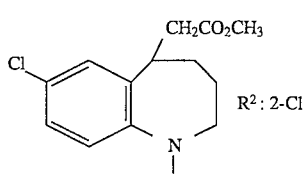

R²: 2-Cl

TABLE 102-continued

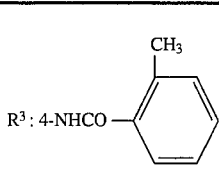

R³: 4-NHCO-

Crystal form: colorless and amorphous
Form: free
NMR: 132)

Example 208
Structure:

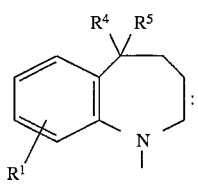

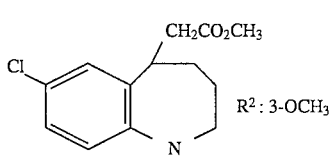

R²: 3-OCH₃

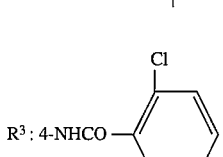

R³: 4-NHCO-

Crystal form: colorless and amorphous
Form: free
NMR: 133)

TABLE 103

Example 209
Structure:

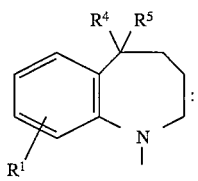

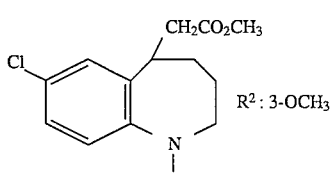

R²: 3-OCH₃

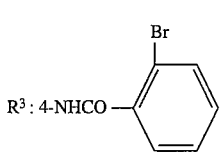

R³: 4-NHCO-

Crystal form: colorless and amorphous
Form free

TABLE 103-continued
NMR: 134)
Example 210
Structure:
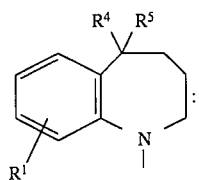
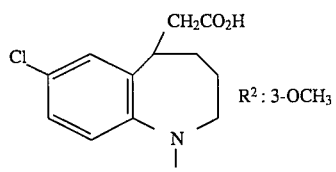  R² : 3-OCH₃
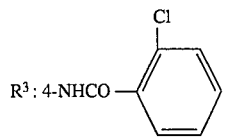  R³ : 4-NHCO—
Crystal form: colorless and amorphous
Form: free
NMR: 135)
TABLE 104
Example 211
Structure:
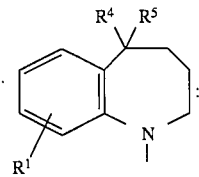
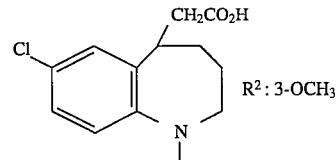  R² : 3-OCH₃
TABLE 104-continued
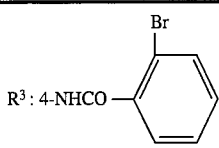  R³ : 4-NHCO—
Crystal form: colorless and amorphous
Form: free
NMR: 136)
Example 212
Structure:
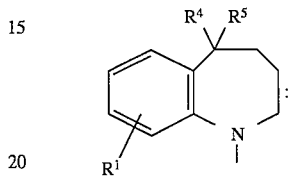
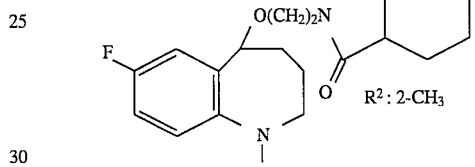  R² : 2-CH₃
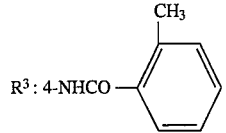  R³ : 4-NHCO—
Crystal form: colorless and amorphous
Form: free
NMR: 137)

TABLE 105

Example 213
Structure:

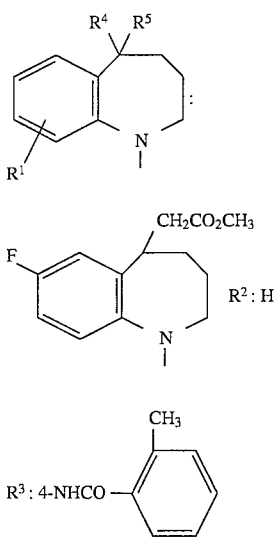

R²: H

R³: 4-NHCO—[phenyl with CH₃]

Crystal form: colorless and amorphous
Form: free
NMR: 138)

Example 214
Structure:

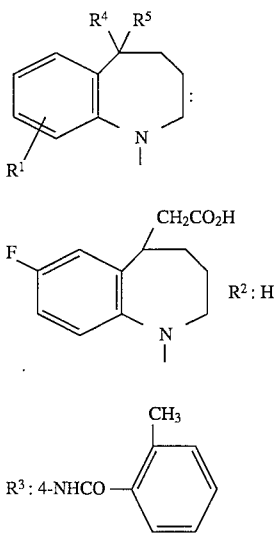

R²: H

R³: 4-NHCO—[phenyl with CH₃]

Crystal form: colorless and amorphous
Form: free
NMR: 139)

TABLE 106

Example 215
Structure:

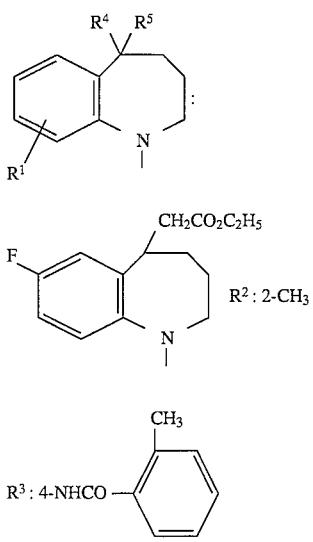

R²: 2-CH₃

R³: 4-NHCO—[phenyl with CH₃]

Crystal form: colorless and amorphous
Form: free
NMR: 140)

Example 216
Structure:

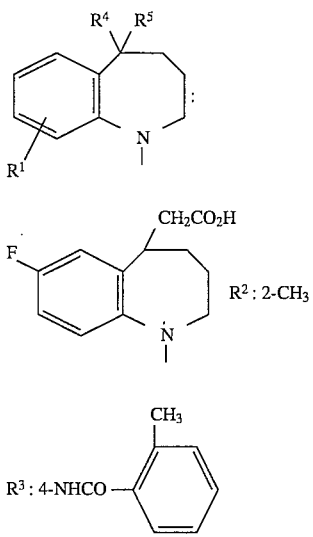

R²: 2-CH₃

R³: 4-NHCO—[phenyl with CH₃]

Crystal form: colorless and amorphous
Form: free
NMR: 141)

TABLE 107

Example 217
Structure:

TABLE 107-continued
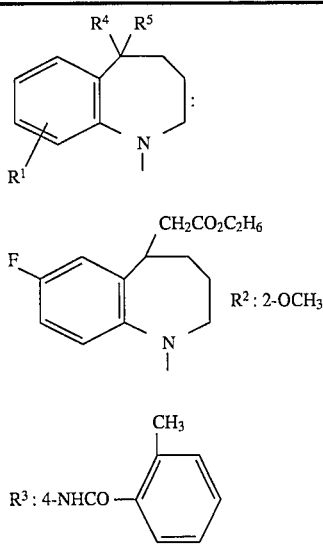
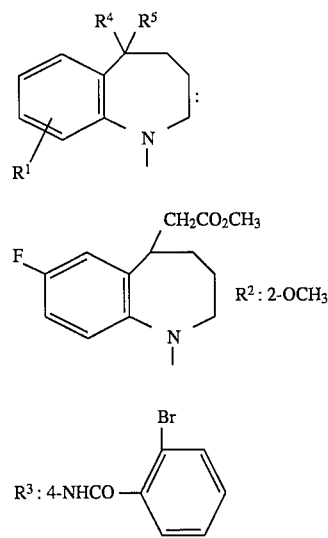
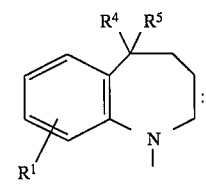
Crystal form: colorless and amorphous
Form: free
NMR: 142)
Example 218
Structure:
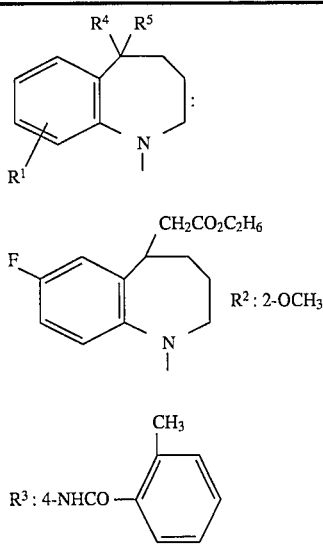
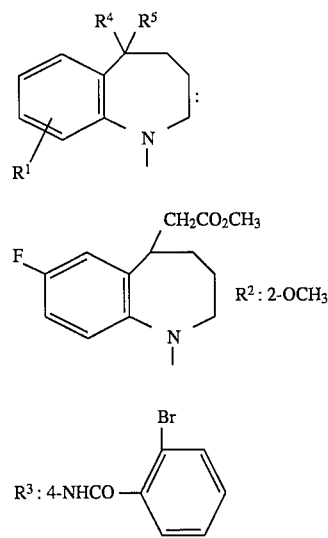
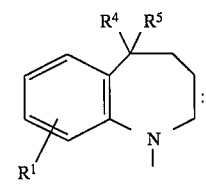
Crystal form: colorless and amorphous
Form: free
NMR: 143)
TABLE 108
Example 219
Structure:
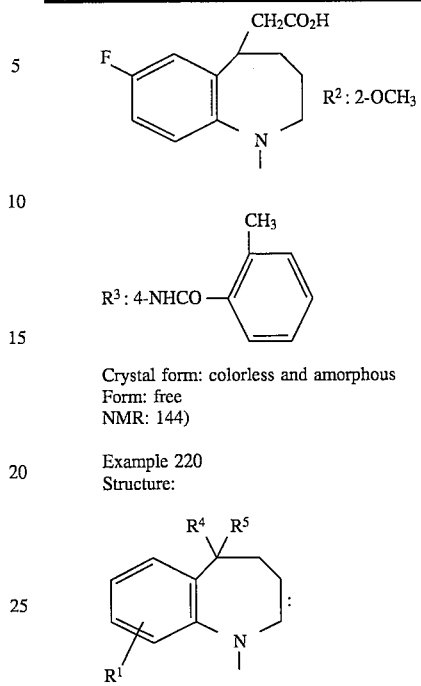
TABLE 108-continued
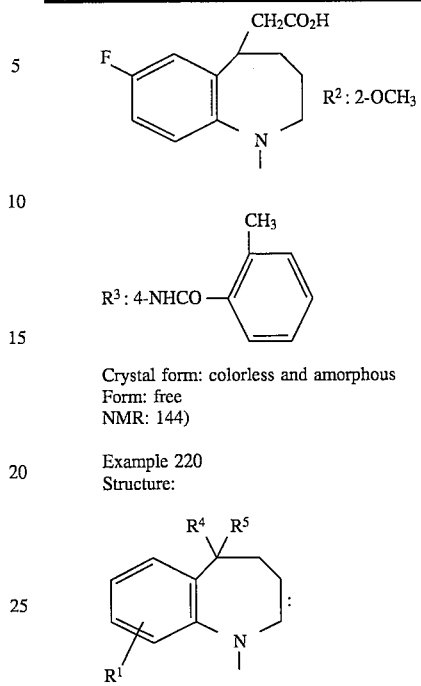
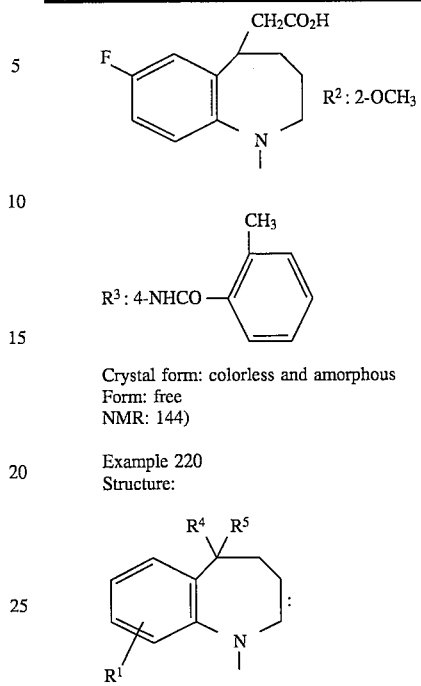
Crystal form: colorless and amorphous
Form: free
NMR: 144)
Example 220
Structure:
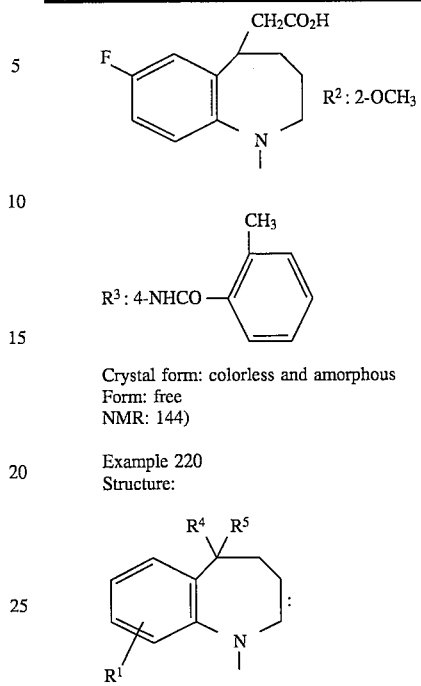
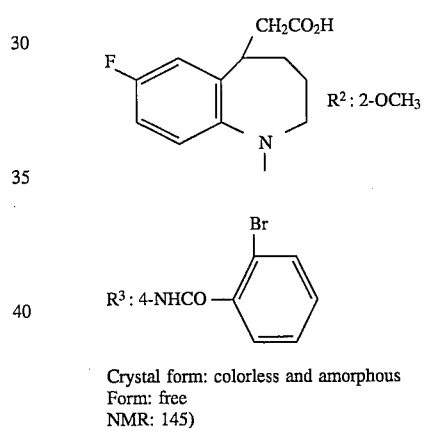
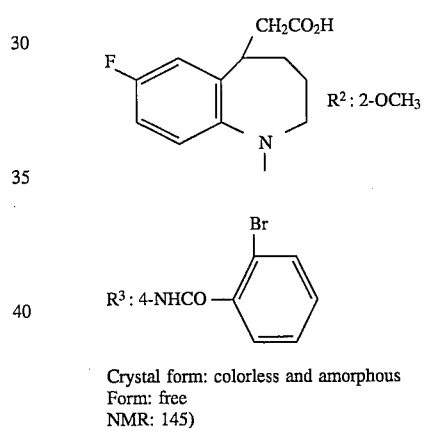
Crystal form: colorless and amorphous
Form: free
NMR: 145)
TABLE 109
Example 221
Structure:
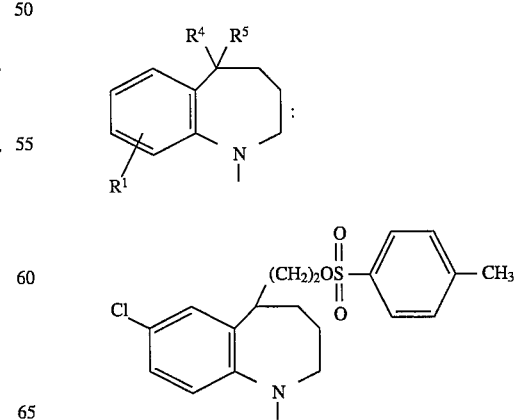
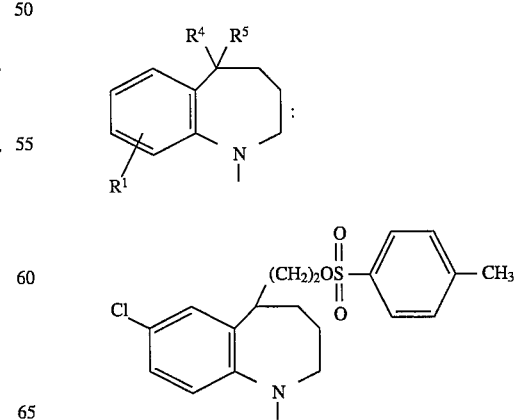

TABLE 109-continued

R²: 2-CH₃

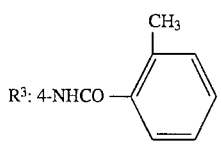

R³: 4-NHCO—

Crystal form: white and amorphous
Form: free
NMR: 146)

46) ¹H-NMR (DMSO-d₆) δ: 1.35–2.45 (12H, m), 2.55–2.95 (3H, m), 3.1–4.0 (4H, m), 4.05–4.45 (1H, m), 4.5–4.8 (1H, m), 5.95–6.3 (1H, m), 6.89 (1H, d, J=8.6 Hz), 7.05–7.8 (9H, m ), 8.17 (3H, brs), 8.90 (3H, brs), 10.25–10.60 (1H, m)

47) ¹H-NMR (CDCl₃) δ: 1.47–2.17 (3H, m), 2.32–2.92 (8H, m), 2.92–4.57 (6H, m), 5.17 (1H, brs), 5.76 (1H, brs), 6.17–8.14 (12H, m)

48) ¹H-MNR (CDCl₃) δ: 1.22–2.52 (10H, m), 2.70–3.05 (1H, m), 3.30–5.10 (8H, m), 6.60–8.05 (12H, m)

49) ¹H-NMR (CDCl₃) δ: 1.21–2.46 (7H, m), 2.70–2.95 (1H, m), 2.95–5.60 (7H, m), 6.60–8.32 (11H, m), 8.60–9.40 (1H, m)

50) ¹H-NMR (CDCl₃) δ: 1.35–2.52 (10H, m), 2.70–3.02 (1H, m), 3.02–5.05 (8H, m), 6.60–7.85 (11H, m), 7.85–8.23 (1H, m)

51) ¹H-NMR (CDCl₃) δ: 1.44–2.51 (11H, m), 2.67–3.77 (7H, m), 3.88–5.00 (4H, m), 6.66–9.05 (11H, m)

52) ¹H-NMR (DMSO-d₆) δ: 1.02–1.43 (3H, m), 1.43–4.98 (10H, m), 6.80–8.25 (11H, m), 10.35–10.72 (1H, m), 12.37–13.00 (1H, m)

53) ¹H-NMR (DMSO-d₆) δ: 1.2–2.2 (3H, m), 2.35 (3H, s), 2.83 (6H, s), 2.7–3.2 (1H, m), 3.3–3.6 (3H, m), 4.29 (2H, s), 4.2–5.1 (2H, 6.80 (1H, d, J=8.2 Hz), 7.0–7.8 (10H, 10.4–10.6 (1H, m), 10.6–10.9 (1H, br)

54) ¹Hs-NMR (CDCl₃) δ: 1.15–5.30 {20H, m [1.28 (3H, t, J=7.1 Hz), 2.50 (s), 3.73 (3H, s)]}, 6.50–7.61 (9H, m), 8.32 (1H, brs), 8.34 (1H, d, J=8.1 Hz)

55) ¹H-NMR (CDCl₃) δ: 1.21–5.34 {15H, m [2.50 (s), 3.78 (s)]}, 5.91–8.78 {13H, m [6.56 (1H, d, J=8.3 Hz)]})}

56) ¹H-NMR (CDCl₃) δ: 1.22–3.04, 3.15–3.89 (total 25H, m), 4.65–5.21 (1H, m), 5.86–6.33 (1H, m), 6.49–7.78 (8H, m), 8.01–8.52 (2H, m)

57) ¹H-NMR (CDCl₃) δ: 1.06–4.66, 5.02–5.26, 5.54–5.79 (total 25H, m [2.48(s), 2.56(s), 3.98(s)]}, 6.61–7.64, 8.04–8.39, 8.57–5.76 8total 12H, m)

58) ¹H-NMR (CDCl₃) δ: 1.23–3.23 (7H, m), 2.35 (3H, m), 4.64–5.01 (1H, m), 6.32 (6H, dd, J=2.6 Hz, 8.4 Hz), 6.50 (1H, d, J=8.4 Hz), 6.66 (6H, d, J=2.6 Hz), 7.08 (2H, d, J=8.6 Hz), 7.14–7.80 (4H, m), 7.54 (2H, d, J=8.4 Hz), 9.40 (1H, brs), 10.32 (1H, s)

59) ¹H-NMR (CDCl₃) δ: 1.26–4.82 (19H, m), 5.68 (1H, t, J=7.1 Hz), 6.64–7.47 (9H, m), 7.80–8.30 (2H, m)

60) ¹H-NMR (CDCl₃) δ: 1.26–4.68 (19H, m), 5.58 (1H, t, J=6.9 Hz), 6.63–8.50 (11H, m)

61) ¹H-NMR (DMSO-d₆) δ: 1.02–2.04 (4H, m), 2.33, 2.40 (total 3H, s), 2.50–4.22 (14H, m), 2.75, 2.77 (total 3H, s), 4.29–4.68 (2H, m), 6.73–7.78 (10H, m), 10.30, 10.50 (total 1H, brs), 11.50 (1H, brs)

62) ¹H-NMR (CDCl₃) δ: 1.0–1.4 (1H, m), 1.4–2.25 (3H, m), 2.25–3.3 (12H, m), 3.35–4.15 (4H, m), 4.3–4.95 (1H, m), 6.6–8.0 (10H, m), 8.6–9.25 (1H, m)

63) ¹H-NMR (CDCl₃) δ: 1.25–3.36 (1.1H, m), 2.31 (6H, s), 2.40 (3H, s), 3.92 (2H, t, J=5.0 Hz), 4.77–5.00 (1H, m), 6.42 (1H, dd, J=2.1 Hz, 6.9 Hz), 6.52 (1H, d, J=6.9 Hz), 6.75 (1H, d, J=2.1 Hz), 6.98–7.61 (8H, m), 8.42 (1H, s)

64) ¹H-NMR (CDCl₃) δ: 1.35–3.16 (9H, m), 1.91 (3H, s), 2.43 (3H, m), 3.25–3.58 (2H, m), 3.76–4.12 (2H, m), 4.80–5.09 (1H, m), 5.06 (1H, brs), 6.42 (1H, dd, J=2.2 Hz, 6.8 Hz), 6.56 (1H, d, J=6.8 Hz), 6.74 (1H, d, J=2.2 Hz), 6.98–7.64 (8H, m), 7.96 (1H, s)

65) ¹H-NMR (CDCl₃) δ: 1.20–3.18 (11H, m), 2.33 (3H, s), 2.47 (3H, s), 2.48 (3H, s), 3.20–5.12 (6H, m), 6.40–7.93 (11H, m)

66) ¹H-NMR (CDCl₃) δ: 1.21–2.22 (2H, m), 2.35–3.21 (3H, m), 2.46 (3H, s), 2.48 (3H, s), 2.98 (3H, s), 3.15 (3H, s), 3.45–4.63 (4H, m), 6.47–7.83 (11H, m)

67) ¹H-NMR (CDCl₃) δ: 1.42–2.95 (16H, m), 2.40 (3H, s), 2.46 (3H, s), 3.35–4.45 (3H, m ), 4.50–5.03 (2H, m), 6.51–8.02 (11H, m)

68) ¹H-NMR (CDCl₃) δ: 1.43–2.96 (12H, m), 7.42 (3H, s), 2.47 (3H, s), 3.36–3.83 (7H, m), 4.32–5.08 (2H, m), 6.51–7.76 (11H, m)

69) ¹H-NMR (CDCl₃) δ: 1.42–2.60 (9H, m), 2.45 (3H, s), 2.66–3.83 4H, m), 4.03–5.13 (3H, m), 6.50–8.39 (14H, m)

70) ¹H-NMR (CDCl₃) δ: 1.2–2.35 (6H, m), 2.35–2.6 (6H, m), 2.6–2.95 (1H, m), 3.1–4.05 (5H, m), 4.05–4.45 (2H, m), 4.45–5.1 (2H, m), 6.55–6.8 (1H, m), 6.8–7.55 (11H, m), 7.6–7.95 (3H, m)

71) ¹H-NMR (DMSO-d₆) δ: 1.3–2.45 (9H, m), 2.6–2.85 (1H, m), 2.9–4.1 (14H, m), 4.4–4.8 (2H, m), 6.88 (1H, d, J=8.4 Hz), 7.0–7.75 (10H, m), 10.25–10.55 (1H, m), 11.01 (1H, brs)

72) ¹H-NMR (DMSO-d₆) δ: 1.2–2.45 (8H, m), 2.6–2.85 (1H, m), 3.2–4.0 (6H, m), 4.2–4.8 (4H, m), 6.87 (1H, d, J=8.4 Hz), 7.0–8.0 (11H, m), 9.05–9.3 (1H, m), 10.2–10.55 (1H, m)

73) ¹H-NMR (DMSO-d₆) δ: 1.10–2.4 (12H, m), 2.65–4.10 (13H, m), 4.48–5.00 (2H, m), 6.58–7.22 (2H, m), 7.22–7.86 (8H, m), 10.29, 10.45 (total 1H, brs), 11.07 (1H, brs)

74) ¹H-NMR (DMSO-d₆) δ: 1.24–1.82 (3H, m), 1.82–2.48 (9H, m), 2.66–3.94 (3H, m), 4.22–4.93 (2H, m), 6.63–7.98 (14H, m), 9.08, 9.18 (total 1H, brs), 10.29, 10.44 (total 1H, brs)

75) ¹H-NMR (DMSO-d₆) δ: 1.2–2.45 (13H, m), 2.6–2.8 (1H, m), 2.8–3.8 (10H, m), 3.83 (1H, d, J=7.2 Hz), 4.4–4.8 (2H, m), 6.88 (1H, d, J=8.4 Hz), 7.0–7.75 (9H, m), 10.2–10.8 (2H, m)

76) ¹H-NMR (DMSO-d₆) δ: 0.96–2.63 (19H, m), 2.63–4.04 (6H, m), 4.07–4.95 (2H, m), 6.57–7.99 (11H, m), 10.29, 10.44 (total 1H, brs), 10.49 (1H, brs)

77) ¹H-NMR (CDCl₃) δ: 1.44–2.59 (10H, m), 2.60–5.25 (3H, m), 6.42–8.33 (11H, m)

78) ¹H-NMR (CDCl₃) δ: 1.06–2.54 (8H, m), 2.33 (3H, s), 2.45 (3H, s), 2.57–5.02 (12H, m), 6.53–8.38 (11, m)

79) ¹H-NMR (DMSO-d₆) δ: 1.2–2.3 (9H, m), 2.3–2.45 (3H, m), 2.6–2.8 (1H, m), 2.8–3.9 (14H, m), 3.9–4.15 (1H, m), 4.3–3.8 (2H, m), 6.88 (1H, d, J=8.4 Hz), 6.95–7.7 (9H, m), 10.2–10.5 (1H, m), 10.95 (1H, brs)

80) ¹H-NMR (DMSO-d₆) δ: 0.97–2.62 {15H, m [2.07(3H, s)]}, 2.63–4.19 (13H, m), 4.31–5.01 (2H, m), 6.54–8.07 (10H, m), 10.30, 10.46 (total 1H, brs), 10.98 (1H, brs)

81) ¹H-NMR (DMSO-d₆) δ: 1.02–2.15 (4H, m), 2.15–2.48 (6H, m), 2.80 (3H, s), 2.64–3.88 {10H, m [2.80 (3H, s-like)]}, 3.95–4.78 (3H, m), 6.45–8.12 (10H, m), 10.26, 10.47 (total 1H, brs), 11.30 (1H, brs)

82) ¹H-NMR (CDCl₃) δ: 1.3–1.8 (2H, m), 1.85–2.35 (2H, m), 2.35–2.6 (6H, m), 2.65–2.9 (1H, m), 3.35–4.0 (5H, m), 4.1–5.05 (4H, m), 6.5–6.8 (1H, m), 6.8–7.6 (10H, m), 7.6–8.05 (4H, m)

83) ¹H-NMR (CDCl₃) δ: 1.10–1.38 (1H, m), 1.23 (6H, d, J=5.6 Hz), 1.53–2.09 (3H, m), 2.13–3.46 (3H, m), 2.53 (3H, s), 3.56–4.52 (6H, m), 6.32–8.21 (12H, m)

84) ¹H-NMR (CDCl₃) δ: 1.45–2.10 (3H, m), 2.13–3.40 (4H, m), 2.39 (3H, d, J=4.7 Hz), 2.53 (3H, s), 3.42–4.68 (5H, m), 6.38–7.59 (10H, m), 7.79 (1H, brs), 8.16 (1H, brs)

85) ¹H-NMR (CDCl₃) δ: 1.13–2.21 (3H, m), 2.41–3.24 82H, m), 2.45 (3H, s), 2.99, 3.14 (total 6H, s), 3.47–4.65 (4H, m), 6.53–8.14 (11H, m)

86) ¹H-NMR (DMSO-d₆) δ: 1.25–2.45 (9H, m), 2.55–2.85 (1H, m), 2.9–4.1 (15H, m), 4.3–4.8 (2H, m), 6.88 (1H, d, J=8.4 Hz), 7.0–7.8 (9H, m), 9.84 (2H, brs), 10.15–10.55 (1H, m), 12.02 (1H, brs)

87) ¹H-NMR (DMSO-d₆) δ: 1.3–2.15 (3H, m), 2.15–2.45 (4H, m), 2.6–2.85 (1H, m), 3.0–4.25 (15H, m), 4.45–4.9 (2H, m), 6.89 (1H, d, J=8.4 Hz), 7.0–7.75 (9H, m), 10.25–10.6 (1H, m), 11.05–11.65 (1H, m)

88) ¹H-NMR (DMSO-d₆) δ: 1.15–2.2 (4H, m), 2.25–2.4 (3H, m), 2.6–2.85 (1H, m), 3.0–3.95 (4H, m), 3.95–4.15 (1H, m), 4.35–4.8 (4H, m), 6.6–6.95 (1H, m), 6.95–8.0 (12H, m), 9.15–9.45 81H, m), 10.25–10.6 (1H, m)

89) ¹H-NMR (DMSO-d₆) δ: 1.3–2.2 (7H, m), 2.2–2.45 (4H, m), 2.55–2.85 (1H, m), 2.85–4.25 (11H, m), 4.25–4.85 (5H, m), 6.89 (1H, d, J=8.4 Hz), 7.0–7.8 (9H, m), 10.25–10.6 (1H, m), 11.45–12.0 (1H, m)

90) ¹H-NMR (DMSO-d₆) δ: 1.3–2.2 (7H, m), 2.2–2.45 (4H, m), 2.55–2.9 (1H, m), 2.9–4.15 (11H, m), 4.4–4.9 (2H, m), 6.8–7.0 (1H, m), 7.0–7.8 (9H, m), 10.2–10.7 (1H, m), 10.88 (1H, brs)

91) ¹H-NMR (DMSO-d₆) δ: 1.3–2.1 (3H, m), 2.15–2.45 (4H, m), 2.55–2.85 (1H, m), 2.9–4.25 (15H, m), 4.4–4.85 (2H, m), 6.75–7.0 (1H, m), 7.0–7.9 (9H, m), 9.90 (2H, brs), 10.2–10.55 (1H, m), 11.65–12.50 (1H, m)

92) ¹H-NMR (DMSO-d₆) δ: 0.91–2.16 (4H, m), 2.22–4.98 (8H, m), 6.61–7.85 (12H, m), 10.35–10.81 (1H, m)

93) ¹H-NMR (DMSO-d₆) δ: 0.94–2.05 (4H, m), 2.45–4.90 (22H, m), 2.77 (3H, s), 6.80 (1H, d, J=8.6 Hz), 6.94–7.77 (9H, m), 10.52, 10.72 (total 1H, brs), 11.47 (1H, brs)

94) ¹H-NMR (DMSO-d₆) δ: 1.0–2.3 (8H, m), 2.4–3.2 (1H, m), 3.2–4.2 (6H, m), 4.2–4.8 (2H, m), 6.80 (1H, d, J=8.4 Hz), 6.95–7.8 (9H, m), 10.5–10.75 (1H, m), 10.86 (1H, brs)

95) ¹H-NMR (DMSO-d₆) δ: 0.9–1.3 (1H, m), 1.3–2.0 (3H, m), 2.05–2.45 (3H, m), 2.55–3.3 (6H, m), 3.3–4.55 (10H, m), 6.8–7.8 (10H, m), 9.51 (2H, brs), 10.2–10.6 (1H, m)

96) ¹H-NMR (CDCl₃) δ: 1.42–2.36 (14H, m), 2.36 (3H, s), 2.46 (3H, s), 2.86–3.96 (5H, m), 4.43–5.03 (1H, m), 6.52–8.33 (11H, m), 6.54–7.58 (10H, m), 7.80 (1H, brs)

97) ¹H-NMR (CDCl₃) δ: 1.37–2.90 (15H, m), 2.33 (3H, s), 2.47 (3H, s), 3.38–3.99 (5H, m), 4.31–5.08 (2H, m), 6.56–7.98 (11H, m)

98) ¹H-NMR (DMSO-d₆) δ: 0.75–2.25 (10H, m), 2.25–4.4 (13H, m), 6.79 (1H, d, J=8.2 Hz), 6.9–7.9 (14H, m), 8.25–8.8 (1H, m), 10.45–10.85 (1H, m), 10.85–11.35 (1H, m)

99) ¹H-NMR (DMSO-d₆) δ: 1.07–2.10 (4H, m), 2.19–2.62 (3H, m), 2.62–4.72 (16H, m), 6.60–7.84 (10H, m), 10.48, 10.68 (total 1H, brs), 11.32 (1H, brs)

100) ¹H-NMR (DMSO-d₆) δ: 1.04–2.68 {[13H, m [2.08 (3H, s)]], 2.68–4.24 (13H, m), 4.32–5.00 (2H, m), 6.54–7.91 (10H, m), 10.29, 10.44 (total 1H, brs), 11.14 (1H, brs)

101) ¹H-NMR (CDCl₃+DMSO-d₆) δ: 1.00–2.21 (4H, m), 2.54–2.99 (2H, m), 2.42, 2.49 (3H, each s), 3.00–5.14 (3H, m), 6.78–8.23 (11H, m), 10.04, 10.29 (1H, each s)

102) ¹H-NMR (DMSO-d₆) δ: 1.06–2.14 (4H, m), 2.39 (3H, s), 2.48–3.65 (4H, 4.21–4.50 (1H, m), 6.75 (1H, d, J=8.2 Hz), 6.94 (1H, d, J=8.2 Hz), 7.07 (1H, dd, J=2.2 Hz, 8.2 Hz), 7.14–7.82 (7H, m), 10.44, 10.64 (1H, each s), 12.42 (1H, brs)

103) ¹H-NMR (CDCl₃) δ: 1.20–2.81 (9H, m), 2.33 (3H, s), 2.47 (3H, s), 2.85–3.93 (7H, m), 4.43–5.21 (1H, m), 6.53–6.87 (3H, m), 7.15–7.86 (9H, m)

104) ¹H-NMR (CDCl₃) δ: 1.22–2.21 (4H, m), 2.42–3.24 (3H, m), 2.47 (3H, s), 2.98 (3H, s), 3.15 (3H, s), 3.58–4.03 (1H, m), 4.40–5.22 (1H, m), 6.53–6.72 (3H, m), 7.13–7.67 (9H, m)

105) ¹H-NMR (CDCl₃) δ: 1.21–2.23 (8H, m), 2.40–4.10 (7H, m), 2.47 (3H, s), 4.35–5.22 (2H, m), 6.53–6.85 (3H, m), 7.13–7.70 (9H, m)

106) ¹H-NMR (CDCl₃) δ: 1.08–2.63 (9H, m), 2.32, 2.34 (total 3H, s), 2.63–4.11 (10H, m), 4.35–5.06 (1H, m), 6.53–8.24 (11H, m)

107) ¹H-NMR (CDCl₃) δ: 1.11–2.28 (4H, m), 2.45–3.23 (3H, m), 3.01 (3H, s), 3.16 (3H, s), 3.45–4.15 (4H, m), 4.38–5.07 (1H, m), 6.53–8.16 (11H, m)

108) ¹H-NMR (CDCl₃) δ: 1.06–2.23 (8H, m), 2.50–4.12 (7H, m), 3.76 (3H, s), 4.34–5.10 (2H, m), 6.52–8.23 (11H, m)

109) ¹H-NMR (DMSO-d₆) δ: 1.02–2.59 {16H, m [2.09 (3H, s-like)]}, 2.59–3.83 (9H, m), 3.87–4.63 (2H, m), 6.56–8.12 (10H, m), 10.27, 10.45 (total 1H, brs), 11.00 (1H, brs)

110) ¹H-NMR (DMSO-d₆) δ: 1.38–5.08 [25H, m (2.36, s-like)], 6.60–9.20 (12H, m), 10.29, 10.43 (total 1H, brs)

111) ¹H-NMR (CDCl₃) δ: 1.04–2.10 (8H, m), 2.16–3.25 (6H, m), 2.28 (3H, s), 2.30 (3H, s), 2.44, 2.51 (total 3H, s), 3.36–4.18 (5H, m), 4.32–5.02 (2H, m), 6.50–7.90 (10H, m), 8.32, 8.64 (total 1H, brs)

112) ¹H-NMR (CDCl₃) δ: 1.06–2.17 (10H, m), 2.45, 2.51 (total 3H, s), 2.47–3.06 (2H, m), 3.13–4.06 (8H, m), 4.30–5.00 (2H, m), 6.52–7.82 (10H, m), 8.36, 8.72 (total 1H, brs)

113) ¹H-NMR (CDCl₃) δ: 1.12–2.20 (8H, m), 1.91, 1.93 (total 3H, s), 2.34–3.41 (5H, m), 2.44 (3H, m), 3.55–4.13 (3H, m), 4.32–5.25 (2H, m), 5.96–7.55 (11H, m), 8.16, 8.23 (total 1H, brs), 8.52 (1H, brs)

114) ¹H-NMR (CDCl₃) δ: 1.06–2.20 (8H, m), 1.92, 1.93 (total 3H, s), 2.36–3.30 (5H, m), 2.43, 2.52 (total 3H, m), 3.46–4.09 (6H, m), 4.35–5.03 (2H, m), 6.00–7.58 8.25 (1H, brs), 8.44 (1H, brs)

115) $^1$H-NMR (CDCl$_3$) δ: 1.06–2.25 (8H, m), 1.90 (3H, s), 2.35–3.30 (5H, m), 3.36–4.07 (7H, m), 4.30–4.97 (1H, m), 6.23–7.92 (10H, m), 8.83 (1H, brs), 9.90 (1H, brs)

116) $^1$H-NMR (CDCl$_3$) δ: 1.34 (3H, t, J=5.6 Hz), 1.55–2.3 (3H, m), 2.46 (3H, s), 2.8–3.9 (6H, m), 4.24 (2H, q, J=5.6 Hz), 5.96 (1H, s), 6.6–7.6 (10H, m), 8.10 (1H, s)

117) $^1$H-NMR (CDCl$_3$) δ: 1.3–2.6 (28H, m), 2.6–2.9 (1H, m), 3.0–4.0 (5H, m), 4.3–5.1 (2H, m), 6.6–7.6 (10H, m), 7.70 (1H, brs)

118) $^1$H-NMR (CDCl$_3$) δ: 1.1–2.25 (4H, m), 2.55–3.15 (3H, m), 3.3–4.0 (7H, m), 4.05–5.1 (1H, m), 6.7–7.9 (10H, m), 8.3–8.75 (1H, m)

119) $^1$H-NMR (CDCl$_3$) δ: 1.3–2.9 (23H, m), 3.25–4.0 (9H, m), 4.3–5.1 (2H, m), 6.6–7.55 (10H, m), .7.6–7.95 (1H, m)

120) $^1$-NMR (CDCl$_3$) δ: 1.15–2.2 (4H, m), 2.5–3.3 (3H, m), 3.4–3.9 (4H, m), 4.3–5.25 (1H, m), 6.45–6.7 (1H, m), 6.8–7.05 (1H, m), 7.05–7.6 (8H, m), 7.6–7.8 (1H, m), 8.1–8.4 (1H, m)

121) $^1$H-NMR (CDCl$_3$) δ: 1.2–2.5 (7H, m), 2.55–3.25 (3H, m), 3.3–3.85 (4H, m), 4.35–5.2 (1H, m), 6.59 (1H, d, J=6.7 Hz), 6.95 (1H, dd, J=6.7 Hz, 1.6 Hz), 7.11 (1H, d, J=1.7 Hz), 7.15–8.05 (9H, m)

122) $^1$H-NMR (CDCl$_3$) δ: 0.95–2.35 (6H, m), 2.35–2.6 (6H, m), 2.6–3.3 (2H, m), 3.35–5.05 (6H, m), 6.55–6.8 (1H, m), 6.8–8.15 (14H, m)

123) $^1$H-NMR (CDCl$_3$) δ: 1.2–2.2 (4H, m), 2.35 (3H, s), 2.55–3.05 (2H, m), 3.05–3.25 (1H, m), 3.45–3.75 (1H, m), 4.2–5.15 (1H, m), 6.45–6.6 (1H, m), 6.75–6.95 (1H, m), 7.0–8.05 (9H, m), 8.15–8.45 (1H, m)

124) $^1$H-NMR (CDCl$_3$) δ: 1.2–2.2 (4H, m), 2.5–3.0 (2H, m), 3.0–3.25 (1H, m), 3.3–3.75 (1H, m), 4.2–5.2 (1H, m), 6.45–6.65 (1H, m), 6.8–7.0 (1H, m), 7.0–7.5 (8H, m), 7.55 (1H, d, J=6.9 Hz), 8.4–8.6 (1H, m)

125) $^1$H-NMR (CDCl$_3$) δ: 1.15–1.45 (1H, m), 1.45–2.4 (5H, m), 2.4–2.7 (3H, m), 3.05–3.35 (2H, m), 3.45–4.1 (5H, m), 4.35–5.2 (1H, m), 6.6–7.6 (10H, m), 7.6–7.8 (3H, m), 7.8–8.05 (2H, m)

126) $^1$H-NMR (CDCl$_3$) δ: 1.23–2.30, 2.56–3.98, 4.27–5.65 [total 16H, 2.47 (3H, s), 3.72 (3H, s)], 6.61 (1H, d, J=8.3Hz), 6.18–7.57 (8H, m), 8.15 (1H, s), 8.31 (1H, d, J=8.1Hz)

127) $^1$H-NMR (CDCl$_3$) δ: 1.56–5.10 (6H, m), 2.50 (3H, s), 3.80 (3H, s), 5.59 (1H, s), 6.51–6.86 (2H, m), 6.91–7.06 (1H, m), 7.13 (1H, dd, J=2.4Hz, 8.4Hz), 7.19–7.58 (5H, m), 8.15 (1H, s), 8.32 (1H, d, J=8.4Hz)

128) $^1$H-NMR (CDCl$_3$) δ: 0.88–4.12 (16H, m), 1.44, 1.46, 1.48 (9H, each s), 2.45, 2.51 (6H, each s), 4.31–4.62 (1H, m), 6.58 (1H, d, J=8.2Hz), 6.78–8.31 (10H, m)

129) $^1$H-NMR (CDCl$_3$) δ: 0.81–2.98 (5H, m), 2.35, 2.37, 2.43, 2.49 (9H, each s), 3.02–4.75 (6H, m), 6.61 (1H, dd, J=18Hz, 8.4Hz), 4.93 (1H, d, J=8.4Hz, 2.3Hz), 7.08–8.40 (9H, m)

130) $^1$H-NMR (CDCl$_3$) δ: 1.33–3.00 (7H, m), 2.41, 2.43, 2.46 (9H, each s), 3.05–5.14 (6H, m), 6.57 (1H, d, J=8.2Hz), 6.71 (1H, d, J=8.2Hz), 6.82–8.28 (13H, m)

131) $^1$H-NMR (CDCl$_3$) δ: 0.83–2.52 (4H, m), 2.42, 2.45 (3H, each s), 2.56–5.18 (5H, m), 3.72 (3H, s), 6.57 (1H, d, J=8.3Hz), 6.87 (1H, d, J=8.3Hz), 7.06 (1H, dd, J=5.7Hz, 2.3Hz), 6.67–8.49 (8H, m)

132) $^1$H-NMR (CDCl$_3$) δ: 1.05–2.23 (4H, m), 2.24–5.07 (5H, m), 2.43, 2.49 (3H, each s), 3.71 (3H, s), 6.75–9.00 (11H, m)

133) $^1$H-NMR (CDCl$_3$) δ: 0.78–2.31 (4H, m), 2.48–3.35 (3H, m), 3.36–5.39 (2H, m), 3.73 (3H, s), 3.75 (3H, s), 6.61 (1H, d, J=8.3Hz), 6.35–7.93 (8H, m), 8.35 (1H, d, J=8.4Hz), 8.61, 8.86 (1H, each s)

134) $^1$H-NMR (CDCl$_3$) δ: 1.03–2.28 (4H, m), 2.50–3.33 (3H, m), 3.34–5.48 (2H, m), 3.73 (3H, s), 3.75 (3H, s), 6.62 (1H, d, J=8.3Hz), 6.43–7.82 (8H, m), 8.18–8.70 (2H, m)

135) $^1$H -NMR (CDCl$_3$) δ: 1.02–2.30 (4H, m), 2.49–3.40 (3H, m), 3.41–5.42 (2H, m), 3.73 (3H, s), 6.61 (1H, d, J=8.2Hz), 6.34–7.99 (8H, m), 8.33 (1H, d, J=8.3Hz), 8.61, 8.86 (1H, each s)

136) $^1$H-NMR (CDCl$_3$) δ: 0.98–2.35 (4H, m), 2.36–5.47 (5H, m), 3.72 (3H, s), 6.61 (1H, d, J=8.2Hz), 6.47–7.91 (9H, m), 8.12–8.72 (1H, m)

137) $^1$H-NMR (CDCl$_3$) δ: 1.28–2.55 (12H, m), 2.34 (3H, s), 2.42 (3H, s), 2.65–2.94 (2H, m), 3.03–3.98 (5H, m), 4.35–5.03 (2H, m), 6.50–8.54 (11H, m)

138) $^1$H-NMR (CDCl$_3$) δ: 1.17–2.17 (4H, m), 2.43 (3H, s), 2.53–3.21 (3H, m), 3.31–3.82 (1H, m), 3.71 (3H, s), 4.31–5.20 (1H, m), 6.50–6.73 (2H, m), 6.77–7.53 (8H, m), 7.99, 8.00, 8.08 (total 1H, brs)

139) $^1$H-NMR (CDCl$_3$) δ: 1.18–2.15 (4H, m), 2.34 (3H, s), 2.52–3.27 (3H, m), 3.47–3.73 (1H, m), 4.22–5.18 (1H, m), 6.50–6.72 (2H, m), 6.78–6.94 (1H, m), 7.07–7.50 (7H, m), 8.45 (2H, brs)

140) $^1$H-NMR (CDCl$_3$) δ: 1.11–2.23 (7H, m), 2.45 (3H, s), 2.46 (3H, s), 2.63–3.82 (4H, m), 4.10–5.20 (3H, m), 6.55–7.83 (10H, m)

141) $^1$H-NMR (CDCl$_1$) δ: 1.13–2.09 (4H, m), 2.36 (6H, s), 2.56–3.68 (4H, m), 4.28–5.13 (1H, m), 5.92 (1H, brs), 6.55–7.66 (10H, m), 8.17 (1H, brs)

142) $^1$H-NMR (CDCl$_3$) δ: 1.12–1.41 (4H, m), 1.43–2.18 (3H, m), 2.28–3.03 (3H, m), 2.44 (3H, s), 3.32–3.90 (1H, m), 3.60 (3H, s), 4.02–4.96 (3H, m), 6.55–7.56 (10H, m), 8.53 (1H, brs)

143) $^1$H-NMR (CDCl$_3$) δ: 1.10–2.12 (4H, m), 2.53–3.03 (3H, m), 3.34–3.95 (1H, m), 4.27–4.95 (1H, m), 6.53–7.70 (10H, m), 8.57, 8.59, 8.86 (total 1H, brs)

144) $^1$H-NMR (CDCl$_3$) δ: 1.13–2.13 (4H, m), 2.45 (3H, s), 2.53–3.14 (3H, m), 3.27–4.10 (4H, m), 4.30–5.02 (1H, m), 6.52–7.05 (5H, m), 7.07–7.53 (5H, m), 8.70 (1H, brs), 9.13 (1H, brs)

145) $^1$H-NMR (CDCl$_3$) δ: 1.08–2.15 (4H, m), 2.50–3.12 (3H, m), 3.25–4.02 (4H, m), 4.28–5.00 (1H, m), 6.52–7.05 (5H, m), 7.11–7.67 (5H, m), 8.91 (1H, brs), 9.13 (1H, brs)

146) $^1$H-NMR (CDCl$_3$) δ: 1.12–2.75 (16H, m), 2.76–3.92 (3H, m), 3.93–4.42 (1H, m), 6.32–8.25 (15H, m)

Example 222

0.41 g of dimethylaminopyridine and 0.35 g of dimethylaminopyridine hydrochloride were added to a solution of 0.4 g of 5-hydroxymethyl-7-chloro-1-[4-(2-methylbenzoylamino)benzoyl]-2,3,4,5-tetrahydro-1H-benzoazepine dissolved in 10 ml of chloroform. The mixture was heated and made into a solution. To the solution were added 0.15 g of N,N-dimethylglycine hydrochloride and 0.46 g of dicyclohexyl-carbodiimide in this order at room temperature with stirring. The mixture was stirred overnight at room temperature. Thereto were added 1.3 ml of methanol and 0.4 ml of acetic acid, and the mixture was stirred at room temperature for 2 hours. The reaction mixture was mixed with a saturated aqueous sodium hydrogencarbonate solution, followed by extraction with dichloromethane. The extract was dried over magnesium sulfate and subjected to vacuum distillation to remove the solvent. The residue was purified by silica gel column chromatography (elutant: methyl acetate) and then mixed with hydrochloric acid-methanol. The mixture was stirred at room temperature for 1 hour to form a hydrochloride and obtain 0.36 g of 5-[(2-dimethylaminoacetyloxy)m-ethyl]-7-chloro-1-[4-(2-methyl-benzoylamino)benzoyl]-2,3,4,5-tetrahydro-1H-benzoazepine hydrochloride.

Colorless and amorphous $^1$H-NMR (DMSO-d$_6$) δ: 1.2–2.2 (3H, m), 2.35 (3H, s), 2.83 (6H, s), 2.7– 3.2 (1H, m), 3.3–3.6 (3H, m), 4.29 (2H, s), 4.2–5.1 (2H, m), 6.80 (1H, d, J=8.2 Hz), 7.0–7.8 (10H, m), 10.4–10.6 (1H, m), 10.6–10.9 (1H, br)

Example 223

0.28 g of lithium borohydride was added to a solution of 2.2 g of 5-ethoxycarbonylmethoxy-7-chloro-1-[4-(2-methylbenzoylamino)benzoyl]-2,3,4,5-tetrahydro-1H-benzoazepine dissolved in 50 ml of tetrahydrofuran, at room temperature with stirring. The mixture was refluxed for 30 minutes. The reaction mixture was poured into a diluted hydrochloric acid. The mixture was subjected to extraction with dichloromethane. The extract was dried over magnesium sulfate and subjected to vacuum distillation to remove the solvent. The residue was purified by silica gel column chromatography (elutant: dichloromethane/methanol=100/1→50/1) and then recrystallized from dichloromethane-diethyl ether to obtain 1.6 g of 5-(2-hydroxyethoxy)-7-chloro-1-[4-(2-methylbenzoylamino)benzoyl]-2,3,4,5-tetrahydro-1H-benzoazepine.

A white powder
Melting point: 185°–187.5° C.

Example 224

In 10 ml of dimethylformamide were dispersed 0.4 g of 5-[2-(p-toluenesulfonyloxy)ethoxy]-7-fluoro-1-[2-methoxy-4-(2-methylbenzoylamino)benzoyl]-2,3,4,5-tetrahydro-1H-benzoazepine, 0.38 ml of N-methylpiperazine and 0.3 g of sodium iodide. The dispersion was stirred at room temperature for 3 days. The reaction mixture was concentrated. The residue was mixed with water and the mixture was subjected to extraction with ethyl acetate. The extract was dried over sodium carbonate and purified by silica gel column chromatography (elutant: dichloromethane/-methanol=10/1) to obtain 1.15 g of 5-[2-(4-methyl-1-piperazinyl)ethoxy]-7-fluoro-1-[2-methoxy-4-(2-methyl-benzoylamino)benzoyl]-2,3,4,5-tetrahydro-1H-benzoazepine.

Colorless and amorphous $^1$H-NMR (CDCl$_3$) δ: 1.37–2.90 (15H, m), 2.33 (3H, s), 2.47 (3H, s), 3.38–3.99 (5H, m), 4.31–5.08 (2H, m), 6.56–7.98 (11H, m)

Example 225

0.178 g of sodium iodide and 0.152 g of 4-acetyl-piperazine were added to a solution of 0.25 g of 5-[2-(p-toluenesulfonyloxy)ethyl]-7-chloro-1-[2-methyl-4-(2-methyl-benzoylamino)benzoyl]-2,3,4,5-tetrahydro-1H-benzoazepine dissolved in 20 ml of dry dimethylformamide. The mixture was stirred at room temperature for 1 hour and heated at 50° C. for 2 hours and at 60° C. for 3 hours. The reaction mixture was mixed with 1N hydrochloric acid and diethyl ether. The aqueous layer was separated, then neutralized with a saturated aqueous sodium bicarbonate solution, and subjected to extraction with dichloromethane. The dichloromethane layer was washed with water, then dried and subjeced to distillation to remove the solvent. The resiude was mixed with hydrochloric acid-ethanol to form a hydrochloride and obtain 150 mg of 5-[2-(4-acetyl-1-piperazinyl)ethyl]-7-chloro-1-[2-methyl-4-(2-methylbenzoylamino)benzoyl]-2,3,4,5-tetrahydro-1H-benzoazepine hydrochloride.

Colorless and amorphous $^1$H-NMR (CDCl$_3$) δ: 1.02–2.59 [16H, m (2.09, 3H, s-like)], 2.59–3.83 (9H, m), 3.87–4.63 (2H, m), 6.56–8.12 (10H, m), 10.27, 10.45 (total 1H, brs), 11.00 (1H, brs)

Tables 110 to 154 (Examples 226 to 314) and their NMR data appear here.

The following compounds were obtained in the same manner as in Examples 1 and 2, using respective raw materials.

TABLE 110

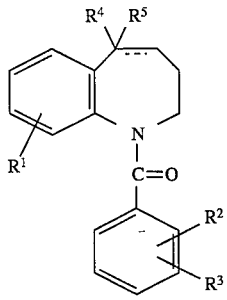

Example 226
Structure:

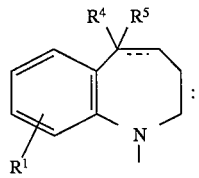

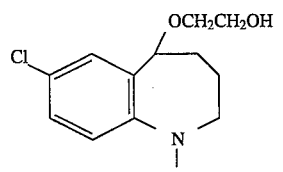

R$^2$: H

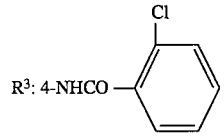

R$^3$: 4-NHCO—

Crystal form: white powder
Recrystallization solvent: dichloromethane-diethyl ether TABLE 110-continued Melting point: 183–185° C.   Form: free

TABLE 111

Example 227
Structure:

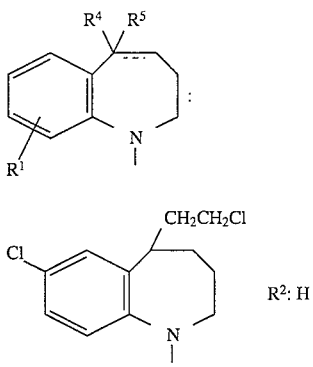

R²: H

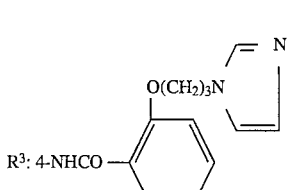

R³: 4-NHCO—

Crystal form: white powder
Recrystallization solvent: dichloromethane-
                        diethyl ether
Melting point: 200–201.5° C.
Form: free Example 228
Structure:

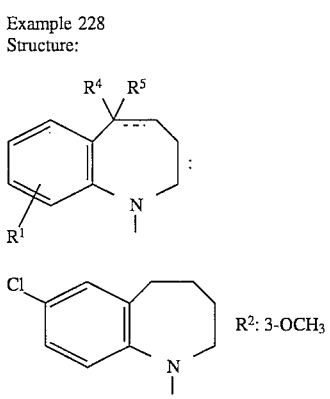

R²: 3-OCH₃

Crystal form: colorless needle
Form: free
NMR: 147)

TABLE 112

Example 229
Structure:

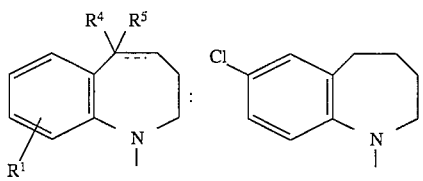

R²: 3-OCH₃

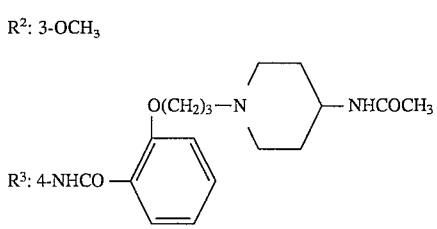

R³: 4-NHCO—

Crystal form: colorless and amorphous
Form: free
NMR: 148)

Example 230
Structure:

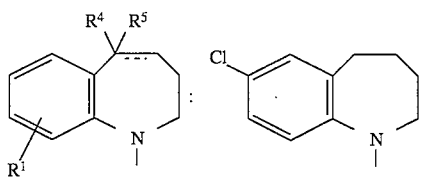

R²: 3-OCH₃

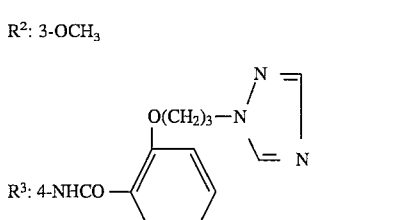

R³: 4-NHCO—

Crystal form: colorless needle
Recrystallization solvent: dichloromethane-
                        diethyl ether
Melting point: 158–160° C.
Form: free

TABLE 113

Example 231
Structure:

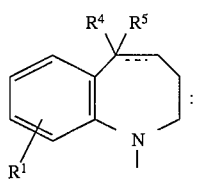

TABLE 113-continued

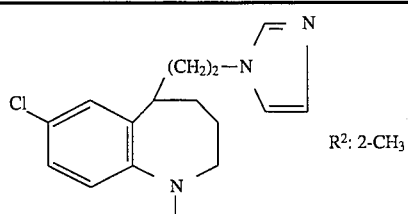

R²: 2-CH₃

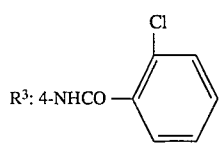

R³: 4-NHCO-[2-Cl-phenyl]

Crystal form: colorless and amorphous
Form: free
NMR: 149)

Example 232
Structure:

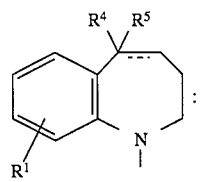

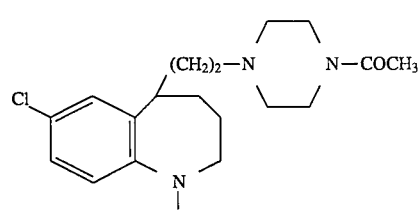

R²: 2-CH₃

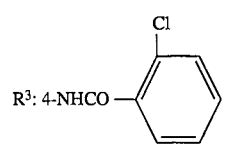

R³: 4-NHCO-[2-Cl-phenyl]

Crystal form: colorless and amorphous
Form: free
NMR: 150)

TABLE 114

Example 233
Structure:

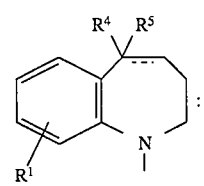

TABLE 114-continued

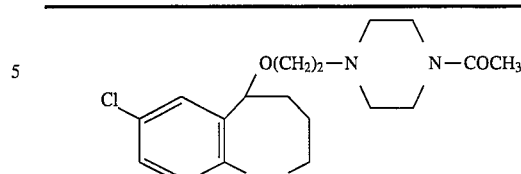

R²: 2-CH₃

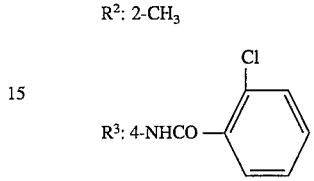

R³: 4-NHCO-[2-Cl-phenyl]

Crystal form: colorless and amorphous
Form: free
NMR: 151)

Example 234
Structure:

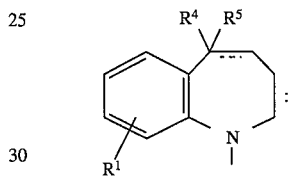

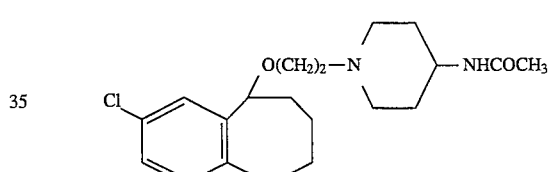

R²: 2-CH₃

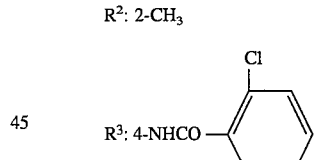

R³: 4-NHCO-[2-Cl-phenyl]

Crystal form: colorless and amorphous
Form: free
NMR: 152)

TABLE 115

Example 235
Structure:

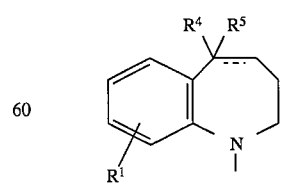

TABLE 115-continued

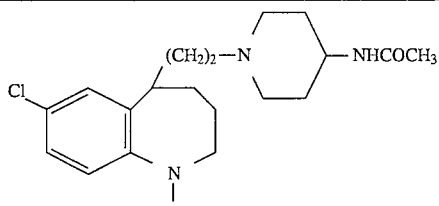

R²: 2-CH₃

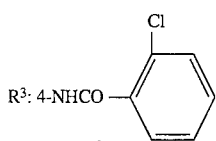

R³: 4-NHCO

Crystal form: colorless and amorphous
Form: free
NMR: 153)

Example 236
Structure:

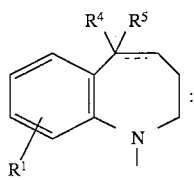

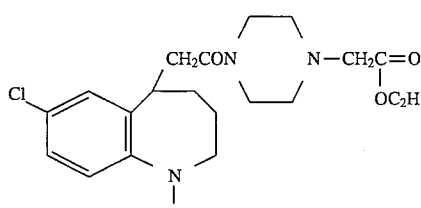

R²: 2-OCH₃

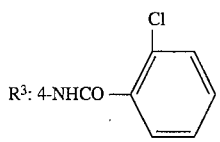

R³: 4-NHCO

Crystal form: colorless and amorphous
Form: free
NMR: 154)

TABLE 116

Example 237
Structure:

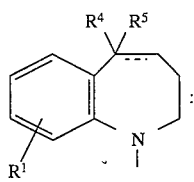

TABLE 116-continued

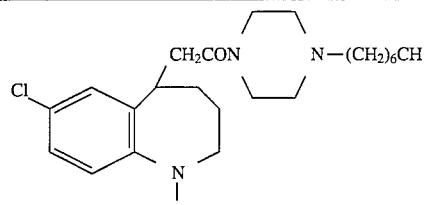

R²: 2-OCH₃

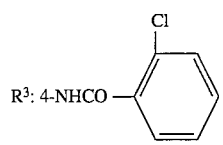

R³: 4-NHCO

Crystal form: colorless and amorphous
Form: hydrochloride
NMR: 155)

Example 238
Structure:

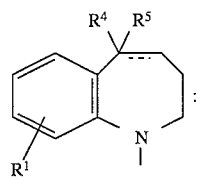

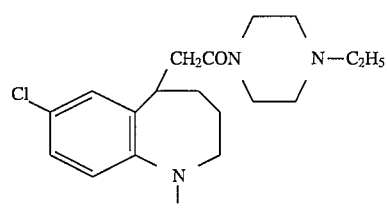

R²: 2-OCH₃

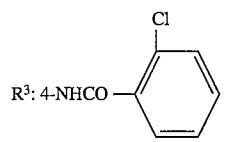

R³: 4-NHCO

Crystal form: white powder
Recrystallization solvent: ethyl acetate-diethyl ether
Melting point: 214–216° C.
Form: free

TABLE 117

Example 239
Structure:

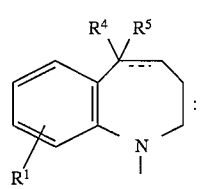

TABLE 117-continued

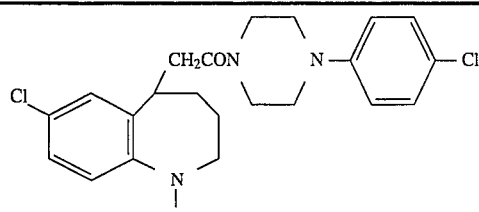

R²: 2-OCH₃

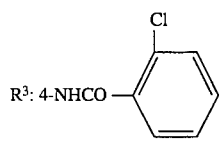

R³: 4-NHCO

Crystal form: white powder
Recrystallization solvent: acetone-n-hexane
Form: free Example 240
Structure:

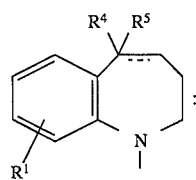

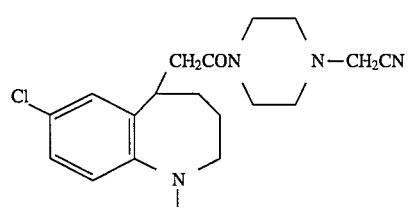

R²: 2-OCH₃

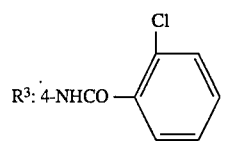

R³: 4-NHCO

Crystal form: white powder
Recrystallization solvent: acetone-diethyl ether
Melting point: 263–264° C.
Form: free

TABLE 118

Example 241
Structure:

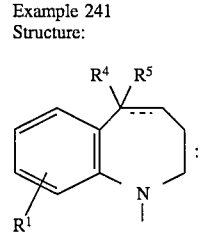

TABLE 118-continued

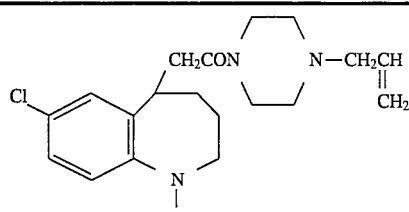

R²: 2-OCH₃

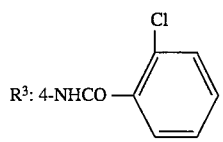

R³: 4-NHCO

Crystal form: white powder
Recrystallization solvent: ethanol-diethyl ether
Melting point: 218–218.5° C.
Form: free Example 242
Structure:

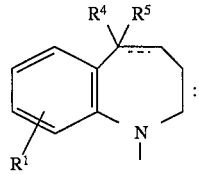

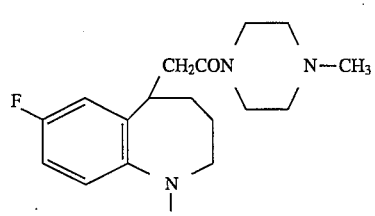

R²: 3-OCH₃

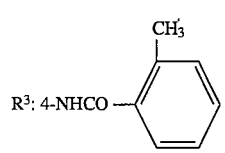

R³: 4-NHCO

Crystal form: colorless and amorphous
Form: free
NMR: 156)

TABLE 119

Example 243
Structure:

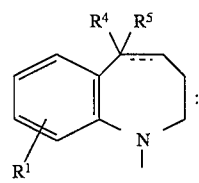

TABLE 119-continued

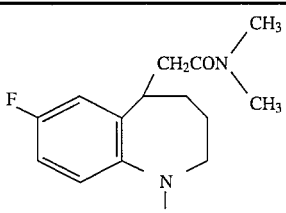

R²: 3-OCH₃

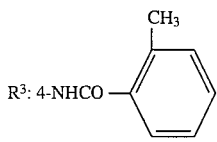

R³: 4-NHCO—

Crystal form: colorless and amorphous
Form: free
NMR: 157)

Example 244
Structure:

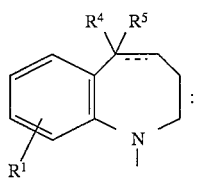

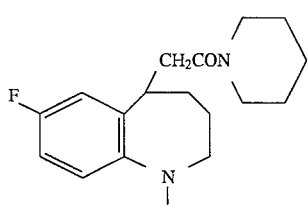

R²: 3-OCH₃

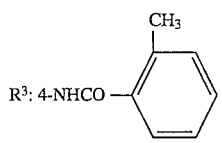

R³: 4-NHCO—

Crystal form: colorless and amorphous
Form: free
NMR: 158)

TABLE 120

Example 245
Structure:

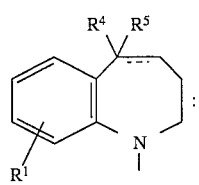

TABLE 120-continued

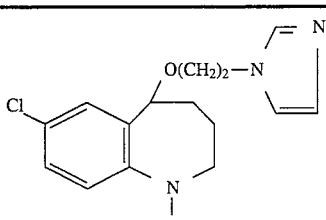

R²: 2-CH₃

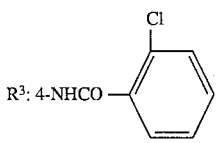

R³: 4-NHCO—

Crystal form: colorless and amorphous
Form: free
NMR: 159)

Example 246
Structure:

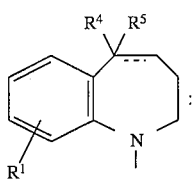

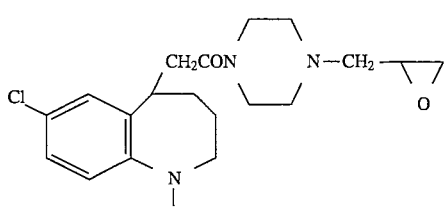

R²: 2-OCH₃

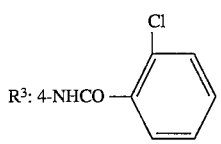

R³: 4-NHCO—

Crystal form: white powder
Recrystallization solvent: acetone-diethyl ether
Melting point: 205–208° C.
Form: free

TABLE 121

Example 247
Structure:

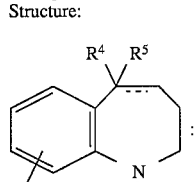

TABLE 121-continued

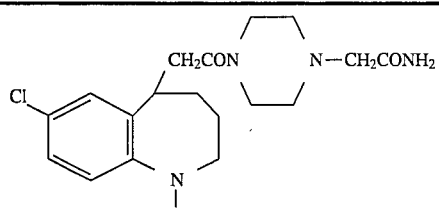

R²: 2-OCH₃

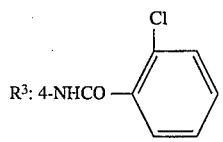

R³: 4-NHCO—

Crystal form: colorless and amorphous
Form: free
NMR: 160)

Example 248
Structure:

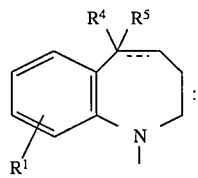

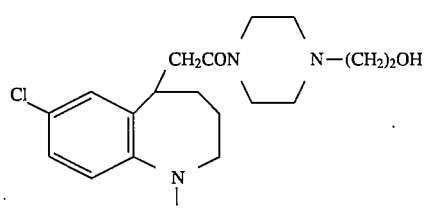

R²: 2-OCH₃

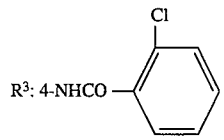

R³: 4-NHCO—

Crystal form: white powder
Recrystallization solvent: acetone-n-hexane
Melting point: 209–209.5° C.
Form: free

TABLE 122

Example 249
Structure:

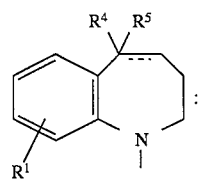

TABLE 122-continued

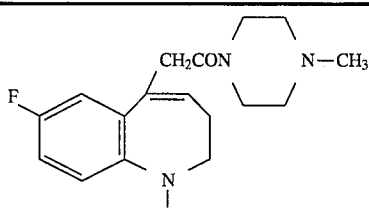

R²: 2-OCH₃

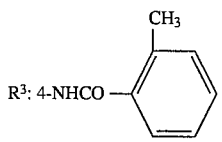

R³: 4-NHCO—

Crystal form: colorless and amorphous
Form: free
NMR: 161)

Example 250
Structure:

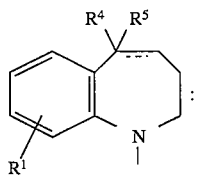

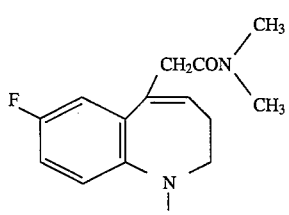

R²: 2-OCH₃

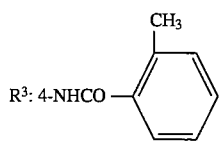

R³: 4-NHCO—

Crystal form: colorless and amorphous
Form: free
NMR: 162)

TABLE 123

Example 251
Structure:

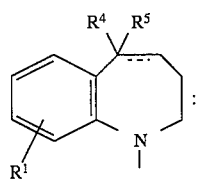

TABLE 123-continued

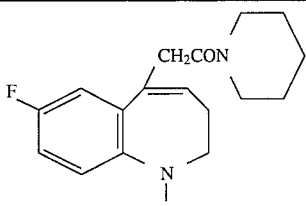

R²: 2-OCH₃

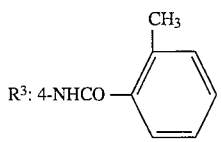

R³: 4-NHCO-

Crystal form: colorless and amorphous
Form: free
NMR: 163)

Example 252
Structure:

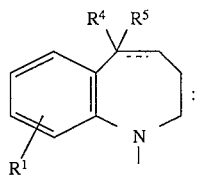

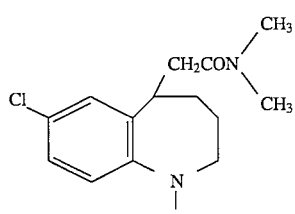

R²: 3-OCH₃

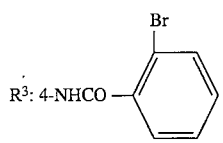

R³: 4-NHCO-

Crystal form: colorless and amorphous
Form: free
NMR: 164)

TABLE 124

Example 253
Structure:

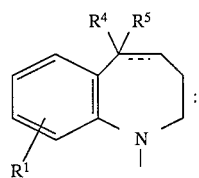

TABLE 124-continued

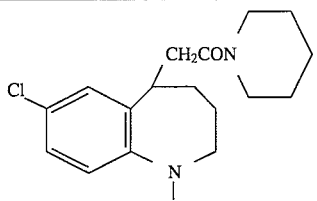

R²: 3-OCH₃

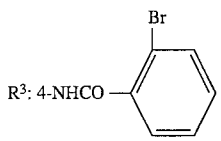

R³: 4-NHCO-

Crystal form: colorless and amorphous
Form: free
NMR: 165)

Example 254
Structure:

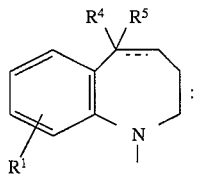

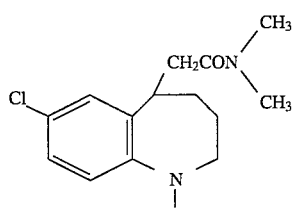

R²: 3-OCH₃

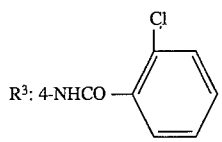

R³: 4-NHCO-

Crystal form: colorless and amorphous
Form: free
NMR: 166)

TABLE 125

Example 255
Structure:

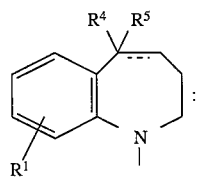

TABLE 125-continued

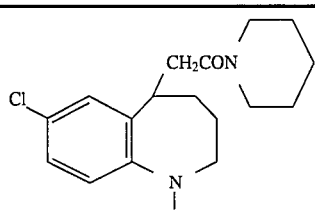

R²: 3-OCH₃

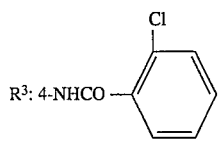

R³: 4-NHCO—

Crystal form: colorless and amorphous
Form: free
NMR: 167)

Example 256
Structure:

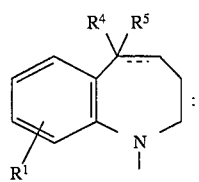

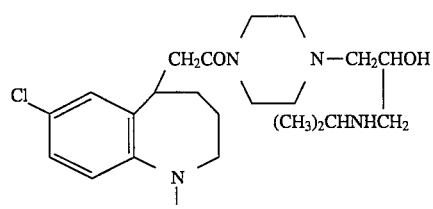

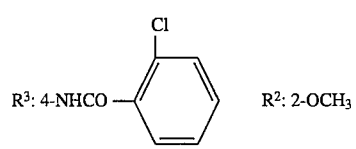

Crystal form: colorless and amorphous
Form: free
NMR: 168)

TABLE 126

Example 257
Structure:

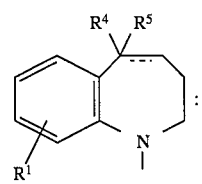

TABLE 126-continued

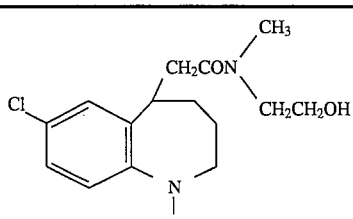

R²: 2-OCH₃

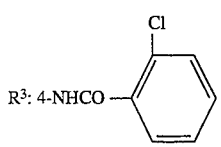

R³: 4-NHCO—

Crystal form: white powder
Recrystallization solvent: ethanol-diethyl ether
Melting point: 223.5–224° C.
Form: free Example 258
Structure:

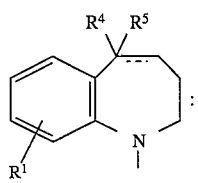

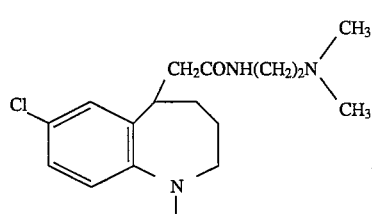

R²: 2-OCH₃

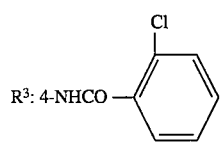

R³: 4-NHCO—

Crystal form: white powder
Recrystallization solvent: ethanol-n-hexane
Melting point: 212–213° C.
Form: hydrochloride

TABLE 127

Example 259
Structure:

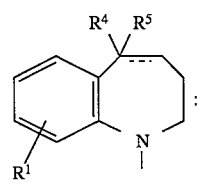

TABLE 127-continued

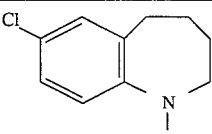

R²: 3-OCH₃

R³: 4-NHCO— 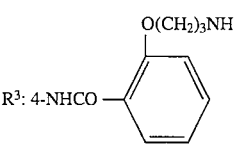 —O(CH₂)₃NHCONHCH₃

Crystal form: colorless needle
Recrystallization solvent: dichloromethane-ethanol
Melting point: 211–213° C.
Form: free Example 260
Structure:

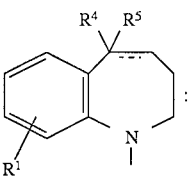

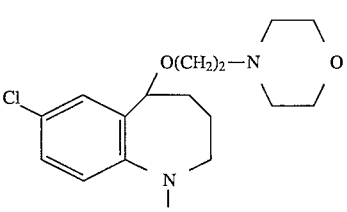

R²: 2-CH₃

R³: 4-NHCO— 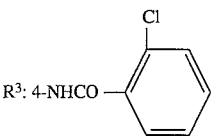 —Cl

Crystal form: colorless and amorphous
Form: free
NMR: 169)

TABLE 128

Example 261
Structure:

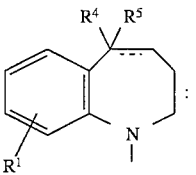

TABLE 128-continued

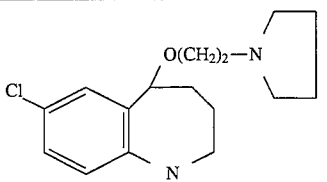

R²: 2-CH₃

R³: 4-NHCO— 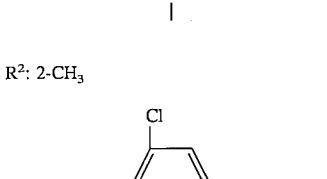 —Cl

Crystal form: light yellow and amorphous
Form: hydrochloride
NMR: 170)

Example 262
Structure:

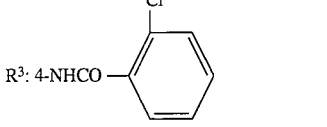

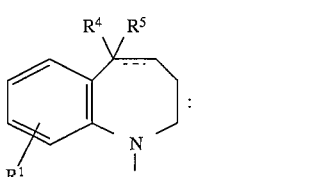

R³: 4-NHCO— 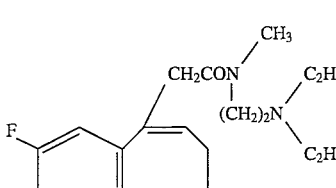 —CH₃   R²: 2-OCH₃

Crystal form: colorless and amorphous
Form: free
NMR: 171)

TABLE 129

Example 263
Structure:

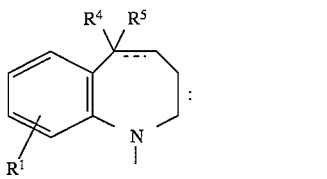

TABLE 129-continued
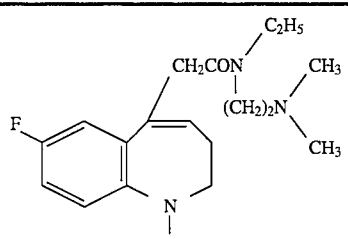
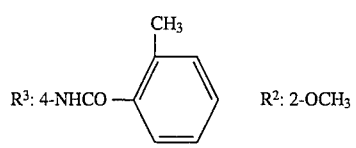
Crystal form: colorless and amorphous
Form: free
NMR: 172)
Example 264
Structure:
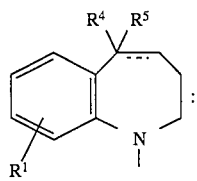
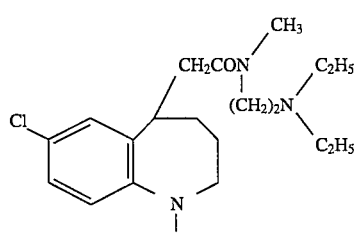
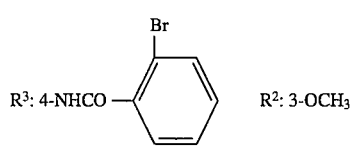
Crystal form: colorless and amorphous
Form: free
NMR: 173)
TABLE 130
Example 265
Structure:
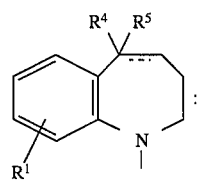
TABLE 130-continued
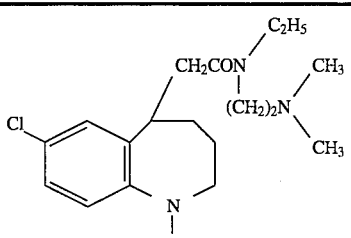
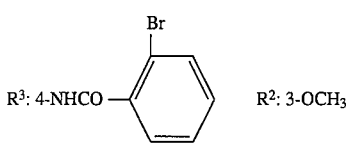
Crystal form: colorless and amorphous
Form: free
NMR: 174)
Example 266
Structure:
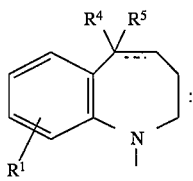
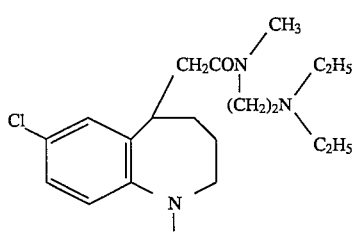
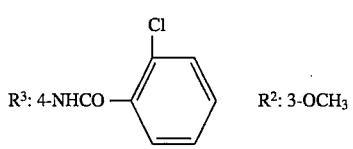
Crystal form: colorless and amorphous
Form: free
NMR: 175)
TABLE 131
Example 267
Structure:
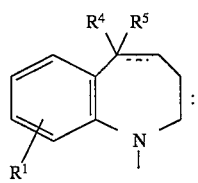

TABLE 131-continued

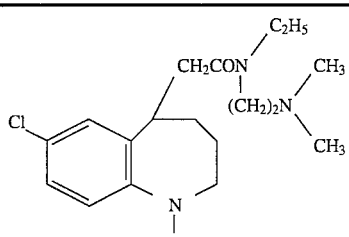

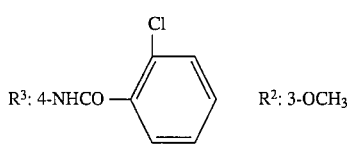

R³: 4-NHCO— (2-Cl phenyl)    R²: 3-OCH₃

Crystal form: colorless and amorphous
Form: free
NMR: 176)

Example 268
Structure:

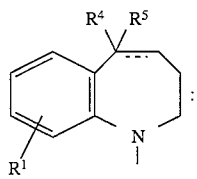

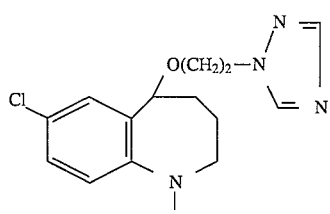

R²: 2-CH₃

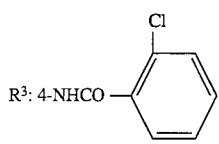

R³: 4-NHCO— (2-Cl phenyl)

Crystal form: colorless and amorphous
Form: free
NMR: 177)

TABLE 132

Example 269
Structure:

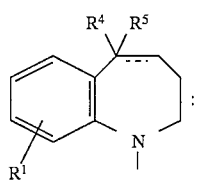

TABLE 132-continued

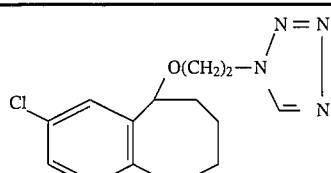

R²: 2-CH₃

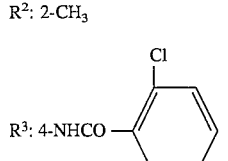

R³: 4-NHCO— (2-Cl phenyl)

Crystal form: colorless and amorphous
Form: free
NMR: 178)

Example 270
Structure:

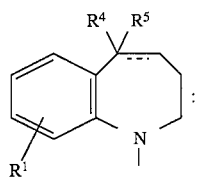

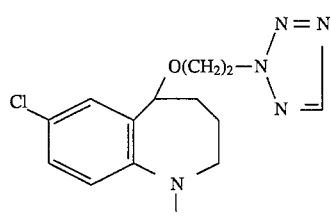

R²: 2-CH₃

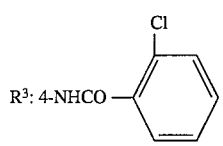

R³: 4-NHCO— (2-Cl phenyl)

Crystal form: colorless and amorphous
Form: free
NMR: 179)

TABLE 133

Example 271
Structure:

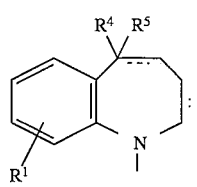

TABLE 133-continued

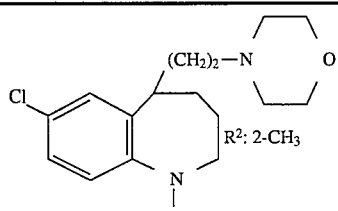
R²: 2-CH₃

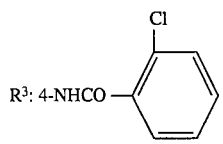
R³: 4-NHCO-

Crystal form: white powder
Recrystallization solvent: acetone-n-hexane
Melting point: 163–165° C.
Form: free Example 272
Structure:

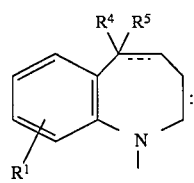

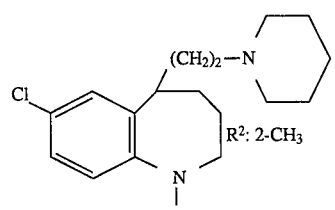
R²: 2-CH₃

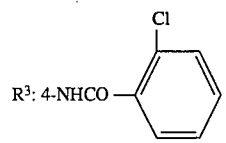
R³: 4-NHCO-

Crystal form: colorless and amorphous
Form: hydrochloride
NMR: 180)

TABLE 134

Example 273
Structure:

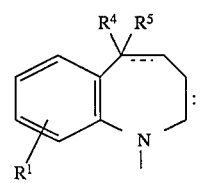

TABLE 134-continued

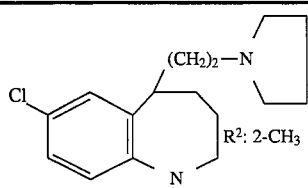
R²: 2-CH₃

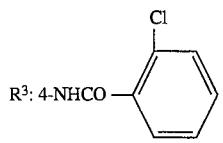
R³: 4-NHCO-

Crystal form: colorless and amorphous
Form: hydrochloride
NMR: 181)

Example 274
Structure:

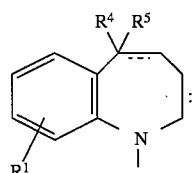

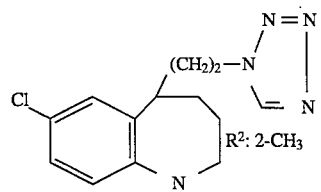
R²: 2-CH₃

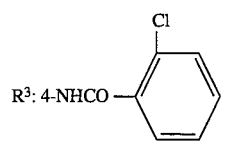
R³: 4-NHCO-

Crystal form: colorless and amorphous
Form: free
NMR: 182)

TABLE 135

Example 275
Structure:

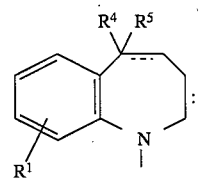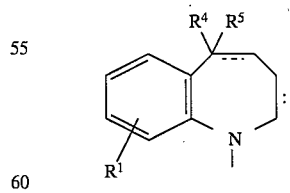

TABLE 135-continued

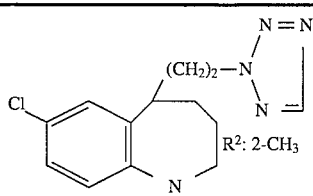

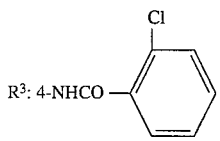

Crystal form: colorless and amorphous
Form: free
NMR: 183)

Example 276
Structure:

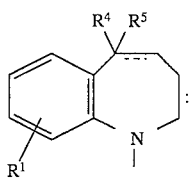

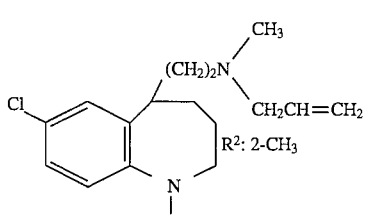

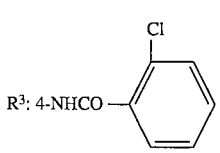

Crystal form: colorless and amorphous
Form: hydrochloride
NMR: 184)

TABLE 136

Example 277
Structure:

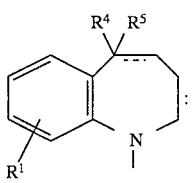

TABLE 136-continued

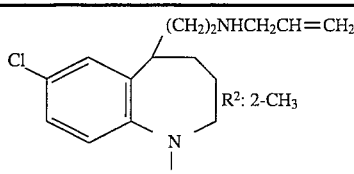

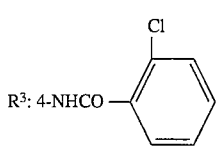

Crystal form: colorless and amorphous
Form: hydrochloride
NMR: 185)

Example 278
Structure:

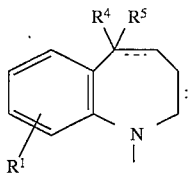

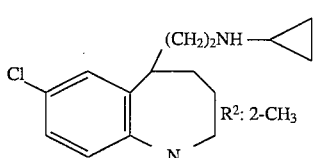

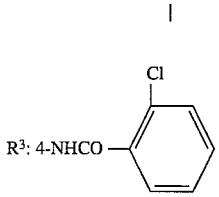

Crystal form: white powder
Recrystallization solvent:
dichloromethane-n-hexane
Melting point: 185–187° C. (decomposed)
Form: hydrochloride

TABLE 137

Example 279
Structure:

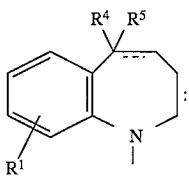

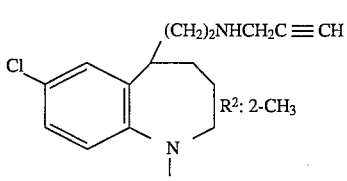

TABLE 137-continued

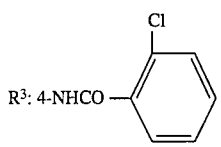
R³: 4-NHCO—(2-Cl-phenyl)

Crystal form: colorless and amorphous
Form: hydrochloride
NMR: 186)

Example 280
Structure:

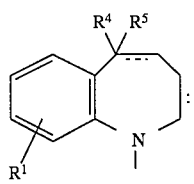

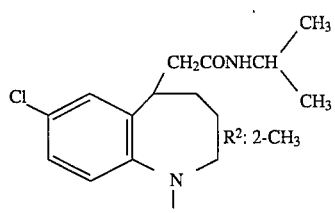
R²: 2-CH₃, CH₂CONHCH(CH₃)₂, Cl

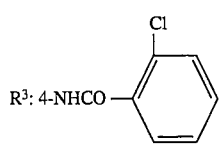
R³: 4-NHCO—(2-Cl-phenyl)

Crystal form: white powder
Recrystallization solvent:
acetone-n-hexane
Melting point: 266.5–267° C.
Form: free

TABLE 138

Example 281
Structure:

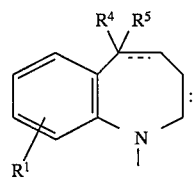

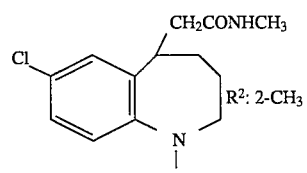
CH₂CONHCH₃, R²: 2-CH₃, Cl

TABLE 138-continued

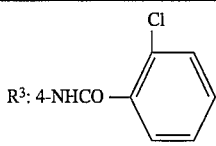
R³: 4-NHCO—(2-Cl-phenyl)

Crystal form: white powder
Recrystallization solvent: acetone
Melting point: 255–257° C.
Form: free Example 282
Structure:

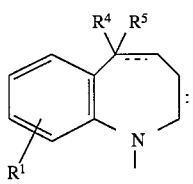

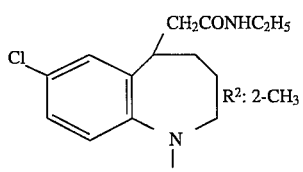
CH₂CONHC₂H₅, R²: 2-CH₃, Cl

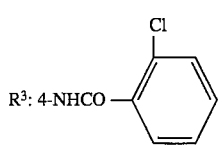
R³: 4-NHCO—(2-Cl-phenyl)

Crystal form: white powder
Recrystallization solvent:
acetone-n-hexane
Melting point: 263.5–264° C.
Form: free

TABLE 139

Example 283
Structure:

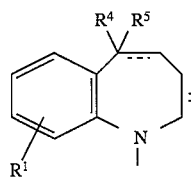

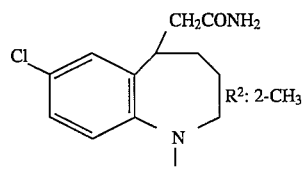
CH₂CONH₂, R²: 2-CH₃, Cl

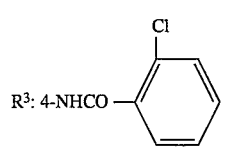
R³: 4-NHCO—(2-Cl-phenyl)

TABLE 139-continued

Crystal form: white powder
Recrystallization solvent: ethanol
Melting point: 240–241.5° C.
Form: free Example 284
Structure:

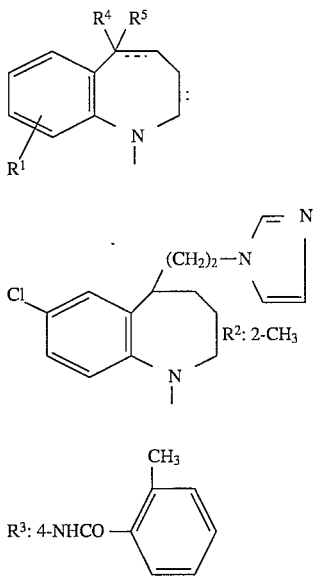

Crystal form: colorless and amorphous
Form: free
NMR: 187)

TABLE 140

Example 285
Structure:

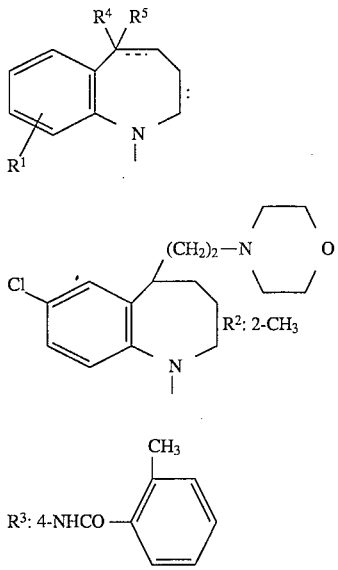

Crystal form: white powder
Recrystallization solvent: diethyl ether
Melting point: 159–163° C. (decomposed)
Form: free

TABLE 140-continued

Example 286
Structure:

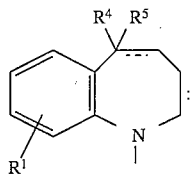

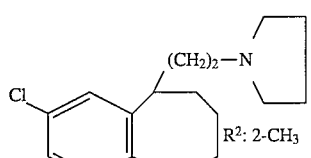

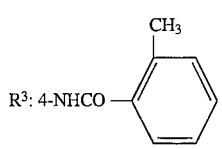

Crystal form: colorless and amorphous
Form: free
NMR: 188)

TABLE 141

Example 287
Structure:

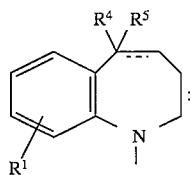

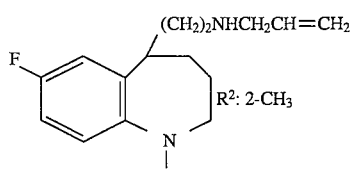

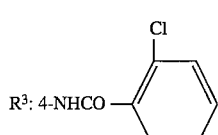

Crystal form: colorless and amorphous
Form: free
NMR: 189)

Example 288
Structure:

TABLE 141-continued

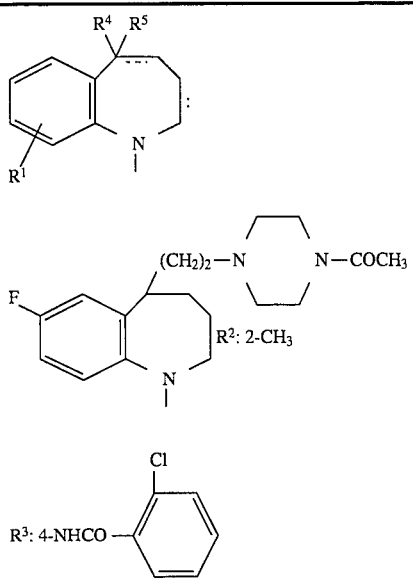

Crystal form: colorless and amorphous
Form: free
NMR: 190)

TABLE 142

Example 289
Structure:

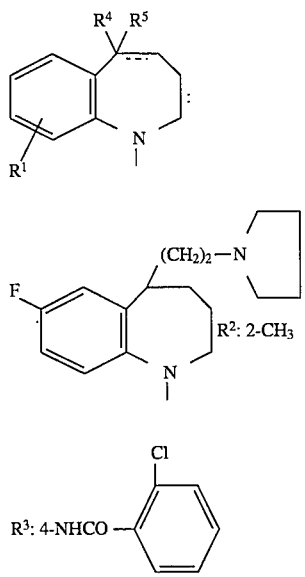

Crystal form: colorless and amorphous
Form: free
NMR: 191)

Example 290
Structure:

TABLE 142-continued

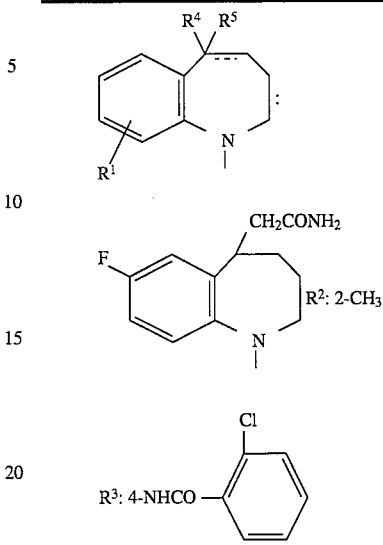

Crystal form: white powder
Recrystallization solvent:
dichloromethane-diethyl ether
Melting point: 247–248° C.
Form: free

TABLE 143

Example 291
Structure:

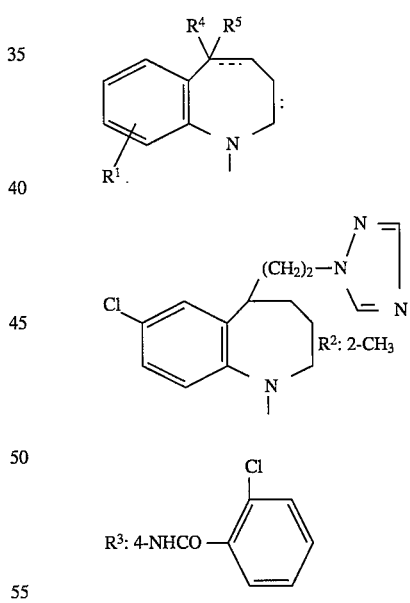

Crystal form: colorless and amorphous
Form: free
NMR: 192)

Example 292
Structure:

TABLE 143-continued

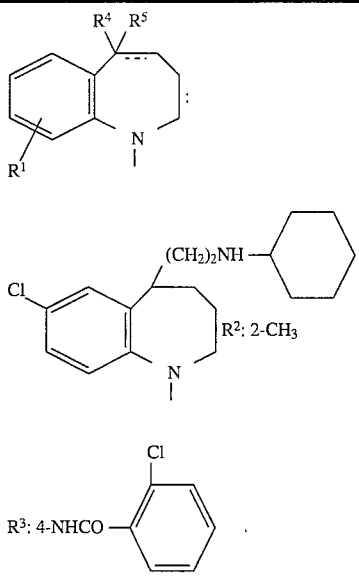

R²: 2-CH₃

R³: 4-NHCO—(2-Cl phenyl)

Crystal form: white powder
Recrystallization solvent:
acetone-diethyl ether
Melting point: 192.5–194° C.
Form: free

TABLE 293

Example 293
Structure:

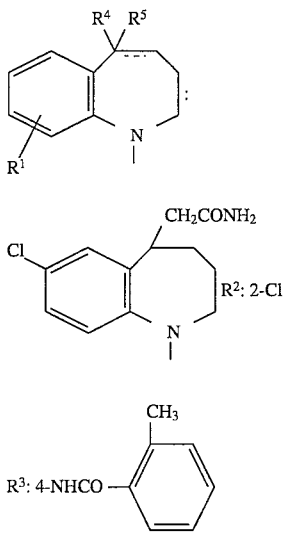

R²: 2-Cl

R³: 4-NHCO—(2-CH₃ phenyl)

Crystal form: white powder
Recrystallization solvent:
dichloromethane-diethyl ether
Melting point: 171–172° C.
Form: free Example 294
Structure:

TABLE 293-continued

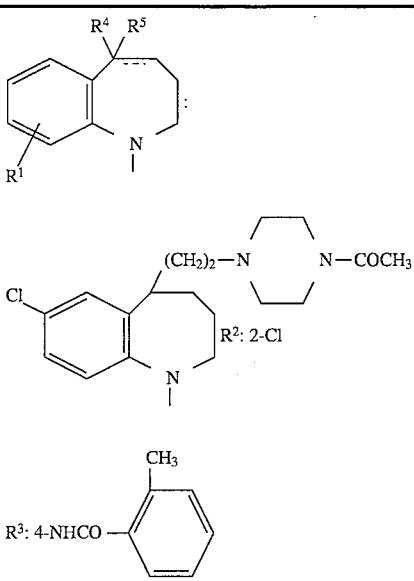

R²: 2-Cl

R³: 4-NHCO—(2-CH₃ phenyl)

Crystal form: colorless and amorphous
Form: free
NMR: 193)

TABLE 145

Example 295
Structure:

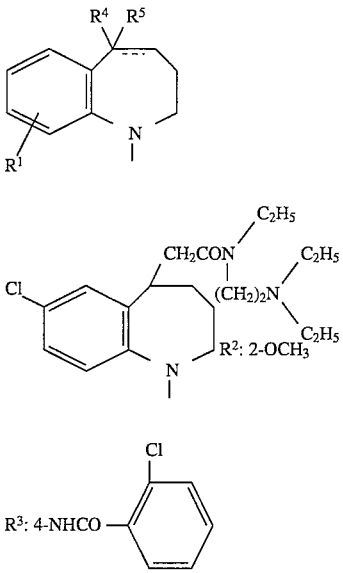

R²: 2-OCH₃

R³: 4-NHCO—(2-Cl phenyl)

Crystal form: colorless and amorphous
NMR: 194)
Form: free

Example 296
Structure:

TABLE 145-continued
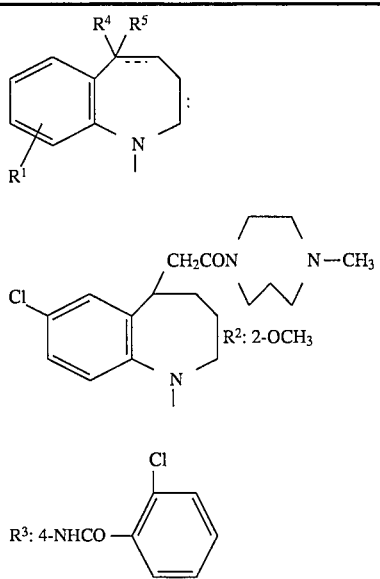
Crystal form: colorless and amorphous
NMR: 195)
Form: free
TABLE 146
Example 297
Structure:
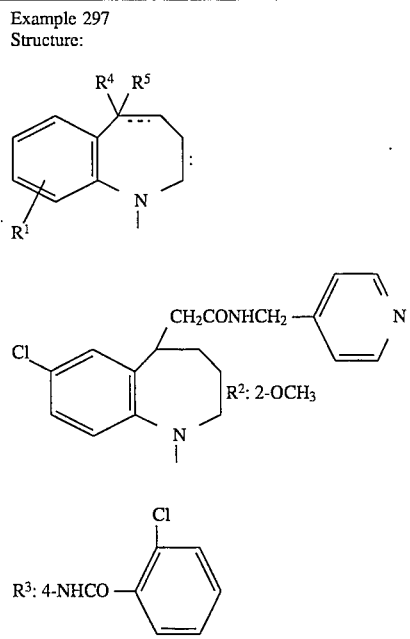
Crystal form: colorless and amorphous
Form: free
NMR: 196)
Example 298
Structure:
TABLE 146-continued
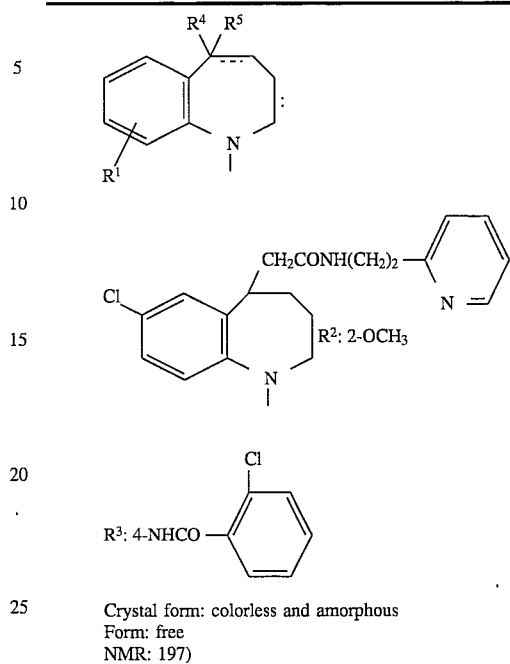
Crystal form: colorless and amorphous
Form: free
NMR: 197)
TABLE 147
Example 299
Structure:
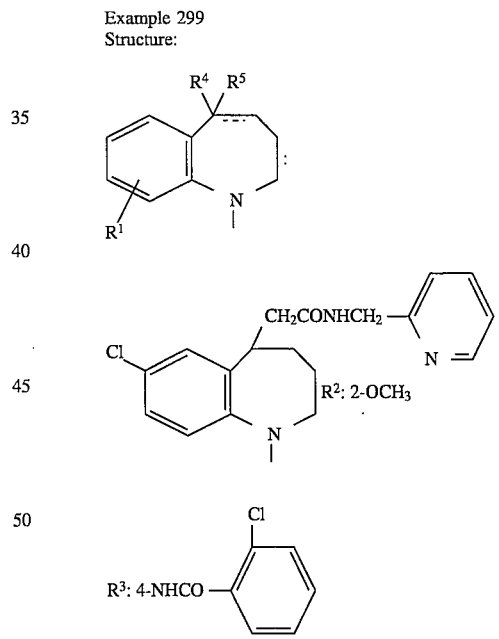
Crystal form: colorless and amorphous
Form: free
NMR: 198)
Example 300
Structure:

TABLE 147-continued

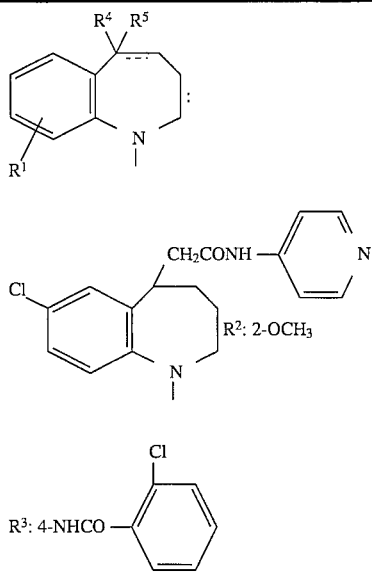

Crystal form: colorless and amorphous
NMR: 199)
Form: free

TABLE 148

Example 301
Structure:

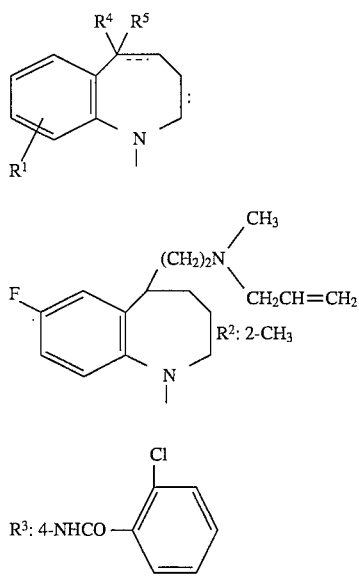

Crystal form: colorless and amorphous
Form: free
NMR: 200)

Example 302
Structure:

TABLE 148-continued

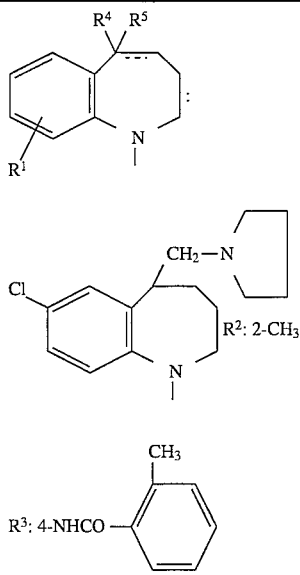

Crystal form: colorless and amorphous
NMR: 201)
Form: free

TABLE 149

Example 303
Structure:

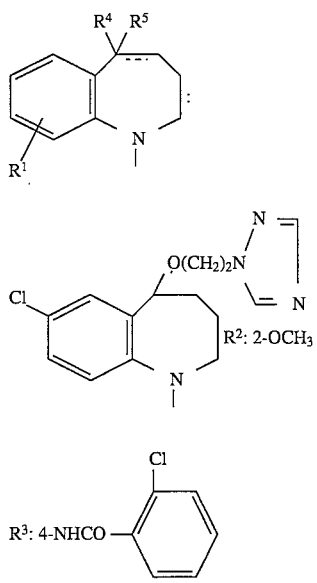

Crystal form: white powder
Recrystallization solvent:
ethanol-n-hexane
Melting point: 214–215° C.
Form: free Example 304
Structure:

TABLE 149-continued

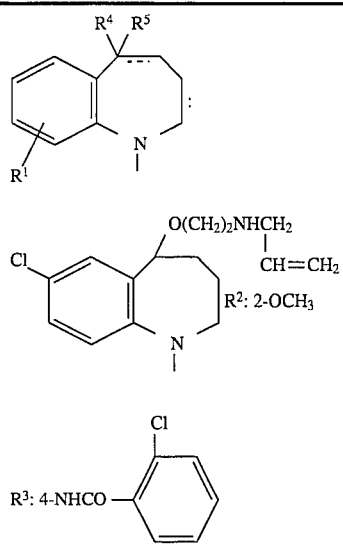

Crystal form: white powder
Recrystallization solvent:
acetone-diethyl ether
Melting point: 193–195° C.
Form: hydrochloride

TABLE 150

Example 305
Structure:

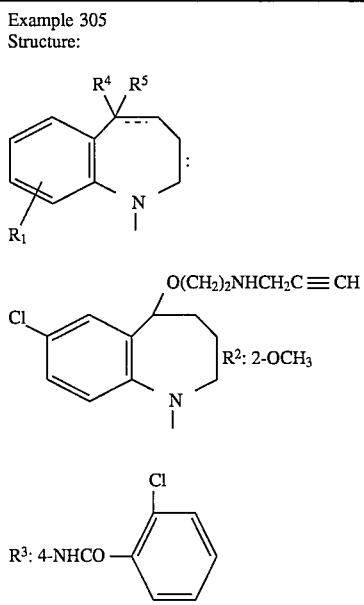

Crystal form: colorless and amorphous
Form: hydrochloride
NMR: 202)

Example 306
Structure:

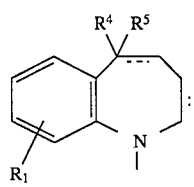

TABLE 150-continued

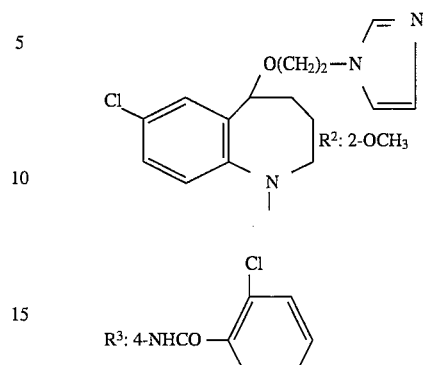

Crystal form: white powder
Recrystallization solvent: acetone-n-hexane
Melting point: 211–212° C.
Form: free

TABLE 151

Example 307
Structure:

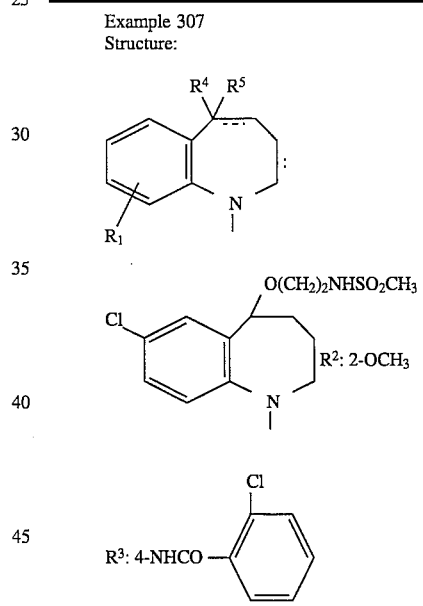

Crystal form: colorless and amorphous
Form: free
NMR: 203)

Example 308
Structure:

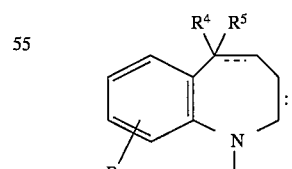

TABLE 151-continued

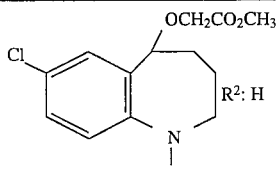

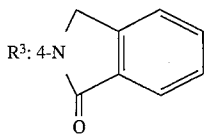

Crystal form: colorless and amorphous
Form: free
NMR: 204)

TABLE 152

Example 309
Structure:

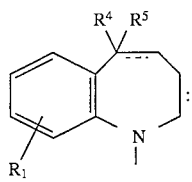

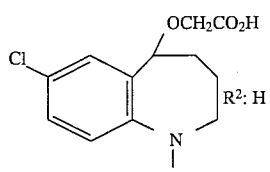

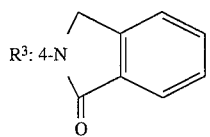

Crystal form: colorless and amorphous
Form: free
NMR: 205)

Example 310
Structure:

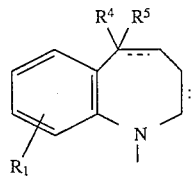

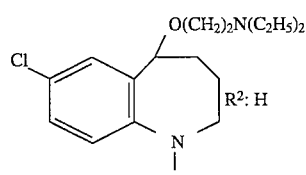

TABLE 152-continued

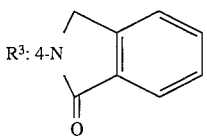

Crystal form: colorless needle
Recrystallization solvent:
dichloromethane-diethyl ether
Melting point: 153–156° C.
Form: free

TABLE 153

Example 311
Structure:

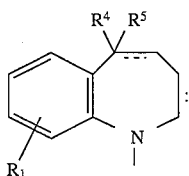

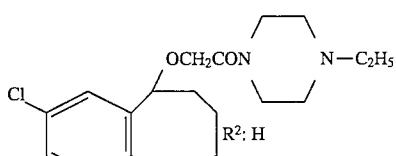

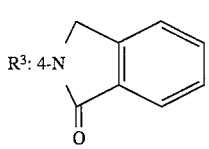

Crystal form: colorless and amorphous
Form: free
NMR: 206)

Example 312
Structure:

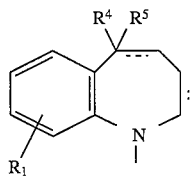

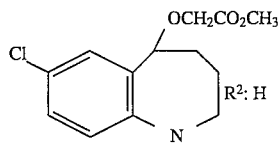

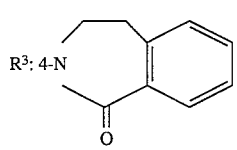

TABLE 153-continued

Crystal form: colorless and amorphous
Form: free
NMR: 207)

TABLE 314

Example 313
Structure:

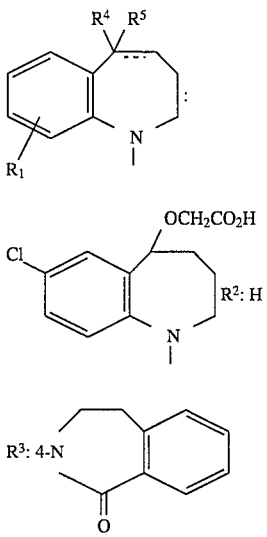

Crystal form: colorless oil
Form: free
NMR: 208)

Example 314
Structure:

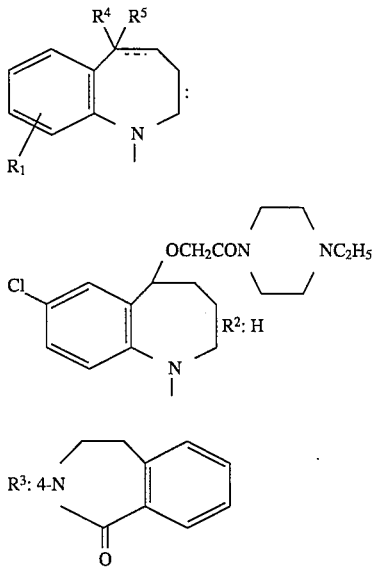

Crystal form: colorless and amorphous
Form: free
NMR: 209)

147) $^1$H-NMR (CDCl$_3$) δ ppm: 1.36–2.23 (4H, m), 2.25–3.20 (5H, m), 3.66 (3H, s), 4.00–4.27 (4H, m), 4.87–5.19 (1H, m), 6.52–7.23 (8H, m), 7.24 (1H, d, J=2.4Hz), 7.31–7.55 (2H, m), 8.18 (1H, dd, J=1.8Hz, 7.8Hz), 8.47 (1H, d, J=8.4Hz), 9.90–10.05 (total 1H, each s)

148) $^1$H-NMR (CDCl$_3$) δ ppm: 1.12–4.32 (28H, m), 4.73–5.12 (1H, m), 6.04 (1H, d, J=7.8Hz), 6.45–7.47 (8H, m), 8.15 (1H, dd, J=1.7Hz, 7.8Hz), 8.38 (1H, d, J=7.8Hz), 10.19, 10.28 (total 1H, each s)

149) $^1$H-NMR (CDCl$_3$) δ ppm: 1.20–3.29, 3.51–4.52, 4.95–5.19 (total 14H, m), 6.37–7.85 (13H, m), 8.54–8.79, 8.91–9.19 (total 1H, m)

150) $^1$H-NMR (CDCl$_3$) δ ppm: 1.15–4.03, 4.12–4.47, 4.91–5.14 (total 22H, m), 2.02 (3H, s), 6.40–7.78 (10H, m), 8.45, 8.69 (total 1H, each s)

151) $^1$H-NMR (CDCl$_3$) δ ppm: 1.40–3.02, 3.09–3.94, 4.27–5.15 (total 25H, m), 6.40–6.83, 7.05–7.78 (total 9H, m), 6.94 (1H, dd, J=2.2Hz, 8.4Hz), 8.56, 8.73, 8.86 (total 1H, each s)

152) $^1$H-NMR (CDCl$_3$) δ ppm: 1.31–3.18, 3.35–3.97, 4.30–4.77, 4.86–5.13 (total 26H, m), 5.49–6.02, 6.18–6.40 (total 1H, m), 6.41–7.00, 7.06–7.84 (total 10H, m), 8.25–8.63 (1H, m)

153) $^1$H-NMR (CDCl$_3$) δ ppm: 1.12–3.91, 4.16–4.92, 4.87–5.11 (total 23H, m), 1.87 (3H, s), 5.85–6.18 (1H, m), 6.35–6.99, 7.04–7.78 (total 10H, m), 8.45–8.96 (1H, m)

154) $^1$H-NMR (CDCl$_3$) δ ppm: 1.00–2.25 (5H, m), 1.28 (3H, t, J=7.1Hz), 2.26–5.08 (17H, m), 4.20 (2H, q, J=7.1Hz), 6.61–7.92 (10H, m), 8.25, 8.47 (total 1H, each brs)

155) $^1$H-NMR (CDCl$_3$) δ ppm: 0.75–1.01 (3H, m), 1.05–2.04 (13H, m), 2.62–4.69 (17H, m), 6.79–7.78 (10H, m), 10.54, 10.76 (total 1H, each brs), 11.17 (1H, brs)

156) $^1$H-NMR (CDCl$_3$) δ ppm: 1.22–1.67 (2H, m), 1.71–3.34 (16H, m), 2.49 (3H, s), 3.53–4.08 (1H, m), 3.64, 3.70 (total 3H, s), 4.37–5.21 (1H, m), 6.55–7.53 (9H, m), 8.03–8.44 (2H, m)

157) $^1$H-NMR (CDCl$_3$) δ ppm: 1.12–4.13 (17H, m), 2.49 (3H, s), 4.37–5.25 (1H, m), 6.54–7.58 (9H, m), 8.04–8.46 (2H, m)

158) $^1$H-NMR (CDCl$_3$) δ ppm: 1.20–4.02 (21H, m), 2.49 (3H, s), 4.40–5.23 (1H, m), 6.53–7.58 (9H, m), 8.03–8.47 (2H, m)

159) $^1$H-NMR (CDCl$_3$) δ ppm: 1.31–4.70, 4.87–5.14 (total 14H, m), 6.48–7.84 (13H, m), 9.15, 9.31, 9.53 (total 1H, each s)

160) $^1$H-NMR (CDCl$_3$) δ ppm: 1.10–5.05 (22H, m), 5.57–5.88 (1H, m), 6.68–7.89 (10H, m), 8.29, 8.50 (total 1H, each brs)

161) $^1$H-NMR (CDCl$_3$) δ ppm: 1.88–2.72 (6H, m) 2.32 (3H, s), 2.46 (3H, s), 3.28–3.97 (10H, m), 4.58–4.82 (1H, m), 5.90–6.18 (1H, m), 6.58–7.56 (10H, m), 8.06, 8.28 (total 1H, brs)

162) $^1$H-NMR (CDCl$_3$) δ ppm: 2.03–2.68 (2H,m), 2.45 (3H, s), 2.99 (3H, s), 3.10 (3H, s), 3.32–3.55 (1H, m), 3.72 (3H, s), 4.57–4.78 (1H, m), 5.88–6.16 (1H, m), 6.57–7.56 (10H, m), 8.25, 8.51 (total 1H, brs)

162) $^1$H-NMR (CDCl$_3$) δ ppm: 2.03–2.68 (2H, m), 2.45 (3H, s), 2.99 (3H, s), 3.10 (3H, s), 3.32–3.55 (1H, m), 3.72 (3H, s), 4.57–4.78 (1H, m), 5.88–6.16 (1H, m), 6.57–7.56 (10H, M), 8.25, 8.51 (total 1H, brs)

163) ¹H-NMR (CDCl₃) δ ppm: 1.44–1.82 (6H, m), 2.16–2.69 (2H, m), 2.46 (3H, s), 3.18–3.93 (7H, m), 3.74 (3H, s), 4.58–4.82 (1H, m), 5.87–6.17 (1H, m), 6.56–7.57 (10H, m), 8.24, 8.51 (total 1H, brs)

164) ¹H-NMR (CDCl₃) δ ppm: 1.21–2.23 (4H, m), 2.56–3.37 (9H, m), 3.57–4.05 (1H, m), 3.64, 3.71 (total 3H, s), 4.37–5.23 (1H, m), 6.52–7.76 (9H, m), 8.23–8.58 (2H, m)

165) ¹H-NMR (CDCl₃) δ ppm: 1.19–2.25 (10H, m), 2.54–4.02 (15H, m), 4.34–5.23 (1H, m), 6.54–7.73 (9H, m), 8.22–8.55 (2H, m)

166) ¹H-NMR (CDCl₃) δ ppm: 1.23–2.27 (4H, m), 2.55–3.37 (9H, m), 3.58–3.99 (1H, m), 3.65, 3.72 (total 3H, s), 4.37–5.23 (1H, m), 6.53–6.68 (1H, m), 6.77–7.93 (8H, m), 8.30–8.95 (2H, m)

167) ¹H-NMR (CDCl₃) δ ppm: 1.18–2.27 (10H, m), 2.52–3.98 (15H, m), 4.35–5.26 (1H, m), 6.52–7.48 (9H, m), 8.29–8.47 (1H, m), 8.60, 8.87 (total 1H, brs)

168) ¹H-NMR (DMSO-d₆) δ ppm: 0.73–2.03 (16H, m), 2.62–4.68 (17H, m), 6.78–7.75 (10H, m), 10.54, 10.76 (total 1H, each brs), 11.17 (1H, brs)

169) ¹H-NMR (CDCl₃) δ: 1.40–3.05, 3.14–4.06 (total 20H, m), 4.31–4.75, 4.82–5.11 (total 2H, m), 6.41–6.82, 7.08–7.80 (total 9H, m), 6.93 (1H, dd, J=2.4Hz, 8.4Hz), 8.22, 8.37, 8.55 (total 1H, each s).

170) ¹H-NMR (DMSO-d₆) δ ppm: 1.35–4.15 (20H, m), 4.46–5.08 (2H, m), 6.55–6.98, 7.04–7.21, 7.22–7.84 (total 10H, m), 10.25–10.91 (2H, m)

171) ¹H-NMR (CDCl₃) δ ppm: 0.88–1.18 (6H, m), 2.05–3.98 (16H, m), 2.46 (3H, s), 3.73 (3H, s), 4.58–4.83 (1H, 5.93–6.23 (1H, m), 6.55–7.58 (10H, m) 7.93, 8.01 (total 1H, brs)

172) ¹H-NMR (CDCl₃) δ ppm: 1.18–4.02 (23H, m), 2.47 (3H, s), 4.68–4.87 (1H, m), 6.03–6.26 (1H, m), 6.57–8.12 (11H, m)

173) ¹H-NMR (CDCl₃) δ ppm: 0.81–4.07 (25H, m), 3.69, 3.73 (total 3H, s), 4.32–5.23 (1H, m), 6.52–6.66 (1H, m), 6.67–7.72 (8H, m), 8.19–8.54 (2H, m)

174) ¹H-NMR (CDCl₃) δ ppm: 0.93–4.13 (17H, m), 2.32 (3H, s), 2.36 (3H, s), 3.70, 3.73 (total 3H, s), 4.35–5.23 (1H, m), 6.53–6.70 (1H, m), 6.72–7.74 (8H, m), 8.26–8.57 (2H, m)

175) ¹H-NMR (CDCl₃) δ ppm: 0.78–4.13 (25H, m), 3.70, 3.75 (total 3H, s), 4.32–5.23 (1H, m), 6.51–6.74 (1H, m), 6.88–7.58 (7H, m), 7.65–7.88 (1H, m), .8.26–8.94 (2H, m)

176) ¹H-NMR (CDCl₃) δ ppm: 0.93–4.13 (17H, m), 2.32 (3H, s), 2.36 (3H, s), 3.71, 3.73 (total 3H, s), 4.36–5.23 (1H, m), 6.52–6.75 (1H, m), 6.80–7.57 (7H, m), 7.65–7.90 (1H, m), 8.27–8.92 (2H, m)

177) ¹H-NMR (CDCl₃) δ ppm: 1.35–4.71, 4.84–5.14 (total 14H, m), 6.41–6.80, 6.80–7.79 (total 10H, m), 7.91, 7.98, 8.04, 8.15, 8.20 (total 2H, each s), 8.46, 8.86 (total 1H, each s)

178) ¹H-NMR (CDCl₃) δ ppm: 1.32–5.12 (14H, m), 6.42–7.88 (10H, m), 8.42–8.57, 8.70, 8.77, 8.83 (total 2H, each s)

179) ¹H-NMR (CDCl₃) δ ppm: 1.31–5.11 (14H, m, 2.35, 2.42 (each s)), 6.41–7.83 (10H, m), 8.32, 8.47, 8.50, 8.57, 8.85 (total 2H, each s)

180) ¹H-NMR (DMSO-d₆) δ ppm: 0.68–2.49 (13H, m), 2.35, 2.41 (total 1H, each s), 2.50–5.09 (8H, m), 6.56–8.08 (10H, m), 10.52, 10.69 (total 1H, each brs), 10.81 (1H, brs)

181) ¹H-NMR (DMSO-d₆) δ ppm: 1.00–2.49 (11H, m), 2.35, 2.41 (total 3H, each s), 2.51–5.13 (8H, m), 6.53–7.82 (10H, m), 10.54 10.71 (total 1H, each brs), 10.73 (1H, brs)

182) ¹H-NMR (CDCl₃) δ ppm: 1.13–3.32 (10H, m), 3.42–5.10 (3H, m), 4.62 (1H, t, J=7Hz), 6.45–7.93 (10H, m), 8.67–9.26 (2H, m)

183) ¹H-NMR (CDCl₃) δ ppm: 1.02–3.35 (10H, m), 3.37–5.12 (3H, m), 4.83 (1H, t, J=6.6Hz), 6.47–7.89 (10H, m), 8.42–9.11 (2H, m)

184) ¹H-NMR (DMSO-d₆) δ ppm: 1.01–2.52 (10H, m), 2.53–5.06 (9H, m), 5.38–5.73 (2H, m), 5.83–6.24 (1H, m), 6.54–7.82 (10H, m), 10.51, 10.69 (total 1H, each brs), 11.10 (1H, brs)

185) ¹H-NMR (DMSO-d₆) δ ppm: 1.00–2.57 (10H, m), 2.58–5.06 (6H, m), 5.15–5.63 (2H, m), 5.82–6.18 (1H, m), 6.52–8.08 (10H, m), 9.15–9.74 (2H, br), 10.51, 10.68 (total 1H, brs)

186) ¹H-NMR (DMSO-d₆) δ ppm: 1.04–2.59 (10H, m), 2.60–5.08 (7H, m), 6.53–7.88 (10H, m), 9.70 (2H, brs), 10.52, 10.68 (total 1H, (each brs)

187) ¹H-NMR (CDCl₃) δ ppm: 1.16–2.63 (5H, m), 2.36, 2.47, 2.52 (total 6H, s), 2.66–3.32 (2H, m), 3.36–5.22 (4H, m), 6.44–8.15 (14H, m)

188) ¹H-NMR (CDCl₃) δ ppm: 1.14–3.92 (18H, m), 2.40 (3H, s), 2.46 (3H, s), 4.23–5.18 (1H, m), 6.41–6.98 (3H, m), 7.02–7.90 (8H, m)

189) ¹H-NMR (CDCl₃) δ ppm: 1.13–3.92 (13H, m), 2.41 (3H, s), 4.27–5.14 (1H, m), 5.10–5.23 (2H, m), 5.78–6.05 (1H, 6.43–8.35 (11H, m)

190) ¹H-NMR (CDCl₃) δ ppm: 1.12–3.87 (18h, m), 2.07 (3H, s), 2.42 (3H, s), 4.28–5.16 (1H, m), 6.46–8.22 (11H, m)

191) ¹H-NMR (CDCl₃) δ ppm: 1.17–3.40 (18H, m), 2.43 (3H, s), 4.30–5.17 (1H, m), 6.45–8.13 (11H, m)

192) ¹H-NMR (CDCl₃) δ ppm: 0.79–5.21 (11H, m), 2.38, 2.44 (total 3H, each s), 6.50–8.30 (13H, m)

193) ¹H-NMR (CDCl₃) δ ppm: 1.14–3.92 (18H, m), 2.04 (3H, s), 2.46 (3H, s), 4.23–5.08 (1H, m), 6.78–8.35 (11H, m)

194) ¹H-NMR (CDCl₃) δ ppm: 0.82–4.01 (30H, m), 4.44–5.06 (1H, m), 6.68–7.80 (10H, m), 8.24, 8.48 (total 1H, brs)

195) ¹H-NMR (CDCl₃) δ ppm: 1.07–4.12 (21H, m), 2.38, 2.41 (total 3H, s), 4.43–5.03 (1H, m), 6.71–7.87 (10H, m), 8.36, 8.58 (total 1H, brs)

196) ¹H-NMR (CDCl₃) δ ppm: 1.13–4.12 (9H, m), 3.92 (3H, brs), 4.25–4.47 (2H, m), 6.45–6.85 (2H, m), 6.88–7.52 (8H, m), 7.56–7.96 (2H, m), 8.27–8.56 (2H, m), 8.23, 9.03 (total 1H, brs)

197) ¹H-NMR (CDCl₃) δ ppm: 1.06–4.08 (15H, m), 4.37–5.03 (1H, m), 6.65–8.56 (16H, m)

198) ¹H-NMR (CDCl₃) δ ppm: 1.14–2.12 (4H, m), 2.28–5.06 (10H, m), 6.51–7.89 (14H, m), 8.28–8.75 (2H, m)

199) ¹H-NMR (CDCl₃) δ ppm: 1.56–2.17 (4H, m), 2.33–3.52 (4H, m), 3.76–4.17 (4H, m), 6.98–7.55 (10H, m), 7.63–7.97 (2H, m), 8.22 (2H, dd, J=4.9Hz, 1.5Hz), 8.68–9.16 (2H, m)

200) ¹H-NMR (CDCl₃) δ ppm: 1.14–3.93 (18H, m), 4.25–5.14 (1H, m), 5.08–5.29 (2H, m), 5.78–6.02 (1H, m), 6.44–7.78 (10H, m), 7.96, 8.21 (total 1H, brs)

201) ¹H-NMR (CDCl₃) δ ppm: 1.10–1.40 (1H, m), 1.50–4.00 (22H, m), 4.50–5.10 (1H, m), 6.40–7.05 (3H, m), 7.10–7.90 (8H, m)

202) ¹H-NMR (DMSO-d₆) δ ppm: 1.05–2.52 (4H, m), 2.53–2.82 (1H, m), 3.01–4.12 (10H, m), 4.48–4.89 (2H, m), 6.76–7.76 (10H, m), 9.68 (2H, brs), 10.59, 10.75 (total 1H, each brs)

203) ¹H-NMR (CDCl₃) δ ppm: 0.78–2.45 (5H, m), 2.46–5.95 (9H, m), 3.02 (3H, s), 6.67–7.92 (10H, m), 8.27, 8.60 (total 1H, each brs)

204) ¹H-NMR (CDCl₃) δ ppm: 1.51–2.59 (4H, m), 2.65–3.07 (1H, m), 3.81 (3H, s), 4.04–5.29 (6H, m), 6.50–6.78, 6.88–7.10, 7.12–8.01 (total 11H, m)
205) ¹H-NMR (CDCl₃) δ ppm: 1.37–3.08 (5H, m), 3.95–5.25 (6H, m), 5.65–6.27 (2H, m), 6.42–6.73, 6.77–7.10, 7.10–8.08 (total 10H, m)
206) ¹H-NMR (CDCl₃) δ ppm: 1.11 (3H, t, J=7.4Hz), 1.50–3.06 (11H, m), 3.35–3.85 (4H, m), 4.07–5.29 (6H, m), 6.46–6.73, 6.86–7.14, 7.14–7.69 (total 8H, m), 7.78 (2H, d, J=8.3Hz), 7.89 (1H, d, J=8.1Hz)
207) ¹H-NMR (CDCl₃) δ ppm: 1.50–3.02 (5H, m), 3.11 (2H, t, J=6.3Hz), 3.78 (3H, s), 3.94 (2H, t, J=6.3Hz), 4.04–5.23 (4H, m), 6.62 (1H, d, J=8.1Hz), 7.02 (1H, d, J=7.9Hz), 7.07–7.80 (8H, m), 8.11 (1H, d, J=7.5Hz)
208) ¹H-NMR (CDCl₃) δ ppm: 1.45–3.32 (7H, m), 3.59–5.22 (6H, m), 6.62 (1H, d, J=8.1Hz), 6.87–7.75 (10H, m), 8.07 (1H, d, J=6.3Hz)
209) ¹H-NMR (CDCl₃) δ ppm: 1.10 (3H, t, J=7.1Hz), 1.50–3.22 (13H, m), 3.32–3.79 (4H, m), 3.94 (2H, t, J=6.2Hz), 4.04–5.25 (4H, m), 6.53–6.75 (1H, m), 6.87–7.67 (9H, m), 8.11 (1H, d, J=7.4Hz)

The compounds shown in Table 155 were obtained in the same manner as in Examples 1 and 2, using respective starting materials.

Table 155 (Examples 315 to 429) and their NMR data appear here.

TABLE 155
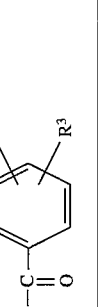
| Example No. | R¹ R⁴ R⁵ | R² R³ | Crystal form (Recrystallization solvent) | Melting point (°C.) (Salt form) |
|---|---|---|---|---|
| 315 | 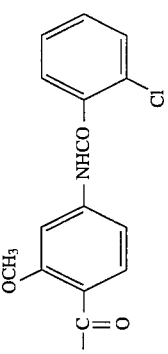 | 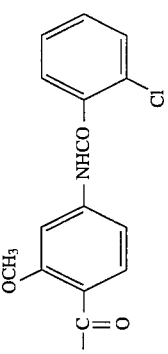 | Colorless and amorphous | (—) |
| 316 | 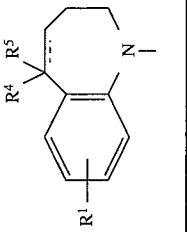 | 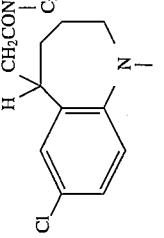 | Colorless and amorphous | (—) |

TABLE 155-continued

| | | | | |
|---|---|---|---|---|
| 317 | (structure with CH₂CONH—CH₂ and pyrazine group) | (2-Cl-phenyl NHCO-, OCH₃, C=O aryl) | Colorless and amorphous | (—) |
| 318 | (structure with O(CH₂)₂NH—C(=NH)—CH₃) | (same aryl) | Colorless and amorphous | (HCl) |
| 319 | (structure with O(CH₂)₂NH—C(=O)—NH₂) | (same aryl) | White powder (Acetone-n-hexane) | 206–207 (—) |
| 320 | (structure with CH₂—tetrazole NH) | (same aryl) | Colorless and amorphous | (—) |
| 321 | (structure with O(CH₂)₂NHCO₂C₂H₅) | (same aryl) | White powder (Acetone-n-hexane) | 192–193 (—) |

TABLE 155-continued

| | | | | |
|---|---|---|---|---|
| 322 | H O(CH₂)₂NH-cyclopropyl, chlorophenyl-azepine | 3-OCH₃, 4-C(=O)-, 4-NHCO-(2-chlorophenyl) | Colorless and amorphous | (HCl) |
| 323 | O(CH₂)₂-N(pyrrolidine), chlorophenyl-azepine | 3-OCH₃, 4-C(=O)-, 4-NHCO-(2-chlorophenyl) | White powder (Acetone-ethyl acetate-n-hexane) | 194–195.5 (–) |
| 324 | O(CH₂)₂-N(piperidine), chlorophenyl-azepine | 3-OCH₃, 4-C(=O)-, 4-NHCO-(2-chlorophenyl) | White powder (Acetone-n-hexane) | 198–199 (decomposed) (–) |
| 325 | O(CH₂)₂-S-(3-pyridyl), chlorophenyl-azepine | 3-OCH₃, 4-C(=O)-, 4-NHCO-(2-chlorophenyl) | White powder (Acetone-n-hexane) | 199–200 (–) |

TABLE 155-continued

| | | | |
|---|---|---|---|
| 326 | [structure] | [structure] | White powder (Acetone-n-hexane) 228–229.5 (−) |
| 327 | [structure] | [structure] | White powder (Acetone-n-hexane) 138–139 (−) |
| 328 | [structure] | [structure] | Colorless and amorphous (−) |
| 329 | [structure] | [structure] | Colorless and amorphous (−) |

TABLE 155-continued

| | | | |
|---|---|---|---|
| 330 | (structure with O(CH₂)₂—SO—pyridyl) | (structure with OCH₃, NHCO-2-chlorophenyl, C=O) | White powder (Ethyl acetate-n-hexane) 192–193.5 (–) |
| 331 | (structure with O(CH₂)₂—SO—imidazolyl) | (structure with OCH₃, NHCO-2-chlorophenyl, C=O) | White powder (Acetone-ethyl acetate-n-hexane) 206–207 (decomposed) (–) |
| 332 | (structure with O(CH₂)₂—SO₂—imidazolyl) | (structure with OCH₃, NHCO-2-chlorophenyl, C=O) | White powder (Acetone-diethyl ether) 247–248 (–) |
| 333 | (structure with (CH₂)₂—N—piperazine-N—SO₂CH₃) | (structure with OCH₃, NHCO-2-chlorophenyl, C=O) | Colorless and amorphous (–) |

TABLE 155-continued

| | | | | |
|---|---|---|---|---|
| 334 | (structure with piperazine N–CO₂C₂H₅ group) | (3-OCH₃, 4-C(=O)–NHCO–(2-Cl-phenyl)) | Colorless and amorphous | (–) |
| 335 | (structure with piperazine N–CONHCH₃ group) | (3-OCH₃, 4-C(=O)–NHCO–(2-Cl-phenyl)) | Colorless and amorphous | (–) |
| 336 | (structure with O(CH₂)₂NH–C(=N–CN)–NHCH₃ group) | (3-OCH₃, 4-C(=O)–NHCO–(2-Cl-phenyl)) | Colorless and amorphous | (–) |
| 337 | (structure with O(CH₂)₂–NH–cyclopentyl group) | (3-OCH₃, 4-C(=O)–NHCO–(2-Cl-phenyl)) | White powder (Acetone-n-hexane) | 169–171 (–) |
| 338 | (structure with O(CH₂)₂–NHCH₂–phenyl group) | (3-OCH₃, 4-C(=O)–NHCO–(2-Cl-phenyl)) | White powder (Acetone-diethyl ether) | 142–144 (–) |

TABLE 155-continued

| | | | |
|---|---|---|---|
| 339 | (structure with O(CH₂)₂—N(piperazine)N—CH₃) | (structure with OCH₃, NHCO, 2-Cl phenyl) | White powder (Ethyl acetate-diethyl ether) 161–163.5 (−) |
| 340 | (structure with O(CH₂)₂—NHCH₂-(2-Cl phenyl)) | (structure with OCH₃, NHCO, 2-Cl phenyl) | Colorless and amorphous (−) |
| 341 | (structure with O(CH₂)₂—NHCH₂CN) | (structure with OCH₃, NHCO, 2-Cl phenyl) | White powder 152.5–153 (−) |
| 342 | (structure with O(CH₂)₂—N(piperidine)) | (structure with OCH₃, NHCO, 2-Br phenyl) | White powder (Acetone-n-hexane) 199.5–222 (decomposed) (−) |
| 343 | (structure with O(CH₂)₂—NH-cyclopropyl) | (structure with OCH₃, NHCO, 2-Br phenyl) | White powder (Ethyl acetate-n-hexane) 177–178 (−) |

TABLE 155-continued

| | | | | |
|---|---|---|---|---|
| 344 | H, O(CH₂)₂—NHSO₂CF₃ on bicyclic Cl-phenyl-N structure | NHCO-(2-Cl-phenyl), 3-OCH₃, 4-C(=O)– | Yellow plate | 140-142.5 (−) |
| 345 | H, O(CH₂)₂NH(CH₂)₃N(C₂H₅)₂ | NHCO-(2-Cl-phenyl), 3-OCH₃, 4-C(=O)– | Colorless and amorphous | (−) |
| 346 | H, O(CH₂)₂NHSO₂CF₃ | NHCO-(2-Br-phenyl), 3-OCH₃, 4-C(=O)– | Yellow plate (Acetone-n-hexane) | 183-184.5 (−) |
| 347 | H, O(CH₂)₂—N(CH₃)(CH₂)₂N(C₂H₅)₂ | NHCO-(2-Cl-phenyl), 3-OCH₃, 4-C(=O)– | Colorless and amorphous | (−) |
| 348 | H, O(CH₂)₂—N(C₂H₅)(CH₂)₂N(C₂H₅)₂ | NHCO-(2-Cl-phenyl), 3-OCH₃, 4-C(=O)– | Colorless and amorphous | (−) |

TABLE 155-continued

| | | | |
|---|---|---|---|
| 349 | (structure) | (structure) | Colorless and amorphous (—) |
| 350 | (structure) | (structure) | Colorless and amorphous (—) |
| 351 | (structure) | (structure) | Colorless and amorphous (—) |
| 352 | (structure) | (structure) | Colorless and amorphous (—) |
| 353 | (structure) | (structure) | Colorless and amorphous (—) |

TABLE 155-continued

| No. | Structure 1 | Structure 2 | Appearance | (–) |
|-----|---|---|---|---|
| 354 | (structure) | (structure) | Colorless and amorphous | (–) |
| 355 | (structure) | (structure) | Colorless and amorphous | (–) |
| 356 | (structure) | (structure) | Colorless and amorphous | (–) |
| 357 | (structure) | (structure) | Colorless and amorphous | (–) |

TABLE 155-continued

| | | | |
|---|---|---|---|
| 358 | (structure with N-methylpiperazine-CH₂CO-NH group on chlorobenzazepine) | (4-benzoyl-NHCO-phenyl group) | Colorless needle (Ethanol-diethyl ether) (—) |
| 359 | (structure with CH₂CONHCH₂-pyridyl group on chlorobenzazepine) | (2-OCH₃, NHCO-o-tolyl group) | Colorless and amorphous (—) |
| 360 | (structure with CH₂CONH(CH₂)₂-pyridyl group on chlorobenzazepine) | (2-OCH₃, NHCO-o-tolyl group) | Colorless and amorphous (—) |
| 361 | (structure with CH₂CO-N(CH₃)(CH₂)₂-pyridyl group on chlorobenzazepine) | (2-OCH₃, NHCO-o-tolyl group) | Colorless and amorphous (—) |

TABLE 155-continued

| | | | |
|---|---|---|---|
| 362 | (structure with CH₂CO-N(C₂H₅)(CH₂)₂-N(C₂H₅)₂ side chain on chlorinated bicyclic core) | (benzamide with OCH₃ and CH₃ substituents) | Colorless and amorphous (−) |
| 363 | (structure with CH₂CONH(CH₂)₂-N-methylpyrrolidine side chain on chlorinated bicyclic core) | (benzamide with OCH₃ and CH₃ substituents) | Colorless and amorphous (−) |
| 364 | (structure with (CH₂)₂-N-piperazine-N-COCH₃ side chain on chlorinated bicyclic core) | (benzamide with OCH₃ and Cl substituents) | Colorless and amorphous (−) |
| 365 | (structure with CH₂CONHCH₂-pyridyl side chain on chlorinated bicyclic core) | (benzamide with Cl substituent) | Colorless and amorphous (−) |

TABLE 155-continued

| | | | |
|---|---|---|---|
| 366 | [structure: chloro-benzazepine with CH₂CONH(CH₂)₂-pyridin-2-yl substituent] | [structure: 4-(2-chlorophenyl-NHCO)-benzoyl] | Colorless and amorphous (−) |
| 367 | [structure: chloro-benzazepine with CH₂CO—N(CH₃)(CH₂)₂-pyridin-2-yl] | [structure: 4-(2-chlorophenyl-NHCO)-benzoyl] | Colorless and amorphous (−) |
| 368 | [structure: chloro-benzazepine with CH₂CO—N(C₂H₅)—(CH₂)₂—N(C₂H₅)₂] | [structure: 4-(2-chlorophenyl-NHCO)-benzoyl] | Colorless and amorphous (−) |
| 369 | [structure: chloro-benzazepine with CH₂CONH(CH₂)₂-(N-methylpyrrolidin-2-yl)] | [structure: 4-(2-chlorophenyl-NHCO)-benzoyl] | Colorless and amorphous (−) |

TABLE 155-continued
| | | | | |
|---|---|---|---|---|
| 370 | 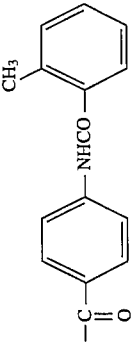 | 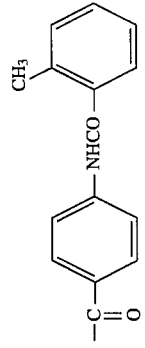 | Light orange powder (Diethyl ether) | 182–183 (–) |
| 371 | | | Light yellow powder (Diethyl ether) | 172–173 (–) |
| 372 | | | White powder (Diethyl ether) | 233–235 (–) |
| 373 | 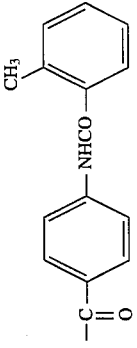 | 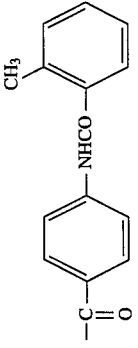 | White powder (Diethyl ether) | 162–164 (–) |

TABLE 155-continued

| | | | |
|---|---|---|---|
| 374 | [structure with CH₂CONH(CH₂)₂-pyrrolidinyl-N-CH₃, chlorophenyl-benzazepine] | [4-(-C(=O)-)-phenyl-NHCO-2-CH₃-phenyl] | White powder (Diethyl ether) 193–196 (−) |
| 375 | [structure with CH₂CO-N(CH₃)-(CH₂)₂N(CH₃)₂, chlorophenyl-benzazepine] | [4-(-C(=O)-)-3-OCH₃-phenyl-NHCO-2-Cl-phenyl] | Colorless and amorphous (−) |
| 376 | [structure with CH₂CONH(CH₂)₂N(C₂H₅)₂, chlorophenyl-benzazepine] | [4-(-C(=O)-)-3-OCH₃-phenyl-NHCO-2-Cl-phenyl] | Colorless and amorphous (−) |
| 377 | [structure with CH₂CONH(CH₂)₃N(C₂H₅)₂, chlorophenyl-benzazepine] | [4-(-C(=O)-)-3-OCH₃-phenyl-NHCO-2-Cl-phenyl] | Colorless and amorphous (−) |
| 378 | [structure with CH₂CONH(CH₂)₂-piperidinyl-N, chlorophenyl-benzazepine] | [4-(-C(=O)-)-3-OCH₃-phenyl-NHCO-2-Cl-phenyl] | Colorless and amorphous (−) |

TABLE 155-continued

| | | | |
|---|---|---|---|
| 379 | (structure) | (structure) | Colorless and amorphous (—) |
| 380 | (structure) | (structure) | White powder (Acetone-n-hexane) 152–153 (—) |
| 381 | (structure) | (structure) | Colorless and amorphous (—) |
| 382 | (structure) | (structure) | Colorless and amorphous (—) |

TABLE 155-continued

| # | Structure 1 | Structure 2 | Description | mp |
|---|---|---|---|---|
| 383 | | | Colorless and amorphous | (—) |
| 384 | | | Colorless and amorphous | (—) |
| 385 | | | Colorless and amorphous | (—) |
| 386 | | | White powder (Acetone-n-hexane) | 269–270 |
| 387 | | | White powder (Diethyl ether) | 162–165 |

TABLE 155-continued

| | | | |
|---|---|---|---|
| 388 | (structure with CH₂CO-N-piperazine-3-chlorophenyl on chlorinated benzazepine) | (structure: OCH₃, NHCO, 2-Cl-phenyl benzamide with -C=O) | White powder (Diethyl ether) 168-171 (-) |
| 390 | CH₂CONH(CH₂)₂-N(CH₃)(CH₂CH₂OH) on chlorinated benzazepine | (structure: OCH₃, NHCO, 2-Cl-phenyl benzamide with -C=O) | Colorless and amorphous (-) |
| 391 | CH₂COOH on chlorinated benzazepine | (structure: OH, NHCO, 2-Cl-phenyl benzamide with -C=O) | Colorless and amorphous (-) |
| 392 | CH₂CONH(CH₂)₂N(CH(CH₃)₂)₂ on chlorinated benzazepine | (structure: OCH₃, NHCO, 2-Cl-phenyl benzamide with -C=O) | Colorless and amorphous (-) |
| 393 | CH₂CON(CH₃)(CH₂)₂N(C₂H₅)₂ on chlorinated benzazepine | (structure: OCH₃, NHCO, 2-CH₃-phenyl benzamide with -C=O) | Colorless and amorphous (-) |

TABLE 155-continued

| | | | | |
|---|---|---|---|---|
| 394 | [structure with (CH₂)₂N(C₂H₅)₂, CH₃, CH₂CO—N, chlorobenzazepine] | [structure: NHCO-phenyl-C(=O)- with Cl] | White powder (Diethyl ether) | 191–192 (—) |
| 395 | [structure with (CH₂)₂N(C₂H₅)₂, CH₃, CH₂CO—N, chlorobenzazepine] | [structure: NHCO-phenyl-C(=O)- with CH₃] | White powder (Diethyl ether) | 181–182 (—) |
| 396 | [structure with N-methylpiperazine-CH₂CO—N, chlorobenzazepine] | [structure: NHCO-phenyl-C(=O)- with O(CH₂)₄NHCH(CH₃)₂] | White powder (Diethyl ether) | 139–142 (decomposed) (—) |
| 397 | [structure with N-methylpiperazine-CH₂CO—N, chlorobenzazepine] | [structure: NHCO-phenyl-C(=O)- with O(CH₂)₄NHC(CH₃)₃] | White powder (Diethyl ether) | 149–152 (—) |

TABLE 155-continued

TABLE 155-continued

| | | | | |
|---|---|---|---|---|
| 403 | [structure: chlorophenyl-azepine with H, CH₂CON(CH₃)₂ substituents; N-aryl with NHCO-phenyl-C(=O)- and O(CH₂)₄NH-C(CH₃)₂-CH₃] | | White powder (Diethyl ether) | 99–102 (–) |
| 404 | [structure: similar azepine; N-aryl with NHCO-phenyl-C(=O)- and O(CH₂)₄-N(piperidinyl-NHCOCH₃)] | | Light yellow and amorphous | (–) |
| 405 | [structure: azepine with CH₂CO-N(4-methylpiperazinyl); N-aryl with Br, NHCO-phenyl-C(=O)-] | | Light yellow and amorphous | (–) |
| 406 | [structure: azepine with CH₂CONH(CH₂)₂N(C₂H₅)₂; N-aryl with Br, OCH₃, NHCO-phenyl-C(=O)-] | | White powder (Diethyl ether) | 141–143 (decomposed) (–) |
| 407 | [structure: azepine with CH₂CONH(CH₂)₃N(C₂H₅)₂; N-aryl with Br, OCH₃, NHCO-phenyl-C(=O)-] | | White powder (Diethyl ether) | 140–142 (–) |

TABLE 155-continued

| | | | |
|---|---|---|---|
| 408 | (structure with Cl-substituted tetrahydroquinoline N-) | (4-substituted phenyl with NHCO linker, Cl, O(CH₂)₄-piperidine-NHCOCH₃) | Colorless and amorphous (−) |
| 409 | (structure with Cl-substituted benzazepine N-, CH₂CO—N(CH₃)₂N(CH₃)₂, CH₃) | (phenyl-NHCO, Br, OCH₃) | Colorless and amorphous (−) |
| 410 | (structure with Cl-substituted benzazepine N-, CH₂CONH(CH₂)₃—N(CH₃)₂) | (phenyl-NHCO, Br, OCH₃) | Colorless and amorphous (−) |
| 411 | (structure with Cl-substituted benzazepine N-, CH₂CONH(CH₂)₂—piperidine) | (phenyl-NHCO, Br, OCH₃) | Colorless and amorphous (−) |
| 412 | (structure with Cl-substituted benzazepine N-, CH₂CONH(CH₂)₂—morpholine) | (phenyl-NHCO, Br, OCH₃) | Colorless and amorphous (−) |

TABLE 155-continued
| | | | |
|---|---|---|---|
| 413 |  |  Colorless and amorphous | (—) |
| 414 | | | (—) |
| 415 | | | (—) |
| 416 | | | (—) |
| 417 | | | (—) |

TABLE 155-continued

| | | | |
|---|---|---|---|
| 418 | H OCH₂CONH(CH₂)₂—N⟨cyclohexyl⟩ on chlorobenzazepine | —C(=O)—Ar (Ar = 2-OCH₃, 3-NHCO-(2-Br-phenyl)) | Colorless and amorphous (−) |
| 419 | H OCH₂CONH(CH₂)₂—N⟨morpholino⟩ on chlorobenzazepine | —C(=O)—Ar | Colorless and amorphous (−) |
| 420 | H CH₂CO—N(CH₃)—(CH₂)₃—N(C₂H₅)₂ on chlorobenzazepine | —C(=O)—Ar | Colorless and amorphous (−) |
| 421 | H OCH₂CO—N(CH₃)(CH₂)₃N(C₂H₅)₂ on chlorobenzazepine | —C(=O)—Ar | Colorless and amorphous (−) |
| 422 | H CH₂CO—N(CH₃)(CH₂)₂—N(C₂H₅)₂ on chlorobenzazepine | —C(=O)—Ar | Colorless and amorphous (−) |

TABLE 155-continued

| | | | | |
|---|---|---|---|---|
| 423 | [structure: chlorobenzazepine with CH₂CON(CH₂)₂—N(CH₃)₂ / C₂H₅ and H] | [structure: OC₂H₅, NHCO-C₆H₄-Br, -C(=O)-] | Colorless and amorphous | (—) |
| 424 | [structure: chlorobenzazepine with CH₂CONH(CH₂)₂—N(C₂H₅)₂ and H] | [structure: OC₂H₅, NHCO-C₆H₄-Br, -C(=O)-] | Colorless and amorphous | (—) |
| 425 | [structure: chlorobenzazepine with CH₂CO-N(piperazinyl)N—CH₃ and H] | [structure: OC₂H₅, NHCO-C₆H₄-Br, -C(=O)-] | Colorless and amorphous | (—) |
| 426 | [structure: chlorobenzazepine with OCH₂CO₂C₂H₅ and H] | [structure: NHCO-C₆H₄-Br, OCH₃, -C(=O)-] | Colorless and amorphous | (—) |
| 427 | [structure: chlorobenzazepine with O(CH₂)₂OH and H] | [structure: NHCO-C₆H₄-Br, OCH₃, -C(=O)-] | White powder | 188–189 (—) |

TABLE 155-continued

| Example | | | |
|---|---|---|---|
| 428 | [structure: chloro-substituted bicyclic with H, (CH₂)₂—N-piperidine NH, N-substituent] | Colorless and amorphous | (—) |
| 429 | [structure: chloro-substituted bicyclic with H, O(CH₂)₂NH₂, N-substituent; aryl group with NHCO, OCH₃, Br] | White powder | 175–177 (—) |

| Example | ¹H-NMR δ ppm |
|---|---|
| 315 | (CDCl₃): 1.05–4.82(17H, m), 6.16–8.42(13H, m) |
| 316 | (CDCl₃): 0.82–2.15(9H, m), 2.18–4.65(14H, m), 2.26, 2.33(total 6H, S), 6.68–7.05(3H, m), 7.05–8.73(8H, m) |
| 317 | (CDCl₃): 0.97–2.11(4H, m), 2.13–3.43(5H, m), 2.38, 2.49(Total 3H, S), 3.65, 3.90(total 3H, brs), 6.64–7.42(11H, m), 8.03–8.56(2H, m), 8.66, 8.92(total 1H, brs) |
| 318 | (DMSO-d₆): 1.08–2.48(4H, m), 2.26(3H, S), 2.57–4.10, 4.41–4.89(total 10H, m), 6.65–7.82(10H, m), 8.97, 9.45, 9.96(each 1H, each brs), 10.63, 10.78(total 1H, each brs) |
| 320 | (CDCl₃): 1.01–5.18(12H, m), 6.48–7.98(11H, m), 8.44, 8.50(total 1H, each brs) |
| 322 | (CDCl₃+DMSO-d₆): 0.58–5.05(22H, m), 6.57–7.95(10H, m), 9.38–10.32(3H, m) |
| 329 | (CDCl₃): 1.12–2.21(4H, m), 2.52–5.01(7H, m), 3.62(3H, S), 6.58–7.91(12H, m), 8.23, 8.35(total 1H, each brs), 8.75–9.02(2H, m) |
| 333 | (CDCl₃): 0.82–5.11(19H, m), 2.80(3H, S), 5.64–7.93(12H, m), 8.12–8.48(1H, m) |
| 334 | (CDCl₃): 1.03–5.14(22H, m), 1.27(3H, t, J=7.12Hz), 4.14(2H, q, J=7.12Hz), 6.62–7.92(10H, m), 7.93–8.82(1H, m) |
| 328 | (CDCl₃): 1.1–4.7, 4.9–5.1(total 29H, m with S at 2.35), 6.6–7.4, 7.6–8.2(total 9H, m), 9.90, 10.05(total 1H, each s) |
| 364 | (CDCl₃): 2.04, 2.05(total 3H, each S), 2.05–2.80(10H, m), 3.40–3.70(5H, m), 3.81, 3.91(total 3H, each S), 4.60–4.75(1H, m), 6.13(1H, t, J=6.3Hz), 6.70–6.95(4H, m), 7.30–7.50(5H, m), 7.68(1H, d, J=6.4Hz), 8.27, 8.45(total 1H, each S) |
| 391 | (CDCl₃): 1.20–2.20(4H, m), 2.50–3.30(3H, m), 3.40–3.80(1H, m), 4.25–4.50, 5.05–5.30(total 1H, m), 5.30–6.20(1H, br), 6.40–6.80(3H, m), 7.00–7.40(6H, m), 7.62(1H, d, J=6.2Hz), 8.08(1H, s) |
| 335 | (CDCl₃): 0.85–5.17(26H, m), 6.65–8.01(10H, m), 8.77–9.24(1H, m) |
| 336 | (CDCl₃): 1.34–2.48(4H, m), 2.49–4.94(13H, m)2.83(3H, d, J=4.86Hz), 5.19–6.23(2H, m), 6.55–8.04(10H, m), 8.30–8.58(1H, m) |
| 340 | (CDCl₃): 1.19–2.52(4H, m), 2.53–5.12(10H, m), 3.61(3H, s), 6.40–7.88(14H, m), 7.93–8.34(1H, m) |
| 345 | (CDCl₃): 1.03(6H, t, J=7.12Hz), 1.39–5.08(25H, m), 6.56–7.87(10H, m), 8.03–8.46(1H, m) |
| 347 | (CDCl₃): 1.03(6H, t, J=7.12Hz), 0.75–5.07(22H, m), 3.65(3H, S), 6.60–7.90(10H, m), 8.12–8.49(1H, m) |
| 348 | (CDCl₃): 1.03(6H, t, J=7.1Hz), 0.79–5.13(27H, m), 6.58–7.88(10H, m), 7.97–8.25(1H, m) |
| 349 | (CDCl₃): 0.95–2.14(4H, m), 2.23–3.18(5H, m), 3.01, 3.06(total 3H, S), 3.42–4.07(3H, m), 4.45–5.08(1H, m), 6.68–7.80(13H, m), 8.02–8.68(2H, m) |
| 350 | (CDCl₃): 1.02–2.36(6H, m), 2.43–3.13(4H, m), 3.21–4.65(3H, m), 3.49, 3.56(total 3H, S), 3.94(3H, brs), 5.75–6.12(2H, m), 6.45–7.53(10H, m), 7.63–7.94(2H, m), 8.15, 8.44(total 1H, brs) |
| 351 | (CDCl₃): 0.71–4.64(20H, m), 2.20, 2.21(total 3H, S), 3.94(3H, brs), 6.37–6.93(2H, m), 6.98–7.53(7H, m), 7.61–7.92(2H, m), 8.36(1H, brs) |
| 352 | (CDCl₃): 0.91–3.23(13H, m), 1.06(6H, t, J=7.1Hz), 2.99, 3.18(total 3H, S), 3.26–5.08(4H, m), 3.72, 3.93(total 3H, brs), 6.67–7.05(3H, m), 7.11–7.83(7H, m), 8.05–8.43(1H, m) |
| 353 | (CDCl₃): 1.22–2.27(4H, m), 2.62–2.97(2H, m), 3.07–4.08(4H, m), 5.66(3H, S), 4.14–5.25(3H, m), 6.53–6.72(1H, m), 6.77–7.87(12H, m), 8.18–8.87(3H, m) |
| 354 | (CDCl₃): 1.16–2.11(4H, m), 2.46–2.82(3H, m), 2.86–4.12(9H, m), 4.35–5.23(1H, m), 6.52–6.67(1H, m), 6.75–7.86(11H, m), 8.27–8.86(3H, m) |
| 355 | (CDCl₃): 1.06–2.13(5H, m), 2.35–3.32(8H, m), 3.41–5.23(6H, m), 6.48(1H, m), 6.73–7.52(9H, m), 7.56–7.92(2H, m), 8.24–8.93(3H, m) |
| 356 | (CDCl₃): 0.85, 1.09, 1.32(total 9H, t, J=7.0Hz), 1.22–1.67(2H, m), 1.74–2.42(3H, m), 2.47–4.14(13H, m), 3.70, 3.74(total 3H, S), 4.35–5.22(1H, m), 6.52–6.68(1H, m), 6.72–7.57(7H, m), 7.67–7.93(1H, m), 8.27–8.93(2H, m) |
| 357 | (CDCl₃): 0.83–4.11(20H, m), 2.34, 2.39(total 3H, S), 3.71, 3.99(total 3H, S), 6.47–6.72(1H, m), 6.77–7.57(7H, m), 7.65–7.91(1H, m), 8.14–8.88(2H, m) |
| 358 | (CDCl₃): 1.1–4.0, 4.3–4.6, 4.95–5.2(total 20H, m with two S at 2.20 and 2.33), 6.57(1H d, J=8.3Hz), 6.8–7.77(9H, m), 7.83(2H, d, J=6.8Hz), 8.42, 8.60(total 1H, each S) |
| 359 | (CDCl₃): 1.18–2.27(4H, m), 2.34–2.98 82H, m), 2.49(3H, S), 3.04–4.07(2H, m), 3.64(3H, S), 4.14–5.23(4H, m), 6.47–7.73(12H, m), 7.97–8.73(3H, m) |

TABLE 155-continued

| | |
|---|---|
| 360 | (CDCl₃): 1.14–2.24(5H, m), 2.32–3.35(3H, m), 2.49(3H, S), 3.00(2H, J, J=6.0Hz), 3.40–5.22(4H, m), 3.69(3H, S), 6.47–7.22(12H, m), 8.03–8.77(3H, m) |
| 361 | (CDCl₃): 1.07–2.26(4H, m), 2.33–3.34(5H, m), 2.50(3H, S), 2.96, 3.06(total 3H, S), 3.44–5.23(4H, m), 3.69, 3.72(total 3H, S), 6.48–6.66(1H, m), 6.71–7.73(11H, m), 8.03–8.69(3H, m) |
| 362 | (CDCl₃): 0.73–1.67(11H, m), 1.74–2.13(2H, m), 2.33, 2.38(total 3H, S), 2.49(3H, S), 3.69, 3.97(total 3H, S), 3.68, 3.74(total 3H, S), 6.53–6.67(1H, m), 6.83–7.55(7H, m), 8.05–8.46(2H, m) |
| 363 | (CDCl₃): 0.64–4.10(19H, m), 2.33, 2.38(total 2H, m), 2.49, 2.50(total 3H, S), 2.49, 2.50(total 3H, S), 3.68, 3.74(total 3H, S), 4.13–5.22(1H, m), 6.51–6.73(1H, m), 6.75–7.65(9H, m), 8.05–8.76(2H, m) |
| 365 | (CDCl₃): 1.21–2.32(4H, m), 2.53–3.02(2H, m), 3.05–5.26(5H, m), 6.59(1H, d, J=8.4Hz), 6.87–8.02(14H, m), 8.39–8.63(1H, m) |
| 366 | (CDCl₃): 1.16–2.18(5H, m), 2.23–3.87(4H, m), 2.99(2H, t, J=6.1Hz), 3.70(2H, t, J=6.1Hz), 4.13–5.18(1H, m), 6.55(1H, t, J=7.8Hz), 6.82–7.73(13H, m), 8.04–8.57(2H, m) |
| 367 | (CDCl₃): 1.04–3.23(9H, m), 2.96, 3.05(total 3H, S), 3.38–4.08(3H, m), 4.28–5.17(1H, m), 6.48–6.73(1H, m), 6.88–7.93(13H, m), 8.34–8.73(2H, m) |
| 368 | (CDCl₃): 0.75–2.22(13H, m), 2.25–3.95(16H, m), 4.32–5.20(1H, m), 6.49–6.63(1H, m), 6.84–7.12(2H, m), 7.15–7.75(8H, m), 8.32–8.73(1H, m) |
| 369 | (CDCl₃): 0.91–3.88(20H, m), 2.30, 2.37(total 3H, S), 4.07–5.18(1H, m), 6.48–7.43(11H, m), 8.29, 8.53(total 3H, brs) |
| 375 | (CDCl₃): 1.10–5.05(13H, m), 2.33, 2.40(total 6H, S), 2.98, 3.17(total 3H, brs), 3.70, 3.91(total 3H, brs), 6.68–7.83(10H, m), 8.27–8.72(1H, m) |
| 376 | (CDCl₃): 0.94–1.37(7H, m), 1.51–2.12(3H, m), 2.13–3.16(8H, m), 3.25–4.12(8H, m), 4.28–5.06(1H, m), 6.65–7.52(8H, m), 7.55–7.98(2H, m) |
| 377 | (CDCl₃): 0.97–2.13(10H, m), 2.38–4.65(18H, m), 6.43–7.98(10H, m), 8.34–8.57(1H, m) |
| 378 | (CDCl₃): 1.17–3.15(20H, m), 3.23–4.64(4H, m), 3.74, 3.95(total 3H, brs), 6.64–8.01(10H, m), 8.10–8.31(1H, m) |
| 379 | (CDCl₃): 1.10–2.28(8H, m), 2.26–5.12(17H, m), 3.16(2H, S), 3.73(3H, brs), 6.72–7.04(3H, m), 7.08–8.88(7H, m), 8.29, 8.53(total 1H, brs) |
| 381 | (CDCl₃): 1.08–2.14(4H, m), 2.28–3.28(3H, m), 2.46, 2.52(total 3H, S), 3.32–4.65(4H, m), 3.70, 3.92(total 3H, S), 6.52–7.72(14H, m), 7.76, 8.08(total 1H, S), 8.33–8.57(1H, m) |
| 382 | (CDCl₃): 1.07–2.76(9H, m), 2.45, 2.53(total 3H, m), 2.83–4.58(8H, m), 6.65–7.87(13H, m), 7.97, 8.22(total 1H, S), 8.38–8.55(1H, m) |
| 383 | (CDCl₃): 0.93–2.17(4H, m), 2.24–3.18(5H, m), 2.49, 2.53(total 3H, S), 3.00, 3.06(total 3H, S), 3.44–4.06(6H, m), 4.07–5.08(1H, m), 6.63–7.75(14H, m), 8.43–8.66(1H, m) |
| 384 | (CDCl₃): 0.92–1.35(9H, m), 1.45–2.24(6H, m), 2.38–2.83(10H, m), 2.89–4.73(9H, m), 6.64–7.04(3H, m), 7.12–7.90(8H, m) |
| 385 | (CDCl₃): 0.97–4.56(20H, m), 2.24, 2.25(total 3H, S), 2.52, 2.65(total 3H, S), 3.92(3H, brs), 6.37–7.58(9H, m), 7.79(1H, brs), 8.13–8.53(1H, m) |
| 389 | (CDCl₃): 1.05–2.39(5H, m), 2.44–4.98(15H, m), 6.68–7.02(2H, m), 7.05–7.83(8H, m), 8.47–8.73(1H, m) |
| 390 | (CDCl₃): 1.43–2.13(6H, m), 2.13–4.65(18H, m), 6.65–7.53(9H, m), 7.55–7.92(2H, m), 8.56–9.05(1H, m) |
| 392 | (CDCl₃): 0.74–1.33(12H, m), 1.45–3.57(11H, m), 3.52–4.63(2H, m), 3.70, 394(total 3H, brs), 6.34–7.55(9H, m), 7.61–8.02(2H, m), 8.25, 8.48(total 1H, m) |
| 393 | (CDCl₃): 0.86–1.33(7H, m), 1.42–2.23(4H, m), 2.28–3.24(11H, m), 2.99, 3.17(total 3H, S), 3.28–5.07(7H, m), 6.61–7.05(3H, m), 7.07–7.57(7H, m), 7.58–7.83(1H, m) |
| 398 | (CDCl₃): 1.12–4.03(31H, m), 2.00(3H, S), 2.35(3H, S), 4.03–4.35(2H, m), 4.35–5.19(1H, m), 5.98–7.66(10H, m), 7.87–8.28(1H, m), 9.96–10.13(1H, m) |
| 399 | (CDCl₃): 1.2–2.5(8H, m), 2.6–3.2(3H, m), 3.90(2H, d, J=6.6Hz), 3.97(2H, m), 3.45(2H, t, J=5Hz), 3.59(2H, t, J=6Hz), 6.4–7.7(13H, m), 9.31(1H, S) |
| 400 | (CDCl₃): 1.3–2.25(8H, m with S at 2.06), 2.25–3.2(9H, m), 3.45(2H, t, J=5Hz), 3.98(2H, t, J=6Hz), 4.8–5.2(1H, m), 8.58(1H, d, J=8.3Hz), 8.92(1H, dd, J=3.3Hz, 8.8Hz), 7.05–7.4(5H, m), 7.48(1H, d, J=8.5Hz), 8.25(1H, S) |
| 404 | (CDCl₃): 1.17–2.22(14H, m), 2.01(3H, S), 2.43(2H, d, J=7.3Hz), 2.56–3.26(5H, m), 2.80, 2.94, 3.01, 3.18(total 6H, S), 3.56–3.94(2H, m), 4.05–4.32(2H, m), 4.48–5.21(1H, m), 6.11–6.33(1H, m), 6.52–6.67(1H, m), 6.87–7.62(9H, m), 8.17–8.26(1H, m), 9.92–10.06(total 1H, brs) |
| 405 | (CDCl₃): 1.18–3.05(12H, m), 2.38, 2.44(total 3H, S), 3.08–5.22(10H, m), 6.60(1H, d, J=8.3Hz), 6.75–7.17(4H, m), 7.26–7.50(2H, m), 7.50–7.73(2H, m), 8.24–8.56(2H, m) |
| 408 | (CDCl₃): 1.2–3.2, 3.6–4.2, 4.8–5.2(total 28H, m with S at 1.92 and two t at 2.37(J=7Hz)and 3.97(J=6Hz)), 5.75(1H, d, J=8.1Hz), 8.57(1H, m), 6.8–7.4(7H, m), 7.49(1H, d, J=8.4Hz), 2.61(1H, S) |
| 409 | (CDCl₃): 1.16–5.26(13H, m), 2.26, 2.36(total 6H, m), 2.94, 3.18(total 3H, m), 3.70(3H, S), 6.59(1H, d, J=8.3Hz), 6.72–7.75(8H, m), 8.25–8.55(2H, m) |
| 410 | (CDCl₃): 1.13–2.86(11H, m), 2.14, 2.28(total 6H, S), 3.03–5.23(4H, m), 3.66, 3.70(total 3H, S), 6.60(1H, d, J=8.3Hz), 6.76–6.77(9H, m), 8.24–8.75(2H, m) |
| 411 | (CDCl₃): 1.18–2.83(18H, m), 2.88–5.23(5H, m), 3.66, 3.70(total 3H, S), 6.32–7.05(4H, m), 7.08–7.53(4H, m), 7.56–7.76(2H, m), 8.23–8.73(2H, m) |
| 412 | (CDCl₃): 1.13–2.85(12H, m), 2.98–5.23(18H, m), 6.17–6.83(2H, m), 6.83–7.05(2H, m), 7.05–7.52(4H, m), 7.52–7.78(2H, m), 8.23–8.76(2H, m) |
| 413 | (CDCl₃): 1.03–1.46(3H, m), 1.52–2.63(6H, m), 2.26(6H, S), 2.68–3.93(5H, m), 3.70, 3.80(total 3H, brs), 3.98–5.21(4H, m), 6.52–7.18(4H, m), 7.22–7.50(5H, m), 8.18–8.53(2H, m) |
| 414 | (CDCl₃): 1.53–2.64(6H, m), 2.24(6H, S), 2.67–4.03(6H, m), 2.97, 3.05(total 3H, S), 4.07–5.25(4H, m), 6.52–7.20(4H, m), 7.26–7.72(5H, m), 8.22–8.57(2H, m) |
| 415 | (CDCl₃): 1.52–3.13(14H, m), 3.23–5.25(8H, m), 3.68, 3.80(total 3H, S), 6.54–7.21(4H, m), 7.24–7.75(5H, m), 8.25–8.57(2H, m) |
| 416 | (CDCl₃): 1.01–2.62(11H, m), 2.67–5.32(9H, m), 2.67–5.32(9H, m), 2.43(2H, d, J=7.3Hz), 3.67, 3.81(total 3H, brs), 6.53–7.22(4H, m), 7.24–7.75(5H, m), 8.24–8.53(2H, m) |
| 417 | (CDCl₃): 0.82–1.15(6H, m), 1.55–5.28(18H, m), 2.22–3.07(7H, m), 3.75(3H, S), 3.93–4.27(2H, m), 4.38–5.23(2H, m), 6.57–7.17(4H, m), 7.23–7.73(6H, m), 8.24–8.56(2H, m) |
| 418 | (CDCl₃): 1.32–3.12(17H, m), 3.16–4.32(4H, m), 3.75(3H, S), 4.36–5.24(2H, m), 6.53–7.18(4H, m), 7.22–7.73(6H, m), 8.24–8.55(2H, m) |
| 419 | (CDCl₃): 1.55–3.07(11H, m), 3.13–4.33(11H, m), 4.38–5.25(2H, m), 6.55–7.53(8H, m), 7.53–7.75(2H, m), 8.25–8.54(2H, m) |
| 420 | (CDCl₃): 0.83–2.31(12H, m), 2.33–5.22(13H, m), 2.93, 3.19(total 3H, S), 3.72, 3.76(total 3H, S), 6.59(1H, d, J=8.3Hz), 6.86–7.14(4H, m), 7.25–7.73(4H, m)8.22–8.56(2H, m) |
| 421 | (CDCl₃): 0.86–1.23(6H, m), 1.47–2.18(4H, m), 2.22–5.23(18H, m), 5.80(3H, S), 6.52–7.18(4H, m), 7.24–7.75(6H, m), 8.34(2H, brs) |
| 422 | (CDCl₃): 0.78–1.67(11H, m), 1.70–5.23(17H, m), 2.95, 3.20(total 3H, S), 6.59(1H, dd, J=8.3, 2.5Hz), 6.73–7.56(6H, m), 7.56–7.73(2H, m), 8.28–8.58(2H, m) |
| 423 | (CDCl₃): 0.92–1.65(5H, m), 1.67–5.21(18H, m), 2.30, 2.36(total 6H, m), 6.15–7.56(8H, m), 6.68–7.22(3H, m), 7.22–7.49(3H, m), 7.57–7.75(2H, m), 8.26–8.55(2H, m) |
| 424 | (CDCl₃): 0.84–2.24(13H, m), 2.24–3.12(18H, m), 3.12–5.25(4H, m), 6.52–7.18(4H, m), 7.56–7.82(2H, m), 8.26–8.76(2H, m) |
| 425 | (CDCl₃): 1.28(3H, t, J=6.9Hz), 2.12–2.18(6H, m), 2.20–5.23(15H, m), 5.60(1H, d, J=8.3Hz), 6.75–7.15(4H, m), 7.26–7.58(2H, m), 7.58–7.42(2H, m), 8.28–8.57(2H, m) |
| 426 | (CDCl₃): 1.25–(3H, t, J=7.13), 1.41–2.92(5H, m), 2.93–5.04(6H, m), 3.64(3H, S), 6.63–7.91(10H, m), 8.14, 8.23, 8.38(total 1H, each brs) |
| 428 | (CDCl₃): 1.09–5.06(23H, m), 6.62–8.14(10H, m), 8.68–9.28(1H, m) |

Example 430

0.13 ml of methyl isothiocyanate was added to 20 ml of a suspension of 0.5 g of 5-(2-aminoethoxy)-7-chloro-1-[2-methoxy-4-(2-chlorobenzoylamino)benzoyl]-2,3,4,5-tetrahydro-1H-benzoazepine in ethanol. The mixture was refluxed for 3 hours. The reaction mixture was subjected to vacuum distillation to remove ethanol. The residue was mixed with a saturated aqueous sodium hydrogencarbonate solution, followed by extraction with ethyl acetate. The organic layer was dried over magnesium sulfate and then subjected to vacuum distillation to remove the solvent. The residue was purified by silica gel column chromatography (elutant: dichloromethane/methanol =50/1) to obtain 0.46 g of 5-(2-methylaminothiocarbonylaminoethoxy)-7-chloro-1-[2-methoxy-4-(2-chlorobenzoylamino)benzoyl]-2,3,4,5-tetrahydro-1H-benzoazepine.

Colorless and amorphous $^1$H-NMR (CDCl$_3$) δppm: 1.05–4.82 (17H, m), 6.16–8.42 (13H, m)

Example 431

0.129 g of ethyl acetoimidate hydrochloride was added to 15 ml of a suspension of 0.5 g of 5-(2-amino-ethoxy)-7-chloro-1-[2-methoxy-4-(2-chlorobenzoylamino)-benzoyl]-2,3,4,5-tetrahydro-1H-benzoazepine in ethanol with ice-cooling. The mixture was stirred overnight at room temperature. Then, 0.163 g of ethyl acetoimidate hydrochloride was further added. The mixture was stirred at 50° C. for 7 hours and then refluxed for 3 hours. After cooling, the reaction mixture was subjected to filtration to remove insolubles. The filtrate was concentrated. The residue was purified by silica gel column chromatography (elutant: dichloromethane/methanol=30/1) to obtain 0.2 g of 5-[2-(1-iminoethyl)aminoethoxy]-7-chloro-1-[2-methoxy-4-(2-chlorobenzoylamino)benzoyl]-2,3,4,5-tetrahydro-1H-benzo-azepine hydrochloride.

Colorless and amorphous $^1$H-NMR (CDCl$_3$) δppm: 1.08–2.48 (4H, m), 2.26 (3H, s), 2.57–4.10, 4.41–4.89 (total 10H, m), 6.65–7.82 (10H, m), 8.79, 9.45, 9.96 (each 1H, each brs), 10.63, 10.78 (total 1H, each brs)

Example 432

0.12 g of sodium cyanate and 0.22 ml of trifluoro-acetic acid were added to a solution of 0.5 g of 5-(2-aminoethoxy)-7-chloro-1-[2-methoxy-4-(2-chlorobenzoylamino)-benzoyl]-2,3,4,5-tetrahydro-1H-benzoazepine dissolved in 15 ml of dry dimethylformamide. The mixture was stirred at 80° C. for 1 hour. After cooling, the reaction mixture was mixed with slight amounts of a saturated aqueous sodium hydrogen-carbonate solution and hexane, followed by extraction with ethyl acetate. The organic layer was water-washed, then dried over magnesium sulfate and subjected to vacuum distillation to remove the solvent. The resiude was recrystallized from acetone-n-hexane to obtain 0.41 g (76%) of 5-(2-ureidoethoxy)-7-chloro-1-[2-methoxy-4-(2-chlorobenzoylamino)benzoyl]-2,3,4,5-tetrahydro-1H-benzoazepine.

A white powder

Melting point: 206°–207° C.

Example 433

0.14 g of ammonium chloride and 0.17 g of sodium azide were added to a solution of 0.7 g of 5-cyanomethyl-7-chloro-1-[2-methyl-4-(2-chlorobenzoylamino)benzoyl]-2,3, 4,5-tetrahydro-1H-benzoazepine dissolved in 10 ml of dry dimethylformamide. The mixture was stirred at 100° C. for 2 hours. To the reaction mixture was added hydrochloric acid to control the pH of the mixture at about 2, followed by extraction with ethyl acetate. The organic layer was water-washed, then dried and subjected to vacuum distillation to remove the solvent. The residue was purified by silica gel column chromatography (elutant: dichloromethane/methanol =30/1) to obtain 0.52 g of 5-(1-methyl-1,2,3,4-tetrazol-5-yl)methyl-7-chloro-1-[2-methyl-4-(2-chlorobenzoylamino)-benzoyl]-2,3,4,5-tetrahydro-1H-benzoazepine.

Colorless and amorphous $^1$H-NMR (CDCl$_3$) δppm: 1.01–5.18 (12H, m), 6.48–7.98 (11H, m), 8.44, 8.50 (total 1H, each brs)

Example 434

An aqueous solution containing 0.27 g of sodium metaperiodate was added, at room temperature, to a suspension of 0.33 g of 5-[2-(4-pyridyl)thioethoxy]-7-chloro-1-[2-methoxy-4-(2-chlorobenzoylamino)benzoyl]-2,3,4,5-tetrahydro-1H-benzoazepine in 20 ml of methanol. The mixture was stirred at 70° C. for 2 hours. The reaction mixture was subjected to vacuum distillation to remove methanol. The residue was mixed with a saturated aqueous sodium chloride solution, followed by extraction with ethyl acetate. The extract was dried over anhydrous magnesium sulfate and then subjected to vacuum distillation to remove the solvent. The residue was purified by silica gel column chromatography (elutant: dichloromethane/methanol=50/1) and recrystallized from ethyl acetate-n-hexane to obtain 0.18 g of 5-[2-(4-pyridyl)sulfinylethoxy]-7-chloro-1-[2-methoxy-4-(2-chlorobenzoylamino)benzoyl-2,3,4,5-tetrahydro-1H-benzoazepine.

A white powder

Melting point: 192°–193.5° C.

The above-mentioned compound of Example 331 was obtained in the same manner as in Example 434 using appropriate starting materials.

Example 435

0.33 g of sodium metaperiodate was added to a suspension of 0.3 g of 5-[2-(4-pyridyl)thioethoxy]-7-chloro-1-[-2-methoxy-4-(2-chlorobenzoylamino)benzoyl]-2,3,4,5-tetrahydro-1H-benzoazepine in 20 ml of methanol. The mixture was refluxed for 5 hours. The reaction mixture was subjected to vacuum distillation to remove methanol. The residue was mixed with a saturated aqueous sodium chloride solution, followed by extraction with dichloromethane. The extract was dried over anhydrous magnesium sulfate and then subjected to vacuum distillation to remove the solvent. The residue was purified by silica gel column chromatography (elutant: dichloromethane/methanol =50/1) to obtain 0.28 g of 5-[2-(4-pyridyl)sulfonylethoxy]-7-chloro-1-[2-methoxy-4-(2-chlorobenzoylamino)benzoyl]-2,3,4,5-tetrahydro-1H-benzo-azepine.

Colorless and amorphous $^1$H-NMR (CDCl$_3$) δppm: 1.12–2.21 (4H, m), 2.52–5.01 (7H, m), 3.62 (3H, s), 6.58–7.91 (12H, m), 8.23, 8.35 (total 1H, each brs), 8.75–9.02 (2H, m)

The above-mentioned compound of Example 332 was obtained in the same manner as in Example 435 using appropriate starting materials.

Example 436

0.18 g of m-chloroperbenzoic acid was added, with ice-cooling, to a suspension of 0.32 g of 5-[2-(2-imidazolyl)thioethoxy]-7-chloro-1-[2-methoxy-4-(2-chloro-benzoylamino)benzoyl]-2,3,4,5-tetrahydro-1H-benzoazepine in 10 ml of dichloromethane. The mixture was stirred at room temperature for 15 minutes. The reaction mixture was mixed with a saturated aqueous sodium chloride solution, followed by extraction with dichloromethane. The extract was washed with a saturated aqeuous sodium hydrogencarbonate solution, then dried over anhydrous magnesium sulfate, and subjected to vacuum distillation to remove the solvent. The residue was purified by silica gel column chromatography (elutant: ethyl acetate/methanol=100/1) and recrystallized from acetone-diethyl ether to obtain 0.27 g of 5-[2-(2-imidazolyl)sulfonylethoxy]-7-chloro-1-[2-methoxy-4-(2-chlorobenzoylamino)benzoyl]-2,3,4,5-tetrahydro-1H-benzo-azepine.

A white powder

Melting point: 247°–248° C.

The above-mentioned compound of Example 329 was obtained in the same manner as in Example 436 using appropriate starting materials.

Example 437

An ethanol solution containing 0.174 g of dimethyl cyanodithioimidocarbonate was added to a solution of 0.6 g of 5-(2-aminoethoxy)-7-chloro-1-[2-methoxy-4-(2-chlorobenzoylamino)benzoyl]-2,3,4,5-tetrahydro-1H-benzoazepine dissolved in 30 ml of ethanol. The mixture was stirred overnight at room temperature. Thereto was added 1.76 ml of a methanol solution containing 40% of methylamine. The mixture was stirred at 40°–50° C. for 3 hours. The reaction mixture was subjected to vacuum distillation to remove ethanol. The residue was purified by silica gel column chromatography (elutant: dichloromethane/methanol=100/1) to obtain 0.46 g of 5-[2-(3-methyl-2-cyanoguanidino)ethoxy]-7-chloro-1-[2-methoxy-4-(2-chlorobenzoylamino)benzoyl]-2,3,4,5-tetrahydro-1H-benzoazepine.
Colorless and amorphous
$^1$H-NMR (CDCl$_3$) δppm: 1.34–2.48 (4H, m), 2.49–4.94 (13H, m), 2.83 (3H, d, J=4.86Hz), 5.19–6.23 (2H, m), 6.55–8.04 (10H, m), 8.30–8.58 (1H, m)

Example 438

0.64 ml of trifluoromethanesulfonic acid anhydride was dropwise added, with ice-cooling, to a solution of 0.4 g of 5-(2-aminoethoxy)-7-chloro-1-[2-methoxy-4-(2-chlorobenzoylamino)benzoyl]-2,3,4,5-tetrahydro-1H-benzoazpine dissolved in 10 ml of pyridine. The mixture was stirred for 1.5 hours at the same temperature. Thereto was added 10% hydrochloric acid, followed by extraction with ethyl acetate. The extract was water-washed, dried and subjected to vacuum distillation to remove the solvent. The residue was purified by silica gel column chromatography (elutant: dichloromethane/methanol=100/1) to obtain 0.18 g of 5-(2-trifluoromethanesulfonylaminoethoxy)-7-chloro-1-[2-methoxy-4-(2-chlorobenzoylamino)benzoyl]-2,3,4,5-tetrahydro-1H-benzoazepine.

A yellow plate

Melting point: 140°–142.5° C.

Example 439

0.01 ml of chloroacetonitrile, 0.22 ml of triethylamine and 0.24 ml of sodium iodide were added to 50 ml of a solution of 0.7 g of 5-(2-aminoethoxy)-7-chloro-1-[2-methoxy-4-(2-chlorobenzoylamino)benzoyl]-2,3,4,5-tetrahydro-1H-benzoazepine dissolved in dimethylformamide. The mixture was stirred at 60° C. for 2 hours. The reaction mixture was mixed with water, followed by extraction with ethyl acetate-n-hexane (10:1). The organic layer was water-washed, dried and subjected to vacuum distilation to remove the solvent. The residue was purified by silica gel column chromatography (elutant: dichloromethane/methanol=50/1) and crystallized from acetone-n-hexane to obtain 0.5 g of 5-(2-cyanomethylaminoethoxy)-7-chloro-1-[2-methoxy-4-(2-chlorobenzoylamino)benzoyl]-2,3,4,5-tetrahydro-1H-benzo-azepine.

A white powder

Melting point: 152.5°–153° C.

The above-mentioned compounds of Examples 321, 322, 337, 338, 340 and 343–349 were obtained in the same manner as in Example 439 using respective starting materials.

Example 440

9.1 ml of 98% boron tribromide was dropwise added, at −10° C. with stirring, to a solution of 10 g of 5-carboxymethyl-7-chloro-1-[2-methoxy-4-(2-chloro-benzoyl-amino)benzoyl]-2,3,4,5-tetrahydro-1H-benzoazepine dissolved in 400 ml of dichloromethane. The mixture was slowly returned to room temperature and stirred overnight at the same temperature. The reaction mixture was mixed with water, followed by extraction with dichloromethane. The extract was water-washed, then dried over anhydrous magnesium sulfate, and subjected to vacuum distillation to remove the solvent. The residue was purified by silica gel column chromatography to obtain 9.08 g of 5-carboxymethyl-7-chloro-1-[2-hydroxy-4-(2-chlorobenzoylamino)benzoyl]-2,3,4,5-tetrahydro-1H-benzoazepine.
Colorless and amorphous
$^1$H-NMR (CDCl$_3$) δppm: 1.20–2.20 (4H, m), 2.50–3.30 (3H, m), 3.40–3.80 (1H, m), 4.25–4.50, 5.05–5.30 (total 1H, m), 5.30–6.20 (1H, br), 6.40–6.80 (3H, m), 7.00–7.40 (6H, m), 7.62 (1H, d, J=6.2Hz), 8.08 (1H, s)

Pharmacological Tests

Test compound No.
1. 5-Dimethylamino-1-[4-(3-carbamoylbenzoylamino)benzoyl]-2,3,4,5-tetrahydro-1H-benzoazepine
2. 5-Dimethylamino-1-{4-[2-(2-methylphenyl)acetylamino]benzoyl}-2,3,4,5-tetrahydro-1H-benzoazepine
3. 5-Dimethylamino-1-{4-[2-(2-chlorophenyl)acetylamino]benzoyl}-2,3,4,5-tetrahydro-1H-benzoazepine
4. 5-Dimethylamino-1-{4-[2-(2-methoxyphenyl)acetylamino]benzoyl}-2,3,4,5-tetrahydro-1H-benzoazepine
5. 5-Dimethylamino-1-{4-[-2-(2-fluorophenyl)acetylamino]benzoyl}-2,3,4,5-tetrahydro-1H-benzoazepine
6. 5-Dimethylamino-1-(4-[2-(2,6-dichlorophenyl)acetylamino]benzoyl}-2,3,4,5-tetrahydro-1H-benzoazepine
7. 5-Dimethylamino-1-{4-[4-(2-nitrophenyl)acetylamino]benzoyl}-2,3,4,5-tetrahydro-1H-benzoazepine
8. 5-Dimethylamino-7-hydroxy-1-[2-chloro-4-(2-chlorobenzoylamino)benzoyl]-2,3,4,5-tetrahydro-1H-benzoazepine
9. 5-(L-Alanyloxy)-1-[2-chloro-4-(2-methylbenzoylamino)benzoyl]-2,3,4,5-tetrahydro-1H-benzoazepine•hydrochloride
10. 5-(L-Methionyloxy)-1-[2-chloro-4-(2-methylbenzoylamino)benzoyl]-2,3,4,5-tetrahydro-1H-benzoazepine•hydrochloride 11. 5-Dimethylamino-7-acetyloxy-1-[2-chloro-[4-(2-chlorobenzoylamino)benzoyl]-2,3,4,5-tetrahydro-1H-benzoazepine
12. 5-(L-Prolyloxy)-1-[2-chloro-4-(2-methylbenzoylamino)benzoyl]-2,3,4,5-tetrahydro-1H-benzoazepine•hydrochloride (Example 64)
13. 5-(L-Methionyloxy)-7-chloro-1-[2-methoxy-4-(2methylbenzoylamino)benzoyl]-2,3,4,5-tetrahydro-1H-benzoazepine-hydrochloride (Example 61)
14. 5-(L-Methionyloxy)-7-chloro-1-[2-methyl-4-(2-methylbenzoylamino)benzoyl]-2,3,4,5-tetrahydro-1H-benzoazepine•hydrochloride (Isomer A of Example 72)
15. 5-(L-Valyloxy)-7-chloro-1-[2-methyl-4-(2-methylbenzoylamino)benzoyl]-2,3,4,5-tetrahydro-1H-benzoazepine hydrochloride (Isomer A of Example 86)
16. 5-Hydroxy-7-chloro-1-{2-methyl-4-[2-(2-methylphenyl)acetylamino]benzoyl}-2,3,4,5-tetrahydro-1H-benzoazepine
17. 5-(2-Morpholinoacetyloxy)-7-chloro-1-[2-methoxy-4-(2-methylbenzoylamino)benzoyl]-2,3,4,5-tetrahydro-1H-benzoazepine
18. 5-Hydroxy-7-chloro-1-{2-methoxy-4-[2-(2-methylphenyl)acetylamino]benzoyl}-2,3,4,5-tetrahydro-1H-benzoazepine
19. 5,7-Dihydroxy-5-hydroxymethyl-1-[2-chloro-4-(2-chlorobenzoylamino)benzoyl]-2,3,4,5-tetrahydro-1H-benzoazepine
20. 5-Dimethylamino-7-dimethylaminocarbonylmethoxy-1-[2-chloro-4-(2-chlorobenzoylamino)benzoyl]-2,3,4,5-tetrahydro-1H-benzoazepine
21. 5-Ethoxycarbonylmethylaminocarbonylmethoxy-7-fluoro-1-[2-chloro-4-[2-methylbenzoylamino)benzoyl]-2,3,4,5-tetrahydro-1H-benzoazepine
22. 5-Carboxymethylaminocarbonylmethoxyl-7-fluoro-1-[2-chloro-4-(2-methylbenzoylamino)benzoyl]-2,3,4,5-tetrahydro-1H-benzoazepine
23. 5-[(2-β-Methoxycarbonyl)-1-pyrrolidinylcarbonylmethoxy]-7-fluoro-1-[2-chloro-4-(2-methylbenzoylamino)benzoyl]-2,3,4,5-tetrahydro-1H-benzoazepine
24. 5-(2-Methoxyacetyloxy)-7-chloro-1-[4-(2-methyl-4-benzoylamino)benzoyl]-2,3,4,5-tetrahydro-1H-benzoazepine
25. 5-{[2-(Dimethylaminoacetyloxy)methyl}-7-chloro-1-[4-(2-methylbenzoylamino)benzoyl]-2,3,4,5-tetrahydro-1H-benzoazepine•hydrochloride
26. 5-Ethoxycarbonylmethyl-7-chloro-1-[2-methoxy-4-(2-methylbenzoylamino)benzoyl]-2,3,4,5-tetrahydro-1H-benzoazepine
27. 5-[(4-Methyl-1-piperazinyl)carbonylmethyl-7-chloro-1-[3-methoxy-4-(2-methylbenzoylamino)benzoyl]-2,3,4,5-tetrahydro-1H-benzoazepine
28. 5-Carbamoylmethoxy-7-chloro-1-[2-methoxy-4-(2-chlorobenzoylamino)benzoyl]-1,2,3,4-tetrahydro-1H-benzoazepine
29. 5-(L-Lysyloxy)-7-chloro-1-[2-methoxyl-4-(2-methylbenzoylamino)benzoyl]-2,3,4,5-tetrahydro-1H-benzoazepine•hydrochloride
30. 5-[(4-Piperidinyl)aminocarbonylmethyl-7-chloro-1-[3-methoxy-4-(2-methylbenzoylamino)-benzoyl]-2,3,4,5-tetrahydro-1H-benzoazepine•hydrochloride
31. 5-Carboxymethyl-7-chloro-1-[2-methoxy-4-(2-chlorobenzoylamino)benzoyl]-2,3,4,5-tetrahydro-1H-benzoazepine
32. 5-Dimethylaminocarbonylmethyl-7-chloro-1-[3-methoxy-4-(2-methylbenzoylamino)benzoyl]-2,3,4,5-tetrahydro-1H-benzoazepine
33. 5-(3-Dimethylaminopropylidene)-7-fluoro-1-[2-chloro-4-(2-methylbenzoylamino)benzoyl]-2,3,4,5-tetrahydro-1H-benzoazepine•hydrochloride
34. 5-[2-(1-Pyrrolidinyl)ethoxy]-7-chloro-1-[2-methoxy-4-(2-methylbenzoylamino)benzoyl]-2,3,4,5-tetrahydro-1H-benzoazepine•hydrochloride
35. 5-(3-Morpholinopropoxy)-7-fluoro-1-[2-methyl-4-(2-methylbenzoylamino)benzoyl]-2,3,4,5-tetrahydro-1H-benzoazepine
36. 5-[3-(1-Imidazolyl)propoxy]-7-fluoro-1-[2-methyl-4-(2-methylbenzoylamino)benzoyl]-2,3,4,5-tetrahydro-1H-benzoazepine
37. 5-[3-(p-Toluenesulfonyloxy)propoxy]-7-chloro-1-[2-methoxy-4-(2-methylbenzoylamino)benzoyl]-2,3,4,5-tetrahydro-1H-benzoazepine
38. 5-Cyano-7-chloro-1-[3-chloro-4-(2-methylbenzoylamino)benzoyl]-2,3,4,5-tetrahydro-1H-benzoazepine
39. 5-Cyanomethyl-7-chloro-1-[3-methoxy-4-(2-methylbenzoylamino)benzoyl]-2,3,4,5-tetrahydro-1H-benzoazepine
40. 5-[2-(4-Acetyl-1-piperazinyl)ethoxy-7-chloro-1-[2-methoxy-4-(2-methylbenzoylamino)benzoyl]-2,3,4,5-tetrahydro-1H-benzoazepine•hydrochloride
41. 5-[(4-Methyl-1-piperazinyl)carbonylmethyl]-7-chloro-1-[2-methyl-4-(methylbenzoylamino)benzoyl]-2,3,4,5-tetrahydro-1H-benzoazepine
42. 5-Methylaminocarbonylmethyl-7-fluoro-1-[2-methoxy-4-(2-methylbenzoylamino)benzoyl]-2,3,4,5-tetrahydro-1H-benzoazepine
43. 5-[2-(1-Piperazinyl)ethoxy]-7-chloro-1-[2-methoxy-4-(2-methylbenzoylamino)benzoyl]-2,3,4,5-tetrahydro-1H-benzoazepine•dihydrochloride
44. 5-[(4-Methyl-1-piperazinyl)carbonylmethyl-7-chloro-1-[2-methoxy-4-(2-chlorobenzoylamino)benzoyl]-2,3,4,5-tetrahydro-1H-benzoazepine•hydrochloride
45. 5-[(4-Dimethylamino-1-piperidinyl)carbonylmethyl-7-chloro-1-[2-methoxy-4-chlorobenzoylamino)benzoyl]-2,3,4,5-tetrahydro-1H-benzoazepine•hydrochloride
46. 5-[(4-Methyl-1-piperazinyl)methyl]-7-fluoro-1-[2-methoxy-4-(2-methylbenzoylamino)benzoyl]-2,3,4,5-tetrahydro-1H-benzoazepine
47. 5-[2-(4-Methyl-1-1-piperazinyl)ethoxy]-7-fluoro-1-[2-methoxy-4-(2-methylbenzoylamino)-benzoyl]-2,3,4,5-tetrahydro-1H-benzoazepine
48. 5-[(1-Benzyl-4-piperidinyl)aminocarbonylmethyl-7-chloro-1-[2-methoxy-4-(2-chlorobenzoylamino)benzoyl]-2,3,4,5-tetrahydro-1H-benzoazepine•hydrochloride
49. 7-Chloro-1-[2-methoxy-4-{2-[4-(4-acetyl-1-piperazinyl)butoxy]benzoylamino}benzoyl]-2,3,4,5-tetrahydro-1H-benzoazepine
50. 5-[(1-Pyrrolidinyl)carbonylmethyl]-7-fluoro-1-[4-(2-methylbenzoylamino)benzoyl]-2,3,4,5-tetrahydro-1H-benzoazepine
51. 5-Dimethylaminocarbonylmethyl-7-fluoro-1-[2-methoxy-4-(2-bromobenzoylamino)benzoyl]-2,3,4,5-tetrahydro-1H-benzoazepine
52. 5-[(1-Piperazinyl)-carbonylmethyl]-7-chloro-1-[2-methoxy-4-(2-methylbenzoylamino)benzoyl]-2,3,4,5-tetrahydro-1H-benzoazepine•hydrochloride
53. 5-[2(1-Acetyl-1-piperazinyl)ethyl]-7-chloro-1-[2-metheyl-4-(2-methylbenzoylamino)benzoyl]-2,3,4,5-tetrahydro-1H-benzoazepine•hydrochloride
54. 5-[2-(4-Dimethyl-1-piperidinyl)ethyl]-7-chloro-1-[2-methoxy-4-(2-methylbenzoylamino)benzoyl]-2,3,4,5-tetrahydro-1H-benzoazepine•dihydrochloride
55. 5-[2-(4-Methyl-1-piperazinyl)ethyl]-7-chloro-1-[2-methoxy-4-(2-methylbenzoylamino)benzoyl]-2,3,4,5-tetrahydro-1H-benzoazepin•hydrochloride
56. 7-Chloro-1-[3-methoxy-4-{2-[4-(4-acetyl-1-piperazinyl)butoxy]benzoylamino}benzoyl]-2,3,4,5-tetrahydro-1H-benzoazepine 57. 7-Chloro-5-[(4-piperidinyl)aminocarbonylmethoxy]-1-[2-methyl-4-(2-methylbenzoylamino)benzoyl]-2,3,4,5-tetrahydro-1H-benzoazepine•hydrochloride
58. 5-[(1-Piperidinyl)carbonylmethyl-7-fluoro-1-[2-methoxy-4-(2-methylbenzoylamino)benzoyl]-2,3,4,5-tetrahydro-1H-benzoazepine
59. 5-[(1-Methyl-4-piperidinyl)aminoarbonylmethoxy]-7-chloro-1-[2-methyl-4-(2-methylbenzoylamino)benzoyl]-2,3,4,5-tetrahydro-1H-benzoazepine
60. 5-[(4-Acetylamino-1-piperidinyl)carbonylmethyl]-7-fluoro-1-[2-methoxy-4-(2-bromobenzoylamino)benzoyl]-2,3,4,5-tetrahydro-1H-benzoazepine
61. 5-(2-Hydroxyethoxy)-7-chloro-1-[4-(2-methylbenzoyamino)benzoyl]-2,3,4,5-tetrahydro-1H-benzoazepine
62. 5-(Carbonylmethylaminocarbonylmethyl)-7-chloro-1-[2-methyl-4-(2-methylbenzoylamino)benzoyl]-2,3,4,5-tetrahydro-1H-benzoazepine
63. 5-[(4-Methyl-1-piperazinyl)carbonylmethyl]-7-chloro-1-[2-methoxy-4-(2-methylbenzoylamino)benzoyl]-2,3,4,5-tetrahydro-1H-benzoazepine
64. 5-Allyloxy-7-chloro-1-[4-(2-methylbenzoylamino)benzoyl]-2,3,4,5-tetrahydro-1H-benzoazepine
65. 5-Ethoxycarbonylmethylidene-7-chloro-1-[2-methyl-4-(2-methylbenzoylamino)benzoyl]-2,3,4,5-tetrahydro-1H-benzoazepine
66. 5-Methylamino-7-chloro-1-{2-chloro-4-[2-(2methylphenyl)acetylamino]benzoyl}-2,3,4,5-tetrahydro-1H-benzoazepine
67. 5-Allylamino-7-chloro-1-{4-[2-(2-methylphenyl)acetylamino]benzoyl}-2,3,4,5-tetrahydro-1H-benzoazepine
68. 5-(2-Dimethylaminoacetyloxy)-7-chloro-1-{2-methoxy-4-[2-(2-methylphenyl)acetylamino]benzoyl}-2,3,4,5-tetrahydro-1H-benzoazepine
69. 5-[2-(1,3-Dioxo-4a,4,5,6,7,7a-hexahydro-isoindolyn-1-yl)ethoxy]-7-fluoro-1-[2-methyl-4-(2-methylbenzoylamino)benzoyl]-2,3,4,5-tetrahydro-1H-benzoazepine
70. 5-(2-Chloroethyl)-7-chloro-1-[4-(4-chlorobenzoylamino)benzoyl]-2,3,4,5-tetrahydro-1H-benzoazepine
71. 7-Chloro-1-[3-methoxy-4-{2-[3-(1-imidazoyl)propoxy]benzoylamino)benzoyl]-2,3,4,5-tetrahydro-1H-benzoazepine
72. 7-Chloro-1-[3-methoxy-4-{2-[3-(4-acetylamino-1-piperidinyl)propoxy]benzoylamino}benzoyl]-2,3,4,5-tetrahydro-1H-benzoazepine
73. 7-Chloro-1-[3-methoxy-4-{2-[3-(1,2,4-triazol-1-yl)propoxy]benzoylamino}benzoyl]-2,3,4,5-tetrahydro-1H-benzoazepine
74. 5-[2-(1-Imidazoyl)ethyl]-7-chloro-1-[2-methyl-4-(2-chlorobenzoylamino)benzoyl]-2,3,4,5-tetrahydro-1H-benzoazepine
75. 5-[2-(4-Acetylamino-1-piperidinyl)ethoxy]-7-chloro-1-[2-methyl-4-(2-chlorobenzoylamino)benzoyl]-2,3,4,5-tetrahydro-1H-benzoazepine
76. 5-[2-(4-Acetylamino-1-piperidinyl)ethyl]-7-chloro-1-[2-methyl-4-(2-chlorobenzoylamino)benzoyl]-2,3,4,5-tetrahydro-1H-benzoazepine
77. 5-(4-Ethoxycarbonylmethyl-1-piperazinyl)carbonyl-methyl-7-chloro-1-[2-methoxy-4-(2-chlorobenzoylamino)benzoyl]-2,3,4,5-tetrahydro-1H-benzoazepine
78. 5-(4-Ethyl-1-piperazinyl)carbonylmethyl-7-chloro-1-[2-methoxy-4-(2-chlorobenzoylamino)benzoyl]-2,3,4,5-tetrahydro-1H-benzoazepine
79. 5-[4-(4-Chlorophneyl)-1-piperazinyl]carbonyl-methyl-7-chloro-1-[2-methoxy-4-(2-chlorobenzoylamino)benzoyl]-2,3,4,5-tetrahydro-1H-benzoazepine
80. 5-(4-Cyanomethyl-1-piperazinyl)carbonylmethyl 7-chloro-1-[2-methoxy-4-(2-chlorobenzoylamino)benzoyl]-2,3,4,5-tetrahydro-1H-benzoazepine
81. 5-(4-Allyl-1-piperazinyl)carbonylmethyl-7-chloro-1-[2-methoxy-4-(2-chlorobenzoylamino)benzoyl]-2,3,4,5-tetrahydro-1H-benzoazepine
82. 5-(1-Piperidinyl)carbonylmethyl-7-fluoro-[3-methoxy-4-(2-methylbenzoylamino)benzoyl-2,3,4,5-tetrahydro-1H-benzoazepine
83. 5-(4-Oxiranyl-1-piperazinyl)carbonylmethyl-7-chloro-1-[2-methoxy-4-(2-carbonylamino)benzoyl]-2,3,4,5-tetrahydro-1H-benzoazepine
84. 5-(4-Carbonylmethyl-1-piperazinyl)carbonylmethyl-7-chloro-1-[2-methoxy-4-(2-chlorobenzoylamino)benzoyl]-2,3,4,5-tetrahydro-1H-benzoazepine
85. 5-[4-(2-Hydroxyethyl)-1-piperazinyl]-carbonylmethyl-7-chloro-1-[2-methoxy-4-(2-chlorobenzoylamino)benzoyl]-2,3,4,5-tetrahydro-1H-benzoazepine
86. 5-(4-Methyl-1-piperazinyl)carbonylmethyl-7-fluoro-1-[2-methoxy-4-(2-methylbenzoylamino)benzoyl]-2,3,-dihydro-1H-benzoazepine
87. 5-[4-(2-Hydroxy-3-isopropylaminopropyl)-1-piperazinyl]carbonylmethyl-7-chloro-1-[2-methoxy-4-(2-chlorobenzoylamino)benzoyl]-2,3,4,5-tetrahydro-1H-benzoazepine
88. 5-[N-Methyl-N-(2-hydroxyethyl)amino]-carbonylmethyl-7-chloro-1-[2-methoxy-4-(2-chlorobenzoylamino)benzoyl]-2,3,4,5-tetrahydo-1H-benzoazepine
89. 5-(2-Dimethylaminoethylamino)carbonylmethyl-7-chloro-1-[2-methoxy-4-(2-chlorobenzoylamino)benzoyl]-2,3,4,5-tetrahydro-1H-benzoazepine•hydrochloride
90. 7-Chloro-1-(3-methoxy-4-[2-(3-[N'-methoxyureido]propoxy)benzoylamino]benzoyl)-2,3,4,5-tetrahydro-1H-benzoazepine
91. 5-[N-Methyl-N-(2-diethylaminoethyl)amino]-carbonylmethyl-7-chloro-1-[3-methoxy-4-(2-bromobenzoylamino)benzoyl]-2,3,4,5-tetrahydro-1H-benzoazepine
92. 5-[2–1,2,4-Triazol-1-yl)ethoxy]-7-chloro-1-[2-methyl-4-(2-chlorobenzoylamino)benzoyl]-2,3,4,5-tetrahydro-1H-benzoazepine
93. 5-[2-(1,2,3,4-Tetrazol-1-yl)ethoxy]-7-chloro-1-[2-methyl-4-(2-chlorobenzoylamino)benzoyl]-2,3,4,5-tetrahydro-1H-benzoazepine
94. 5-[2-(1,2,3,4-Tetrazol-1-yl)ethoxy-7-chloro-1-[2-methyl-4-(2-chlorobenzoylamino)benzoyl]-2,3,4,5-tetrahydro-1H-benzoazepine
95. 5-(2-Morpholinoethyl)-7-chloro-1-[2-methyl-4-(2-chlorobenzoylamino)benzoyl-2,3,4,5-tetrahydro-1H-benzoazepine
96. 5-[2-(1-Piperidinyl)ethyl]-7-chloro-1-[2-methyl-4-(2-chlorobenzoylamino)benzoyl]-2,3,4,5-tetrahydro-1H-benzoazepine•hydrochloride
97. 5-[2-(1-Pyrrolidinyl)ethyl]-7-chloro-1-[2-methyl-4-(2-chlorobenzoylamino)benzoyl]-2,3,4,5-tetrahydro-1H-benzoazepine•hydrochloride
98. 5-[2-(1,2,3,4-Tetrazol-1-yl)ethyl]-7-chloro-1-[2-methyl-4-(2-chlorobenzoylamino)benzoyl-2,3,4,5-tetrahydro-1H-benzoazepine
99. 5-[2-(1,2,3,5-Tetrazol-1-yl)ethyl]-7-chloro-1-[2-methyl-4-(2-chlorobenzoylamino)benzoyl]-2,3,4,5-tetrahydro-1H-benzoazepine
100. 5-[2-(N-Methyl-N-allylamino)ethyl]-7-chloro 1-[2-methyl-4-(2-chlorobenzoylamino)benzoyl-2,3,4,5-tetrahydro-1H-benzoazepine•hydrochloride
101. 5-(2-Allylaminoethyl)-7-fluoro-1-[2-methyl-4-(2-chlorobenzoylamino)benzoyl]-2,3,4,5-tetrahydro-1H-benzoazepine
102. 5-(2-Cyclopropylaminoethyl)-7-chloro-1-[2-methyl-4-(2-chlorobenzoylamino)benzoyl]-2,3,4,5-tetrahydro-1H-benzoazepine•hydrochloride 103. 5-(2-Propargylaminoethyl)-7-chloro-1-[2-methyl-4-(2-chlorobenzoylamino)benzoyl]-2,3,4,5-tetrahydro-1H-benzoazepine•hydrochloride
104. 5-[2-(1-Imidazolyl)ethyl]-7-chloro-1-[2-methyl-4-(methylbenzoylamino)benzoyl]-2,3,4,5-tetrahydro-1H-benzoazepine
105. 5-[2-(1,2,4-Triazol-1-yl)ethyl]-7-chloro-1-[2-methyl-4-(2-chlorobenzoylamino)benzoyl]-2,3,4,5-tetrahydro-1H-benzoazepine
106. 5-Hydroxy-7-chloro-1-{4-[2-(2-methylphenyl)acetylamino]benzoyl}-2,3,4,5-tetrahydro-1H-benzoazepine
107. 5-(L-Lysyloxy)-7-chloro-1-[3-methoxy-4-(2methylbenzoylamino)benzoyl]-2,3,4,5-tetrahydro-1H-benzoazepine•dihydrochloride
108. 5-(4-Methyl-1-piperazinyl)carbonylmethyl-7-chloro-1-[2-chloro-4-(2-methylbenzoylamino)benzoyl]-2,3,4,5-tetrahydro-1H-benzoazepine•hydrochloride
109. 5-(4-Methyl-1-piperazinyl)carbonylmethyl-7-chloro-1-[4-(2-methylbenzoylamino)benzoyl]-2,3,4,5-tetrahydro-1H-benzoazepine•hydrochloride
110. 5-(4-Dimethylamino-1-piperidinyl)carbonylmethyl-7-fluoro-1-[2-methoxy-4-(2-methylbenzoylamino)benzoyl]-2,3,4,5-tetrahydro-1H-benzoazepine
111. 5-Dimethylaminocarbonylmethyl-7-chloro-1-[4-(2-methylbenzoylamino)benzoyl]-2,3,4,5-tetrahydro-1H-benzoazepine
112. 5-Carbamoylmethyl-7-chloro-1-[4-(2-methylbenzoylamino)benzoyl]-2,3,4,5-tetrahydro-1H-benzoazepine
113. 5-(2-Hydroxyethoxy)-7-chloro-1-[4-(2chlorobenzoylamino)benzoyl]-2,3,4,5-tetrahydro-1H-benzoazepine
114. 5-(1-Pyrrolidinyl)carbonylmethyl-7-fluoro-1-[2-methoxy-4-(2-bromobenzoylamino)benzoyl]-2,3,4,5-tetrahydro-1H-benzoazepine
115. 5-(1-Piperazinyl)carbonylmethyl-7-chloro-1-[2-methyl-4-(2-methylbenzoylamino)benzoyl]-2,3,4,5-tetrahydro-1H-benzoazepine•hydrochloride
116. 5-(4-Methyl-1-piperazinyl)carbonylmethyl-7-chloro-1-[4-(2-chlorobenzoylamino)benzoyl]-2,3,4,5-tetrahydro-1H-benzoazepine•hydrochloride
117. 5-(4-Methyl-1-piperazinyl)carbonylmethyl-7-chloro-1-[3-methoxy-4-(2-chlorobenzoylamino)benzoyl]-2,3,4,5-tetrahydro-1H-benzoazepine•hydrochloride
118. 5-(4-Dimethylamino-1-piperidinyl)carbonylmethyl-7-chloro-1-[2-methyl-4-(2-methylbenzoylamino)benzoyl]-2,3,4,5-tetrahydro-1H-benzoazepine•hydrochloride
119. 5-(4-Methyl-1-piperazinyl)carbonylmethyl-7-chloro-1-[3-methoxy-4-(2-bromobenzoylamino)benzoyl]-2,3,4,5-tetrahydro-1H-benzoazepine
120. 5-Dimethylaminocarbonylmethyl-7-chloro-1-[3-methoxy-4-(2-bromobenzoylamino)benzoyl]-2,3,4,5-tetrahydro-1H-benzoazepine
121. 5-(2-Allylaminoethyl)-7-chloro-1-[2-methyl-4-(2-chlorobenzoylamino)benzoyl]-2,3,4,5-tetrahydro-1H-benzoazepine
122. 5-Methylaminocarbonylmethyl-7-chloro-1-[2-methyl-4-(2-chlorobenzoylamino)benzoyl]-2,3,4,5-tetrahydro-1H-benzoazepine
123. 5-Carbamoylmethyl-7-chloro-1-[2-methyl-4-(2-chlorobenzoylamino)benzoyl-2,3,4,5-tetrahydro-1H-benzoazepine
124. 5-Morpholinoethyl-7-chloro-1-[2-methyl-4-(2-methylbenzoylamino)benzoyl]-2,3,4,5-tetrahydro-1H-benzoazepine
125. 5-(4-Methyl-1-homopiperazinyl)carbonylmethyl-7-chloro-1-[2-methoxy-4-(2-chlorobenzoylamino)benzoyl]-2,3,4,5-tetrahydro-1H-benzoazepine
126. 5-(2-Pyridylmethyl)aminocarbonylmethyl-7-chlor-[2-methoxy-4-(2-chlorobenzoylamino)benzoyl]-2,3,4,5-tetrahydro-1H-benzoazepine
127. 5-(4-Pyridyl)aminocarbonylmethyl-7-chloro-1-[2-methoxy-4-(2-chlorobenzoylamino)benzoyl]-2,3,4,5-tetrahydro-1H-benzoazepine
128. 5-(4-Ethyl-1-piperazinyl)carbonylmethoxy-7-chloro-1-[4-(1-oxo-1,2,3,4-tetrahydroisoquinolin-2-yl)benzoyl]-2,3,4,5-tetrahydro-1H-benzoazepine
129. 5-[2-(N-Allyl-N-methylamino)ethyl]-7-fluoro-1-[2-methyl-4-(2-chlorobenzoylamino)benzoyl]-2,3,4,5-tetrahydro-1H-benzoazepine
130. 5-[2-(2-Pyridyl)ethyl]aminocarbonylmethyl-7-chloro-1-[2-methoxy-4-(2-chlorobenzoylamino)benzoyl]-2,3,4,5-tetrahydro-1H-benzoazepine
131. 5-(2-Diethylaminoethoxy)-7-chloro-1-[4-(1-oxoisoindolin-2-yl)benzoyl]-2,3,4,5-tetrahydro-1H-bezoazepine
132. 5-(4-Ethyl-1-piperazinyl)carbonylethoxy-7-chloro-1-[4-(1-oxoisoindolin-2-yl)benzoyl]-2,3,4,5-tetrahydro-1H-benzoazepine
133. 5-(2-Methylaminothiocarbonylaminoethoxy)-7-chloro-1-[2-methoxy-4-(2-chlorobenzoylamino)benzoyl]-2,3,4,5-tetrahydro-1H-benzoazepine
134. 5-(5-Methyl-2-pyrazinyl)methylaminocarbonylmethyl-7-chloro-1-[2-methoxy-4-(2-chlorobenzoylamino)benzoyl]-2,3,4,5-tetrahydro-1H-benzoazepine
135. 5-[2-(1-Iminoethyl)aminoethoxy]-7-chloro-1-[2-methoxy-4-(2-chlorobenzoylamino)benzoyl]-2,3,4,5-tetrahydro-1H-benzoazepine•hydrochloride
136. 5-(2-Ureidoethoxy)-7-chloro-1-[2-methoxy-4-(2-chlorobenzoylamino)benzoyl]-2,3,4,5-tetrahydro-1H-benzoazepine
137. 5-(2-Ethoxycarbonylaminoethoxy)-7-chloro-1-[2-methoxy-4-(2-chlorobenzoylamino)benzoyl]-2,3,4,5-tetrahydro-1H-benzoazepine
138. 5-(2-Cyclopropylaminoethoxy)-7-chloro-1-[2-methoxy-4-(2-chlorobenzoylamino)benzoyl]-2,3,4,5-tetrahydro-1H-benzoazepine•hydrochloride
139. 5-[2-(4-Pyridyl)thioethoxy]-7-chloro-1-[2-methoxy-4-(2-chlorobenzoylamino)benzoyl]-2,3,4,5-tetrahydro-1H-benzoazepine
140. 5-[2-(6-Methyl-2-pyrimidinyl)thioethoxy-7-chloro-1-[2-methoxy-4-(2-chlorobenzoylamino)benzoyl]-2,3,4,5-tetrahydro-1H-benzoazepine
141. 5-[2-(2-Imidazolyl)thioethoxy]-7-chloro-1-[2-methoxy-4-(2-chlorobenzoylamino)benzoyl]-2,3,4,5-tetrahydro-1H-benzoazepine
142. 5-[2-(4-Pyridyl)sulfonylethoxy]-7-chloro-1-[2-methoxy-4-(2-chlorobenzoylamino)benzoyl]-2,3,4,5-tetrahydro-1H-benzoazepine
143. 5-[2-(4-Pyridyl)sulfinylethoxy]-7-chloro-1-[2-methoxy-4-(2-chlorobenzoylamino)benzoyl]-2,3,4,5-tetrahydro-1H-benzoazepine
144. 5-[2-(2-Imidazolyl)sulfinylethoxy]-7-chloro-1-[2-methoxy-4-(2-chlorobenzoylamino)benzoyl] 2,3,4,5-tetrahydro-1H-benzoazepine
145. 5-[2-(2-Imidazolyl)sulfonylethoxy]-7-chloro-1-[2-methoxy-4-(2-chlorobenzoylamino)benzoyl]-2,3,4,5-tetrahydro-1H-benzoazepine
146. 5-[2-(4-Methanesulfonyl-1-piperazinyl)ethyl]-7-chloro-1-[2-methoxy-4-(2-chlorobenzoylamino)-benzoyl]-2,3,4,5-tetrahydro-1H-benzoazepine
147. 5-[2-(4-Ethoxycarbonyl-1-piperazinyl)ethyl]-7-chloro-1-[2-methoxy-4-(2-chlorobenzoylamino)-benzoyl]-2,3,4,5-tetrahydro-1H-benzoazepine
148. 5-[2-(4-Methylaminocarbonyl-1-piperazinyl)ethyl]-7-chloro-1-[2-methoxy-4-(2-chlorobenzoylamino)benzoyl]-2,3,4,5-tetrahydro-1H-benzoazepine
149. 5-[2-(3-Methyl-2-cyanogianidino)ethoxy]-7-chloro-1-[2-methoxy-4-(2-chlorobenzoylamino)benzoyl]-2,3,4,5-tetrahydro-1H-benzoazepine 150. 5-(2-Benzylaminoethoxy)-7-chloro-1-[2-methoxy-4-(2-chlorobenzoylamino)benzoyl]-2,3,4,5-tetrahydro-1H-benzoazepine
151. 5-(2-Cyanomethylaminoethoxy)-7-chloro-1-[2-methoxy-4-(2-chlorobenzoylaminobenzoyl]-2,3,4,5-tetrahydro-1H-benzoazepine
152. 5-(2-Trifluoromethylsulfonylaminoethoxy)-7-chloro-1-[2-methoxy-4-(2-bromobenzoylamino)benzoyl]-2,3,4,5-tetrahydro-1H-benzoazepine
153. 5-[2-(3-Diethylaminopropyl)aminoethoxy]-7-chloro-1-[2-methoxy-4-(2-chlorobenzoylamino)benzoyl]-2,3,4,5-tetrahydro-1H-benzoazepine
154. 5-[2-(1-Methyl-2-pyrrolyl)ethyl]aminocarbonyl-methyl-7-chloro-1-[2-methoxy-4-(2-chlorobenzoylamino)benzoyl]-2,3,4,5-tetrahydro-1H-benzoazepine
155. 5-[2-(1-Methyl-2-pyrrolidinyl)ethyl]-aminocarbonylmethyl-7-chloro-1-[2-methoxy-4-(2-chlorobenzoylamino)benzoyl]-2,3,4,5-tetrahydro-1H-benzoazepine
156. 5-[2-(1-Piperidinyl)ethyl]aminocarbonylmethyl-7-chloro-1-[2-methoxy-4-(2-chlorobenzoylamino)benzoyl]-2,3,4,5-tetrahydro-1H-benzoazepine
157. 5-{4-[(1-Pyrrolidynyl)carbonylmethyl]-1-piperazinyl}carbonylmethyl-7-chloro-1-[2-methoxy-4-(2-chlorobenzoylamino)benzoyl]-2,3,4,5-tetrahydro-1H-benzoazepine
158. 5-(2-Chloroanilino)carbonylmethyl-7-chloro-1-[2-methoxy-4-(2-chlorobenzoylamino)benzoyl]-2,3,4,5-tetrahydro-1H-benzoazepine
159. 5-(2-Chlorobenzoylamino)-7-chloro-1-[2-methoxy-4-(2-chlorobenzoylamino)benzoyl]-2,3,4,5-tetrahydro-1H-benzoazepine
160. 5-{2-[N-(2-Hydroxyethyl)-N-methylamino]ethyl}-aminocarbonylmethyl-7-chloro-1-[2-methoxy-4-(2-chlorobenzoylamino)benzoyl]-2,3,4,5-tetrahydro-1H-benzoazepine
161. 5-Carboxymethyl-7-chloro-1-[2-hydroxy-4-(2-chlorobenzoylamino)benzoyl]-2,3,4,5-tetrahydro-1H-benzoazepine
162. 5-Dimethylaminocarbonylmethyl-7-chloro-1-{4-[2-(4-isopropylaminobutoxy)benzoylamino]-benzoyl}-2,3,4,5-tetrahydro-1H-benzoazepine
163. 5-[N-(2-Dimethylaminoethyl)-N-methylamino]-carbonylmethyl-7-chloro-1-[3-methoxy-4-(2-bromobenzoylamino)benzoyl]-2,3,4,5-tetrahydro-1H-benzoazepine
164. 5-(2-Morpholinoethyl)aminocarbonylmethyl-7-chlorolo-[3-methoxy-4-(2-bromobenzoylamino)-benzoyl]-2,3,4,5-tetrahydro-1H-benzoazepine
165. 5-[N-(2-Dimethylaminoethyl)-N-ethylamino]-carbonylmethoxy-7-chloro-[3-methoxy-4-(2-bromobenzoylamino)benzoyl]-2,3,4,5-tetrahydro-1H-benzoazepine
166. 5-(4-Methyl-1-homopiperazinyl)carbonylmethoxy-7-chloro-1-[3-methoxy-4-(2-bromobenzoylamino)benzoyl]-2,3,4,5-tetrahydro-1H-benzoazepine
167. 5-[2-(1-Piperidinyl)ethyl]aminocarbonylmethoxy-7-chloro-1-[3-methoxy-4-(2-bromobenzoylamino)benzoyl]-2,3,4,5-tetrahydro-1H-benzoazepine
168. 5-(2-Morpholinoethyl)aminocarbonylmethoxy-7-chloro-1-[3-methoxy-4-(2-bromobenzoylamino)benzoyl]-2,3,4,5-tetrahydro-1H-benzoazepine
169. 5-(2-Allylaminoethoxy)-7-chloro-1-[2-methoxy-4-(2-chlorobenzoylamino)benzoyl]-2,3,4,5-tetrahydro-1H-benzoazepine•hydrochloride
170. 5-(2-Propargylaminoethoxy)-7-chloro-1-[2-methoxy-4-(2-chlorobenzoylamino)benzoyl]-2,3,4,5-tetrahydro-1H-benzoazepine•hydrochloride
171. 5-[2-(1-Imidazolyl)ethoxy]-7-chloro-1-[2-methoxy-4-(2-chlorobenzoylamino)benzoyl]-2,3,4,5-tetrahydro-1H-benzoazepine
172. 5-(2-Methanesulfonylaminoethoxy)-7-chloro-1-[2-methoxy-4-(2-chlorobenzoylamino)benzoyl]-2,3,4,5-tetrahydro-1H-benzoazepine
173. 5-Carbamoylmethyl-7-chloro-1-[2-chloro-4-(2-methylbenzoylamino)benzoyl]-2,3,4,5-tetrahydro-1H-benzoazepine
174. 5-[2-(4-Acetyl-1-piperazinyl)ethyl]-7-chloro-1-[2-chloro-4-(2-methylbenzoylamino)benzoyl]-2,3,4,5-tetrahydro-1H-benzoazepine
175. 5-[N-(2-Diethylaminoethyl)-N-ethylamino]-carbonylmethyl-7-chloro-1-[2-methoxy-4-(2-chlorobenzoylamino)benzoyl]-2,3,4,5-tetrahydro-1H-benzoazepine
176. 5-[2-(1,2,4-Triazol-1-yl)ethoxy]-7-chloro-1-[2-methoxy-4-(2-chlorobenzoylamino)benzoyl]-2,3,4,5-tetrahydro-1H-benzoazepine
177. 5-(2-Cyclopentylaminoethoxy)-7-chloro-1-[2-methoxy-4-(2-chlorobenzoylamino)benzoyl]-2,3,4,5-tetrahydro-1H-benzoazepine
178. 5-(4-Methyl-1-piperazinyl)carbonylmethyl-7-chloro-1-(4-benzoylaminobenzoyl)-2,3,4,5-tetrahydro-1H-benzoazepine
179. 5-[2-(4-Acetyl-1-piperazinyl)ethyl]-7-chloro-1-[2-methoxy-4-(2-chlorobenzoylamino)benzoyl]-2,3,-dihydro-1H-benzoazepine
180. 5-[2-(4-Methyl-1-homopiperazinyl)ethoxy]-7-chloro-1-[2-methoxy-4-(2-chlorobenzoylamino)benzoyl]-2,3,4,5-tetrahydro-1H-benzoazepine
181. 5-[4-(2-Chlorophenyl)-1-piperazinyl]-carbonylmethyl-7-chloro-1-[2-methoxy-4-(2-chlorobenzoylamino)benzoyl]-2,3,4,5-tetrahydro-1H-benzoazepine
182. 5-Dimethylaminocarbonylmethyl-7-chloro-1-{4-[2-(4-tert-butylaminobutoxy)benzoylamino]benzoyl}-2,3,4,5-tetrahydro-1H-benzoazepine
183. 5-(4-Methyl-1-piperazinyl)carbonylmethyl-7-chloro-1-{2-methoxy-4-[(2,3-dihydro-4H-chromen-8-yl)carbonylamino]benzoyl}-2,3,4,5-tetrahydro-1H-benzoazepine
184. 7-Chloro-1-[4-{3-[4-(4-Acetylamino-1-piperidinyl)butoxy]-6-chlorobenzoylamino}benzoyl]-2,3,4,5-tetrahydro-1H-benzoazepine
185. 5-(4-Methyl-1-homopiperazinyl)carbonylmethyl-7-chloro-1-[3-methoxy-4-(2-bromobenzoylamino)benzoyl]-2,3,4,5-tetrahydro-1H-benzoazepine Test-1: $V_1$ Recepter binding assay By using rat liver plasma membrane preparations prepared according to Ichiraha's method [by Akira Ichihara: J. Bio. Chem., 258, 9283 (1983)], the plasma membrane (50,000 dpm, $2\times10^{-10}$M) of [$^3$H]-Arg-vasopressin and a test compound (60 µg, $10^{-8}$ to $10^{-4}$M) were incubated at 37° C. for 10 minutes in 250 µl (in total volume) of 100 mM Tris-HCl buffer (pH=8.0), containing 5 mM MgCl$_2$, 1 mM EDTA and 0.1% BSA. After the incubation, the mixture was filtered three times by using a glass filter (GF/F) so as to separate the membrane preparation by combining with vasopressin and then washed with the buffer (5 ml). This glass filter was taken out and mixed with a liquid of scintillation cocktail. The amount of [$^3$H]-vasopressin combining with the membrane was measured by liquid scintillation counter and the rate of inhibitory effect of the test compound was calculated according to the following equation:

Rate of inhibitory effect (%)=100-[($C_1$-$B_1$)/($C_0$-$B_1$)]×100 wherein, $C_1$: the amount of [$^3$H]-vasopressin combining with the membrane in the presence of the test compound of a known amount, $C_0$: the amount of [$^3$H]-vasopressin combining with the membrane in the absence of the test compound, $B_1$: the amount of [$^3$H]-vasopressin combining with the membrane in the presence of the excess amount of vasopressin ($10^{-6}$M).

The results are expressed as $IC_{50}$ value, which is the concentration of the test compound required to achieve the inhitory effect in the rate of 50%, and are shown in the following Table 156.

TABLE 156

| Test compound No. | $IC_{50}$ (μM) | Test compound No. | $IC_{50}$ (μM) |
|---|---|---|---|
| 64 | 0.045 | 70 | 0.13 |
| 71 | 0.025 | 70 | 0.13 |
| 73 | 0.007 | 72 | 0.0012 |
| 80 | 0.016 | 77 | 0.029 |
| 82 | 0.057 | 79 | 0.065 |
| 84 | 0.019 | 81 | 0.023 |
| 87 | 0.007 | 83 | 0.025 |
| 89 | 0.009 | 85 | 0.016 |
| 91 | 0.0026 | 88 | 0.010 |
| 126 | 0.024 | 90 | 0.0055 |
| 128 | 0.014 | 125 | 0.008 |
| 131 | 0.032 | 127 | 0.023 |
| 133 | 0.020 | 130 | 0.018 |
| 135 | 0.018 | 132 | 0.090 |
| 137 | 0.017 | 134 | 0.012 |
| 139 | 0.12 | 136 | 0.037 |
| 141 | 0.056 | 138 | 0.005 |
| 143 | 0.013 | 140 | 0.28 |
| 145 | 0.091 | 142 | 0.098 |
| 147 | 0.039 | 144 | 0.055 |
| 149 | 0.09 | 146 | 0.054 |
| 151 | 0.046 | 148 | 0.054 |
| 153 | 0.036 | 150 | 0.016 |
| 155 | 0.007 | 152 | 0.041 |
| 157 | 0.016 | 154 | 0.021 |
| 159 | 0.28 | 156 | 0.0055 |
| 162 | 0.0092 | 158 | 0.031 |
| 164 | 0.0026 | 160 | 0.006 |
| 166 | 0.0048 | 163 | 0.0018 |
| 168 | 0.01 | 165 | 0.0036 |
| 170 | 0.024 | 167 | 0.0055 |
| 172 | 0.005 | 169 | 0.007 |
|  |  | 171 | 0.11 |

Test^2: $V_2$ Recepter binding assay

By using rat kidney plasma membrane preparations prepared according to Hechter's method [by O. Hechter: J. Bio. Chem., 2.53, 3211 (1978)], the plasma membrane (100,000 dpm, $4\times10^{-10}$M) of [$^3$H]-Arg-vasopressin and a test compound (0.6 mg, $10^{-10}$ to $10^{-5}$M) were incubated at 4° C. for 3 hours in 250 μl (in total volume) of 100 mM Tris-HCl buffer (pH=8.0), containing, 5 mM $MgCl_2$, 1 mM EDTA and 0.1% BSA. After the incubation, the mixture, the mixture was filtered by using a glass filter (GF/F) so as to separate the membrane preparation combining with vasopressin, then washed twice with the buffer (5 ml). This glass filter was taken out and mixed with liquid scintillation cocktail. The amount of [$^3$H]-vasopressin combining with the membrane was measured by a liquid scintillation counter and the rate of inhibitory effect of the test compound was calculated according to the following equation: Rate of the inhibitory effect (%)=100-[$(C_1-B_1)/(C_0-B_1)$]×100 wherein, $C_1$: the amount of [$^3$H]-vasopressin combining with the membrane in the presence of the testcompound of a known amount, $C_0$: the amount of [$^3$H]-vasopressin combining with the membrane in the absence of the test compound, $B_1$: the amount of [$^3$H]-vasopressin combining with the mebrane in the presence of the excess amount of of vasopressin ($10^{-6}$M).

The results are expressed as $IC_{50}$ value, which is the concentration of the test compound required to achieve the inhibitory effect in the rate of 50%, and are shown in the following Table 157.

TABLE 157

| Test compound No. | $IC_{50}$ (μM) | Test compound No. | $IC_{50}$ (μM) |
|---|---|---|---|
| 70 | 0.015 | 69 | 0.024 |
| 72 | 0.074 | 71 | 0.28 |
| 74 | 0.032 | 73 | 0.080 |
| 76 | 0.014 | 75 | 0.032 |
| 80 | 0.009 | 77 | 0.022 |
| 84 | 0.005 | 79 | 0.15 |
| 86 | 0.059 | 81 | 0.010 |
| 88 | 0.002 | 83 | 0.007 |
| 90 | 0.14 | 85 | 0.008 |
| 92 | 0.0074 | 87 | 0.002 |
| 94 | 0.014 | 89 | 0.0025 |
| 96 | 0.009 | 91 | 0.0035 |
| 98 | 0.009 | 93 | 0.014 |
| 100 | 0.0047 | 95 | 0.017 |
| 102 | 0.0071 | 97 | 0.0072 |
| 104 | 0.009 | 99 | 0.012 |
| 125 | 0.004 | 101 | 0.007 |
| 127 | 0.004 | 103 | 0.008 |
| 129 | 0.012 | 105 | 0.0075 |
| 131 | 0.17 | 126 | 0.005 |
| 133 | 0.049 | 128 | 0.013 |
| 135 | 0.0049 | 130 | 0.004 |
| 137 | 0.005 | 132 | 0.12 |
| 139 | 0.012 | 134 | 0.004 |
| 141 | 0.0076 | 136 | 0.0043 |
| 143 | 0.022 | 138 | 0.003 |
| 145 | 0.014 | 140 | 0.046 |
| 147 | 0.014 | 142 | 0.038 |
| 149 | 0.045 | 144 | 0.0099 |
| 151 | 0.008 | 146 | 0.01 |
| 153 | 0.005 | 148 | 0.005 |
| 155 | 0.0019 | 150 | 0.009 |
| 157 | 0.0073 | 152 | 0.061 |
| 159 | 0.025 | 154 | 0.012 |
| 163 | 0.008 | 156 | 0.003 |
| 165 | 0.0043 | 158 | 0.014 |
| 167 | 0.0085 | 160 | 0.0033 |
| 169 | 0.0056 | 162 | 0.13 |
| 171 | 0.015 | 164 | 0.0085 |
|  |  | 166 | 0.01 |
|  |  | 168 | 0.019 |
|  |  | 170 | 0.007 |
|  |  | 172 | 0.0039 |

Test-3: Vasopressin antagonistic activity in vivo

In order to test the vasopressin antagonistic activity of the compound of the present invention when admistered orally to rats under awaking, the following experiment was conducted. Cannulas were inserted into the aorta abdominalis and the carotid arteries of male SD-rats (body weight: 300–450 g) under pentobarbital-anesthetization. A few days thereafter, vasopressin (30 mU/kg) was administered intravenously to the rats under awaking with measuring the blood pressure at the cannula inserted into the arorta abdominalis by a piezo-electric transducer. The test compound was dissolved in polyethylene glycol or water, or suspended in 5% gum arabic solution, and orally administered by force to the rats.

The increase in the diastolic pressure of the rat was periodically mesured at 30 minutes' interval after the administration of vasopressin for 8 hours. The rate of inhibitory effect (%) of the test compound on the increase in the diastolic pressure caused by vasopressin (30 mU/kg) was calculated based on the increase in the diastolic pressure when vasopressin (30 mU/kg) was intravenously administered without a test compound.

The test result is expressed as ID50 value, which is the oral dose of the test compound required to achieve the inhibitory effect in the rate of 50% and is shown in Table 158 as follows:

TABLE 158

| Test compound No. | $ID_{50}$ (mg/kg) |
|---|---|
| 63 | 3.4 |

Test-4: Anti-antiduretic water diuretic/activity in vivo

The test compound of the present invention was dissolved in polyethylene glycol 400 or water or suspended in 5% gum arabic aqueous solution, and the mixture was orally administered by force to male SD-rats (body weight: 300 to 400 g) under untreated and unrestrained. After administration the rats were kept in a metabolism cage and the amount of urine spontaneously excreted by the rats was measured at 2 hours' interval, during which the rats could freely be given feed and water.

In the cotrol group, a solvent was administered instead of a test compound solution (or suspension).

The test results are expressed as $ED_3$, which is the oral dose of the test compound which is required to increase the amount of the urine excreted from the rat in the test compound-treated group for the first 2 hours by time based on the amount of urine excreted from the rat for the first 2 hours in the control group. The results are shown in Table 159 as follows:

TABLE 159

| Test compound No. | $ED_3$ (mg/kg) |
|---|---|
| 41 | 1.4 |
| 63 | 3.2 |

Test-5 Oxytocin receptor binding assay

In accordance with Chan's method [by W. Y. Chan, et al.: Endocrinology, 126, 2095–2101 (1990)], the uterin muscle benn injected subcutaneously with diethylstilbe-sterol (DES) the day before and was homogenized, which was used as a membrane prepara tion. The membrane preparation (0.2 mg), [$^3$H]-oxytocin (100,000 dpm, $10^{-9}$M), a test compound ($10^{-9}$ to $10^{-5}$M) were incubated at 25°. for one hour in 100 mM Tris-HCl buffer (pH=8.0, 250 µl) containing 5 mM $MgCl_2$, 1 mM EDTA and 0.1% BSA. The mixture was filtered through a glass filter (GF/F) so as to separate the membrane preparation combining with [$^3$H]-oxytocin, then, was washed twicw with the buffer (5 ml). The glass filter was put into a vial and mixed with Aquasole (a liquid scintillation cocktail). The amount of [$^3$H]-oxytocin combining w ith the membrane was measured by a liquid scintillation counter. The rate of the inhibitory effect of the test compound was calculated according to the equation as follows:

Rate of the inhibitory effect (%)=100−[$(C_1-B)/(C_0-B)$]×100 wherein, $C_1$: the amount of [$^3$H]-oxytocin combining with the membrane in the presence of a test compound (in known amount), $C_0$: the amount of [$^3$H]-oxytocin combinig with the membrane in the absence of a test compound, B: the amount of [$^3$H]-oxytocin combining with the membrane in the presence of the excess amount of oxytocin ($5\times10^{-6}$M).

The results are expressed as $IC_{50}$ values, which is the concentration of the test compound required to achieve the inhibitory effect in the rate of 50%. The results are shown in Table 160 as follows:

TABLE 160

| Test compound No. | $IC_{50}$ (µM) | Test compound No. | $IC_{50}$ (µM) |
|---|---|---|---|
| 17 | 0.046 | 29 | 0.11 |
| 32 | 0.61 | 47 | 1.6 |
| 53 | 1.9 | 54 | 0.30 |
| 57 | 2.7 | 58 | 0.094 |
| 59 | 1.9 | 60 | 0.099 |
| 61 | 0.23 | 68 | 0.23 |
| 80 | 0.084 | 81 | 0.10 |
| 83 | 0.076 | 84 | 0.045 |
| 85 | 0.094 | 87 | 0.070 |
| 88 | 0.058 | 96 | 4.4 |
| 97 | 4.066 | 99 | 2.8 |
| 100 | 4.045 | 101 | 5.3 |
| 102 | 2.9 | 103 | 3.0 |
| 104 | 1.6 | 106 | 0.60 |
| 107 | 1.3 | 108 | 1.9 |
| 109 | 0.36 | 110 | 0.22 |
| 111 | 0.25 | 112 | 0.28 |
| 113 | 0.25 | 114 | 0.17 |
| 115 | 2.1 | 116 | 0.38 |
| 117 | 0.32 | 118 | 3.2 |
| 119 | 0.27 | 120 | 0.19 |
| 121 | 2.3 | 122 | 2.2 |
| 123 | 2.2 | 124 | 2.8 |
| 125 | 0.037 | 126 | 0.073 |
| 127 | 0.032 | 128 | 0.095 |
| 130 | 0.115 | 131 | 1.790 |
| 132 | 0.478 | 133 | 0.072 |
| 134 | 0.096 | 135 | 0.146 |
| 136 | 0.151 | 137 | 0.451 |
| 138 | 0.233 | 139 | 1.003 |
| 140 | 4.288 | 141 | 0.193 |
| 142 | 1.132 | 143 | 0.200 |
| 144 | 0.354 | 145 | 0.849 |
| 146 | 0.154 | 147 | 0.504 |
| 148 | 0.225 | 150 | 0.471 |
| 152 | 1.643 | 153 | 0.248 |
| 154 | 0.197 | 155 | 0.055 |
| 156 | 0.070 | 157 | 0.047 |
| 158 | 0.130 | 159 | 1.696 |
| 160 | 0.084 | 164 | 0.041 |
| 167 | 0.177 | 168 | 0.085 |
| 169 | 0.147 | 170 | 0.416 |
| 171 | 0.317 | 172 | 0.133 |
| 173 | 2.187 | 174 | 1.055 |
| 175 | 0.013 | 176 | 0.387 |
| 177 | 0.258 | 178 | 0.969 |
| 179 | 2.604 | 180 | 0.284 |
| 181 | 0.606 | 182 | 4.710 |
| 183 | 4.409 | 184 | 3.669 |
| 185 | 0.162 | | |

What is claimed is:

1. A benzoheterocyclic compound or a salt thereof represented by the formula (1A):

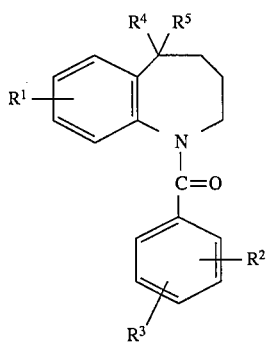
(1A)

wherein $R^1$ is selected from the group consisting of a hydrogen atom, a halogen atom, a hydroxyl group, a lower alkanoyloxy group, an amino-lower alkoxy group which may have a substituent selected from the group consisting of a lower alkyl group, a lower alkanoyl group, a carboxy-substituted lower alkoxy group, and a lower alkoxycarbonyl-substituted lower alkoxy group, and an aminocarbonyl-lower alkoxy group which may have a lower alkyl group as a substituent;

$R^4$ is selected from the group consisting of:
(a) a group of the formula:

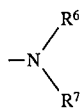

wherein $R^6$ is a hydrogen atom, a lower alkyl group or a lower alkenyl group; and $R^7$ is a benzoyl group having a halogen atom as a substituent on the phenyl ring,
(b) a group of the formula:

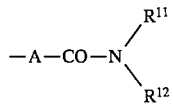

wherein A is a lower alkylene group, $R^{11}$ is a hydrogen atom or a lower alkyl group, and $R^{12}$ is selected from the group consisting of a hydroxyl group-substituted lower alkyl group, a pyridyl-substituted lower alkyl group, a pyridyl group, a group of the formula:

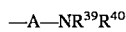

wherein A is the same as defined above, and $R^{39}$ and $R^{40}$ are the same or different, and are each a hydrogen atom or a lower alkyl group which may have a hydroxyl group as a substituent; further $R^{39}$ and $R^{40}$ may form a 5- or 6-membered saturated heterocyclic group, by combining with the adjacent nitrogen atom bonded thereto, together with or without another nitrogen atom or oxygen atom, said heterocyclic ring may have a member selected from the group consisting of a lower alkyl group on the heterocyclic ring, a pyrazinyl-substituted lower alkyl group which may have as a substituent a lower alkyl group on the pyrazine ring, a pyrrolyl-substituted lower alkyl group which may have as a substituent a lower alkyl group on the pyrrole ring, a pyrrolidinyl-substituted lower alkyl group which may have as a substituent a lower alkyl group on the pyrrolidine ring, and a phenyl group which may have a halogen atom on the phenyl ring, further, $R^{11}$ and $R^{12}$ may form a 5- to 7-membered saturated heterocyclic group, by combining with the adjacent nitrogen atom bonded thereto, together with or without another nitrogen atom or oxygen atom; said heterocyclic group may be substituted with a member selected from the group consisting of a lower alkyl group, a lower alkoxy-carbonyl group and an amino group which may have a substituent selected from the group consisting of a lower alkyl group, a lower alkanoyl group, a lower alkoxycarbonyl-substituted lower alkyl group, a phenyl group which may have a halogen atom on the phenyl ring, a cyano-substituted lower alkyl group, a lower alkenyl group, an oxyranyl-substituted lower alkyl group, a carbamoyl-substituted lower alkyl group and a lower alkyl group having 1 to 2 substituents selected from the group consisting of a hydroxyl group and an amino group which may have a lower alkyl group, or a pyrrolidinylcarbonyl-lower alkyl group,
(c) a group of the formula:

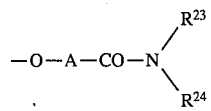

wherein A is the same as defined above, $R^{23}$ is a hydrogen atom or a lower alkyl group, and $R^{24}$ is a group of the formula:

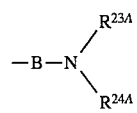

wherein B is an alkylene group, $R^{23A}$ and $R^{24A}$ are the same or different, and are each a hydrogen atom or a lower alkyl group,
further $R^{23A}$ and $R^{24A}$ may form a 5- to 6-membered saturated heterocyclic group, by combining with the adjacent nitrogen atom bonded thereto, together with or without another nitrogen atom or oxygen atom, further $R^{23}$ and $R^{24}$ may form a 5- to 7-membered saturated heterocyclic group, by combining with the adjacent nitrogen atom bonded thereto, together with or without another nitrogen atom or oxygen atom, said heterocyclic group may have a lower alkyl groups as a substituent,
(d) a group of the formula:

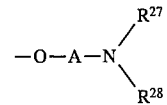

wherein A is the same as defined above; $R^{27}$ and $R^{28}$ are the same or different, and are each a member selected from the group consisting of a hydrogen atom, a lower alkyl group, a lower alkenyl group, a lower alkynyl group, a lower alkylsulfonyl group, an aminothiocarbonyl group which may have a lower alkyl group as a substituent, a group of the formula:

wherein $R^{41}$ is a hydrogen atom or a cyano group; $R^{42}$ is a lower alkyl group or an amino group which may have a lower alkyl group as a substituent,
a carbamoyl group, a lower alkoxycarbonyl group, a cycloalkyl group, a phenyl-lower alkyl group which may have a halogen atom as a substituent on the phenyl ring, a cyano-substituted lower alkyl group, a halogen atom-substituted lower alkylsulfonyl group, and an amino group-substituted lower alkyl group which may have a lower alkyl group as a substituent, further, $R^{27}$ and $R^{28}$ may form a 5- to 10-membered single ring or binary ring saturated or unsaturated heterocyclic group, by combining with the adjacent nitrogen atom bonded thereto, together with or without another nitrogen atom or oxygen atom, said heterocyclic group may be substituted with a lower alkanoylamino group on the heterocyclic ring, (e) a group of the formula:

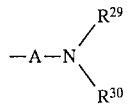

wherein A is the same as defined above, $R^{29}$ is a hydrogen atom or a lower alkyl group, and $R^{30}$ is a lower alkenyl group, a cycloalkyl group or a lower alkynyl group, further $R^{29}$ and $R^{30}$ may form a 5- to 6-membered saturated heterocyclic group, by combining with the adjacent nitrogen atom bonded thereto, together with or without another nitrogen atom or oxygen atom; said heterocyclic group is substituted with a member of the group consisting of an amino group having a lower alkanoyl group, a lower alkylsulfonyl group, a lower alkoxycarbonyl group and an aminocarbonyl group which may have a lower alkyl group as a substituent, (f) a 1,2,4-triazolyl-substituted lower alkoxy group,
(g) a 1,2,3,4-tetrazolyl-substituted lower alkoxy group,
(h) a 1,2,3,5-tetrazolyl-substituted lower alkoxygroup,
(i) a 1,2,3,4-tetrazolyl-substituted lower alkyl group,
(j) a 1,2,3,5-tetrazolyl-substituted lower alkyl group,
(k) 1,2,4-triazolyl-substituted lower alkyl group,
(l) a pyridylthio-substituted lower alkoxy group,
(m) a pyrimidinylthio-substituted lower alkoxy group which may have a lower alkyl group on the pyrimidine ring,
(n) an imidazolthio-substituted lower alkoxy group,
(o) a pyridylsulfinyl-substituted lower alkoxy group,
(p) a pyridylsulfonyl-substituted lower alkoxy group,
(q) an imidazolylsulfinyl-substituted lower alkoxy group, and
(r) an imidazolylsulfonyl-substituted lower alkoxy group;

$R^5$ is a hydrogen atom or a hydroxyl group;

$R^2$ is selected from the group consisting of a hydrogen atom, a lower alkyl group, a hydroxyl group, a halogen atom and a lower alkoxy group; and $R^3$ is selected from the group consisting of:
(a) a group of the formula:

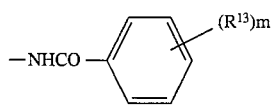

wherein $R^{13}$ is selected from the group consisting of a halogen atom, a hydroxyl group, a carbamoyl group, a lower alkyl group, a piperazinyl-lower alkoxy group having a lower alkanoyl group at 4-position in the piperazine ring, an imidazolyl-substituted lower alkoxy group, a piperidinyl-lower alkoxy group having lower alkanoylamino groups on the piperidine ring, a 1,2,4-triazolyl-substituted lower alkoxy group, an ureido-substituted lower alkoxygroup which may have a lower alkyl group, and an amino-substituted lower alkoxy group which may have a lower alkyl group as a substituent, and m is 0 or an integer of 1 to 3, (b) a group of the formula:

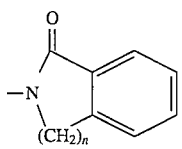

wherein n is 1 or 2, provided that when $R^1$ is a hydrogen atom or a halogen atom, then $R^4$ is a group of the formula:

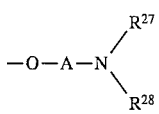

wherein A is the same as defined above, $R^{27}$ and $R^{28}$ are the same or different, and are each a hydrogen atom or a lower alkyl group; and $R^5$ is a hydrogen atom or a hydroxyl group, further, when $R^3$ is a group of the formula:

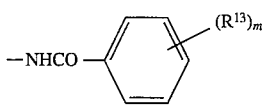

then $R^{13}$ is selected from the group consisting of a carbamoyl group, a piperazinyl-lower alkoxy group having a lower alkanoyl group at the 4-position in the piperazine ring, an imidazolyl-substituted lower alkoxy group, a piperidinyl-substituted lower alkoxy group having a lower alkanoylamino group on the piperidine ring, a 1,2,4-triazolyl-substituted lower alkoxy group and an ureido-substituted-lower alkoxy group which may have a lower alkyl as a substituent; and m is an integer of 1 to 3, or further, when $R^{11}$ and $R^{12}$ form a saturated heterocyclic group, by combining together with the adjacent nitrogen atom with or without another nitrogen atom or oxygen atom, and said heterocyclic group may have as a substituent a substituent selected from the group consisting of a lower alkyl group, a lower alkoxycarbonyl group and an amino group which may have, as a substituent a lower alkyl group or a lower alkanoyl group;

then said saturated heterocyclic group formed by combining $R^{11}$ and $R^{12}$ is a 7-membered heterocyclic group.

2. A benzoheterocyclic compound or salt thereof represented by the formula (1B):

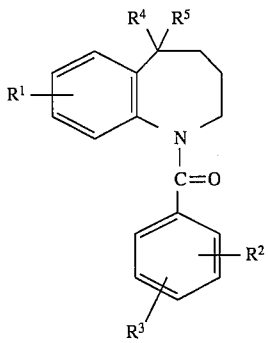 (1B)

wherein, $R^1$ is selected from the group consisting of a hydrogen atom and a halogen atom, $R^4$ is a hydrogen atom, or a group of the formula:

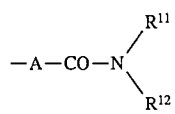

wherein A is a lower alkylene group; $R^{11}$ and $R^{12}$ are the same or different, and are each selected from the group consisting of a hydrogen atom, a lower alkyl group, a piperidinyl group which may have a phenyl-lower alkyl group on the piperidine ring, and a carbamoyl-substituted lower alkyl group, further, $R^{11}$ an $R^{12}$ may form a 5- to 6-membered saturated heterocyclic group, by combining with the adjacent nitrogen atom bonded thereto, together with or without another nitrogen atom or oxygen atom; said heterocyclic group may be substituted with a lower alkyl group, a lower alkoxycarbonyl group, or an amino group which may have as a substituent a lower alkyl group or a lower alkanoyl group, $R^5$ is a hydrogen atom;

$R^2$ is Selected from the group consisting of a hydrogen atom, a lower alkyl group, a hydroxyl group, a halogen atom and a lower alkoxy group; and $R^3$ is a group of the formula:

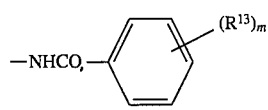

wherein $R^{13}$ is selected from the group consisting of a hydroxyl group, an imidazolyl-substituted lower alkoxy group, a piperidinyl-lower alkoxy group having a lower alkanoylamino group on the piperidine ring, a 1,2,4-triazolyl-substituted lower alkoxy group, an ureido-substituted lower alkoxy group which may have lower alkyl groups, and an amino-substituted lower alkoxy group which may have a lower alkyl group as a substituent; and m is 0 or an integer of 1 to 3, provided that when $R^1$ is a hydrogen atom or a halogen atom; $R^4$ is a hydrogen atom, and $R^5$ is a hydrogen atom; and provided further that when $R^3$ is a group of the formula:

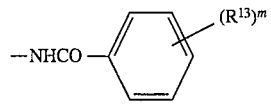

then $R^{13}$ is selected from the group consisting of an imidazolyl-substituted lower alkoxy group, a piperidinyl-substituted lower alkoxy group having a lower alkanoylamino group on the piperidine ring, an 1,2,4-triazolyl-substituted lower alkoxy group and an ureido-substituted lower alkoxy group which may have a lower alkyl as a substituent; and m is an integer of 1 to 3.

3. A benzoheterocyclic compound or a salt thereof represented by the formula (1C):

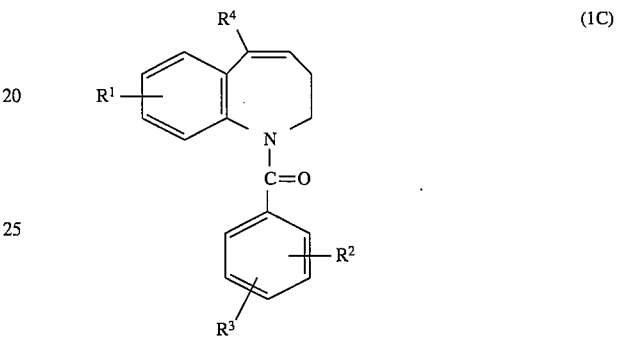 (1C)

wherein, $R^1$ is a hydrogen atom or a halogen atom;

$R^4$ is a group of the formula:

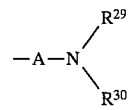

wherein A is a lower alkylene group; $R^{29}$ is a hydrogen atom or a lower alkyl group; $R^{30}$ is a lower alkenyl group, a cycloalkyl group or a lower alkynyl group; further $R^{29}$ and $R^{30}$ may form a 5- to 6-membered saturated heterocyclic group, by combining with the adjacent nitrogen atom bonded thereto, together with or without another nitrogen atom or oxygen atom; said heterocyclic group may be substituted with a member of the group consisting of a lower alkyl group, a lower alkanoyl group, and an amino group which may have a substituent selected from the group consisting of a lower alkyl group, a lower alkanoyl group, a lower alkylsulfonyl group, a lower alkoxycarbonyl group and an aminocarbonyl group which may have a lower alkyl group as a substituent, $R^2$ is selected from the group consisting of a hydrogen atom, a lower alkyl group, a hydroxyl group, a halogen atom and a lower alkoxy group;

$R^3$ is a group of the formula:

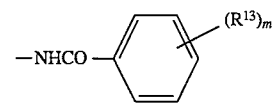

wherein $R^{13}$ is selected from the group consisting of a halogen atom, a hydrogen group, a hydroxyl group, a carbamoyl group, a lower alkyl group, a piperazinyl-lower alkoxy group having a lower alkanoyl group at the 4-position in the piperazine ring, an imidazolyl-substituted lower alkoxy group, a piperidinyl-lower alkoxy group having a lower alkanoylamino group on the piperidine ring, a 1,2,4-triazolyl-substituted lower alkoxy group, an ureido-substituted lower alkoxy group which may have a lower alkyl group, and an amino-substituted lower alkoxy group which may have lower alkyl groups as a substituent; and m is 0 or an integer of 1 to 3.

4. The benzoheterocyclic compound or a salt thereof according to claim 1, wherein $R^1$ is a hydrogen atom or a halogen atom.

5. The benzoheterocyclic compound or a salt thereof according to claim 1, wherein $R^1$ is selected from the group consisting of a hydroxyl group, a lower alkanoyloxy group, an amino-lower alkoxy group which may have as a substituent a lower alkyl group or a lower alkanoyl group, a carboxy-substituted lower alkoxy group, a lower alkoxycarbonyl-substituted lower alkoxy group, and an aminocarbonyl-lower alkoxy group which may have a lower alkyl group as a substituent.

6. The benzoheterocyclic compound or a salt thereof according to claim 4, wherein $R^4$ is a group of the formula:

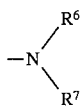

wherein $R^6$ and $R^7$ are the same as defined in claim 1; an imidazolyl-substituted lower alkyl group,
a 1,2,4-triazolyl-substituted lower alkoxy group,
a 1,2,3,4-tetrazolyl-substituted lower alkoxy group,
a 1,2,3,5-tetrazolyl-substituted lower alkoxy group,
a 1,2,3,4-tetrazolyl-substituted lower alkyl group,
a 1,2,3,5-tetrazolyl-substituted lower alkyl group,
1,2,4-triazolyl-substituted lower alkyl group,
a pyridylthio-substituted lower alkoxy group,
a pyrimidinylthio-substituted lower alkoxy group which may have lower alkyl groups on the pyrimidine ring, an imidazolthio-substituted lower alkoxygroup, a pyridylsulfinyl-substituted lower alkoxygroup, a pyridylsulfonyl-substituted lower alkoxygroup, an imidazolylsulfinyl-substituted lower alkoxy group, and an imidazolylsulfonyl-substituted lower alkoxy group.

7. The benzoheterocyclic compound or a salt thereof according to claim 1, wherein $R^1$ is a hydrogen atom or a halogen atom, and $R^4$ is a group of the formula:

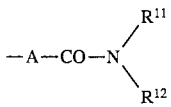

wherein A, $R^{11}$ and $R^{12}$ are the same as defined in claim 1.

8. The benzoheterocyclic compound or a salt thereof according to claim 1, wherein $R^1$ is a hydrogen atom or a halogen atom, and $R^4$ is a group of the formula:

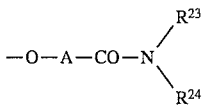

wherein A, $R^{23}$ and $R^{24}$ are the same as defined in claim 1.

9. The benzoheterocyclic compound or a salt thereof according to claim 1, wherein $R^1$ is a hydrogen atom or a halogen atom, and $R^4$ is a group of the formula:

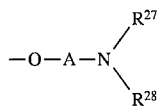

wherein A, $R^{27}$ and $R^{28}$ are the same as defined in claim 1.

10. The benzoheterocyclic compound or a salt thereof according to claim 1, wherein $R^1$ is a hydrogen atom or a halogen atom, and $R^4$ is a group of the formula:

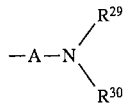

wherein A, $R^{29}$ and $R^{30}$ are the same as defined in claim 1.

11. The benzoheterocyclic compound or a salt thereof according to claim 1, wherein $R^1$ is selected from the group consisting of a hydroxyl group, a lower alkanoyloxy group, an amino-lower alkoxy group which may have as a substituent a lower alkyl group or a lower alkanoyl group, a carboxy-substituted lower alkoxy group, a lower alkoxycarbonyl-substituted lower alkoxy group, and an aminocarbonyl-lower alkoxy group which may have a lower alkyl group as a substituent; and $R^4$ is a group of the formula:

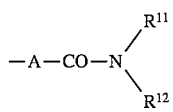

wherein A, $R^{11}$ and are the same as defined in claim 1.

12. The benzoheterocyclic compound or a salt thereof according to claim 1, wherein $R^1$ is selected from the group consisting of a hydroxyl group, a lower alkanoyloxy group, an amino-lower alkoxy group which may have as a substituent a lower alkyl group or a lower alkanoyl group, a carboxy-substituted lower alkoxy group, a lower alkoxycarbonyl-substituted lower alkoxy group, and an aminocarbonyl-lower alkoxy group which may have a lower alkyl group as a substituent; and $R^4$ is a group of the formula:

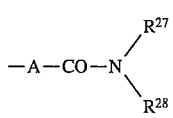

wherein A, $R^{27}$ and $R^{28}$ are the same as defined in claim 1.

13. The benzoheterocyclic compound or a salt thereof according to claim 1, wherein $R^1$ is selected from the group consisting of a hydroxyl group, a lower alkanoyloxy group, an amino-lower alkoxy group which may have as a substituent a lower alkyl group or a lower alkanoyl group, a carboxy-substituted lower alkoxy group, a lower alkoxycarbonyl-substituted lower alkoxy group, and an aminocarbonyl-lower alkoxy group which may have a lower alkyl group as a substituent; and $R^4$ is a group of the formula:

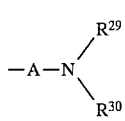

wherein A, $R^{29}$ and $R^{30}$ are the same as defined in claim 1.

14. The benzoheterocyclic compound or a salt thereof according to any one of claims 6 to 13, wherein $R^5$ is a hydrogen atom, $R^2$ is a lower alkyl group or a lower alkoxy group, and $R^3$ is a group of the formula:

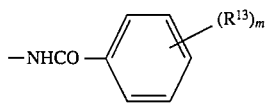

wherein $R^{13}$ is a halogen atom or a lower alkyl group, and m is 0 or an integer of 1 to 3.

15. The benzoheterocyclic compound or a salt thereof according to any one of claims 1 to 13, wherein $R^5$ is a hydrogen atom, $R^2$ is a hydrogen atom, a hydroxyl group or a halogen atom, and $R^3$ is a group of the formula:

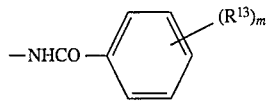

wherein $R^{13}$ is a halogen atom or a lower alkyl group, and m is 0 or an integer of 1 to 3.

16. The benzoheterocyclic compound or a salt thereof according to any one of claims 6 to 13, wherein $R^5$ is a hydrogen atom, $R^2$ is a lower alkyl group or a lower alkoxy group, and $R^3$ is a group of the formula:

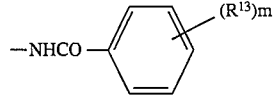

wherein $R^{13}$ is selected from the group consisting of a hydroxyl group, a carbamoyl group, a piperazinyl-lower alkoxy group having a lower alkanoyl group at the 4-position in the piperazine ring, an imidazolyl-substituted lower alkoxy group, a piperidinyl-substituted lower alkoxy group having a lower alkanoylamino group on the piperidine ring, a 1,2,4-triazolyl-substituted lower alkoxy group, an ureido-substituted lower alkoxy group which may have a lower alkyl groups, and an amino-substituted lower alkoxy group which may have a lower alkyl group as a substituent; and m is 0 or an integer of 1 to 3.

17. The benzoheterocyclic compound or a salt thereof according to any one of claims 6 to 13, wherein $R^5$ is a hydrogen atom, $R^2$ is a hydrogen atom, a hydroxyl group or a halogen atom; and $R^3$ is a group of the formula:

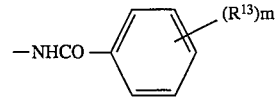

wherein $R^{13}$ is selected from the group consisting of a hydroxyl group, a carbamoyl group, a piperazinyl-lower alkoxy group having a lower alkanoyl group at the 4-position in the piperazine ring, an imidazolyl-substituted lower alkoxy group, a piperidinyl-substituted lower alkoxy group having a lower alkanoylamino group on the piperidine ring, a 1,2,4-triazolyl-substituted lower alkoxy group, an ureido-substituted lower alkoxy group which may have a lower alkyl group, and an amino-substituted lower alkoxy group which may have a lower alkyl group as a substituent; and m is 0 or an integer of 1 to 3.

18. The benzoheterocyclic compound or a salt thereof according to any one of claims 4 or 5, wherein $R^5$ is a hydroxyl. group.

19. The benzoheterocyclic compound or a salt thereof according to any one of claims 4 or 5, wherein $R^3$ is a phenyl-lower alkanoylamino group having 1 to 3 substituents selected from the group consisting of a halogen atom, a lower alkoxy group, a lower alkyl group and a nitro group on the phenyl ring.

20. The benzoheterocyclic compound or a salt thereof according to claim 5, wherein $R^{11}$ is a hydrogen atom or a lower alkyl group, $R^{12}$ is selected from the group consisting of a hydroxy-substituted lower alkyl group, a pyridyl-substituted lower alkyl group, a pyridyl group, a piperazinyl-substituted lower alkyl group which may have as a substituent a lower alkyl group on the piperazine ring, a pyrrolyl-substituted lower alkyl group which may have as a substituent a lower alkyl group on the pyrrole ring, a pyrrolidinyl-substituted lower alkyl group which may have as a substituent a lower alkyl group on the pyrrolidine ring, and a phenyl group which may have a halogen atom on the phenyl ring.

21. The benzoheterocyclic compound or a salt thereof according to claim 5, wherein $R^{11}$ is a hydrogen atom or a lower alkyl group, $R^{12}$ is a group of the formula:

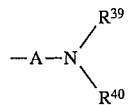

wherein A is the same as defined above; $R^{39}$ and $R^{40}$ are the same or different, and are each a hydrogen atom or a lower alkyl group which may have a hydroxyl group as a substituent, $R^{39}$ and $R^{40}$ may form a 5- to 6-membered saturated heterocyclic group, by combining with the adjacent nitrogen atoms, together with or without another nitrogen atom or oxygen atom, said heterocyclic group may be substituted with a lower alkyl group thereon.

22. The benzoheterocyclic compound or a salt thereof according to claim 5, wherein $R^{11}$ and $R^{12}$ may form a 5- to 7-membered saturated heterocyclic group, by combining with the adjacent nitrogen atom being bonded thereto, together with or without another nitrogen atom or oxygen atom; said heterocyclic group may be substituted with a member selected from the group consisting of a lower alkyl group, a lower alkoxycarbonyl group, an amino group which may have a substituent selected from the group consisting of a lower alkyl group, a lower alkanoyl group, a lower alkoxycarbonyl-substituted lower alkyl group, a phenyl group which may have a halogen atom on the phenyl ring, a cyano-substituted lower alkyl group, a lower alkenyl group, and a oxyranyl-substituted lower alkyl group, a carbamoyl-substituted lower alkyl group, a lower alkyl group having 1 to 2 substituents selected from the group consisting of a hydroxyl group, and an amino group which may have lower alkyl group or a pyrrolidinyl-carbonyl-lower alkyl group.

23. The benzoheterocyclic compound or a salt thereof according to claim 2, wherein $R^1$ is a hydrogen atom or a halogen atom; $R^2$ is a hydrogen atom, a lower alkyl group or a lower alkoxy group, or a salt thereof.

24. The benzoheterocyclic compound or a salt thereof according to claim 3, wherein $R^1$ is a hydrogen atom or a halogen atom; $R^2$ is a hydrogen atom, a lower alkyl group or a lower alkoxy group.

25. The benzoheterocyclic compound or a salt thereof according to claim 2, wherein $R^1$ is a hydrogen atom or a halogen atom, $R^2$ is a hydrogen atom, a lower alkyl group or a lower alkoxy group, or a salt thereof, and $R^4$ is a hydrogen atom or a group of the formula:

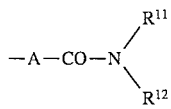

wherein A, $R^{11}$ and $R^{12}$ are the same as defined in claim 2.

26. The benzoheterocyclic compound or a salt thereof according to claim 3, wherein $R^1$ is a hydrogen atom or a halogen atom, $R^2$ is a hydrogen atom, a lower alkyl group or a lower alkoxy group, and $R^3$ is a group of the formula:

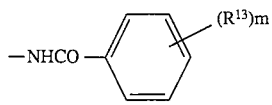

wherein $R^{13}$ and m are the same as defined in claim 3.

27. A compound that is 7-chloro-5-[N-(2-dimethylaminoethyl)-N- methylamino]carbonylmethyl-1-[3-methoxy-4-(2-bromobenzoylamine)benzoyl]-2,3,4,5-tetrahydro-1H-benzoazepine.

28. A vasopressin antagonistic composition which comprises, as an active ingredient, a benzoheterocyclic compound represented by the formula (1A), (1B) or (1C) as defined, respectively in claims 1, 2 or 3, or a pharmaceutically acceptable salt thereof in admixture with a pharmaceutically acceptable carrier or diluent.

* * * * *